US012583825B2

(12) United States Patent
Weiler et al.

(10) Patent No.: US 12,583,825 B2
(45) Date of Patent: Mar. 24, 2026

(54) BENZO[H]QUINAZOLIN-4-AMINE AND THIENO[3,2-H]QUINAZOLIN-4-AMINE DERIVATIVES FOR THE TREATMENT OF CANCER

(71) Applicant: Redona Therapeutics, Inc., Watertown, MA (US)

(72) Inventors: Sven Weiler, Allschwil (CH); Bérangère Gaucher, Allschwil (CH); Florian Richalet, Allschwil (CH); Stefan Reinelt, Allschwil (CH); Thomas Radimerski, Allschwil (CH); Andrea Aloia, Allschwil (CH)

(73) Assignee: Redona Therapeutics, Inc., Watertown, MA (US)

( * ) Notice: Subject to any disclaimer, the term of this patent is extended or adjusted under 35 U.S.C. 154(b) by 527 days.

(21) Appl. No.: 18/030,702

(22) PCT Filed: Oct. 7, 2021

(86) PCT No.: PCT/EP2021/077757

§ 371 (c)(1),
(2) Date: Apr. 6, 2023

(87) PCT Pub. No.: WO2022/074143

PCT Pub. Date: Apr. 14, 2022

(65) Prior Publication Data

US 2023/0365509 A1 Nov. 16, 2023

(30) Foreign Application Priority Data

Oct. 8, 2020 (EP) .................................... 20200850
Dec. 11, 2020 (EP) .................................... 20213590
Mar. 25, 2021 (EP) .................................... 21165054

(51) Int. Cl.
*A61P 35/00* (2006.01)
*C07D 239/94* (2006.01)
(Continued)

(52) U.S. Cl.
CPC ............ *C07D 239/94* (2013.01); *A61P 35/00* (2018.01); *C07D 401/12* (2013.01); (Continued)

(58) Field of Classification Search
CPC ...... C07D 239/94; C07D 401/12; A61P 35/00
See application file for complete search history.

(56) References Cited

U.S. PATENT DOCUMENTS 5,405,851 A 4/1995 Pendergast et al.
6,762,188 B1 * 7/2004 Pendergast ........... C07D 403/12 514/267

(Continued)

FOREIGN PATENT DOCUMENTS

CA 3021185 A1 11/2017
CN 1058208 A 1/1992
(Continued)

OTHER PUBLICATIONS

Markosyan et al., Synthesis of Triazoles and Tetrazoles Condensed with Spiro(Benzo[h]Quinazoline-5,1'-Cycloalkanes. Chemistry of Heterocyclic Compounds. 1999;35(11):1345-1348.

(Continued)

*Primary Examiner* — Sarah Pihonak
*Assistant Examiner* — Mikhail O'Donnel Robinson
(74) *Attorney, Agent, or Firm* — McCarter & English, LLP; Steven G. Davis

(57) ABSTRACT

The invention provides compounds of formula (IA) and compounds of formula (IB) and pharmaceutically acceptable salts thereof; wherein A is selected from group (A1) and group (A2): wherein #1 is attached to the carbon atom forming the oxime moiety and wherein group (A1) is optionally substituted by one or two R10 and group (A2) is optionally substituted by one R10, and wherein R1, X, R2 and R10 are as defined in the claims, as well as methods of using the compounds to treat neoplastic diseases, in particular cancer.

(IA)

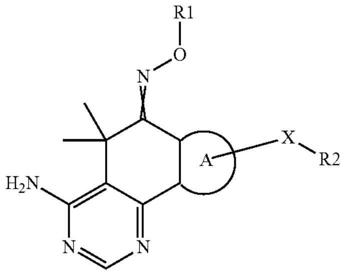

(IB)

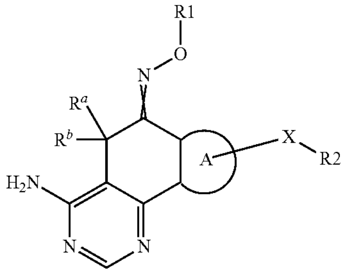

(A1)

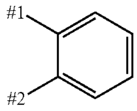

(A2)

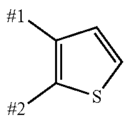

20 Claims, 2 Drawing Sheets

(51) Int. Cl.

| | |
|---|---|
| ***C07D 401/12*** | (2006.01) |
| ***C07D 403/12*** | (2006.01) |
| ***C07D 413/12*** | (2006.01) |
| ***C07D 495/04*** | (2006.01) |

(52) U.S. Cl.

CPC ......... *C07D 403/12* (2013.01); *C07D 413/12* (2013.01); *C07D 495/04* (2013.01)

(56) References Cited

U.S. PATENT DOCUMENTS

| | | | |
|---|---|---|---|
| 2005/0148603 | A1 | 7/2005 | Jimenez et al. |
| 2007/0270362 | A1 | 11/2007 | Harlan et al. |
| 2008/0188452 | A1 | 8/2008 | Altenbach et al. |
| 2008/0292626 | A1 | 11/2008 | Wang et al. |
| 2011/0097305 | A1 | 4/2011 | Connors et al. |
| 2014/0200206 | A1 | 7/2014 | Calabrese et al. |
| 2015/0132352 | A1 | 5/2015 | Sun et al. |
| 2019/0106437 | A1 | 4/2019 | Kawakita et al. |
| 2020/0039989 | A1 | 2/2020 | Hulme et al. |

FOREIGN PATENT DOCUMENTS

| | | | |
|---|---|---|---|
| CN | 102079746 | A | 6/2011 |
| CN | 102325755 | A | 1/2012 |
| CN | 108602780 | A | 9/2018 |
| WO | 2004/039786 | A1 | 5/2004 |
| WO | 2005/037843 | A1 | 4/2005 |
| WO | 2008/086158 | A1 | 7/2008 |
| WO | 2009/055674 | A1 | 4/2009 |
| WO | 2009/094123 | A1 | 7/2009 |
| WO | 2010/003133 | A2 | 1/2010 |
| WO | 2010/078421 | A1 | 7/2010 |
| WO | 2015/002915 | A1 | 1/2015 |
| WO | 2017/055530 | A1 | 4/2017 |
| WO | 2017/188374 | A1 | 11/2017 |
| WO | 2019/034890 | A1 | 2/2019 |
| WO | 2020/006115 | A1 | 1/2020 |
| WO | 2020/150545 | A1 | 7/2020 |
| WO | 2020/150552 | A2 | 7/2020 |
| WO | 2020/163248 | A1 | 8/2020 |
| WO | 2020/163323 | A1 | 8/2020 |
| WO | 2020/163375 | A1 | 8/2020 |
| WO | 2020/163382 | A1 | 8/2020 |
| WO | 2020/163401 | A1 | 8/2020 |
| WO | 2020/163405 | A1 | 8/2020 |
| WO | 2020/163406 | A1 | 8/2020 |
| WO | 2020/163409 | A1 | 8/2020 |
| WO | 2020/163541 | A1 | 8/2020 |
| WO | 2020/163544 | A1 | 8/2020 |
| WO | 2020/163647 | A1 | 8/2020 |

OTHER PUBLICATIONS

Markosyan et al., Synthesis and Psychotropic Activity of Triazoles and Tetrazoles Condensed with Spyro(Benzo[H] Quinazoline-5,1'-Cycloalkanes). Pharmaceutical Chemistry Journal. 1996;30(8):498-502.

Chung et al., SM08502, a novel, small-molecule CDC-like kinase (CLK) inhibitor, demonstrates strong antitumor effects and Wnt and cyclin D-CDK4/6-RB pathway inhibition in hormone-receptor-positive (HR+) breast cancer models. Cancer Res. 2020;80(Suppl 16): Abstract 6401, 4 pages.

Colwill et al., The Clk/Sty protein kinase phosphorylates SR splicing factors and regulates their intranuclear distribution. EMBO J. Jan. 15, 1996;15(2):265-75.

Iwai et al., Anti-tumor efficacy of a novel CLK inhibitor via targeting RNA splicing and MYC-dependent vulnerability. EMBO Mol Med. Jun. 2018;10(6):e8289, 15 pages.

Jarhad et al., Dual-Specificity Tyrosine Phosphorylation-Regulated Kinase 1A (DYRK1A) Inhibitors as Potential Therapeutics. J Med Chem. Nov. 21, 2018;61(22):9791-9810.

Koyama et al., Polycyclic N-Hetero Compunds VL. Synthesis of 11,13,15-Triazasteroidal Compounds and Correction of the Structures of Its Intermediates. Chem Pharm Bull. 1975;23(9):2015-2018.

Yoshida et al., CLK2 Is an Oncogenic Kinase and Splicing Regulator in Breast Cancer. Cancer Res. Apr. 1, 2015;75(7):1516-26.

Fukuda et al., Discovery of DS42450411 as a potent orally active hepcidin production inhibitor: Design and optimization of novel 4-aminopyrimidine derivatives. Bioorg Med Chem Lett. Nov. 1, 2018;28(20):3333-3337.

Markosyan et al., Synthesis of triazoles and tetrazoles condensed with spiro(benzo[ h ]quinazoline-5,1'-cycloalkanes). Pharma. Chem. J. Aug. 1, 1996;30(8):498-502.

Mott et al., Evaluation of substituted 6-arylquinazolin-4-amines as potent and selective inhibitors of cdc2-like kinases (Clk). Bioorg Med Chem Lett. Dec. 1, 2009;19(23):6700-5.

Pan et al., Pharmacophore and 3D-QSAR characterization of 6-arylquinazolin-4-amines as Cdc2-like kinase 4 (Clk4) and dual specificity tyrosine-phosphorylation-regulated kinase 1A (Dyrk1A) inhibitors. J Chem Inf Model. Apr. 22, 2013;53(4):938-47.

Tazarki et al., New pyrido[3,4-g]quinazoline derivatives as CLK1 and DYRK1A inhibitors: synthesis, biological evaluation and binding mode analysis. Eur J Med Chem. Mar. 15, 2019;166:304-317.

Zhu et al., Synthetic Lethal Strategy Identifies a Potent and Selective TTK and CLK1/2 Inhibitor for Treatment of Triple-Negative Breast Cancer with a Compromised G1-S Checkpoint. Mol Cancer Ther. Aug. 2018;17(8):1727-1738.

International Preliminary Report on Patentability for Application No. PCT/EP2021/077757, dated Apr. 20, 2023, 9 pages.

International Search Report and Written Opinion for Application No. PCT/EP2021/077757, dated Nov. 23, 2021, 15 pages.

* cited by examiner

BENZO[H]QUINAZOLIN-4-AMINE AND THIENO[3,2-H]QUINAZOLIN-4-AMINE DERIVATIVES FOR THE TREATMENT OF CANCER

CROSS-REFERENCE TO RELATED APPLICATIONS

This application is a 35 U.S.C. § 371 national stage filing of International Application No. PCT/EP2021/077757 filed on Oct. 7, 2021, which claims priority from European Patent Application No. 21165054.4, filed Mar. 25, 2021, European Patent Application No. 20213590.1 filed, Dec. 11, 2020 and European Patent Application No. 20200850.4, filed on Oct. 8, 2020. The entire contents of each of the foregoing applications are expressly incorporated herein by reference.

The present invention relates to compounds targeting the family of CDC2-like kinases (CLKs) and their use in the treatment of neoplastic diseases such as cancer.

Recurrent mutations in components of the splicing machinery have been reported in diseases like cancer. CLKs belong to the CMGC group of kinases and include four family members: CLK1, -2, -3 and -4. CLKs are known to play a key role in regulating alternative splicing (AS) through phosphorylation of splicing factors of the serine-arginine-rich (SR) family. Alternative splicing of transcripts is an important regulatory mechanism in eukaryotes that allows a single gene to generate multiple protein isoforms with distinct functions. CLK-mediated phosphorylation of SR proteins is implicated in their redistribution from speckles to a diffuse nucleoplasmic distribution pattern (Colwill et al., EMBO J. 1996, 15(2):265-75). SR protein phosphorylation has to be tightly regulated for nuclear import, spliceosome assembly, and ultimately for correct splicing, in particular to promote exon inclusion. Expression levels of CLKs have been reported to be elevated in a number of cancers and small molecule inhibitors of CLKs have been described to be efficacious in preclinical animal models of cancer (Yoshida T et al., Cancer Res. 2015, 75(7):1516-26; Iwai K et al., EMBO Mol Med. 2018 10 (6): e8289; Zhu D et al., Mol Cancer Ther. 2018, 17(8):1727-1738). Therefore, targeting of CLKs offers potential for anti-cancer therapy, for instance in splicing factor mutant cancers, where there is a compelling rationale to exploit aberrant splicing as a vulnerability and therapeutic opportunity.

In a first aspect the present invention provides compounds of formula (IA) and formula (IB)

(IA)

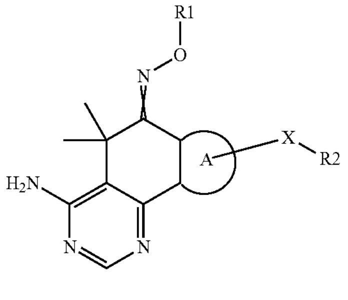

-continued (IB)

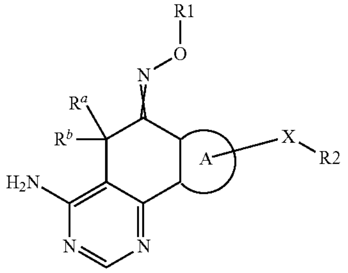

and pharmaceutically acceptable salts thereof, wherein A is selected from group (A1) and group (A2):

(A1)

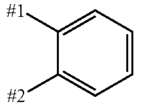

(A2)

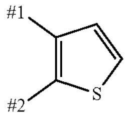

wherein #1 is attached to the carbon atom forming the oxime moiety and wherein group (A1) is optionally substituted by one or two R10 and group (A2) is optionally substituted by one R10;

each R10 is independently halogen or $—NH_2$;

X is —O—, —C(═O)—, $—C(═CH_2)—$, $—CH_2—$, —NH— or —N(C1-C4alkyl)- and wherein X is a bond when R2 is halogen or —CN and wherein when X is —C(═O)— R2 is not hydrogen;

or X—R2 is hydrogen;

Ra and Rb together form a $—CH_2—CH_2—CH_2—$ or a $—CH_2—CH_2—CH_2—CH_2—$ bridging moiety;

R1 is —Y—R3;

Y is a bond or C1-C6alkylene wherein one non-terminal $—CH_2—$ moiety may be replaced by —O—;

R3 is hydrogen, —CN, —OH, C1-C4haloalkyl, C2-C4alkenylene-R4, C2-C4alkynylene-R4, —O—C1-C4alkylene-R4, —O—C1-C4haloalkyl, $—NH_2$, —NH(C1-C4alkylene-R4), $—N(C1-C4alkylene-R4)_2$, —C(═O)—OH, —C(═O)—O—C1-C4alkylene-R4, $—C(═O)—NH_2$, —C(═O)—NH(C1-C4alkylene-R4), $—C(═O)—N(C1-C4alkylene-R4)_2$, Cycle P, Cycle Q, —O—Cycle P, —O—Cycle Q or $—S(O_2)—C1-C4alkyl$;

R4 is hydrogen, $—NH_2$, —NH(C1-C2alkyl) or $—N(C1-C2alkyl)_2$;

Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5; each R5 is independently $—NH_2$, —OH, —CN, C1-C4alkyl (e.g. C1-C2alkyl), C1-C4alkylene-R11 (e.g. C1-C2alkylene-R11), —O—C1-C2alkyl or oxo;

each R11 is independently halogen, $—NH_2$, —OH, —CN or —O—C1-C2alkyl;

- Cycle Q is phenyl optionally substituted by one to three R6, or is a 5-6-membered heteroaryl containing one to two heteroatoms selected from N, S and O optionally substituted by one to three R6;
- each R6 is independently —$NH_2$, —OH, —CN, C1-C2alkyl or —O—C1-C2alkyl;
- R2 is hydrogen, halogen, —CN, C1-C4alkyl optionally substituted by one or two R7, or is a 4- to 7-membered saturated carbocyclic ring optionally substituted by one or two R8, or is a 4- to 7-membered saturated heterocyclic ring containing one —N(R9)-moiety as ring member and otherwise containing only carbon atoms as ring members;
- each R7 is independently —OH, halogen, —$NH_2$, —NH(C1-C2alkyl), —N(C1-C2alkyl)$_2$ or —NH(—C(=O)—C1-C2alkyl);
- each R8 is independently —OH, halogen, —$NH_2$, —NH(C1-C2alkyl), —N(C1-C2alkyl)$_2$, —NH(—C(=O)—C1-C2alkyl) or C1-C2alkyl; and
- R9 is hydrogen, C1-C4alkyl or —C(=O)—C1-C2alkyl.

In a further aspect, the invention provides compounds of formula (IA) and compounds of formula (IB) and pharmaceutically acceptable salts thereof for use in the treatment of neoplastic diseases in a subject selected from a mammal, in particular a human.

In a further aspect, the invention provides use of compounds of formula (IA) and compounds of formula (IB) and pharmaceutically acceptable salts thereof in the manufacture of a medicament for the treatment of neoplastic diseases in a subject selected from a mammal, in particular a human.

In a further aspect, the invention provides methods of treating neoplastic diseases in a subject selected from a mammal, in particular a human, comprising administering a compound of formula (IA) or a compound of formula (IB) or pharmaceutically acceptable salt thereof, e.g. in a therapeutically acceptable amount, to said subject.

In a further aspect, the invention provides pharmaceutical compositions comprising a compound of formula (IA) or a compound of formula (IB) or pharmaceutically acceptable salt thereof and optionally one or more pharmaceutically acceptable excipients.

Each alkyl moiety either alone or as part of a larger group such as alkoxy is a straight or branched chain. Examples include methyl, ethyl, n-propyl, prop-2-yl, n-butyl, but-2-yl, 2-methyl-prop-1-yl or 2-methyl-prop-2-yl.

Each alkylene moiety either alone or part of a larger group is a straight or branched chain and is, for example, —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$— or —$CH_2CH(CH_3)CH_2$—.

Each alkenyl moiety either alone or as part of a larger group such as alkenyloxy is a straight or branched chain. Each moiety can be of either the (E)- or (Z)-configuration. Examples include vinyl and allyl.

Each alkenylene moiety either alone or as part of a larger group such as alkenyloxy is a straight or branched chain and is, for example, —$CH_2$—CH=CH—. Each moiety can be of either the (E)- or (Z)-configuration.

Each alkynyl moiety either alone or as part of a larger group such as alkynyloxy is a straight or branched chain and is preferably C2-C4alkynyl. Examples are ethynyl and propargyl.

Each alkynylene moiety either alone or as part of a larger group is a straight or branched chain and is, for example, —$CH_2$—C≡C—.

Each haloalkyl moiety either alone or as part of a larger group such as haloalkoxy is an alkyl group substituted by one or more of the same or different halogen atoms. Examples include difluoromethyl, trifluoromethyl, chlorodifluoromethyl and 2,2,2-trifluoro-ethyl. Haloalkyl moieties include for example 1 to 5 halo substituents, or 1 to 3 halo substituents.

Each cycloalkyl moiety (also referred to as carbocyclic ring moieties) may be saturated or partially unsaturated (unless otherwise stated) and can be in mono- or bi-cyclic form, preferably in mono-cyclic form. Examples of monocyclic cycloalkyl groups include cyclobutyl, cyclopentyl and cyclohexyl. An example of a bicyclic cycloalkyl group is bicyclo[2.2.1]heptan-2-yl.

Halogen is fluorine, chlorine, bromine or iodine.

Heteroaryl refers to an aromatic ring system containing the stated number of heteroatoms selected from nitrogen, oxygen and sulfur as ring members. Heteroaryl rings do not contain adjacent oxygen atoms, adjacent sulfur atoms, or adjacent oxygen and sulfur atoms within the ring or together with the atom outside the ring connecting the ring to the rest of the molecule.

The term "heterocyclic ring" refers to a saturated or partially unsaturated carbocyclic ring (unless otherwise stated) additionally containing the stated number of heteroatoms selected from nitrogen, oxygen and sulfur as ring members. Such rings do not contain adjacent oxygen atoms, adjacent sulfur atoms, or adjacent oxygen and sulfur atoms within the ring or together with the atom outside the ring connecting the ring to the rest of the molecule.

Oxo is an =O group. Where a moiety is said to be "substituted by oxo" it is counted as substitution by one substituent, e.g. when Cycle P may be substituted by one to three R5 and R5 may be oxo, then Cycle P may be substituted by oxo and two further R5 groups.

Where a group is said to be optionally substituted, it may be unsubstituted or substituted with the specified number of substituents.

Where ring nomenclature is provided for a specific moiety it is applied assuming no substituents on the ring. For example piperidin-1-yl places the nitrogen atom at the point of attachment irrespective of the identity of any substituents which might be present on the piperidine moiety.

The compounds of the invention include all (E) and (Z) isomers as well as mixtures thereof in any ratio. In particular, the oxime moiety may be in the (E) or (Z) configuration, giving rise to the following isomers.

(IA-(Z))

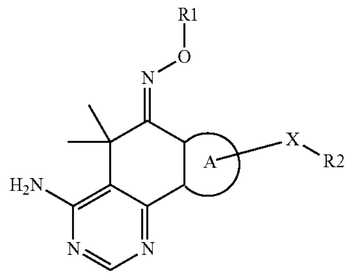

-continued (IA-(*E*))

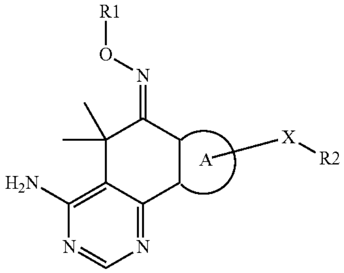

(IB-(*Z*))

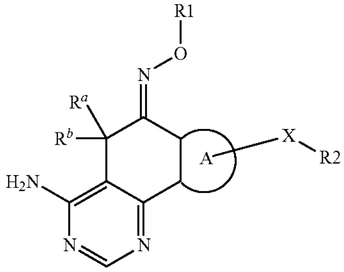

(IB-(*E*))

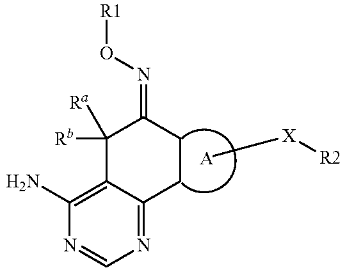

Both (Z) and (E) isomers are included within the scope of the compounds of formula (IA) and compounds of formula (IB), with the Z isomer preferred. Likewise, where cis and trans isomers are possible, e.g. when R2 is cyclohex-4-ylamine, both cis and trans isomers are included in the scope of formula (IA) and formula (IB). Whenever compounds of formula (IA) or compounds of formula (IB) contain one or two or more centers of chirality (for example when Y is branched alkylene) such compounds may be provided as pure enantiomers or pure diastereoisomers as well as mixtures thereof in any ratio and all such isomers are included within the scope of the compounds of formula (IA) and compounds of formula (IB). The compounds of the invention also include all tautomeric forms of the compounds of formula (IA) and compounds of formula (IB) where such possibilities exist, e.g. when a saturated ring is substituted by oxo. Isotopically labeled compounds including deuterium substitutions as well as carbon-13 and/or carbon-14 labels are also included within the scope of compounds of formula (IA) and compounds of formula (IB).

The compounds of formula (IA) and compounds of formula (IB) may also be solvated, especially hydrated, which are also included in the compounds of formula (IA) and compounds of formula (IB). Solvation and hydration may take place during the preparation process. Reference to compounds of the invention includes pharmaceutically acceptable salts of said compounds. Such salts may also exist as hydrates and solvates. Examples of pharmacologically acceptable salts of the compounds of formula (IA) and compounds of formula (IB) are salts of physiologically acceptable mineral acids, such as hydrochloric acid, sulfuric acid and phosphoric acid, or salts of organic acids, such as methane-sulfonic acid, p-toluenesulfonic acid, lactic acid, formic acid, acetic acid, trifluoroacetic acid, citric acid, succinic acid, fumaric acid, maleic acid and salicylic acid. Further examples of pharmacologically acceptable salts of the compounds of formula (IA) and compounds of formula (IB) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts.

The following examples of substituent definitions and embodiments may be combined in any combination where possible.

A is selected from group (A1) and group (A2), wherein #1 is attached to the carbon atom forming the oxime moiety and wherein group (A1) is optionally substituted by one or two R10 and group (A2) is optionally substituted by one R10. The carbon atom forming the oxime moiety is the carbon atom depicted as "C" in the unit >C(=N—O—R1).

Preferably A is selected from group (A1) optionally substituted by one R10, and group (A2) unsubstituted.

More preferably A is group (A1) optionally substituted by one R10.

Preferably when A is group (A1) X is connected to the carbon atom which is at the para position relative to #2, i.e. at the position depicted below in the compound of formula (IAa and IBa).

Preferably when A is group (A2) X is connected to the carbon atom adjacent to the S atom, i.e. at the position depicted below in the compound of formula (IAb).

Each R10 is independently halogen or $—NH_2$.

Preferably each R10 is independently fluoro, chloro or $—NH_2$, more preferably chloro or $—NH_2$.

Specific examples of R10 are fluoro, chloro and $—NH_2$.

X is —O—, —C(=O)—, $—C(=CH_2)—$, $—CH_2—$, —NH— or —N(C1-C4alkyl)- and wherein X is a bond when R2 is halogen or —CN and wherein when X is —C(=O)— R2 is not hydrogen; or X—R2 is hydrogen.

Specific examples of X are —O—, —C(=O)—, $—C(=CH_2)—$, $—CH_2—$, —NH— and $—N(CH_3)—$ (and a bond when R2 is halogen, e.g. chloro, bromo or iodo, or —CN).

Ra and Rb together form a $—CH_2—CH_2—CH_2—$ or a $—CH_2—CH_2—CH_2—CH_2—$ bridging moiety.

Preferably Ra and Rb together form a $—CH_2—CH_2—CH_2—CH_2—$ bridging moiety, i.e. to create a five membered fused carbocyclic ring as depicted in formula (IBa) below.

R1 is —Y—R3.

Preferably R1 is hydrogen, C1-C6alkylene-R3 wherein one non-terminal $—CH_2—$ moiety may be replaced by —O—, or R1 is Cycle P. Reference to a "non-terminal $—CH_2—$ moiety" refers a $—CH_2—$ moiety which is not at either end of the alkylene moiety (i.e. not the terminal $—CH_2—$ moiety which is proximal relative to the oxime moiety and not the terminal $—CH_2—$ moiety which is distal relative to the oxime moiety).

More preferably R1 is hydrogen or C1-C6alkylene-R3.

Even more preferably R1 is hydrogen or C1-C6alkylene-R3 wherein there are no more than three carbon atom spacers between the oxime oxygen atom and R3. In other more preferred embodiments R1 may be C1-C3alkylene-R3.

Specific examples of R1 are hydrogen, $—CH_3$, $—CH(CH_3)CH_3$, $—CH_2CH(CH_3)CH_3$, $—CH_2CH=CH_2$, $—CH_2C≡CH$, $—CH_2CH_2CH_2CN$, $—CH_2CH_2CH_2N$ $(CH_2CH_3)CH_2CH_3$, —$CH_2CH_2CH_2O$-benzyl, —$CH_2CH(CH_3)OH$, —$CH_2CH_2CH_2OH$, —$CH_2CH_2NH_2$, —$CH_2CH_2CH_2NH_2$, —$CH_2CH_2C$(=O)$OCH_2CH_3$, —$CH_2CH_2C$(=O)$OCH_3$, —$CH_2CH_2N(CH_2CH_3)CH_2CH_3$, —$CH_2CH_2N(CH_3)CH_3$, —$CH_2CH_2OH$, —$CH_2CH_2OCH_3$, —$CH_2CH_3$, —$CH_2CN$, —$CH_2CH_2CN$, —$CH_2C$(=O)$NH_2$, —$CH_2C$(=O)$NHCH_3$, —$CH_2C$(=O)$NHCH_2CH_2NH_2$, —$CH_2C$(=O)OH, —$CH_2C$(=O)$OCH_3$, 4-aminocyclohexyl, —$CH_2CH_2$-piperidinyl (e.g. —$CH_2CH_2$-piperidin-1-yl), —$CH_2CH_2$-pyrrolidinyl (e.g. —$CH_2CH_2$-pyrrolidin-1-yl), 4-cyanobenzyl, benzyl, —$CH_2$-3,5-dimethyl-isoxazolyl (e.g. —$CH_2$-3,5-dimethyl-isoxazol-4-yl), —$CH_2$-4-amino-cyclohexyl, —$CH_2$-oxazolidinyl-2-one (e.g. —$CH_2$-oxazolidin-5-yl-2-one), —$CH_2$—N-methyl-oxazolidinyl-2-one, e.g. (—$CH_2$—N-methyl-oxazolidin-5-yl-2-one), —$CH_2$—N-(1-hydroxyeth-2-yl)-oxazolidinyl-2-one (e.g. —$CH_2$—N-(1-hydroxyeth-2-yl)-oxazolidin-5-yl-2-one), —$CH_2$—N-(1-methoxyeth-2-yl)-oxazolidinyl-2-one (e.g. —$CH_2$—N-(1-methoxyeth-2-yl)-oxazolidin-5-yl-2-one), —$CH_2$—N-methyl-pyrrolidinyl (e.g. —$CH_2$—N-methyl-pyrrolidin-3-yl), —$CH_2$—N-methyl-pyrrolidinyl-2-one (e.g. —$CH_2$—N-methyl-pyrrolidin-4-yl-2-one), —$CH_2$-pyrrolidinyl (e.g. —$CH_2$-pyrrolidin-3-yl), —$CH_2$-pyrrolidinyl-2-one (e.g. —$CH_2$-pyrrolidin-4-yl-2-one), —$CH_2CH_2OCF_3$, —$CH_2CH_2CF_3$, —$CH_2CH_2$-phenyl, —$CH_2CH_2O$-phenyl, —$CH_2CH_2CH_2$-pyridinyl (e.g. —$CH_2CH_2CH_2$-pyridin-3-yl), —$CH_2CH_2OCH_2CH_3$, —$CH_2CH_2CH_2S(O_2)CH_3$, —$CH_2CH_2C(CH_3)_2CN$, —$CH_2CH_2OCH_2CF_3$, —$CH_2CH_2CF_2CH_3$, —$CH_2CH_2CH_2CH_2F$, and —$CH_2CH_2CH_2CF_3$.

In general, preferably there is at least a two carbon spacer unit (e.g. —$CH_2CH_2$—) between the oxime oxygen atom and any oxygen atom present in R1.

Y is a bond or C1-C6alkylene wherein one non-terminal —$CH_2$— moiety may be replaced by —O—. Reference to a "non-terminal —$CH_2$— moiety" refers a —$CH_2$— moiety which is not at either end of the alkylene moiety (i.e. not the terminal —$CH_2$— moiety which is proximal relative to the oxime moiety and not the terminal —$CH_2$— moiety which is distal relative to the oxime moiety).

Preferably Y is a bond or C1-C6alkylene, more preferably Y is a bond or C1-C6alkylene wherein there are no more than three carbon atom spacers between the oxime oxygen atom and R3. In other preferred embodiments Y is C1-C3alkylene.

Specific examples of Y are a bond, —$CH_2$—, —$CH_2CH_2$—, —$CH_2CH_2CH_2$—, —$CH(CH_3)CH_2$—, —$CH_2CH(CH_3)$—, —$CH_2CH(CH_3)CH_2$—, —$CH_2CH_2C(CH_3)(CH_3)$—, —$CH_2CH_2OCH_2$—, —$CH_2CH_2OCH_2CH_2$— and —$CH_2CH_2CH_2OCH_2$—.

R3 is hydrogen, —CN, —OH, C1-C4haloalkyl, C2-C4alkenylene-R4, C2-C4alkynylene-R4, —O—C1-C4alkylene-R4, —O—C1-C4haloalkyl, —$NH_2$, —NH(C1-C4alkylene-R4), —N(C1-C4alkylene-R4$)_2$, —C(=O)—OH, —C(=O)—O—C1-C4alkylene-R4, —C(=O)—$NH_2$, —C(=O)—NH(C1-C4alkylene-R4), —C(=O)—N(C1-C4alkylene-R4$)_2$, Cycle P, Cycle Q, —O—Cycle P, —O—Cycle Q or —$S(O_2)$—C1-C4alkyl.

Preferably R3 is hydrogen, —CN, —OH, C1-C4haloalkyl, C2-C4alkenyl, C2-C4alkynyl, —O—C1-C4alkyl, —O—C1-C4haloalkyl, —$NH_2$, —C(=O)—OH, —C(=O)—O—C1-C4alkyl, —C(=O)—$NH_2$, —C(=O)—NH(C1-C4alkylene-R4), Cycle P, Cycle Q, —O—Cycle P, —O—Cycle Q or —$S(O_2)$—C1-C4alkyl.

More preferably R3 is hydrogen, —CN, —OH, C1-C4haloalkyl, —O—C1-C4alkyl, —O—C1-C4haloalkyl, C2-C4alkynyl, —C(=O)—OH, —C(=O)—O—C1-C4alkyl, —C(=O)—$NH_2$, —C(=O)—NH(C1-C4alkyl), phenyl or oxazolidinyl-2-one (e.g. oxazolidin-5-yl-2-one) optionally substituted by one R5, (e.g. by one methyl (e.g. N-methyl-oxazolidin-5-yl-2-one), by one —$CH_2CH_2OH$ (e.g. N-(1-hydroxyeth-2-yl)-oxazolidin-5-yl-2-one) or by one —$CH_2CH_2OCH_3$ (e.g. N-(1-methoxy-eth-2-yl)-oxazolidin-5-yl-2-one)).

Preferably R3 is hydrogen or Cycle P when Y is a bond.

Specific examples of R3 are hydrogen, —CN, —OH, —$NH_2$, —CH=$CH_2$, —C≡CH, —N$(CH_2CH_3)_2$, —N$(CH_3)CH_3$, —$OCH_3$, —C(=O)$NHCH_2CH_2NH_2$, —C(=O)$NH_2$, —C(=O)$NHCH_3$, —C(=O)$OCH_2CH_3$, —C(=O)OH, —C(=O)$OCH_3$, 4-amino-cyclohexyl, piperidinyl (e.g. piperidin-1-yl), pyrrolidinyl (e.g. pyrrolidin-1-yl, pyrrolidin-3-yl), N-methylpyrrolidinyl, (e.g. N-methylpyrrolidin-3-yl), pyrrolidinyl-2-one (e.g. pyrrolidin-4-yl-2-one), N-methyl-pyrrolidinyl-2-one (e.g. N-methylpyrrolidin-4-yl-2-one), 3,5-dimethyl-isoxazolyl (e.g. 3,5-dimethyl-isoxazol-4-yl), oxazolidinyl-2-one (e.g. oxazolidin-5-yl-2-one), oxazolidinyl-2-one substituted by one methyl (e.g. N-methyl-oxazolidin-5-yl-2-one), N-(1-methoxyeth-2-yl)-oxazolidinyl-2-one (e.g. N-(1-methoxyeth-2-yl)-oxazolidin-5-yl-2-one), N-(1-hydroxyeth-2-yl)-oxazolidinyl-2-one (e.g. N-(1-hydroxyeth-2-yl)-oxazolidin-5-yl-2-one), 4-CN-phenyl, phenyl, —$OCF_3$, —$CF_3$, —O-phenyl, pyridinyl (e.g. pyridin-3-yl), —$OCH_2CH_3$, —$S(O)_2CH_3$, —$OCH_2CF_3$, —$CF_2CH_3$, $CH_2F$.

R4 is hydrogen, —$NH_2$, —NH(C1-C2alkyl) or —N(C1-C2alkyl$)_2$.

Preferably R4 is hydrogen, —$NH_2$ or —NH$(CH_3)$.

Specific examples of R4 are hydrogen and —$NH_2$.

Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5.

Preferably Cycle P is a 6-membered saturated carbocyclic ring optionally substituted by one to two R5 or is a 5-membered saturated heterocyclic ring containing one to two heteroatoms selected from N and O optionally substituted by one to two R5.

More preferably Cycle P is oxazolidinyl optionally substituted by one or two R5, in particular oxazolidinyl-2-one optionally substituted by one R5, preferably wherein R5 is not oxo.

Specific examples of Cycle P are aminocyclohexyl (e.g. 4-amino-cyclohexyl), piperidinyl (e.g. piperidin-1-yl), pyrrolidinyl (e.g. pyrrolidin-1-yl, pyrrolidin-3-yl, N-methyl-pyrrolidin-3-yl), pyrrolidinyl-2-one (e.g. pyrrolidin-4-yl-2-one, N-methyl-pyrrolidin-4-yl-2-one) and oxazolidinyl-2-one (e.g. oxazolidin-5-yl-2-one, N-(1-hydroxyeth-2-yl)-oxazolidin-5-yl-2-one, N-(1-methoxyeth-2-yl)-oxazolidin-5-yl-2-one, N-methyl-oxazolidin-5-yl-2-one).

Each R5 is independently —$NH_2$, —OH, —CN, C1-C4alkyl (e.g. C1-C2alkyl), C1-C4alkylene-R11 (e.g. C1-C2alkylene-R11), —O—C1-C2alkyl or oxo.

Preferably each R5 is independently —$NH_2$, C1-C2alkyl, —C1-C2alkyl-R11 or oxo. More preferably each R5 is independently C1-C2alkyl, —C1-C2alkyl-R11 or oxo. Preferably when a moiety is substituted by R5 no more than one R5 is oxo. In particular, preferably an oxazolidinyl-2-one moiety is not further substituted by oxo.

Specific examples of R5 are —$NH_2$, —$CH_3$, oxo, $CH_2CH_2OH$ and —$CH_2CH_2OCH_3$.

Each R11 is independently halogen, —$NH_2$, —OH, —CN or —O—C1-C2alkyl.

Specific examples of R1 are —OH and —$OCH_3$.

Cycle Q is phenyl optionally substituted by one to three R6, or is a 5-6-membered heteroaryl containing one to two heteroatoms selected from N, S and O optionally substituted by one to three R6.

Preferably Cycle Q is phenyl optionally substituted by one or two R6, or is a 6-membered heteroaryl containing one to two heteroatoms selected from N, S and O optionally substituted by one or two R6, e.g. pyridinyl, e.g. pyridin-3-yl.

Specific examples of Cycle Q are phenyl, 4-CN-phenyl, 3,5-dimethylisoxazolyl (e.g. 3,5-dimethylisoxazol-4-yl) and pyridinyl (e.g. pyridin-3-yl).

Each R6 is independently —$NH_2$, —OH, —CN, C1-C2alkyl or —O—C1-C2alkyl.

Preferably each R6 is independently —$NH_2$, —OH, —CN, —$CH_3$ or —$OCH_3$. Specific examples of R6 are —CN and —$CH_3$.

R2 is hydrogen, halogen, —CN, C1-C4alkyl optionally substituted by one or two R7, or is a 4- to 7-membered saturated carbocyclic ring optionally substituted by one or two R8, or is a 4- to 7-membered saturated heterocyclic ring containing one —N(R9)-moiety as ring member and otherwise containing only carbon atoms as ring members, wherein X is a bond when R2 is halogen.

Preferably R2 is hydrogen, halogen, C1-C4alkyl optionally substituted by one or two R7, or is a 6-membered saturated carbocyclic ring optionally substituted by one or two R8 (preferably substituted by at least one R8 which is —$NH_2$), or is a 6-membered saturated heterocyclic ring containing one —N(R9)-moiety as ring member and otherwise containing only carbon atoms as ring members.

More preferably R2 is bromo, iodo, —$CH_3$, C1-C4alkylene-R7, or is a 6-membered saturated carbocyclic ring substituted by one or two R8 wherein at least one R8 is —$NH_2$ and is at the para position with respect to X (e.g. 4-aminocyclohexyl (e.g. selected from cis-4-amino-cyclohexyl and trans-4-amino-cyclohexyl), 4-amino-3-fluoro-cyclohexyl (e.g. trans-4-amino-3-fluoro-cyclohexyl), 4-amino-4-methyl-cyclohexyl (e.g. cis-4-amino-4-methyl-cyclohexyl)) or piperidin-4-yl.

Specific examples of R2 are hydrogen, —CN, chloro, bromo, iodo, —$CH_3$, —$CH_2CH_2OH$, 4-amino-cyclohexyl (e.g. selected from cis-4-amino-cyclohexyl and trans-4-amino-cyclohexyl), 4-amino-3-fluoro-cyclohexyl (e.g. trans-4-amino-3-fluoro-cyclohexyl), piperidin-4-yl and 4-amino-4-methyl-cyclohexyl (e.g. cis-4-amino-4-methyl-cyclohexyl).

Specific examples of —X—R2 are —O-(4-amino-cyclohexyl) (e.g. selected from —O-(cis-4-amino-cyclohexyl and —O-(trans-4-amino-cyclohexyl)), —C(=$CH_2$)-(4-amino-cyclohexyl) (e.g. —C(=$CH_2$)-(trans-4-amino-cyclohexyl), —O—$CH_3$, —N($CH_3$)-(4-amino-cyclohexyl) (e.g. —N($CH_3$)-(trans-4-amino-cyclohexyl), bromo, —O-(4-amino-3-fluoro-cyclohexyl) (e.g. O-(trans-4-amino-3-fluoro-cyclohexyl), —O-piperidin-4-yl, —N($CH_3$)-piperidin-4-yl, —$CH_2$-(4-amino-cyclohexyl) (e.g. —$CH_2$-(trans-4-amino-cyclohexyl), chloro, —OH, —$CH_2$-piperidin-4-yl, —CN, iodo, —O—$CH_2CH_2OH$, —NH-(4-amino-cyclohexyl) (e.g. selected from —NH-(cis-4-amino-cyclohexyl and —NH-(trans-4-amino-cyclohexyl), —C(=O)—$CH_3$ and —O-(4-amino-4-methyl-cyclohexyl) (e.g. —O-(cis-4-amino-4-methyl-cyclohexyl).

Each R7 is independently —OH, halogen, —$NH_2$, —NH (C1-C2alkyl), —N(C1-C2alkyl)$_2$ or —NH(—C(=O)—C1-C2alkyl).

Preferably each R7 is independently halogen, —$NH_2$ or —OH (e.g. halogen or —$NH_2$).

More preferably each R7 is independently fluoro, —$NH_2$ or —OH (e.g. fluoro or —$NH_2$).

A specific example of R7 is —OH.

Each R8 is independently —OH, halogen, —$NH_2$, —NH (C1-C2alkyl), —N(C1-C2alkyl)$_2$, —NH(—C(=O)—C1-C2alkyl) or C1-C2alkyl.

Preferably each R8 is independently halogen, —$NH_2$ or —$CH_3$ (e.g. halogen or —$NH_2$) and preferably at least one R8 is —$NH_2$.

More preferably each R8 is independently fluoro, —$NH_2$ or —$CH_3$ (e.g. fluoro or —$NH_2$) and preferably at least one R8 is —$NH_2$.

Specific examples of R8 are fluoro, —$NH_2$ and $CH_3$ (e.g. fluoro and —$NH_2$).

R9 is hydrogen, C1-C4alkyl or —C(=O)—C1-C2alkyl.

Preferably R9 is hydrogen or —$CH_3$. A specific example of R9 is hydrogen.

In some embodiments the compounds of the invention are compounds of formula (IA).

In some embodiments the compounds the invention are compounds of formula (IB).

In some embodiments the compounds of the invention are compounds of formula (IB-1)

(IB-1)

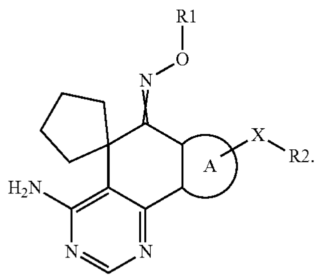

In some embodiments A is group (A1).

In some embodiments A is group (A2).

In some embodiments X is —O—.

In some embodiments X is —C(=$CH_2$)—.

In some embodiments X is —$CH_2$—.

In some embodiments X is —N($CH_3$)—.

In some embodiments X is —C(=O)—.

In some embodiments X is —NH—.

In some embodiments X is a bond and R2 is halogen (e.g. chloro, bromo or iodo).

In some embodiments X is a bond and R2 is —CN.

In some embodiments A is group (A1) and X is —O—.

In some embodiments A is group (A1) and X is —C(=$CH_2$)—.

In some embodiments A is group (A1) and X is —$CH_2$—.

In some embodiments A is group (A1) and X is —N($CH_3$)—.

In some embodiments A is group (A1) and X is —C(=O)—.

In some embodiments A is group (A1) and X is —NH—.

In some embodiments A is group (A1), X is a bond and R2 is —CN.

In some embodiments A is group (A1), X is a bond and R2 is halogen (e.g. chloro, bromo or iodo).

In some embodiments A is group (A2) and X is —O—.

In some embodiments A is group (A2) and X is —C(=$CH_2$)—.

In some embodiments A is group (A2) and X is —$CH_2$—.

In some embodiments A is group (A2) and X is —N($CH_3$)—.

In some embodiments A is group (A2), X is a bond and R2 is halogen.

In some embodiments R1 is hydrogen or C1-C6alkylene-R3 and R3 is hydrogen, —CN, —OH, C1-C4haloalkyl, C2-C4alkenyl, C2-C4alkynyl, —O—C1-C4alkyl, —O—C1-C4haloalkyl, —$NH_2$, —C(═O)—OH, —C(═O)—O—C1-C4alkyl, —C(═O)—$NH_2$, —C(═O)—NH(C1-C4alkylene-R4), Cycle P, Cycle Q, —O—Cycle P, —O—Cycle Q or —S($O_2$)—C1-C4alkyl.

In some embodiments R1 is hydrogen or C1-C6alkylene-R3 wherein there are no more than three carbon atom spacers between the oxime oxygen atom and R3 is hydrogen, —CN, —OH, C1-C4haloalkyl, —O—C1-C4alkyl, —O—C1-C4haloalkyl, C2-C4alkynyl, —C(═O)—OH, —C(═O)—O—C1-C4alkyl, —C(═O)—$NH_2$, —C(═O)—NH(C1-C4alkyl), phenyl or oxazolidinyl-2-one (e.g. oxazolidin-5-yl-2-one) optionally substituted by one R5, (e.g. by one methyl (e.g. N-methyl-oxazolidin-5-yl-2-one), by one —$CH_2CH_2OH$ (e.g. N-(1-hydroxyeth-2-yl)-oxazolidin-5-yl-2-one) or by one —$CH_2CH_2OCH_3$ (e.g. N-(1-methoxyeth-2-yl)-oxazolidin-5-yl-2-one).

In some embodiments R1 is hydrogen or C1-C3alkylene-R3 and R3 is hydrogen, —CN, —OH, C1-C4haloalkyl, —O—C1-C4alkyl, —O—C1-C4haloalkyl, C2-C4alkynyl, —C(═O)—OH, —C(═O)—O—C1-C4alkyl, —C(═O)—$NH_2$, —C(═O)—NH(C1-C4alkyl), phenyl or oxazolidinyl-2-one (e.g. oxazolidin-5-yl-2-one) optionally substituted by one R5, (e.g. by one methyl (e.g. N-methyl-oxazolidin-5-yl-2-one), by one —$CH_2CH_2OH$ (e.g. N-(1-hydroxyeth-2-yl)-oxazolidin-5-yl-2-one) or by one —$CH_2CH_2OCH_3$ (e.g. N-(1-methoxyeth-2-yl)-oxazolidin-5-yl-2-one).

In some embodiments R1 is hydrogen.

In some embodiments R1 is C1-C6alkylene-R3 wherein one non-terminal —$CH_2$— moiety may be replaced by —O— and wherein R3 is hydrogen, —CN, —OH, C1-C4haloalkyl, C2-C4alkenylene-R4, C2-C4alkynylene-R4, —O—C1-C4alkylene-R4, —O—C1-C4haloalkyl, —$NH_2$, —NH(C1-C4alkylene-R4), —N(C1-C4alkylene-R4)$_2$, —C(═O)—OH, —C(═O)—O—C1-C4alkylene-R4, —C(═O)—$NH_2$, —C(═O)—NH(C1-C4alkylene-R4), —C(═O)—N(C1-C4alkylene-R4)$_2$ or —S($O_2$)—C1-C4alkyl and R4 has the meaning as described herein.

In some embodiments R1 is C1-C6alkylene-R3 and wherein R3 is hydrogen, —CN, —OH, C1-C4haloalkyl, C2-C4alkenyl, C2-C4alkynyl, —O—C1-C4alkyl, —O—C1-C4haloalkyl, —C(═O)—OH, —C(═O)—O—C1-C4alkyl, —C(═O)—$NH_2$, —C(═O)—NH(C1-C4alkylene-R4), or —S($O_2$)—C1-C4alkyl and R4 has the meaning as described herein.

In some embodiments R1 is C1-C6alkylene-R3 wherein there are no more than three carbon atom spacers between the oxime oxygen atom and R3 and wherein R3 is hydrogen, —CN, —OH, C1-C4haloalkyl —O—C1-C4alkyl, —O—C1-C4haloalkyl, C2-C4alkynyl, —C(═O)—OH, —C(═O)—O—C1-C4alkyl, —C(═O)—$NH_2$ or —C(═O)—NH(C1-C4alkyl). In some embodiments R1 is C1-C3alkylene-R3 and wherein R3 is hydrogen, —CN, —OH, C1-C4haloalkyl —O—C1-C4alkyl, —O—C1-C4haloalkyl, C2-C4alkynyl, —C(═O)—OH, —C(═O)—O—C1-C4alkyl, —C(═O)—$NH_2$ or —C(═O)—NH(C1-C4alkyl).

In some embodiments R1 is C2-C3alkylene-R3 and wherein R3 is —CN, —OH or —O—C1-C4alkyl.

In some embodiments R1 is C1-C6alkylene-R3 wherein one non-terminal —$CH_2$— moiety may be replaced by —O— and wherein R3 is Cycle P, Cycle Q, —O—Cycle P or —O—Cycle Q.

In some embodiments R1 is C1-C6alkylene-R3 and wherein R3 is Cycle P, Cycle Q, —O—Cycle P or —O—Cycle Q.

In some embodiments R1 is C1-C6alkylene-R3 wherein there are no more than three carbon atom spacers between the oxime oxygen atom and R3 and wherein R3 is Cycle P or Cycle Q.

In some embodiments R1 is C1-C3alkylene-R3 and wherein R3 is Cycle P or Cycle Q.

In some embodiments R1 is C1-C3alkylene-R3 wherein there are no more than three carbon atom spacers between the oxime oxygen atom and R3 and wherein R3 is phenyl or oxazolidinyl-2-one optionally substituted by one R5, preferably C1-C4alkyl or C1-C4alkylene-R11, and preferably R5 is attached to the nitrogen atom of the oxazolidinyl-2-one and R11 has the meaning as described herein.

In some embodiments R1 is C1-C3alkylene-R3 and wherein R3 is phenyl or oxazolidinyl-2-one optionally substituted by one R5, preferably C1-C4alkyl or C1-C4alkylene-R11, and preferably R5 is attached to the nitrogen atom of the oxazolidinyl-2-one and R11 has the meaning as described herein.

In some embodiments R1 is —$CH_2$-oxazolidinyl-2-one optionally substituted by one R5 and R5 has the meaning as described herein, preferably wherein R5 is not oxo.

In some embodiments R1 is —$CH_2$-oxazolidinyl-2-one optionally substituted by one R5 and wherein the R5 when present has the meaning as described herein but is not oxo and is attached to the nitrogen atom of the oxazolidinyl-2-one moiety.

In some embodiments R1 is —$CH_2CH_2CN$, —$CH_2CH_2OH$, —$CH_2CH_2OCH_3$ or $CH_2$-oxazolidinyl-2-one optionally substituted by one R5 and wherein the R5 when present is attached to the nitrogen atom of the oxazolidinyl-2-one moiety and wherein R5 is —$CH_2CH_2OH$ or —$CH_2CH_2OCH_3$.

In an embodiment (Embodiment A1) the compound is a compound of formula (IA) or a compound of formula (IB), wherein A is selected from group (A1) and group (A2) and wherein group (A1) is optionally substituted by one or two R10 and group (A2) is optionally substituted by one R10;

each R10 is independently fluoro, chloro or —$NH_2$;

X is —O—, —C(═O)—, —C(═$CH_2$)—, —$CH_2$—, —NH— or —N(C1-C4alkyl)- and wherein X is a bond when R2 is halogen or —CN and wherein when X is —C(═O)— R2 is not hydrogen;

Ra and Rb together form a —$CH_2$—$CH_2$—$CH_2$—$CH_2$— bridging moiety;

R1 is —Y—R3;

Y is a bond or C1-C6alkylene wherein one non-terminal —$CH_2$— moiety may be replaced by —O—;

R3 is hydrogen, —CN, —OH, C1-C4haloalkyl, C2-C4alkenyl, C2-C4alkynyl, —O—C1-C4alkyl, —O—C1-C4haloalkyl, —$NH_2$, —C(═O)—OH, —C(═O)—O—C1-C4alkyl, —C(═O)—$NH_2$, —C(═O)—NH(C1-C4alkylene-R4), Cycle P, Cycle Q, —O—Cycle P, —O—Cycle Q or —S($O_2$)—C1-C4alkyl;

R4 is hydrogen, —$NH_2$ or —NH($CH_3$);

Cycle P is a 6-membered saturated carbocyclic ring optionally substituted by one to two R5 or is a 5-membered saturated heterocyclic ring containing one to two heteroatoms selected from N and O optionally substituted by one to two R5;

each R5 is independently —$NH_2$, —OH, —CN, C1-C2alkyl (e.g. —$CH_3$), —C1-C2alkyl-R11, —O—C1-C2alkyl (e.g. —$OCH_3$) or oxo;

each R11 is independently halogen, —$NH_2$, —OH, —CN or —O—C1-C2alkyl;

Cycle Q is phenyl optionally substituted by one or two R6, or is a 6-membered heteroaryl containing one to two heteroatoms selected from N, S and O optionally substituted by one or two R6;

each R6 is independently —$NH_2$, —OH, —CN, —$CH_3$ or —$OCH_3$;

R2 is hydrogen, halogen, C1-C4alkyl optionally substituted by one or two R7, or is a 6-membered saturated carbocyclic ring optionally substituted by one or two R8 (preferably substituted by at least one R8 which is —$NH_2$), or is a 6-membered saturated heterocyclic ring containing one —N(R9)-moiety as ring member and otherwise containing only carbon atoms as ring members;

each R7 is independently halogen —$NH_2$ or —OH (e.g. halogen or —$NH_2$);

each R8 is independently halogen, —$NH_2$ or —$CH_3$ (e.g. halogen or —$NH_2$); and R9 is hydrogen or —$CH_3$.

The above examples of substituent definitions and embodiments given for the compound of formula (IA) and compounds of formula (IB) may be combined with Embodiment A1 in any combination where feasible.

In an embodiment (Embodiment A1-A) the compounds of the invention are compounds of formula (IA) defined as for Embodiment A1.

In an embodiment (Embodiment A1-B) the compounds of the invention are compounds of formula (IB) defined as for Embodiment A1.

In an embodiment (Embodiment A2) the compound is a compound of formula (IA) or a compound of formula (IB), wherein A is selected from group (A1) and group (A2) and wherein group (A1) is optionally substituted by one or two R10 and group (A2) is optionally substituted by one R10;

each R10 is independently fluoro, chloro or —$NH_2$;

preferably X is connected to the carbon atom which is at the para position relative to #2;

X is —O—, —C(═O)—, —C(═$CH_2$)—, —$CH_2$—, —NH— or —N(C1-C4alkyl)- and wherein X is a bond when R2 is halogen or —CN and wherein when X is —C(═O)— R2 is not hydrogen;

Ra and Rb together form a —$CH_2$—$CH_2$—$CH_2$—$CH_2$— bridging moiety;

R1 is hydrogen, C1-C6alkylene-R3 wherein one non-terminal —$CH_2$— moiety may be replaced by —O—, or R1 is Cycle P;

R3 is hydrogen, —CN, —OH, C1-C4haloalkyl, C2-C4alkenyl, C2-C4alkynyl, —O—C1-C4alkyl, —O—C1-C4haloalkyl, —$NH_2$, —C(═O)—OH, —C(═O)—O—C1-C4alkyl, —C(═O)—$NH_2$, —C(═O)—NH(C1-C4alkylene-R4), Cycle P, Cycle Q, —O—Cycle P, —O—Cycle Q or —S($O_2$)—C1-C4alkyl;

R4 is hydrogen, —$NH_2$ or —NH($CH_3$);

Cycle P is a 6-membered saturated carbocyclic ring optionally substituted by one to two R5 or is a 5-membered saturated heterocyclic ring containing one to two heteroatoms selected from N and O optionally substituted by one to two R5;

each R5 is independently —$NH_2$, —OH, —CN, C1-C2alkyl (e.g. —$CH_3$), —C1-C2alkyl-R11, —O—C1-C2alkyl (e.g. —$OCH_3$) or oxo;

Cycle Q is phenyl optionally substituted by one or two R6, or is a 6-membered heteroaryl containing one to two heteroatoms selected from N, S and O optionally substituted by one or two R6;

each R6 is independently —$NH_2$, —OH, —CN, —$CH_3$ or —$OCH_3$;

R2 is hydrogen, halogen, C1-C4alkyl optionally substituted by one or two R7, or is a 6-membered saturated carbocyclic ring optionally substituted by one or two R8 (preferably substituted by at least one R8 which is —$NH_2$), or is a 6-membered saturated heterocyclic ring containing one —N(R9)-moiety as ring member and otherwise containing only carbon atoms as ring members;

each R7 is independently halogen —$NH_2$ or —OH (e.g. halogen or —$NH_2$);

each R8 is independently halogen, —$NH_2$ or —$CH_3$ (e.g. halogen or —$NH_2$); and R9 is hydrogen or —$CH_3$.

The above examples of substituent definitions and embodiments given for the compound of formula (IA) and compounds of formula (IB) may be combined with Embodiment A2 in any combination where feasible.

In an embodiment (Embodiment A2-A) the compounds of the invention are compounds of formula (IA) defined as for Embodiment A2.

In an embodiment (Embodiment A2-B) the compounds of the invention are compounds of formula (IB) defined as for Embodiment A2.

In an embodiment (Embodiment B1) the compound is a compound of formula (IA) or a compound of formula (IB), wherein A is group (A1) optionally substituted by one R10;

R10 is chloro or —$NH_2$;

preferably X is connected to the carbon atom which is at the para position relative to #2;

X is —O—, —C(═O)—, —C(═$CH_2$)—, —$CH_2$— or —N($CH_3$)— and wherein X is a bond when R2 is halogen and wherein when X is —C(═O)— R2 is not hydrogen;

Ra and Rb together form a —$CH_2$—$CH_2$—$CH_2$—$CH_2$— bridging moiety;

R1 is —Y—R3;

Y is a bond or C1-C6alkylene, preferably wherein there are no more than three carbon atom spacers between the oxime oxygen atom and R3, more preferably a bond or C1-C3alkylene;

R3 is hydrogen, —CN, —OH, C1-C4haloalkyl, —O—C1-C4alkyl, —O—C1-C4haloalkyl, C2-C4alkynyl, —C(═O)—OH, —C(═O)—O—C1-C4alkyl, —C(═O)—$NH_2$, —C(═O)—NH(C1-C4alkyl), phenyl, oxazolidinyl-2-one (e.g. oxazolidin-3-yl-2-one, oxazolidin-5-yl-2-one) or oxazolidinyl-2-one substituted by one R5 (e.g. by one methyl (e.g. N-methyl-oxazolidin-5-yl-2-one), by one —$CH_2CH_2OH$ (e.g. N-(1-hydroxyeth-2-yl)-oxazolidin-5-yl-2-one) or by one —$CH_2CH_2OCH_3$ (e.g. N-(1-methoxyeth-2-yl)-oxazolidin-5-yl-2-one)), and preferably wherein R3 is hydrogen when Y is a bond;

R5 is C1-C2alkyl or —C1-C2alkyl-R11;

R11 is halogen, $—NH_2$, —OH, —CN or —O—C1-C2alkyl;

R2 is fluoro, chloro, bromo, iodo, $—CH_3$, C1-C4alkyl-R7, a 6-membered saturated carbocyclic ring substituted by one or two R8 wherein at least one R8 is $—NH_2$ and is at the para position with respect to X (e.g. 4-amino-cyclohexyl, 4-amino-3-fluoro-cyclohexyl, 4-amino-4-methyl-cyclohexyl) or piperidin-4-yl;

R7 is fluoro, $—NH_2$ or —OH; and each R8 is independently halogen, $—NH_2$ or $—CH_3$.

The above examples of substituent definitions and embodiments given for the compound of formula (IA) and compounds of formula (IB) may be combined with Embodiment B1 in any combination where feasible.

In an embodiment (Embodiment B1-A) the compounds of the invention are compounds of formula (IA) defined as for Embodiment B1.

In an embodiment (Embodiment B1-B) the compounds of the invention are compounds of formula (IB) defined as for Embodiment B1.

In an embodiment (Embodiment B2) the compound is a compound of formula (IA) or a compound of formula (IB), wherein A is group (A1) optionally substituted by one R10;

R10 is chloro or $—NH_2$;

preferably X is connected to the carbon atom which is at the para position relative to #2;

X is —O—, —C(═O)—, $—C(═CH_2)—$, $—CH_2—$ or $—N(CH_3)—$ and wherein X is a bond when R2 is halogen and wherein when X is —C(═O)— R2 is not hydrogen;

Ra and Rb together form a $—CH_2—CH_2—CH_2—CH_2—$ bridging moiety;

R1 is hydrogen or C1-C6alkylene-R3, preferably wherein there are no more than three carbon atom spacers between the oxime oxygen atom and R3, more preferably hydrogen or C1-C3alkylene-R3;

R3 is hydrogen, —CN, —OH, C1-C4haloalkyl, —O—C1-C4alkyl, —O—C1-C4haloalkyl, C2-C4alkynyl, —C(═O)—OH, —C(═O)—O—C1-C4alkyl, $—C(═O)—NH_2$, —C(═O)—NH(C1-C4alkyl), phenyl, oxazolidinyl-2-one (e.g. oxazolidin-3-yl-2-one, oxazolidin-5-yl-2-one) or oxazolidinyl-2-one substituted by one R5 (e.g. by one methyl (e.g. N-methyl-oxazolidin-5-yl-2-one), by one $—CH_2CH_2OH$ (e.g. N-(1-hydroxyeth-2-yl)-oxazolidin-5-yl-2-one) or by one $—CH_2CH_2OCH_3$ (e.g. N-(1-methoxyeth-2-yl)-oxazolidin-5-yl-2-one));

R5 is C1-C2alkyl or —C1-C2alkyl-R11;

R11 is halogen, $—NH_2$, —OH, —CN or —O—C1-C2alkyl;

R2 is fluoro, chloro, bromo, iodo, $—CH_3$, C1-C4alkyl-R7, a 6-membered saturated carbocyclic ring substituted by one or two R8 wherein at least one R8 is $—NH_2$ and is at the para position with respect to X (e.g. 4-amino-cyclohexyl, 4-amino-3-fluoro-cyclohexyl, 4-amino-4-methyl-cyclohexyl) or piperidin-4-yl;

R7 is fluoro, $—NH_2$ or —OH; and each R8 is independently halogen, $—NH_2$ or $—CH_3$.

The above examples of substituent definitions and embodiments given for the compound of formula (IA) and compounds of formula (IB) may be combined with Embodiment B2 in any combination where feasible.

In an embodiment (Embodiment B2-A) the compounds of the invention are compounds of formula (IA) defined as for Embodiment B2.

In an embodiment (Embodiment B2-B) the compounds of the invention are compounds of formula (IB) defined as for Embodiment B2.

In an embodiment (Embodiment C1) the compound is a compound of formula (IA) or a compound of formula (IB), wherein A is selected from group (A1) and group (A2) and wherein group (A1) is optionally substituted by one R10 and group (A2) is unsubstituted;

R10 is chloro or $—NH_2$;

preferably when A is group (A1) X is connected to the carbon atom which is at the para position relative to #2, and preferably when A is group (A2) X is connected to the carbon atom adjacent to the S atom;

X is —O—, —C(═O)—, $—C(═CH_2)—$, $—CH_2—$, —NH— or $—N(CH_3)—$ and wherein X is a bond when R2 is halogen and wherein when X is —C(═O)— R2 is not hydrogen;

Ra and Rb together form a $—CH_2—CH_2—CH_2—CH_2—$ bridging moiety;

R1 is —Y—R3;

Y is a bond, $—CH_2—$, $—CH_2CH_2—$, $—CH_2CH_2CH_2—$, $—CH(CH_3)CH_2—$, $—CH_2CH(CH_3)—$, $—CH_2CH(CH_3)CH_2—$, $—CH_2CH_2C(CH_3)(CH_3)—$, $—CH_2CH_2OCH_2—$, $—CH_2CH_2OCH_2CH_2—$ or $—CH_2CH_2CH_2OCH_2—$;

R3 is hydrogen, —CN, —OH, $—NH_2$, $—CH═CH_2$, —C≡CH, $—N(CH_2CH_3)_2$, $—N(CH_3)CH_3$, $—OCH_3$, $—C(═O)NHCH_2CH_2NH_2$, $—C(═O)NH_2$, $—C(═O)NHCH_3$, $—C(═O)OCH_2CH_3$, —C(═O)OH, $—C(═O)OCH_3$, 4-amino-cyclohexyl, piperidinyl (e.g. piperidin-1-yl), pyrrolidinyl (e.g. pyrrolidin-1-yl, pyrrolidin-3-yl), pyrrolidinyl-2-one (e.g. pyrrolidin-4-yl-2-one), N-methylpyrrolidinyl, (e.g. N-methylpyrrolidin-3-yl), N-methyl-pyrrolidinyl-2-one (e.g. N-methylpyrrolidin-4-yl-2-one), 3,5-dimethyl-isoxazolyl (e.g. 3,5-dimethyl-isoxazol-4-yl), oxazolidinyl-2-one (e.g. oxazolidin-3-yl-2-one, oxazolidin-5-yl-2-one), oxazolidinyl-2-one substituted by one methyl (e.g. N-methyl-oxazolidin-5-yl-2-one), N-(1-methoxyeth-2-yl)-oxazolidinyl-2-one (e.g. N-(1-methoxyeth-2-yl)-oxazolidin-5-yl-2-one), N-(1-hydroxyeth-2-yl)-oxazolidinyl-2-one (e.g. N-(1-hydroxyeth-2-yl)-oxazolidin-5-yl-2-one), 4-CN-phenyl, phenyl, $—OCF_3$, $—CF_3$, —O-phenyl, pyridinyl (e.g. pyridin-3-yl), $—OCH_2CH_3$, $—S(O)_2CH_3$, $—OCH_2CF_3$, $—CF_2CH_3$ or $—CH_2F$; and R2 is hydrogen, —CN, chloro, bromo, iodo, $—CH_3$, $—CH_2CH_2OH$, 4-amino-cyclohexyl, 4-amino-3-fluoro-cyclohexyl, piperidin-4-yl or 4-amino-4-methyl-cyclohexyl.

The above examples of substituent definitions and embodiments given for the compound of formula (IA) and compounds of formula (IB) may be combined with Embodiment C1 in any combination where feasible.

In an embodiment (Embodiment C1-A) the compounds of the invention are compounds of formula (IA) defined as for Embodiment C1.

In an embodiment (Embodiment C1-B) the compounds of the invention are compounds of formula (IB) defined as for Embodiment C1.

In an embodiment (Embodiment C2) the compound is a compound of formula (IA) or a compound of formula (IB), wherein A is selected from group (A1) and group (A2) and wherein group (A1) is optionally substituted by one R10 and group (A2) is unsubstituted;

R10 is chloro or $—NH_2$;

preferably when A is group (A1) X is connected to the carbon atom which is at the para position relative to #2, and preferably when A is group (A2) X is connected to the carbon atom adjacent to the S atom;

X is —O—, —C(═O)—, —C(═$CH_2$)—, —$CH_2$— or —N($CH_3$)— and wherein X is a bond when R2 is halogen and wherein when X is —C(═O)— R2 is not hydrogen;

Ra and Rb together form a —$CH_2$—$CH_2$—$CH_2$—$CH_2$— bridging moiety;

R1 is hydrogen, —$CH_3$, —CH($CH_3$)$CH_3$, —$CH_2$CH($CH_3$)$CH_3$, —$CH_2$CH═$CH_2$, —$CH_2$C≡CH, —$CH_2CH_2CH_2$CN, —$CH_2CH_2CH_2$N($CH_2CH_3$)$CH_2CH_3$, —$CH_2CH_2CH_2$O-benzyl, —$CH_2$CH($CH_3$)OH, —$CH_2CH_2CH_2$OH, —$CH_2CH_2NH_2$, —$CH_2CH_2CH_2NH_2$, —$CH_2CH_2$C(═O)$OCH_2CH_3$, —$CH_2CH_2$C(═O)$OCH_3$, —$CH_2CH_2$N($CH_2CH_3$)$CH_2CH_3$, —$CH_2CH_2$N($CH_3$)$CH_3$, —$CH_2CH_2$OH, —$CH_2CH_2$OMe, —$CH_2CH_3$, —$CH_2$CN, —$CH_2CH_2$CN, —$CH_2$C(═O)$NH_2$, —$CH_2$C(═O)$NHCH_3$, —$CH_2$C(═O)$NHCH_2CH_2NH_2$, —$CH_2$C(═O)OH, —$CH_2$C(═O)$OCH_3$, 4-aminocyclohexyl, —$CH_2CH_2$-piperidinyl (e.g. —$CH_2CH_2$-piperidin-1-yl), —$CH_2CH_2$-pyrrolidinyl (e.g. —$CH_2CH_2$-pyrrolidin-1-yl), 4-cyanobenzyl, benzyl, —$CH_2$-3,5-dimethyl-isoxazolyl (e.g. —$CH_2$-3,5-dimethyl-isoxazol-4-yl), —$CH_2$-4-aminocyclohexyl, —$CH_2$-oxazolidinyl-2-one (e.g. —$CH_2$-oxazolidin-5-yl-2-one), —$CH_2$—N-methyl-oxazolidinyl-2-one, e.g. (—$CH_2$—N-methyl-oxazolidin-5-yl-2-one), —$CH_2$—N-(1-hydroxyeth-2-yl)-oxazolidinyl-2-one (e.g. —$CH_2$—N-(1-hydroxyeth-2-yl)-oxazolidin-5-yl-2-one), —$CH_2$—N-(1-methoxyeth-2-yl)-oxazolidinyl-2-one (e.g. —$CH_2$—N-(1-methoxyeth-2-yl)-oxazolidin-5-yl-2-one), —$CH_2$—N-methyl-pyrrolidinyl (e.g. —$CH_2$—N-methyl-pyrrolidin-3-yl), —$CH_2$—N-methyl-pyrrolidinyl-2-one (e.g. —$CH_2$—N-methyl-pyrrolidin-4-yl-2-one), —$CH_2$-pyrrolidinyl (e.g. —$CH_2$-pyrrolidin-3-yl), —$CH_2$— pyrrolidinyl-2-one (e.g. —$CH_2$-pyrrolidin-4-yl-2-one), —$CH_2CH_2OCF_3$, —$CH_2CH_2CF_3$, —$CH_2CH_2$-phenyl, —$CH_2CH_2$O-phenyl, —$CH_2CH_2CH_2$-pyridinyl (e.g. —$CH_2CH_2CH_2$-pyridin-3-yl), —$CH_2CH_2OCH_2CH_3$, —$CH_2CH_2CH_2$S($O_2$)$CH_3$, —$CH_2CH_2$C($CH_3$)$_2$CN, —$CH_2CH_2OCH_2CF_3$, —$CH_2CH_2CF_2CH_3$, —$CH_2CH_2CH_2CH_2$F or —$CH_2CH_2CH_2CF_3$; and R2 is hydrogen, —CN, chloro, bromo, iodo, —$CH_3$, —$CH_2CH_2$OH, 4-amino-cyclohexyl, 4-amino-3-fluoro-cyclohexyl, piperidin-4-yl or 4-amino-4-methyl-cyclohexyl.

The above examples of substituent definitions and embodiments given for the compound of formula (IA) and compounds of formula (IB) may be combined with Embodiment C2 in any combination where feasible.

In an embodiment (Embodiment C2-A) the compounds of the invention are compounds of formula (IA) defined as for Embodiment C2.

In an embodiment (Embodiment C2-B) the compounds of the invention are compounds of formula (IB) defined as for Embodiment C2.

In an embodiment (Embodiment D) the compound is a compound of formula (IAa)

(IAa)

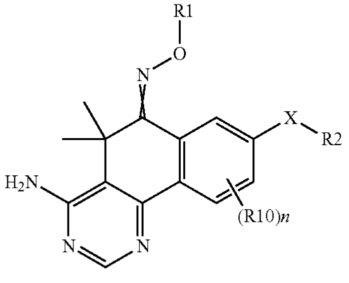

wherein R1, X, R2 and R10 are as defined for the compound of formula (IA) and n is 0, 1 or 2, preferably 0 or 1.

The above examples of substituent definitions and embodiments given for the compound of formula (IA) may be combined with Embodiment D in any combination where feasible.

In an embodiment (Embodiment D1) the compound is a compound of formula (IAa) wherein R1, X, R2 and R10 are as defined in Embodiment A1-A or Embodiment A2-A and n is 0, 1 or 2.

The above examples of substituent definitions and embodiments given for the compound of formula (IA) may be combined with Embodiment D1 in any combination where feasible.

In an embodiment (Embodiment D2) the compound is a compound of formula (IAa) wherein R1, X, R2 and R10 are as defined in Embodiment B1-A or Embodiment B2-A and n is 0 or 1.

The above examples of substituent definitions and embodiments given for the compound of formula (IA) may be combined with Embodiment D2 in any combination where feasible.

In an embodiment (Embodiment D3) the compound is a compound of formula (IAa) wherein R1, X, R2 and R10 are as defined in Embodiment C1-A or Embodiment C2-A and n is 0 or 1.

The above examples of substituent definitions and embodiments given for the compound of formula (IA) may be combined with Embodiment D3 in any combination where feasible.

In an embodiment (Embodiment E) the compound is a compound of formula (IAb)

(IAb)

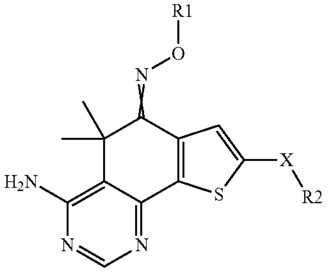

wherein R1, X and R2 are as defined for the compound of formula (IA).

The above examples of substituent definitions and embodiments given for the compound of formula (IA) may be combined with Embodiment E in any combination where feasible.

In an embodiment (Embodiment E1) the compound is a compound of formula (IAb) wherein R1, X and R2 are as defined in Embodiment A1-A or Embodiment A2-A.

The above examples of substituent definitions and embodiments given for the compound of formula (IA) may be combined with Embodiment E1 in any combination where feasible.

In an embodiment (Embodiment E2) the compound is a compound of formula (IAb) wherein R1, X and R2 are as defined in Embodiment B1-A or Embodiment B2-A.

The above examples of substituent definitions and embodiments given for the compound of formula (IA) may be combined with Embodiment E2 in any combination where feasible.

In an embodiment (Embodiment E3) the compound is a compound of formula (IAb) wherein R1 and R2 are as defined in Embodiment C1-A or Embodiment C2-A.

The above examples of substituent definitions and embodiments given for the compound of formula (IA) may be combined with Embodiment E3 in any combination where feasible.

In an embodiment (Embodiment F) the compound is a compound of formula (IBa)

(IBa)

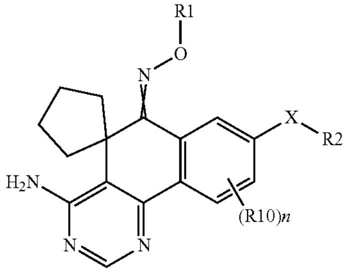

wherein R1, X, R2 and R10 are defined as for the compound of formula (IB) and n is 0, 1 or 2, preferably 0 or 1.

The above examples of substituent definitions and embodiments given for the compound of formula (IB) may be combined with Embodiment F in any combination where feasible.

In an embodiment (Embodiment F1) the compound is a compound of formula (IBa) wherein R1, X and R2 are as defined in Embodiment A1-B or Embodiment A2-B and n is 0, 1 or 2.

The above examples of substituent definitions and embodiments given for the compound of formula (IB) may be combined with Embodiment F1 in any combination where feasible.

In an embodiment (Embodiment F2) the compound is a compound of formula (IBa) wherein R1, X, and R2 are as defined in Embodiment B1-B or Embodiment B2-B and n is 0 or 1.

The above examples of substituent definitions and embodiments given for the compound of formula (IB) may be combined with Embodiment F2 in any combination where feasible.

In an embodiment (Embodiment F3) the compound is a compound of formula (IBa) wherein R1, X and R2 are as defined in Embodiment C1-B or Embodiment C2-B and n is 0 or 1.

The above examples of substituent definitions and embodiments given for the compound of formula (IB) may be combined with Embodiment F3 in any combination where feasible.

In some embodiments the invention may be described by the following paragraphs, which may be combined with any of the above substituent definitions and embodiments in any combination where feasible:

Paragraph 1A: A compound of formula (IA) or a pharmaceutically acceptable salt thereof; wherein wherein #1 is attached to the carbon atom forming the oxime moiety and wherein group (A1) is optionally substituted by one or two R10 and group (A2) is optionally substituted by one R10; each R10 is independently halogen or $—NH_2$;

X is —O—, $—C(=CH_2)—$, $—CH_2—$, —NH— or —N(C1-C4alkyl)-;

R1 is —Y—R3;

Y is a bond or C1-C6alkylene wherein one non-terminal $—CH_2—$ moiety may be replaced by —O—;

R3 is hydrogen, —CN, —OH, —C2-C4alkenylene-R4, C2-C4alkynylene-R4, —O—C1-C4alkylene-R4, $—NH_2$, —NH(C1-C4alkylene-R4), $—N(C1-C4alkylene-R4)_2$, —C(=O)—OH, —C(=O)—O—C1-C4alkylene-R4, $—C(=O)—NH_2$, —C(=O)—NH(C1-C4alkylene-R4), $—C(=O)—N(C1-C4alkylene-R4)_2$, Cycle P, Cycle Q, —O—Cycle P or —O—Cycle Q;

R4 is hydrogen, $—NH_2$, —NH(C1-C2alkyl) or $—N(C1-C2alkyl)_2$;

Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5;

each R5 is independently $—NH_2$, —OH, —CN, C1-C2alkyl, —O—C1-C2alkyl or oxo;

Cycle Q is phenyl optionally substituted by one to three R6, or is a 5-6-membered heteroaryl containing one to two heteroatoms selected from N, S and O optionally substituted by one to three R6;

each R6 is independently $—NH_2$, —OH, —CN, C1-C2alkyl or —O—C1-C2alkyl;

R2 is hydrogen, C1-C4alkyl optionally substituted by one or two R7, or is a 4- to 7-membered saturated carbocyclic ring optionally substituted by one or two R8, or is a 4- to 7-membered saturated heterocyclic ring containing one —N(R9)-moiety as ring member and otherwise containing only carbon atoms as ring members;

each R7 is independently —OH, halogen, $—NH_2$, —NH(C1-C2alkyl), $—N(C1-C2alkyl)_2$ or —NH(—C(=O)—C1-C2alkyl);

each R8 is independently —OH, halogen, $—NH_2$, —NH(C1-C2alkyl), $—N(C1-C2alkyl)_2$ or —NH(—C(=O)—C1-C2alkyl); and R9 is hydrogen, C1-C4alkyl or —C(=O)—C1-C2alkyl.

Paragraph 2A. The compound of paragraph 1A or a pharmaceutically acceptable salt thereof, wherein when A is group (A1) X is connected to the carbon atom which is at the para position relative to #2 and when A is group (A2) X is connected to the carbon atom adjacent to the S atom.

Paragraph 3A. The compound of paragraph 1A or paragraph 2A or a pharmaceutically acceptable salt thereof, wherein A is group (A1).

Paragraph 4A. The compound of paragraph 1A or paragraph 2A or a pharmaceutically acceptable salt thereof, wherein A is group (A2).

Paragraph 5A. The compound of any one of paragraphs 1A to 4A or a pharmaceutically acceptable salt thereof, wherein X is —O—, $—C(=CH_2)—$ or $—N(CH_3)—$.

Paragraph 6A. The compound of any one of paragraphs 1A to 5A or a pharmaceutically acceptable salt thereof, wherein R1 is hydrogen, C1-C6alkylene-R3 wherein one non-terminal —$CH_2$— moiety may be replaced by —O—, or R1 is Cycle P or Cycle Q.

Paragraph 7A. The compound of any one of paragraphs 1A to 6A or a pharmaceutically acceptable salt thereof, wherein R3 is hydrogen, —CN, —OH, C2-C4alkenyl, C2-C4alkynyl, —O—C1-C4alkyl, —C(═O)—OH, —C(═O)—O—C1-C4alkyl, —C(═O)—$NH_2$, —C(═O)—NH(C1-C4alkylene-R4), Cycle P, Cycle Q, —O—Cycle P or —O—Cycle Q.

Paragraph 8A. The compound of any one of paragraphs 1A to 7A or a pharmaceutically acceptable salt thereof, wherein R2 is C1-C4alkyl optionally substituted by one or two R7, or is a 6-membered saturated carbocyclic ring optionally substituted by one or two R8.

Paragraph 9A. The compound of paragraph 1A or a pharmaceutically acceptable salt thereof, wherein A is selected from group (A1) and group (A2) and wherein group (A1) is optionally substituted by one or two R10 and group (A2) is optionally substituted by one R10;

each R10 is independently fluoro, chloro or —$NH_2$;

X is —O—, —C(═$CH_2$)—, —$CH_2$—, —NH— or —N(C1-C4alkyl)-;

R1 is —Y—R3;

Y is a bond or C1-C6alkylene wherein one non-terminal —$CH_2$— moiety may be replaced by —O—;

R3 is hydrogen, —CN, —OH, C2-C4alkenyl, C2-C4alkynyl, —O—C1-C4alkyl, —C(═O)—OH, —C(═O)—O—C1-C4alkyl, —C(═O)—$NH_2$, —C(═O)—NH(C1-C4alkylene-R4), Cycle P, Cycle Q, —O—Cycle P or —O—Cycle Q;

R4 is hydrogen, —$NH_2$ or —NH($CH_3$);

Cycle P is a 6-membered saturated carbocyclic ring optionally substituted by one to two R5 or is a 5-membered saturated heterocyclic ring containing one to two heteroatoms selected from N and O optionally substituted by one to two R5;

each R5 is independently —$NH_2$, —OH, —CN, —$CH_3$, —$OCH_3$ or oxo;

Cycle Q is phenyl optionally substituted by one to three R6, or is a 5-membered heteroaryl containing one to two heteroatoms selected from N, S and O optionally substituted by one to three R6;

each R6 is independently —$NH_2$, —OH, —CN, —$CH_3$ or —$OCH_3$;

R2 is C1-C4alkyl optionally substituted by one or two R7, or is a 6-membered saturated carbocyclic ring optionally substituted by one or two R8;

each R7 is independently halogen or —$NH_2$; and each R8 is independently halogen or —$NH_2$.

Paragraph 10A. The compound of paragraph 1A or a pharmaceutically acceptable salt thereof, wherein A is group (A1) optionally substituted by one R10;

R10 is chloro or —$NH_2$;

X is —O—, —C(═$CH_2$)— or —N($CH_3$)—; R1 is hydrogen or C1-C6alkylene-R3;

R3 is hydrogen, —CN, —OH, —O—C1-C4alkyl, C2-C4alkynyl, —C(═O)—OH, —C(═O)—O—C1-C4alkyl, —C(═O)—$NH_2$, —C(═O)—NH(C1-C4alkyl) or oxazolidinyl-2-one optionally substituted by one methyl; and R2 is —$CH_3$ or 4-amino-cyclohexyl.

Paragraph 11A. The compound of any one of paragraphs 1A to 10A or a pharmaceutically acceptable salt thereof, wherein the compound of formula (IA) is the Z isomer of the oxime moiety.

Paragraph 1B. A compound of formula (IA) or a pharmaceutically acceptable salt thereof, wherein A is selected from group (A1) and group (A2) wherein #1 is attached to the carbon atom forming the oxime moiety and wherein group (A1) is optionally substituted by one or two R10 and group (A2) is optionally substituted by one R10;

each R10 is independently halogen or —$NH_2$;

X is —O—, —C(═$CH_2$)—, —$CH_2$—, —NH— or —N(C1-C4alkyl)- and wherein X is a bond when R2 is halogen;

R1 is —Y—R3;

Y is a bond or C1-C6alkylene wherein one non-terminal —$CH_2$— moiety may be replaced by —O—;

R3 is hydrogen, —CN, —OH, —C2-C4alkenylene-R4, C2-C4alkynylene-R4, —O—C1-C4alkylene-R4, —$NH_2$, —NH(C1-C4alkylene-R4), —N(C1-C4alkylene-R4)$_2$, —C(═O)—OH, —C(═O)—O—C1-C4alkylene-R4, —C(═O)—$NH_2$, —C(═O)—NH(C1-C4alkylene-R4), —C(═O)—N(C1-C4alkylene-R4)$_2$, Cycle P, Cycle Q, —O—Cycle P or —O—Cycle Q;

R4 is hydrogen, —$NH_2$, —NH(C1-C2alkyl) or —N(C1-C2alkyl)$_2$;

Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5;

each R5 is independently —$NH_2$, —OH, —CN, C1-C2alkyl, —O—C1-C2alkyl or oxo;

Cycle Q is phenyl optionally substituted by one to three R6, or is a 5-6-membered heteroaryl containing one to two heteroatoms selected from N, S and O optionally substituted by one to three R6;

each R6 is independently —$NH_2$, —OH, —CN, C1-C2alkyl or —O—C1-C2alkyl;

R2 is hydrogen, halogen, C1-C4alkyl optionally substituted by one or two R7, or is a 4- to 7-membered saturated carbocyclic ring optionally substituted by one or two R8, or is a 4- to 7-membered saturated heterocyclic ring containing one —N(R9)-moiety as ring member and otherwise containing only carbon atoms as ring members;

each R7 is independently —OH, halogen, —$NH_2$, —NH(C1-C2alkyl), —N(C1-C2alkyl)$_2$ or —NH(—C(═O)—C1-C2alkyl);

each R8 is independently —OH, halogen, —$NH_2$, —NH(C1-C2alkyl), —N(C1-C2alkyl)$_2$ or —NH(—C(═O)—C1-C2alkyl); and R9 is hydrogen, C1-C4alkyl or —C(═O)—C1-C2alkyl.

Paragraph 2B. The compound of paragraph 1B or a pharmaceutically acceptable salt thereof, wherein when A is group (A1) X is connected to the carbon atom which is at the para position relative to #2 and when A is group (A2) X is connected to the carbon atom adjacent to the S atom.

Paragraph 3B. The compound of paragraph 1B or paragraph 2B or a pharmaceutically acceptable salt thereof, wherein A is group (A1).

Paragraph 4B. The compound of paragraph 1B or paragraph 2B or a pharmaceutically acceptable salt thereof, wherein A is group (A2).

Paragraph 5B. The compound of any one of paragraphs 1B to 4B or a pharmaceutically acceptable salt thereof, wherein X is —O—, —C(=$CH_2$)— or —N($CH_3$)— and wherein X is a bond when R2 is halogen.

Paragraph 6B. The compound of any one of paragraphs 1B to 5B or a pharmaceutically acceptable salt thereof, wherein R1 is hydrogen, C1-C6alkylene-R3 wherein one non-terminal —$CH_2$— moiety may be replaced by —O—, or R1 is Cycle P or Cycle Q.

Paragraph 7B. The compound of any one of paragraphs 1B to 6B or a pharmaceutically acceptable salt thereof, wherein R3 is hydrogen, —CN, —OH, C2-C4alkenyl, C2-C4alkynyl, —O—C1-C4alkyl, —C(=O)—OH, —C(=O)—O—C1-C4alkyl, —C(=O)—$NH_2$, —C(=O)—NH(C1-C4alkylene-R4), Cycle P, Cycle Q, —O—Cycle P or —O—Cycle Q.

Paragraph 8B. The compound of any one of paragraphs 1B to 7B or a pharmaceutically acceptable salt thereof, wherein R2 is halogen, C1-C4alkyl optionally substituted by one or two R7, or is a 6-membered saturated carbocyclic ring optionally substituted by one or two R8.

Paragraph 9B. The compound of paragraph 1B or a pharmaceutically acceptable salt thereof, wherein

- A is selected from group (A1) and group (A2) and wherein group (A1) is optionally substituted by one or two R10 and group (A2) is optionally substituted by one R10;
- each R10 is independently fluoro, chloro or —$NH_2$;
- X is —O—, —C(=$CH_2$)—, —$CH_2$—, —NH— or —N(C1-C4alkyl)- and wherein X is a bond when R2 is halogen;
- R1 is —Y—R3;
- Y is a bond or C1-C6alkylene wherein one non-terminal —$CH_2$— moiety may be replaced by —O—;
- R3 is hydrogen, —CN, —OH, C2-C4alkenyl, C2-C4alkynyl, —O—C1-C4alkyl, —C(=O)—OH, —C(=O)—O—C1-C4alkyl, —C(=O)—$NH_2$, —C(=O)—NH(C1-C4alkylene-R4), Cycle P, Cycle Q, —O—Cycle P or —O—Cycle Q;
- R4 is hydrogen, —$NH_2$ or —NH($CH_3$);
- Cycle P is a 6-membered saturated carbocyclic ring optionally substituted by one to two R5 or is a 5-membered saturated heterocyclic ring containing one to two heteroatoms selected from N and O optionally substituted by one to two R5;
- each R5 is independently —$NH_2$, —OH, —CN, —$CH_3$, —$OCH_3$ or oxo;
- Cycle Q is phenyl optionally substituted by one to three R6, or is a 5-membered heteroaryl containing one to two heteroatoms selected from N, S and O optionally substituted by one to three R6;
- each R6 is independently —$NH_2$, —OH, —CN, —$CH_3$ or —$OCH_3$;
- R2 is halogen, C1-C4alkyl optionally substituted by one or two R7, or is a 6-membered saturated carbocyclic ring optionally substituted by one or two R8;
- each R7 is independently halogen or —$NH_2$; and
- each R8 is independently halogen or —$NH_2$.

Paragraph 10B. The compound of paragraph 1B or a pharmaceutically acceptable salt thereof, wherein

- A is group (A1) optionally substituted by one R10;
- R10 is chloro or —$NH_2$;
- X is —O—, —C(=$CH_2$)— or —N($CH_3$)— and wherein X is a bond when R2 is halogen;
- R1 is hydrogen or C1-C6alkylene-R3:
- R3 is hydrogen, —CN, —OH, —O—C1-C4alkyl, C2-C4alkynyl, —C(=O)—OH, —C(=O)—O—C1-C4alkyl, —C(=O)—$NH_2$, —C(=O)—NH(C1-C4alkyl) or oxazolidinyl-2-one optionally substituted by one methyl; and
- R2 is fluoro, chloro, bromo, —$CH_3$, 4-amino-cyclohexyl or 4-amino-3-fluoro-cyclohexyl.

Paragraph 11B. The compound of any one of paragraphs 1B to 10B or a pharmaceutically acceptable salt thereof, wherein the compound of formula (IA) is the Z isomer of the oxime moiety.

Paragraph 1C. A compound of formula (IA) or a pharmaceutically acceptable salt thereof, wherein

- A is selected from group (A1) and group (A2) wherein #1 is attached to the carbon atom forming the oxime moiety and wherein group (A1) is optionally substituted by one or two R10 and group (A2) is optionally substituted by one R10;
- each R10 is independently halogen or —$NH_2$;
- X is —O—, —C(=$CH_2$)—, —$CH_2$—, —NH— or —N(C1-C4alkyl)- and wherein X is a bond when R2 is halogen or —CN;
- R1 is —Y—R3;
- Y is a bond or C1-C6alkylene wherein one non-terminal —$CH_2$— moiety may be replaced by —O—;
- R3 is hydrogen, —CN, —OH, —C2-C4alkenylene-R4, C2-C4alkynylene-R4, —O—C1-C4alkylene-R4, —$NH_2$, —NH(C1-C4alkylene-R4), —N(C1-C4alkylene-R4)$_2$, —C(=O)—OH, —C(=O)—O—C1-C4alkylene-R4, —C(=O)—$NH_2$, —C(=O)—NH(C1-C4alkylene-R4), —C(=O)—N(C1-C4alkylene-R4)$_2$, Cycle P, Cycle Q, —O—Cycle P or —O—Cycle Q;
- R4 is hydrogen, —$NH_2$, —NH(C1-C2alkyl) or —N(C1-C2alkyl)$_2$;
- Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5;
- each R5 is independently —$NH_2$, —OH, —CN, C1-C2alkyl, C1-C2alkyl-R11, —O—C1-C2alkyl or oxo; each R11 is independently halogen, —$NH_2$, —OH, —CN or —O—C1-C2alkyl;
- Cycle Q is phenyl optionally substituted by one to three R6, or is a 5-6-membered heteroaryl containing one to two heteroatoms selected from N, S and O optionally substituted by one to three R6;
- each R6 is independently —$NH_2$, —OH, —CN, C1-C2alkyl or —O—C1-C2alkyl;
- R2 is hydrogen, halogen, —CN, C1-C4alkyl optionally substituted by one or two R7, or is a 4- to 7-membered saturated carbocyclic ring optionally substituted by one or two R8, or is a 4- to 7-membered saturated heterocyclic ring containing one —N(R9)-moiety as ring member and otherwise containing only carbon atoms as ring members;
- each R7 is independently —OH, halogen, —$NH_2$, —NH(C1-C2alkyl), —N(C1-C2alkyl)$_2$ or —NH(—C(=O)—C1-C2alkyl);
- each R8 is independently —OH, halogen, —$NH_2$, —NH(C1-C2alkyl), —N(C1-C2alkyl)$_2$ or —NH(—C(=O)—C1-C2alkyl); and
- R9 is hydrogen, C1-C4alkyl or —C(=O)—C1-C2alkyl.

Paragraph 2C. The compound of paragraph 1C or a pharmaceutically acceptable salt thereof, wherein when A is group (A1) X is connected to the carbon atom which is at the para position relative to #2 and when A is group (A2) X is connected to the carbon atom adjacent to the S atom.

Paragraph 3C. The compound of paragraph 1C or paragraph 2C or a pharmaceutically acceptable salt thereof, wherein A is group (A1).

Paragraph 4C. The compound of paragraph 1C or paragraph 2C or a pharmaceutically acceptable salt thereof, wherein A is group (A2).

Paragraph 5C. The compound of any one of paragraphs 1C to 4C or a pharmaceutically acceptable salt thereof, wherein X is —O—, —C(=$CH_2$)—, —$CH_2$— or —N($CH_3$)— and wherein X is a bond when R2 is halogen.

Paragraph 6C. The compound of any one of paragraphs 1C to 5C or a pharmaceutically acceptable salt thereof, wherein R1 is hydrogen, C1-C6alkylene-R3 wherein one non-terminal —$CH_2$— moiety may be replaced by —O—, or R1 is Cycle P or Cycle Q.

Paragraph 7C. The compound of any one of paragraphs 1C to 5C or a pharmaceutically acceptable salt thereof, wherein R1 is hydrogen or C1-C3alkylene-R3.

Paragraph 8C. The compound of paragraph 7C or a pharmaceutically acceptable salt thereof, wherein R3 is hydrogen, —CN, —OH, —O—C1-C4alkyl, C2-C4alkynyl, —C(=O)—OH, —C(=O)—O—C1-C4alkyl, —C(=O)—$NH_2$, —C(=O)—NH(C1-C4alkyl).

Paragraph 9C. The compound of paragraph 7C or a pharmaceutically acceptable salt thereof, wherein R3 is oxazolidinyl-2-one optionally substituted by one R5.

Paragraph 10C. The compound of any one of paragraphs 1C to 9C or a pharmaceutically acceptable salt thereof, wherein R3 is hydrogen, —CN, —OH, C2-C4alkenyl, C2-C4alkynyl, —O—C1-C4alkyl, —$NH_2$, —C(=O)—OH, —C(=O)—O—C1-C4alkyl, —C(=O)—$NH_2$, —C(=O)—NH(C1-C4alkylene-R4), Cycle P, Cycle Q, —O—Cycle P or —O—Cycle Q.

Paragraph 11C. The compound of any one of paragraphs 1C to 1° C. or a pharmaceutically acceptable salt thereof, wherein R2 is halogen, C1-C4alkyl optionally substituted by one or two R7, or is a 6-membered saturated carbocyclic ring optionally substituted by one or two R8, or is a 6-membered saturated heterocyclic ring containing one —N(R9)-moiety as ring member and otherwise containing only carbon atoms as ring members.

Paragraph 12C. The compound of paragraph 1C or a pharmaceutically acceptable salt thereof, wherein

- A is selected from group (A1) and group (A2) and wherein group (A1) is optionally substituted by one or two R10 and group (A2) is optionally substituted by one R10;
- each R10 is independently fluoro, chloro or —$NH_2$;
- X is —O—, —C(=$CH_2$)—, —$CH_2$—, —NH— or —N(C1-C4alkyl)- and wherein X is a bond when R2 is halogen or —CN;
- R1 is —Y—R3;
- Y is a bond or C1-C6alkylene wherein one non-terminal —$CH_2$— moiety may be replaced by —O—;
- R3 is hydrogen, —CN, —OH, C2-C4alkenyl, C2-C4alkynyl, —O—C1-C4alkyl, —$NH_2$, —C(=O)—OH, —C(=O)—O—C1-C4alkyl, —C(=O)—$NH_2$, —C(=O)—NH(C1-C4alkylene-R4), Cycle P, Cycle Q, —O—Cycle P or —O—Cycle Q;
- R4 is hydrogen, —$NH_2$ or —NH($CH_3$);
- Cycle P is a 6-membered saturated carbocyclic ring optionally substituted by one to two R5 or is a 5-membered saturated heterocyclic ring containing one to two heteroatoms selected from N and O optionally substituted by one to two R5;
- each R5 is independently —$NH_2$, —OH, —CN, C1-C2alkyl, —C1-C2alkyl-R11, —O—C1-C2alkyl or oxo;
- each R11 is independently halogen, —$NH_2$, —OH, —CN or —O—C1-C2alkyl;
- Cycle Q is phenyl optionally substituted by one to three R6, or is a 5-membered heteroaryl containing one to two heteroatoms selected from N, S and O optionally substituted by one to three R6;
- each R6 is independently —$NH_2$, —OH, —CN, —$CH_3$ or —$OCH_3$;
- R2 is halogen, C1-C4alkyl optionally substituted by one or two R7, or is a 6-membered saturated carbocyclic ring optionally substituted by one or two R8, or is a 6-membered saturated heterocyclic ring containing one —N(R9)-moiety as ring member and otherwise containing only carbon atoms as ring members;
- each R7 is independently halogen or —$NH_2$; and
- each R8 is independently halogen or —$NH_2$.

Paragraph 13C. The compound of paragraph 1C or a pharmaceutically acceptable salt thereof, wherein

- A is group (A1) optionally substituted by one R10;
- R10 is chloro or —$NH_2$;
- X is —O—, —C(=$CH_2$)—, —$CH_2$— or —N($CH_3$)— and wherein X is a bond when R2 is halogen;
- R1 is hydrogen or C1-C6alkylene-R3;
- R3 is hydrogen, —CN, —OH, —O—C1-C4alkyl, C2-C4alkynyl, —C(=O)—OH, —C(=O)—O—C1-C4alkyl, —C(=O)—$NH_2$, —C(=O)—NH(C1-C4alkyl) or oxazolidinyl-2-one optionally substituted by one R5;
- R5 is C1-C2alkyl or —C1-C2alkyl-R11;
- R11 is halogen, —$NH_2$, —OH, —CN or —O—C1-C2alkyl;

and

- R2 is fluoro, chloro, bromo, —$CH_3$, 4-amino-cyclohexyl or 4-amino-3-fluoro-cyclohexyl.

Paragraph 14C. The compound of paragraph 1C or a pharmaceutically acceptable salt thereof, wherein the compound of formula (IA) is a compound of formula (IAa)

- R10 is chloro or —$NH_2$;
- X is —O—, —C(=$CH_2$)—, —$CH_2$— or —N($CH_3$)— and wherein X is a bond when R2 is halogen;
- R1 is hydrogen or C1-C3alkylene-R3;
- R3 is hydrogen, —CN, —OH, —O—C1-C4alkyl, C2-C4alkynyl, —C(=O)—OH, —C(=O)—O—C1-C4alkyl, —C(=O)—$NH_2$, —C(=O)—NH(C1-C4alkyl) or oxazolidinyl-2-one optionally substituted by one R5;
- R5 is C1-C2alkyl or —C1-C2alkyl-R11;
- R11 is halogen, —$NH_2$, —OH, —CN or —O—C1-C2alkyl;
- R2 is fluoro, chloro, bromo, —$CH_3$, 4-amino-cyclohexyl or 4-amino-3-fluoro-cyclohexyl; and
- n is 0 or 1:

In further embodiments the invention provides the following compounds and pharmaceutically acceptable salts thereof:

(6E)-8-(trans-4-aminocyclohexoxy)-6-methoxyimino-5,5-dimethyl-benzo[h]quinazolin-4-amine;

(6Z)-8-(trans-4-aminocyclohexoxy)-6-benzyloxyimino-5,5-dimethyl-benzo[h]quinazolin-4-amine;

(6Z)-8-(trans-4-aminocyclohexoxy)-6-methoxyimino-5,5-dimethyl-benzo[h]quinazolin-4-amine;

(6E)-4-amino-8-(trans-4-aminocyclohexoxy)-5,5-dimethyl-benzo[h]quinazolin-6-one oxime;

(6Z)-4-amino-8-(trans-4-aminocyclohexoxy)-5,5-dimethyl-benzo[h]quinazolin-6-one oxime;

methyl 3-[(Z)-[4-amino-8-(trans-4-aminocyclohexoxy)-5,5-dimethyl-benzo[h]quinazolin-6-ylidene]amino]oxypropanoate;

3-[(Z)-[4-amino-8-(trans-4-aminocyclohexoxy)-5,5-dimethyl-benzo[h]quinazolin-6-ylidene]amino]oxypropan-1-ol;

(6Z)-8-(trans-4-aminocyclohexoxy)-5,5-dimethyl-6-[2-(1-piperidyl)ethoxyimino]benzo[h]quinazolin-4-amine;

(6Z)-8-(trans-4-aminocyclohexoxy)-6-[3-(diethylamino)propoxyimino]-5,5-dimethyl-benzo[h]quinazolin-4-amine;

(6Z)-8-(trans-4-aminocyclohexoxy)-6-[2-(diethylamino)ethoxyimino]-5,5-dimethyl-benzo[h]quinazolin-4-amine;

2-[(Z)-[4-amino-8-(trans-4-aminocyclohexoxy)-5,5-dimethyl-benzo[h]quinazolin-6-ylidene]amino]oxyethanol;

4-[[(Z)-[4-amino-8-(trans-4-aminocyclohexoxy)-5,5-dimethyl-benzo[h]quinazolin-6-ylidene]amino]oxymethyl]benzonitrile;

(6Z)-8-(trans-4-aminocyclohexoxy)-5,5-dimethyl-6-prop-2-ynoxyimino-benzo[h]quinazolin-4-amine;

[(Z)-[4-amino-8-(trans-4-aminocyclohexoxy)-5,5-dimethyl-benzo[h]quinazolin-6-ylidene]amino]oxyacetonitrile;

ethyl 3-[(Z)-[4-amino-8-(trans-4-aminocyclohexoxy)-5,5-dimethyl-benzo[h]quinazolin-6-ylidene]amino]oxypropanoate;

(6Z)-8-(trans-4-aminocyclohexoxy)-6-ethoxyimino-5,5-dimethyl-benzo[h]quinazolin-4-amine;

(6Z)-8-(trans-4-aminocyclohexoxy)-6-[(3,5-dimethylisoxazol-4-yl)methoxyimino]-5,5-dimethyl-benzo[h]quinazolin-4-amine;

(6Z)-8-(trans-4-aminocyclohexoxy)-6-(3-benzyloxypropoxyimino)-5,5-dimethyl-benzo[h]quinazolin-4-amine;

4-[(Z)-[4-amino-8-(trans-4-aminocyclohexoxy)-5,5-dimethyl-benzo[h]quinazolin-6-ylidene]amino]oxybutanenitrile;

(6Z)-8-(trans-4-aminocyclohexoxy)-5,5-dimethyl-6-(2-pyrrolidin-1-ylethoxyimino)benzo[h]quinazolin-4-amine;

(6Z)-8-(trans-4-aminocyclohexoxy)-6-(2-methoxyethoxyimino)-5,5-dimethyl-benzo[h]quinazolin-4-amine;

(6Z)-8-(trans-4-aminocyclohexoxy)-6-isobutoxyimino-5,5-dimethyl-benzo[h]quinazolin-4-amine;

methyl 2-[(Z)-[4-amino-8-(trans-4-aminocyclohexoxy)-5,5-dimethyl-benzo[h]quinazolin-6-ylidene]amino]oxyacetate;

2-[(Z)-[4-amino-8-(trans-4-aminocyclohexoxy)-5,5-dimethyl-benzo[h]quinazolin-6-ylidene]amino]oxyacetamide;

2-[(Z)-[4-amino-8-(trans-4-aminocyclohexoxy)-5,5-dimethyl-benzo[h]quinazolin-6-ylidene]amino]oxy-N-methyl-acetamide;

5-[[(Z)-[4-amino-8-(trans-4-aminocyclohexoxy)-5,5-dimethyl-benzo[h]quinazolin-6-ylidene]amino]oxymethyl]oxazolidin-2-one;

(6Z)-8-(trans-4-aminocyclohexoxy)-6-[2-(dimethylamino)ethoxyimino]-5,5-dimethyl-benzo[h]quinazolin-4-amine;

(6Z)-8-[1-(trans-4-aminocyclohexyl)vinyl]-6-methoxyimino-5,5-dimethyl-benzo[h]quinazolin-4-amine;

(6E)-8-[1-(trans-4-aminocyclohexyl)vinyl]-6-methoxyimino-5,5-dimethyl-benzo[h]quinazolin-4-amine;

2-[(Z)-(4-amino-8-methoxy-5,5-dimethyl-benzo[h]quinazolin-6-ylidene)amino]oxyacetic acid;

(6Z)-6-[(trans-4-aminocyclohexyl)methoxyimino]-8-methoxy-5,5-dimethyl-benzo[h]quinazolin-4-amine;

(6Z)-6-(cis-4-aminocyclohexoxy)imino-8-methoxy-5,5-dimethyl-benzo[h]quinazolin-4-amine;

(6Z)-6-(trans-4-aminocyclohexoxy)imino-8-methoxy-5,5-dimethyl-benzo[h]quinazolin-4-amine;

2-[(Z)-(4-amino-8-methoxy-5,5-dimethyl-benzo[h]quinazolin-6-ylidene)amino]oxyacetamide;

4-[(Z)-(4-amino-8-methoxy-5,5-dimethyl-benzo[h]quinazolin-6-ylidene)amino]oxybutanenitrile;

N-(2-aminoethyl)-2-[(Z)-(4-amino-8-methoxy-5,5-dimethyl-benzo[h]quinazolin-6-ylidene)amino]oxyacetamide;

(5S)-5-[[(Z)-[4-amino-8-(trans-4-aminocyclohexoxy)-5,5-dimethyl-benzo[h]quinazolin-6-ylidene]amino]oxymethyl]oxazolidin-2-one;

(5R)-5-[[(Z)-(4-amino-8-methoxy-5,5-dimethyl-benzo[h]quinazolin-6-ylidene)amino]oxymethyl]oxazolidin-2-one;

(5S)-5-[[(Z)-(4-amino-8-methoxy-5,5-dimethyl-benzo[h]quinazolin-6-ylidene)amino]oxymethyl]oxazolidin-2-one;

(6Z)-8-methoxy-6-methoxyimino-5,5-dimethyl-benzo[h]quinazolin-4-amine;

(6Z)-8-(trans-4-aminocyclohexoxy)-10-chloro-6-methoxyimino-5,5-dimethyl-benzo[h]quinazolin-4-amine;

(5R)-5-[[(Z)-[4-amino-8-(trans-4-aminocyclohexoxy)-5,5-dimethyl-benzo[h]quinazolin-6-ylidene]amino]oxymethyl]oxazolidin-2-one;

(6Z)-9-chloro-8-methoxy-6-methoxyimino-5,5-dimethyl-benzof[h]quinazolin-4-amine;

(6E)-7-chloro-8-methoxy-6-methoxyimino-5,5-dimethyl-benzo[h]quinazolin-4-amine;

(6E)-8-methoxy-6-methoxyimino-5,5-dimethyl-benzo[h]quinazoline-4,7-diamine;

(6Z)-8-methoxy-6-methoxyimino-5,5-dimethyl-benzo[h]quinazoline-4,9-diamine;

(6Z)-7-chloro-8-methoxy-6-methoxyimino-5,5-dimethyl-benzo[h]quinazolin-4-amine;

(6Z)—N8-(trans-4-aminocyclohexyl)-6-methoxyimino-N8-,5,5-trimethyl-benzo[h]quinazoline-4,8-diamine;

(6Z)-8-(trans-4-aminocyclohexoxy)-6-methoxyimino-5,5-dimethyl-thieno[3,2-h]quinazolin-4-amine;

(5S)-5-[[(Z)-(4-amino-8-methoxy-5,5-dimethyl-benzo[h]quinazolin-6-ylidene)amino]oxymethyl]-3-methyl-oxazolidin-2-one;

(5S)-5-[[(Z)-(4-amino-8-bromo-5,5-dimethyl-benzo[h]quinazolin-6-ylidene)amino]oxymethyl]oxazolidin-2-one;

(5S)-5-[[(Z)-(4-amino-8-chloro-5,5-dimethyl-benzo[h]quinazolin-6-ylidene)amino]oxymethyl]-3-methyl-oxazolidin-2-one;

(5S)-5-[[(Z)-(4-amino-8-bromo-5,5-dimethyl-benzo[h]quinazolin-6-ylidene)amino]oxymethyl]-3-methyl-oxazolidin-2-one;

(6Z)-8-(cis-4-aminocyclohexoxy)-6-methoxyimino-5,5-dimethyl-benzo[h]quinazolin-4-amine 3-[(Z)-[4-amino-8-(trans-4-aminocyclohexoxy)-5,5-dimethyl-benzo[h]quinazolin-6-ylidene]amino]oxypropanenitrile;

(5S)-5-[[(Z)-[4-amino-8-(trans-4-aminocyclohexoxy)-5,5-dimethyl-benzo[h]quinazolin-6-ylidene]amino]oxymethyl]-3-methyl-oxazolidin-2-one;

(6Z)-6-methoxyimino-5,5-dimethyl-8-[-(1R,3S,4R)-4-amino-3-fluoro-cyclohexoxy]benzo[h]quinazolin-4-amine;

(6Z)-6-(2-aminoethoxyimino)-8-methoxy-5,5-dimethyl-benzo[h]quinazolin-4-amine;

(6Z)-6-(3-aminopropoxyimino)-8-methoxy-5,5-dimethyl-benzo[h]quinazolin-4-amine;

3-[(E)-[4-amino-8-(trans-4-aminocyclohexoxy)-5,5-dimethyl-benzo[h]quinazolin-6-ylidene]amino]oxypropanenitrile;

(6Z)-4-amino-6-methoxyimino-5,5-dimethyl-benzo[h]quinazolin-8-ol;

(6Z)-8-methoxy-5,5-dimethyl-6-[[(3R)-pyrrolidin-3-yl]methoxyimino]benzo[h]quinazolin-4-amine;

(6E)-8-methoxy-5,5-dimethyl-6-[[(3R)-pyrrolidin-3-yl]methoxyimino]benzo[h]quinazolin-4-amine;

(6Z)-6-allyloxyimino-8-(trans-4-aminocyclohexoxy)-5,5-dimethyl-benzo[h]quinazolin-4-amine;

(6E)-6-allyloxyimino-8-(trans-4-aminocyclohexoxy)-5,5-dimethyl-benzo[h]quinazolin-4-amine;

(6Z)-6-methoxyimino-5,5-dimethyl-8-(4-piperidyloxy)benzo[h]quinazolin-4-amine;

(6Z)-8-(trans-4-aminocyclohexoxy)-6-isopropoxyimino-5,5-dimethyl-benzo[h]quinazolin-4-amine;

(6E)-8-(trans-4-aminocyclohexoxy)-6-isopropoxyimino-5,5-dimethyl-benzo[h]quinazolin-4-amine;

(6Z)-6-methoxyimino-N8,5,5-trimethyl-N8-(4-piperidyl)benzo[h]quinazoline-4,8-diamine;

(6Z)-6-methoxyimino-5,5-dimethyl-8-(4-piperidylmethyl)benzo[h]quinazolin-4-amine;

(6Z)-8-methoxy-5,5-dimethyl-6-[[(3S)-1-methylpyrrolidin-3-yl]methoxyimino]benzo[h]quinazolin-4-amine;

(4S)-4-[[(Z)-(4-amino-8-methoxy-5,5-dimethyl-benzo[h]quinazolin-6-ylidene)amino]oxymethyl]pyrrolidin-2-one;

(4R)-4-[[(Z)-(4-amino-8-methoxy-5,5-dimethyl-benzo[h]quinazolin-6-ylidene)amino]oxymethyl]pyrrolidin-2-one;

(6Z)-8-[(trans-4-aminocyclohexyl)methyl]-6-methoxyimino-5,5-dimethyl-benzo[h]quinazolin-4-amine;

(6Z)-8-[(cis-4-aminocyclohexyl)methyl]-6-methoxyimino-5,5-dimethyl-benzo[h]quinazolin-4-amine;

(4S)-4-[[(Z)-(4-amino-8-methoxy-5,5-dimethyl-benzo[h]quinazolin-6-ylidene)amino]oxymethyl]-1-methyl-pyrrolidin-2-one;

(6Z)-10-fluoro-8-methoxy-6-methoxyimino-5,5-dimethyl-benzo[h]quinazolin-4-amine;

(2R)-1-[(Z)-[4-amino-8-(trans-4-aminocyclohexoxy)-5,5-dimethyl-benzo[h]quinazolin-6-ylidene]amino]oxypropan-2-ol;

(2S)-1-[(Z)-[4-amino-8-(trans-4-aminocyclohexoxy)-5,5-dimethyl-benzo[h]quinazolin-6-ylidene]amino]oxypropan-2-ol;

(6Z)-8-bromo-6-(2-methoxyethoxyimino)-5,5-dimethyl-benzo[h]quinazolin-4-amine;

3-[(Z)-(4-amino-8-bromo-5,5-dimethyl-benzo[h]quinazolin-6-ylidene)amino]oxypropanenitrile;

(6Z)-8-(cis-4-aminocyclohexoxy)-6-(2-methoxyethoxyimino)-5,5-dimethyl-benzo[h]quinazolin-4-amine;

3-[(Z)-[4-amino-8-(cis-4-aminocyclohexoxy)-5,5-dimethyl-benzo[h]quinazolin-6-ylidene]amino]oxypropanenitrile;

(Z)-4-amino-8-bromo-5,5-dimethyl-benzo[h]quinazolin-6-one oxime;

(E)-4-amino-8-bromo-5,5-dimethyl-benzo[h]quinazolin-6-one oxime;

2-[(Z)-(4-amino-8-bromo-5,5-dimethyl-benzo[h]quinazolin-6-ylidene)amino]oxyethanol;

2-[(Z)-[4-amino-8-(cis-4-aminocyclohexoxy)-5,5-dimethyl-benzo[h]quinazolin-6-ylidene]amino]oxyethanol;

(5S)-5-[[(Z)-[4-amino-8-(cis-4-aminocyclohexoxy)-5,5-dimethyl-benzo[h]quinazolin-6-ylidene]amino]oxymethyl]-3-methyl-oxazolidin-2-one;

(6Z)-8-bromo-6-methoxyimino-5,5-dimethyl-benzo[h]quinazolin-4-amine;

(5S)-5-[[(Z)-(4-amino-8-bromo-5,5-dimethyl-benzo[h]quinazolin-6-ylidene)amino]oxymethyl]-3-(2-methoxyethyl)oxazolidin-2-one;

(5S)-5-[[(Z)-(4-amino-8-bromo-5,5-dimethyl-benzo[h]quinazolin-6-ylidene)amino]oxymethyl]-3-(2-hydroxyethyl)oxazolidin-2-one;

(6Z)-4-amino-5,5-dimethyl-6-[[(5S)-2-oxooxazolidin-5-yl]methoxyimino]benzo[h]quinazoline-8-carbonitrile;

(5S)-5-[[(Z)-(4-amino-8-iodo-5,5-dimethyl-benzo[h]quinazolin-6-ylidene)amino]oxymethyl]oxazolidin-2-one;

(5S)-5-[[(Z)-[4-amino-8-(2-hydroxyethoxy)-5,5-dimethyl-benzo[h]quinazolin-6-ylidene]amino]oxymethyl]oxazolidin-2-one;

(6Z)—N8-(trans-4-aminocyclohexyl)-6-(2-methoxyethoxyimino)-5,5-dimethyl-benzo[h]quinazoline-4,8-diamine;

(6Z)—N8-(cis-4-aminocyclohexyl)-6-(2-methoxyethoxyimino)-5,5-dimethyl-benzo[h]quinazoline-4,8-diamine;

(5S)-5-[[(Z)-(4-amino-8-iodo-5,5-dimethyl-benzo[h]quinazolin-6-ylidene)amino]oxymethyl]-3-(2-hydroxyethyl)oxazolidin-2-one;

(5S)-5-[[(Z)-(8-acetyl-4-amino-5,5-dimethyl-benzo[h]quinazolin-6-ylidene)amino]oxymethyl]oxazolidin-2-one;

(6Z)-8-(trans-4-aminocyclohexoxy)-6-(2-methoxyethoxyimino)spiro[benzo[h]quinazoline-5,1'-cyclopentane]-4-amine;

(6Z)-8-(cis-4-aminocyclohexoxy)-6-(2-methoxyethoxyimino)spiro[benzo[h]quinazoline-5,1'-cyclopentane]-4-amine;

3-[(Z)-[4-amino-8-(cis-4-aminocyclohexoxy)spiro[benzo[h]quinazoline-5,1'-cyclopentane]-6-ylidene]amino]oxypropanenitrile;

3-[(Z)-[4-amino-8-(trans-4-aminocyclohexoxy)spiro[benzo[h]quinazoline-5,1'-cyclopentane]-6-ylidene]amino]oxypropanenitrile;

(6Z)-8-(cis-4-amino-4-methyl-cyclohexoxy)-6-(2-methoxyethoxyimino)-5,5-dimethyl-benzo[h]quinazoline-4-amine;

4-amino-8-(cis-4-minocyclohexoxy)spiro[benzo[h]quinazoline-5,1'-cyclopentane]-6-one oxime;

(6Z)-8-(cis-4-aminocyclohexoxy)-5,5-dimethyl-6-[2-(trifluoromethoxy)ethoxyimino]benzo[h]quinazoline-4-amine;

(6Z)-8-(cis-4-aminocyclohexoxy)-5,5-dimethyl-6-(2-phenylethoxyimino)benzo[h]quinazoline-4-amine;

(6Z)-8-(cis-4-aminocyclohexoxy)-5,5-dimethyl-6-(2-phenoxyethoxyimino)benzo[h]quinazoline-4-amine;

(6Z)-8-(cis-4-aminocyclohexoxy)-5,5-dimethyl-6-[3-(3-pyridyl)propoxyimino]benzo[h]quinazoline-4-amine;

(6Z)-8-(cis-4-aminocyclohexoxy)-6-(2-ethoxyethoxyimino)-5,5-dimethyl-benzo[h]quinazoline-4-amine;

(6Z)-8-(cis-4-aminocyclohexoxy)-5,5-dimethyl-6-(3-methylsulfonylpropoxyimino)benzo[h]quinazoline-4-amine;

4-[(Z)-[4-amino-8-(cis-4-aminocyclohexoxy)-5,5-dimethyl-benzo[h]quinazolin-6-ylidene]amino]oxy-2,2-dimethyl-butanenitrile;

(6Z)-8-(cis-4-aminocyclohexoxy)-5,5-dimethyl-6-[2-(2,2,2-trifluoroethoxy)ethoxyimino]benzo[h]quinazolin-4-amine;

(6Z)-8-(cis-4-aminocyclohexoxy)-6-(4-fluorobutoxyimino)-5,5-dimethyl-benzo[h]quinazolin-4-amine;

(6Z)-8-(cis-4-aminocyclohexoxy)-5,5-dimethyl-6-(4,4,4-trifluorobutoxyimino)benzo[h]quinazolin-4-amine;

(6Z)-8-(cis-4-aminocyclohexoxy)-6-(3,3-difluorobutoxyimino)-5,5-dimethyl-benzo[h]quinazolin-4-amine; and (6Z)-8-(cis-4-aminocyclohexoxy)-5,5-dimethyl-6-(3,3,3-trifluoropropoxyimino)benzo[h]quinazoline-4-amine.

Some intermediates useful for the preparation of compounds of formula (IA) and compounds of formula (IB) are new and form further aspects of the invention. Accordingly, in a further aspect the invention provides compounds of formula (Int-IA)

(Int-IA)

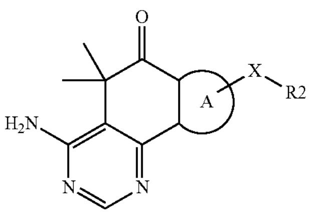

and salts thereof, wherein A, X and R2 are as defined for compounds of formula (IA), including as defined in preferred definitions and embodiments thereof (e.g. as defined in Embodiment A1-A, Embodiment A2-A, Embodiment B1-A, Embodiment B2-A, Embodiment C1-A, Embodiment C2-A, Embodiment D1, Embodiment D2, Embodiment D3, Embodiment E1, Embodiment E2, Embodiment E3).

in a further aspect the invention provides compounds of formula (Int-IB)

(Int-IB)

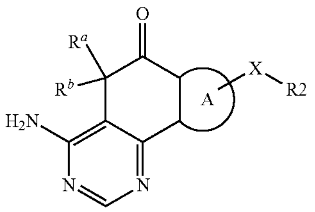

and salts thereof, wherein A, Ra, Rb, X and R2 are as defined for compounds of formula (IB), including as defined in preferred definitions and embodiments thereof (e.g. as defined in Embodiment A1-B, Embodiment A2-B, Embodiment B1-B, Embodiment B2-B, Embodiment C1-B, Embodiment C2-B, Embodiment F1, Embodiment F2, Embodiment F3).

In a further aspect the invention provides compounds of formula (Int-IIA)

(Int-IIA)

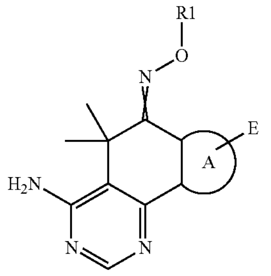

and salts thereof, wherein A and R1 are as defined for compounds of formula (IA), including as defined in preferred definitions and embodiments thereof (e.g. as defined in Embodiment A1-A, Embodiment A2-A, Embodiment B1-A, Embodiment B2-A, Embodiment C1-A, Embodiment C2-A, Embodiment D1, Embodiment D2, Embodiment D3, Embodiment E1, Embodiment E2, Embodiment E3) and E is halogen e.g. chloro, bromo or iodo, preferably chloro or bromo, or —O-L1 and —O-L1 is a leaving group in which L1 is selected from a perfluoroalkylsulfonyl such as triflyl (trifluoromethansulfonyl) and a sulfonyl such as tosyl (p-toluenesulfonyl) or mesyl (methanesulfonyl).

In a further aspect the invention provides compounds of formula (Int-IIB)

(Int-IIB)

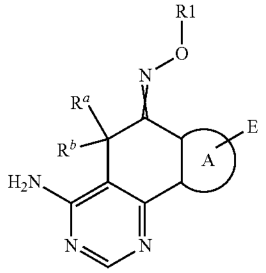

and salts thereof, wherein A, Ra, Rb and R1 are as defined for compounds of formula (IB), including as defined in preferred definitions and embodiments thereof (e.g. as defined in Embodiment A1-B, Embodiment A2-B, Embodiment B1-B, Embodiment B2-B, Embodiment C1-B, Embodiment C2-B, Embodiment F1, Embodiment F2, Embodiment F3) and E is halogen e.g. chloro, bromo or iodo, preferably chloro or bromo, or —O-L1 and —O-L1 is a leaving group in which L1 is selected from a perfluoroalkylsulfonyl such as triflyl (trifluoromethansulfonyl) and a sulfonyl such as tosyl (p-toluenesulfonyl) or mesyl (methanesulfonyl).

The present invention relates also to pharmaceutical compositions that comprise a compound of formula (IA) or a compound of formula (IB) as active ingredient or a pharmaceutically acceptable salt thereof, which can be used especially in the treatment of neoplastic diseases, in particular cancer, as described herein. Compositions may be formulated for non-parenteral administration, such as nasal, buccal, rectal, pulmonary, vaginal, sublingual, topical, transdermal, ophthalmic, or, especially, for oral administration, e.g. in the form of oral solid dosage forms, e.g. granules, pellets, powders, tablets, film or sugar-coated tablets, effervescent tablets, hard and soft gelatin or hydroxypropylmethylcellulose (HPMC) capsules, coated as applicable, orally disintegrating tablets, oral solutions, lipid emulsions or suspensions, or for parenteral administration, such as intravenous, intramuscular, or subcutaneous, intrathecal, intradermal or epidural administration, to mammals, especially humans, e.g. in the form of solutions, lipid emulsions or suspensions containing microparticles or nanoparticles. The compositions may comprise the active ingredient alone or, preferably, together with a pharmaceutically acceptable carrier.

The compounds of formula (IA) and compound of formula (IB) or pharmaceutically acceptable salts thereof can be processed with pharmaceutically inert, inorganic or organic excipients for the production of oral solid dosage forms, e.g. granules, pellets, powders, tablets, film or sugar coated tablets, effervescent tablets, hard gelatin or HPMC capsules or orally disintegrating tablets. Fillers e.g. lactose, cellulose, mannitol, sorbitol, calcium phosphate, starch or derivatives thereof, binders e.g. cellulose, starch, polyvinylpyrrolidone, or derivatives thereof, glidants e.g. talcum, stearic acid or its salts, flowing agents e.g. fumed silica, can be used as such excipients for formulating and manufacturing of oral solid dosage forms, such as granules, pellets, powders, tablets, film or sugar-coated tablets, effervescent tablets, hard gelatin or HPMC capsules, or orally disintegrating tablets. Suitable excipients for soft gelatin capsules are e.g. vegetable oils, waxes, fats, semisolid and liquid polyols etc.

Suitable excipients for the manufacture of oral solutions, lipid emulsions or suspensions are e.g. water, alcohols, polyols, saccharose, invert sugar, glucose etc.

Suitable excipients for parenteral formulations are e.g. water, alcohols, polyols, glycerol, vegetable oils, lecithin, surfactants etc.

Moreover, the pharmaceutical preparations can contain preservatives, solubilizers (e.g. cyclodextrin), stabilizers, wetting agents, emulsifiers, sweeteners, colorants, flavorants, salts for varying the osmotic pressure, buffers, masking agents or antioxidants. They can also contain other therapeutically valuable substances.

The dosage can vary within wide limits and will, of course, be fitted to the individual requirements in each particular case. In general, in the case of oral administration a daily dosage of about 1 to 1000 mg per person of a compound of general formula (IA) or a compound of formula (IB) should be appropriate, although the above lower or upper limit can also be exceeded when necessary.

The compounds of formula (IA) and compounds of formula (IB) can also be used in combination with one or more other pharmaceutically active compounds, which are either effective against the same disease, preferably using a different mode of action, or which reduce or prevent possible undesired side effects of the compounds of formula (IA) and compounds of formula (IB). The combination partners can be administered in such a treatment either simultaneously, e.g. by incorporating them into a single pharmaceutical formulation, or consecutively by administration of two or more different dosage forms, each containing one or more than one of the combination partners.

Compounds of formula (IA) and compounds of formula (IB) according to the invention as described above or pharmaceutically acceptable salts thereof are particularly useful for the treatment of neoplastic diseases such as cancer, in particular when administered in therapeutically effective amounts. In some embodiments, the cancer to be treated by the compounds of the present invention may be treatable by inhibiting one or more CLK enzymes. In some embodiments, the cancer to be treated by the compounds of the present invention may be treatable by inhibiting aberrant splicing. The cancer may be driven by aberrant splicing, e.g. the cancer may be a splicing factor mutant cancer. The cancer may be dependent on an oncogenic splice variant.

Examples of proliferation disorders and diseases for treatment by compounds of the invention include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial-like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous and neuroendocrine neoplasms, meningiomas, nerve sheath tumours, granular cell tumours and alveolar soft part sarcomas, Hodgkin's and non-Hodgkin's lymphomas, B-cell lymphoma, T-cell lymphoma, hairy-cell lymphoma, Burkitts lymphoma and other lymphoreticular neoplasms, plasma cell tumours, mast cell tumours, immunoproliferative diseases, leukemias, miscellaneous myeloproliferative disorders, lymphoproliferative disorders and myelodysplastic syndromes.

Examples of cancers in terms of the organs and parts of the body affected include, but are not limited to, the breast, cervix, ovaries, colon, rectum (including colon and rectum i.e. colorectal cancer), lung (including small cell lung cancer, non-small cell lung cancer, large cell lung cancer and mesothelioma), endocrine system, bone, adrenal gland, thymus, liver, stomach (gastric cancer), intestine, pancreas, bone marrow, hematological malignancies (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, bladder cancer, mesothelioma, hematological malignancies, melanomas and sarcomas.

Further examples of proliferation disorders and diseases for treatment by compounds of the invention are hematological malignancies, e.g. acute myeloid leukemia, myelodysplastic syndromes, chronic myelomonocytic leukemia, chronic lymphocytic leukemia, non-Hodgkin's lymphoma; solid tumors, e.g. mucosal melanoma, uveal melanoma, medulloblastoma, hepatocellular carcinoma, endometrial carcinoma, bladder cancer, cutaneous melanoma, lung adenocarcinoma, pancreatic cancer, breast cancer; cancers with splicing gene mutations, e.g. cancers with splicing factor amplification or fusions, cancers driven by oncogenic transcription factor signaling, cancers driven by oncogenic splice variants, cancers with partial or complete deletion of splicing factors and/or genes implicated in splicing regulation.

The term "treatment" or "treating" as used herein in the context of treating a disease or disorder, pertains generally to treatment and therapy, whether of a human or an animal (e.g. in veterinary applications), in which some desired therapeutic effect is achieved, for example, the inhibition of the progress of the disease or disorder, and includes a reduction in the rate of progress, a halt in the rate of progress, alleviation of symptoms of the disease or disorder, amelioration of the disease or disorder, and cure of the disease or disorder. Treatment as a prophylactic measure (i.e. prophylaxis) is also included. For example, use with patients who have not yet developed the disease or disorder, but who are at risk of developing the disease or disorder, is encompassed by the term "treatment". For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "pharmaceutical composition" is defined herein to refer to a solid or liquid formulation containing at least one therapeutic agent to be administered to a subject, e.g. a mammal or human, optionally with one or more pharmaceutically acceptable excipients, in order to prevent or treat a particular disease or condition affecting the mammal.

The term "pharmaceutically acceptable" as used herein refers to items such as compounds and salts thereof, materials, compositions and/or dosage forms, which are, within the scope of sound medical judgment, suitable for contact with the tissues of a warm-blooded animal, e.g., a mammal or human, without excessive toxicity or other complications commensurate with a reasonable benefit/risk ratio.

The compounds of formula (IA) and compounds of formula (IB) can be synthesized by methods given below, by methods given in the experimental part below or by analogous methods. The schemes described herein are not intended to present an exhaustive list of methods for preparing the compounds of formula (IA) and compounds of formula (IB); rather, additional techniques of which the skilled chemist is aware may be also used for the compound synthesis.

It is understood by one skilled in the art of organic synthesis that optimum reaction conditions may vary with the particular reactants or solvents used, but such conditions can be determined by routine optimization procedures. In some cases, the order of performing the following reaction schemes, and/or reaction steps, may be varied to facilitate the reaction or to avoid the formation of unwanted side products. In addition, the functionality present at various positions of the molecule must be compatible with the reagents and reactions proposed. Such restrictions to the substituents, which are compatible with the reaction conditions, will be readily apparent to one skilled in the art and alternate methods must then be used. Furthermore in some of the reactions mentioned herein it may be necessary or desirable to protect any sensitive groups in compounds and it will be assumed that such protecting groups (PG) as necessary are in place. Conventional protecting groups may be used in accordance with standard practice, well known in the art (for illustration see Greene T. W, Wuts P. G. M, Protective Groups in Organic Synthesis, 5th Edition, Publisher: John Wiley & Sons, 2014). The protecting groups may be removed at any convenient stage in the synthesis using conventional techniques well known in the art, or they may be removed during a later reaction step or work-up.

In the general sequence of reactions outlined below, the abbreviations X and ring A and the generic groups, Ra, Rb, R1 and R2 are as defined for formula (IA) and formula (IB), unless otherwise specified. Other abbreviations used herein are explicitly defined, or are as defined in the experimental section.

The necessary starting materials for the synthetic methods as described herein, if not commercially available, may be made by procedures which are described in the scientific literature, or may be made from commercially available compounds using adaptations of processes reported in the scientific literature. The reader is further referred to e.g. March J., Smith M., Advanced Organic Chemistry, 7th Edition, Publisher: John Wiley & Sons, 2013 for general guidance on reaction conditions and reagents.

The compounds according to the present invention, pharmaceutically acceptable salts, solvates, and hydrates thereof can be prepared according to the general sequence of reactions outlined below in Schemes 1 and 2, followed, if necessary, by:

- manipulation of substituents to give a new final product. These manipulations may include, but are not limited to, reduction, oxidation, alkylation, acylation, substitution, coupling including transition-metal catalyzed coupling and hydrolysis reactions which are commonly known by those skilled in the art;
- removing any protecting groups;
- forming a pharmaceutically acceptable salt; or
- forming a pharmaceutically acceptable solvate or hydrate.

Scheme 1

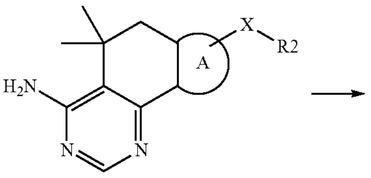

(IIA)

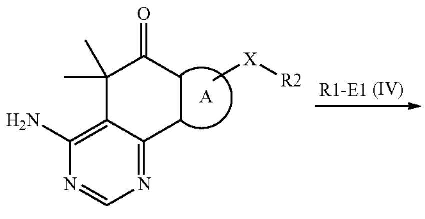

(Int-IA)

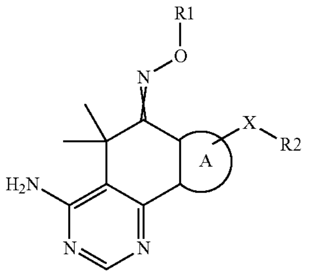

(IA)

Scheme 2

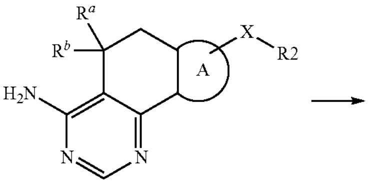

(IIB)

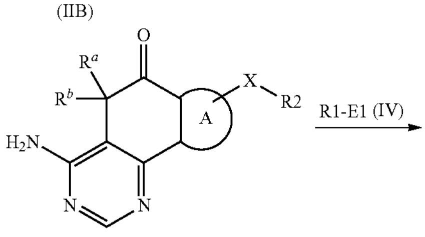

(Int-IB)

-continued

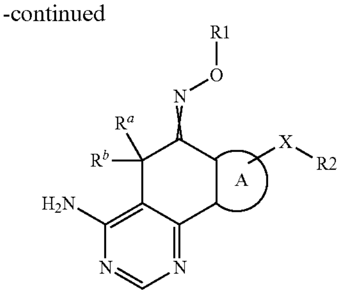

(IB)

Compounds of formulas (IIA), (IIB) and (IV) can be obtained from commercial sources, or are prepared following procedures described in literature (see e.g. Fukuda et al. Bioorg. Med. Chem. Lett. 2018, 1; 28(20):3333-3337), or by procedures known by a person skilled in the art.

Compounds of formula (Int-IA) and formula (Int-IB) can be prepared from compounds of formula (IIA) and formula (IIB) via oxidation performed at a temperature between room temperature and 100° C. using e.g. potassium permanganate as oxidative agent in water and acetone.

Compounds of formula (Int-IA) and formula (Int-IB) wherein X is —O— and R2 is hydrogen can be prepared from compound of formula (Int-IA) and formula (Int-IB) wherein X is —O— and R2 is $CH_3$ via demethylation performed at a temperature between 0° C. and 100° C. in presence of a Lewis acid such as aluminium chloride, boron tribromide or boron trifluoride in a solvent like dichloromethane.

Compounds of formula (IA) and formula (IB) can be prepared from compounds of formula (Int-IA) and formula (Int-IB) and a compound of formula (IV) wherein E1 is O—$NH_2$ via condensation reaction. The reaction is performed at a temperature between room temperature and 150° C. in a solvent like methanol, ethanol or water with or without an organic base such as sodium acetate, triethylamine, pyridine.

Alternatively, compounds of formula (IA) and formula (IB) wherein X is —O— can be prepared via substitution reaction from compounds of formula (IA) and formula (IB) wherein X is —O— and R1 is hydrogen and a compound of formula (IV) wherein E1 is an halogen
or a leaving group —O-L1 wherein L1 is a methanesulfonyl, p-toluenesulfonyl or trifluoromethanesulfonyl group. The reaction is generally performed at a temperature between −20° C. and 100° C. in a dry aprotic solvent like dichloromethane, acetonitrile, N,N-dimethylformamide, dimethyl sulfoxide or tetrahydrofuran without or with an inorganic base such as potassium carbonate or cesium carbonate, or an organic base such as triethylamine or N,N-diisopropylethylamine. Formation of the mesylate, tosylate or triflate compound can be achieved by reacting the corresponding alcohol with methanesulfonyl chloride or methanesulfonic anhydride, p-toluenesulfonyl chloride, trifluoromethanesulfonyl chloride or trifluoromethanesulfonic anhydride, respectively, in presence of a base such as triethylamine or the like in a dry aprotic solvent such as pyridine, acetonitrile, tetrahydrofuran or dichloromethane between −30° C. and 80° C.

Alternatively, compounds of formula (IA) and formula (IB) wherein X is —O— can be prepared from compounds of formula (IA) and formula (IB) wherein X is —O— and R2 is hydrogen and an alcohol via Mitsunobu coupling (as reviewed in O. Mitsunobu, Synthesis, Vol. 1, pages 1-28, 1981). The reaction is performed in the presence of diethyl or diisopropyl azodicarboxylate and triphenylphosphine, in a wide range of solvents such as N,N-dimethylformamide, tetrahydrofuran, 1,2-dimethoxyethane or dichloromethane and within a wide range of temperatures (e.g. between −20° C. and 60° C.). The reaction might also be performed using polymer-supported triphenylphosphine.

Alternatively, compounds of formula (IA) and formula (IB) wherein X is —O— can be prepared from compounds of formula (IA) and formula (IB) wherein X is —O— and R2 is hydrogen and an halide or an alcohol that is previously converted into the corresponding mesylate, tosylate or triflate via substitution reaction, using conditions previously described.

Compounds of formula (IA) and formula (IB) wherein X is —NH— or —N(C1-C4alkyl)-can be prepared from compounds of formula (Int-IIA) and formula (Int-IIB) as previously defined and an amine via a substitution reaction, using conditions previously described.

Compounds of formula (Int-IIA) and formula (Int-IIB) can be prepared from compounds of formula (IA) and formula (IB) wherein X is —O— and R2 is hydrogen via substitution reaction, using conditions previously described.

Alternatively, compounds of formula (IA) and formula (IB) wherein X is —NH— or —N(C1-C4alkyl)-can be prepared from compounds of formula (Int-IIA) and formula (Int-IIB) as previously defined and an amine via a transition-metal catalyst reaction coupling. Typical catalysts include palladium(II) acetate, tris(dibenzylideneacetone)dipalladium(0) or alike. The reaction is typically run at a temperature from 0° C. to 150° C., more frequently from 80° C. to 110° C. Usually the reaction is performed in the presence of a ligand such as di-tert-butyl-[3,6-dimethoxy-2-(2,4,6-triisopropylphenyl)phenyl]phosphane, di-tert-butyl-[2,3,4,5-tetramethyl-6-(2,4,6-triisopropylphenyl)phenyl]phosphane, 2-(dicyclohexylphosphino)biphenyl, 4,5-bis(diphenylphospheno)-9,9-dimethylxanthene or the like and a base such as sodium tert-butylate, cesium carbonate, potassium carbonate, more frequently cesium carbonate in a large variety of inert solvents such as toluene, tetrahydrofuran, dioxane, 1,2-dichloroethane, N,N-dimethylformamide, dimethylsulfoxide, water and acetonitrile, or a mixture of solvents, more frequently in dioxane. As there are numerous components in transition-metal catalyst reaction couplings such as the particular palladium catalyst, the ligand, additives, solvent, temperature, numerous protocols have been identified. One skilled in the art will be able to identify a satisfactory protocol without undue experimentation.

Compounds of formula (IA) and formula (IB) wherein X is —$CH_2$— or —C(=$CH_2$)— can be prepared from compounds of formula (Int-IIA) and formula (Int-IIB) as previously defined and a boronic acid via Suzuki reaction. The Suzuki reaction is a palladium-catalyzed cross coupling between organoboronic acids and aryl or vinyl halides or triflates. Typical catalysts include palladium(II) acetate, tetrakis(triphenylphosphine)palladium(O), bis(triphenylphosphine)palladium(II) dichloride and [1,1'bis(diphenylphosphino)ferrocene]dichloropalladium(II). The reaction can be carried out in a variety of organic solvents including toluene, tetrahydrofuran, dioxane, 1,2-dichloroethane, N,N-dimethylformamide, dimethylsulfoxide and acetonitrile, aqueous solvents and under biphasic conditions. Reactions are typically run from room temperature to 150° C. Additives such as cesium fluoride, potassium fluoride, potassium hydroxide or sodium ethylate frequently accelerate the coupling. Potassium trifluoroborates and organoboranes or boronate esters may be used in place of boronic acids. Although there are numerous components in the Suzuki reaction such as the particular palladium catalyst, the ligand, additives, solvent, temperature, numerous protocols have been identified. One skilled in the art will be able to identify a satisfactory protocol without undue experimentation.

Alternatively, compounds of formula (IA) and formula (IB) wherein X is —$CH_2$— or —C(=$CH_2$)— can be prepared from compounds of formula (Int-IIA) and formula (Int-IIB) wherein E is a boronic acid and an halogen or a triflate via Suzuki reaction, using conditions previously described. Compounds of formula (IA) and formula (IB) wherein X is a bond and R2 is halogen can be prepared from compounds of formula (Int-I) wherein X is a bond and R2 is halogen using methods previously described.

Oxime of compounds of formulas (IA) and formula (IB) exist in 2 isomeric forms, and each isomer can be isolated at any convenient stage of the general sequence of reactions outlined in Schemes 1 and 2.

The skilled chemist will appreciate that different protecting groups (e.g. for R1 and R2) may have to be applied during synthesis to come up with compounds of formula (IA) and formula (IB).

The schemes and processes described herein are not intended to present an exhaustive list of methods for preparing the compounds of formula (IA) and formula (IB); rather, additional techniques of which the skilled chemist is aware of may be also used for the compound synthesis.

All aspects and embodiments of the invention described herein may be combined in any combination where possible.

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Particular embodiments of the invention are described in the following Examples, which serve to illustrate the invention in more detail and should not be construed as limiting the invention in any way.

BRIEF DESCRIPTION OF THE FIGURES

FIG. 1 provides a representative Western blot showing reduction of phosphorylated-SRSF6 (P-SRSF6) in MDA-MB 468 cells by compounds of the invention. GAPDH was probed for by Western blotting to control for equal protein loading and for normalization of samples. The numbers below the blots show percent intensity of P-SRSF6 signal at 100 nM compared to DMSO control.

FIG. 2 shows tumor growth and body weight changes of female NCG mice treated with vehicle or different doses and schedules of Example 29. NCG mice (8-12 weeks of age) were inoculated $1\times10^7$ CAL-51 human triple-negative breast cancer cells in 50% Matrigel™ subcutaneously in the flank. A pair match was performed when tumors reached an average volume of 100-150 $mm^3$ to distribute animals into treatment groups (n=8/group), and treatment of the respective groups was initiated. Tumor volumes (expressed in $mm^3$) were measured twice weekly using a caliper on days 1, 3, 7, 10, 14, 17 and 21 of the treatment period. (A) The average tumor volumes (±SEM) of each treatment group are shown, and at the end of the study (day 21) a significant (*P<0.05, one-way ANOVA) tumor volume reduction versus the vehicle-treated group was observed in groups treated with Example 29 at 60 mg/kg thrice weekly, and at 85 mg/kg twice weekly. (B) Average body weights (expressed in g, ±SEM) on days 1, 2, 3, 4, 5, 7, 10, 14, 17 and 21 of the treatment period.

PREPARATION OF EXAMPLES

Figure 1:
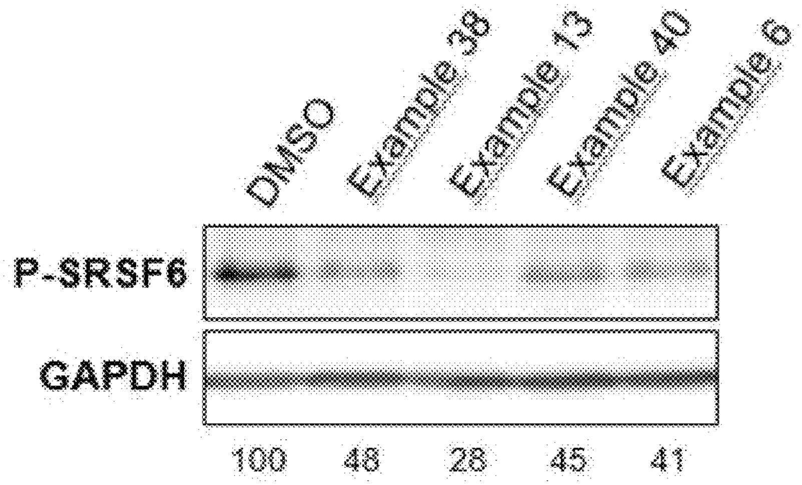
FIG. 1.

All reagents and solvents are generally used as received from the commercial supplier; reactions are routinely performed with anhydrous solvents in well-dried glassware under an argon or nitrogen atmosphere, unless otherwise specified;

evaporations are carried out by rotary evaporation under reduced pressure and work-up procedures are carried out after removal of residual solids by filtration;

all temperatures are given in degree Celsius (° C.) and are approximate temperatures; unless otherwise noted, operations are carried out at room temperature (rt), that is typically in the range 18° C.-25° C.;

column chromatography (by the flash procedure) is used to purify compounds;

classical flash chromatography is often replaced by automated systems. This does not change the separation process per se. A person skilled in the art will be able to replace a classical flash chromatography process by an automated one, and vice versa. Typical automated systems can be used, as they are provided by Buchi or Isco (combiflash) for instance;

reaction mixture can often be separated by preparative HPLC using e.g. water and acetonitrile as system of eluents, unless otherwise stated. A person skilled in the art will find suitable conditions for each separation; the compounds are isolated after purification as a parent compound or in a form of the corresponding trifluoroacetic acid (TFA) salt or the respective formic acid salt;

reactions, which required higher temperature, are usually performed using classical heating instruments; but can also be performed using microwave apparatus (CEM Explorer) at a power of 250 W, unless otherwise noted;

hydrogenation or hydrogenolysis reactions can be performed using hydrogen gas in balloon or using Parr-apparatus system or other suitable hydrogenation equipment;

concentration of solutions and drying of solids are performed under reduced pressure unless otherwise stated;

in general, the course of reactions is followed by TLC, HPLC, or LC/MS and reaction times are given for illustration only; yields are given for illustration only and are not necessarily the maximum attainable;

the structure and purity of the final products of the invention are generally confirmed by NMR spectroscopy, HPLC and mass spectral techniques.

Proton NMR spectra are recorded on a Bruker 400 MHz spectrometer. Chemical shifts (6) are reported in ppm relative to $Me_4Si$ or the solvent peak as internal standard, and NMR coupling constants (Jvalues) are in Hertz (Hz). Each peak is denoted as a broad singlet (br), singlet (s), doublet (d), triplet (t), quadruplet (q), doublet of doublets (dd), triplet of doublets (td) or multiplet (m).

HPLC of the final products are generated using a Dionex Ultimate 3000 instrument coupled with Dionex MSQ ESI mode and the following conditions:
Mobile Phase A: Water with 0.1% Formic acid
Mobile Phase B: Acetonitrile with 0.1% Formic acid
Column: YMC-Triart C18 5 μm 100 mm×4.6 mm
Column Temperature: 25° C.
Detection: UV 250 nm
Injection: 2 μL of 10 mM sample DMSO solution
Flow: 1.6 mL/min
Gradient Time (min) % Mobile Phase B

| Gradient | Time (min) | % Mobile Phase B |
|---|---|---|
| | 0 | 5 |
| | 8 | 95 |
| | 10 | 95 |
| | 10.1 | 5 equilibration |
| | 13 | 5 equilibration |

Mass spectra are generated using a q-Tof Ultima (Waters AG or Thermo Scientific MSQ Plus) mass spectrometer in the positive or negative ESI mode. The system is equipped with the standard Lockspray interface;

each intermediate is purified to the standard required for the subsequent stage and is characterized in sufficient detail to confirm that the assigned structure is correct;

analytical and preparative HPLC on non-chiral phases are performed using RP-C18 based columns;

the following abbreviations may be used (reference can also be made to The *Journal of Organic Chemistry* Guidelines for Authors, for a comprehensive list of standard abbreviations and acronyms):

AcOH Acetic acid
ACN Acetonitrile
Bn Benzyl
BOC tert-butoxy carbonyl group
$BOC_2O$ Di-tert-butyl dicarbonate
BOP (Benzotriazol-1-yloxy)tris(dimethylamino)phosphonium hexafluorophosphate
t-Brettphos 2-(Di-tert-butylphosphino)-2',4',6'-triisopropyl-3,6-dimethoxy-1,1'-biphenyl
t-BuOH tert-Butanol
t-BuONa Sodium tert-butoxide
$B_2Pin_2$ Bis(pinacolato)diboron
CAS compound having Chemical Abstracts Services registry number
$CDCl_3$ Deuterated chloroform
DBU 1,8-Diazabicyclo(5.4.0)undec-7-ene
DCE 1,2-Dichloroethane
DCM Dichloromethane
DEAD Diethyl azodicarboxylate
Diox 1,4-Dioxane
DIPEA N,N-Diisopropylethylamine
DMA Dimethylacetamide
DMAP 4-Dimethylaminopyridine
DMF N,N-Dimethylformamide
DMSO Dimethyl sulfoxide
DMSO-$d_6$ Deuterated dimethyl sulfoxide
$D_2O$ Deuterium oxide
EA Ethyl acetate
ELSD Evaporative light scattering detection
$Et_2O$ Diethyl ether
EtOH Ethanol
Ex. Example
HATU 1-[Bis(dimethylamino)methylene]-1H-1,2,3-triazolo[4,5-b]pyridinium 3-oxide hexafluorophosphate
HPLC High performance liquid chromatography
KOAc Potassium acetate
LAH Lithium aluminium hydride
LC/MS Liquid chromatography coupled to mass spectroscopy
LDA Lithium diisopropylamide
$Me_4$tBuXPhos 2-Di-tert-butylphosphino-3,4,5,6-tetramethyl-2',4',6'-triisopropyl-1,1'-biphenyl
MeOH Methanol
$Me_4Si$ Tetramethylsilane
MS Mass spectrometry
MSA Methanesulfonic acid
MW Microwave
$NaBH_3CN$ Sodium cyanoborohydride
$NaBH(OAc)_3$ Sodium triacetoxyborohydride
NaHMDS Sodium bis(trimethylsilyl)amide
NCS N-Chlorosuccinimide
NFSI N-Fluorobenzenesulfonimide
NMR Nuclear magnetic resonance
Pd/C Palladium on activated carbon
$Pd_2(dba)_3$ Tris(dibenzylideneacetone)dipalladium(0)
$Pd_2(dppf)Cl_2$ [1,1'-Bis(diphenylphosphino)ferrocene]dichloropalladium (II)
$Pd(OAc)_2$ Palladium (II) acetate
PE Petroleum Ether
$PhCF_3$ Benzotrifluoride
$PhNTf_2$ N-Phenyl-bis(trifluoromethanesulfonimide)
PhOK Potassium phenolate
TBAI Tetrabutylammonium iodide
TBS tert-Butyldimethylsilyl
TEA Triethylamine
TES Triethylsilane
TFA Trifluoroacetic acid
Tf Triflate
TfOH Trifluoromethanesulfonic acid
THF Tetrahydrofuran
Tol Toluene
Ts Tosyl (4-toluenesulfonyl)
TsCl 4-Toluenesulfonyl chloride
v/v volume ratio
XPhos Dicyclohexyl[2',4',6'-tris(propan-2-yl) [1,1'-biphenyl]-2-yl]phosphane
$Zn(CN)_2$ Zinc cyanide The following Examples refer to the compounds of formula (IA) and formula (IB) as indicated in Table 1. The Examples listed in the following table can be prepared using procedures described above, and detailed synthesis methodology is described in detail below. The Example numbers used in the leftmost column are used in the application text for identifying the respective compounds.

TABLE 1

| Ex. | Formula | Reference for Preparation | 1H NMR (400 MHz) δ ppm | HPLC Retention time (min) | MS m/z (+ESI) | Salt Form* |
|---|---|---|---|---|---|---|
| 1 | 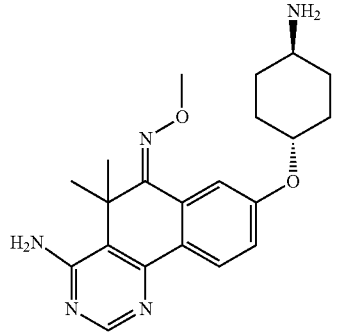 [SMILES: CO/N=C1\c2cc(O[C@H]3CC[C@H](N)CC3)ccc2-c2ncnc(N)c2C1(C)C] | — | DMSO-$d_6$ + $D_2O$: 8.51 (s, 1H), 7.98 (d, J = 9.2 Hz, 1H), 7.55 (d, J = 2.8 Hz, 1H), 7.29 (dd, J = 9.2 Hz, 2.8 Hz, 1H), 4.43 (m, 1H), 3.86 (s, 3H), 3.08 (m, 1H), 2.14 (m, 2H), 1.98 (m, 2H), 1.50 (m, 10H) | 2.90 | 382.3 [M + H]$^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 2 | 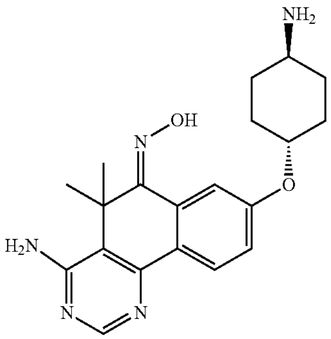 [SMILES: CC1(C)/C(=N/O)c2cc(O[C@H]3CC[C@H](N)CC3)ccc2-c2ncnc(N)c21] | Example 1 (steps 1-7 & 9) | DMSO-$d_6$ + $D_2O$: 8.43 (s, 1H), 8.02 (d, J = 8.8 Hz, 1H), 7.66 (d, J = 2.4 Hz, 1H), 7.22 (dd, J = 8.8 Hz, 2.4 Hz, 1H), 4.39 (m, 1H), 3.08 (m, 1H), 2.14 (m, 2H), 1.98 (m, 2H), 1.48 (m, 10H) | 2.35 | 368.3 $[M + H]^+$ | TFA |
| 3 | 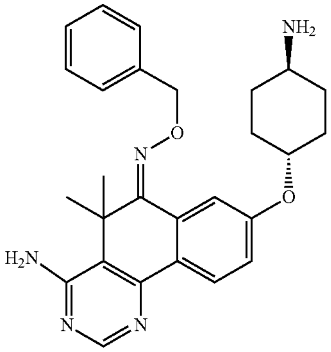 [SMILES: CC1(C)/C(=N/OCc2ccccc2)c2cc(O[C@H]3CC[C@H](N)CC3)ccc2-c2ncnc(N)c21] | Example 1 (steps 1-9) using CAS 100-39-0 | DMSO-$d_6$ + $D_2O$: 8.44 (s, 1H), 8.00 (d, J = 8.8 Hz, 1H), 7.56 (d, J = 2.4 Hz, 1H), 7.34 (m, 5H), 7.20 (dd, J = 8.8 Hz, 2.4 Hz, 1H), 5.13 (s, 2H), 4.30 (m, 1H), 3.05 (m, 1H), 2.00 (m, 4H), 1.49 (s, 6H), 1.15 (m, 4H) | 3.69 | 458.5 $[M + H]^+$ | TFA |
| 4 | 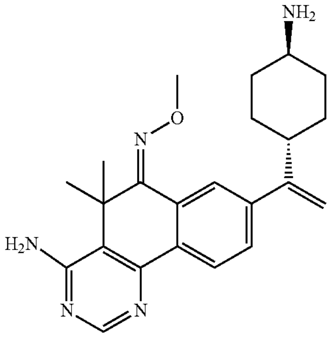 [SMILES: C=C(c1ccc2c(c1)/C(=N\OC)C(C)(C)c1c(N)ncnc1-2)[C@H]1CC[C@H](N)CC1] | — | DMSO-$d_6$ + $D_2O$: 8.42 (s, 1H), 8.11 (d, J = 8.4 Hz, 1H), 8.02 (d, J = 1.6 Hz, 1H), 7.65 (dd, J = 8.4 Hz, 1.6 Hz, 1H), 5.38 (s, 1H), 5.16 (s, 1H), 3.85 (s, 3H), 3.01 (m, 1H), 2.50 (m, 1H, overlapped with DMSO peak), 1.98 (m, 2H), 1.87 (m, 2H), 1.50 (s, 6H), 1.37 (m, 2H), 1.30 (m, 2H) | 3.44 | 392.4 $[M + H]^+$ | TFA |
| 5 | 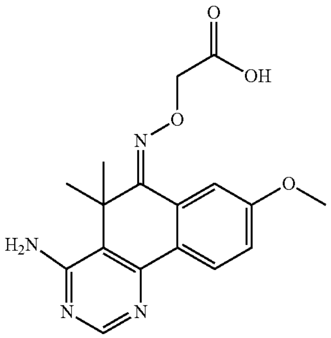 [SMILES: COc1ccc2c(c1)/C(=N\OCC(=O)O)C(C)(C)c1c(N)ncnc1-2] | — | DMSO-$d_6$ + $D_2O$: 8.48 (s, 1H), 7.99 (d, J = 8.8 Hz, 1H), 7.85 (d, J = 2.8 Hz, 1H), 7.27 (dd, J = 8.8 Hz, 2.8 Hz, 1H), 4.67 (s, 2H), 3.85 (s, 3H), 1.47 (s, 6H) | 3.45 | 343.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 6 | 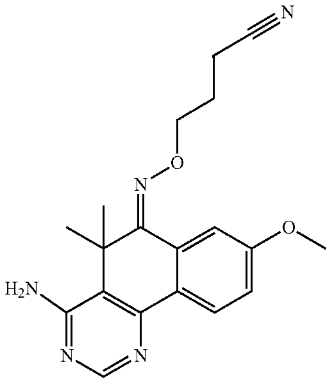 [SMILES: COc1ccc2c(c1)/C(=N\OCCCC#N)C(C)(C)c1c(N)ncnc1-2] | Example 5 (step 2) using CAS 5332-06-9 | DMSO-$d_6$ + $D_2O$: 8.50 (s, 1H), 8.01 (d, J = 8.8 Hz, 1H), 7.64 (d, J = 2.8 Hz, 1H), 7.26 (dd, J = 8.8 Hz, 2.8 Hz, 1H), 4.16 (t, J = 6.0 Hz, 2H), 3.86 (s, 3H), 2.54 (t, J = 6.8 Hz, 2H), 1.95 (m, 2H), 1.50 (s, 6H) | 4.21 | 352.2 $[M + H]^+$ | TFA |
| 7 | 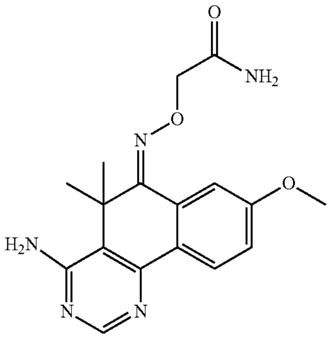 | — | DMSO-$d_6$ + $D_2O$: 8.52 (s, 1H), 8.00 (d, J = 8.8 Hz, 1H), 7.92 (d, J = 2.8 Hz, 1H), 7.28 (dd, J = 8.8 Hz, 2.8 Hz, 1H), 4.47 (s, 2H), 3.87 (s, 3H), 1.48 (s, 6H) | 3.11 | 342.3 $[M + H]^+$ | TFA |
| 8 | 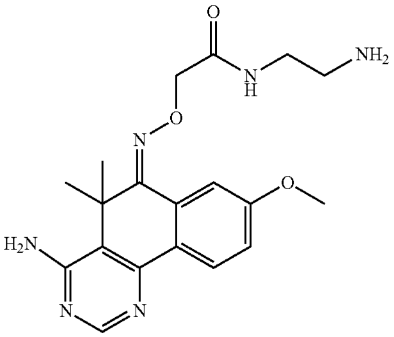 [SMILES: COc1ccc2c(c1)/C(=N\OCC(=O)NCCN)C(C)(C)c1c(N)ncnc1-2] | Example 1 (step 9) | DMSO-$d_6$ + $D_2O$: 8.44 (s, 1H), 8.06 (d, J = 8.8 Hz, 1H), 7.86 (d, J = 2.8 Hz, 1H), 7.25 (dd, J = 8.8 Hz, 2.8 Hz, 1H), 4.53 (s, 2H), 3.86 (s, 3H), 3.34 (t, J = 6.4 Hz, 2H), 2.85 (t, J = 6.4 Hz, 2H), 1.48 (s, 6H) | 2.59 | 385.3 $[M + H]^+$ | TFA |
| 9 | 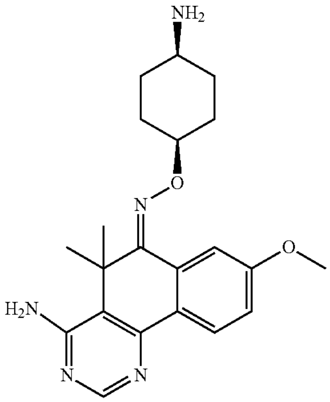 [SMILES: COc1ccc2c(c1)/C(=N\O[C@H]1CC[C@@H](N)CC1)C(C)(C)c1c(N)ncnc1-2] | Example 1 (steps 8 & 9) | DMSO-$d_6$ + $D_2O$: 8.45 (s, 1H), 8.07 (d, J = 8.8 Hz, 1H), 7.77 (d, J = 2.8 Hz, 1H), 7.23 (dd, J = 8.8 Hz, 2.4 Hz, 1H), 4.25 (m, 1H), 3.86 (s, 3H), 3.06 (m, 1H), 2.05 (m, 2H), 1.67 (m, 4H), 1.50 (s, 6H), 1.44 (m, 2H) | 2.96 | 382.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 10 | 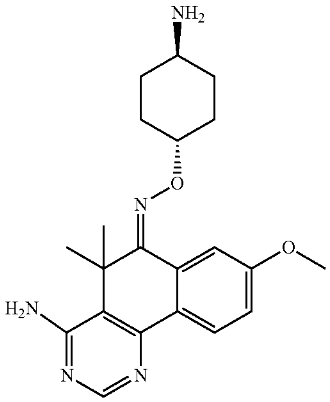 [SMILES: COc1ccc2c(c1)/C(=N\O[C@H]1CC[C@H](N)CC1)C(C)(C)c1c(N)ncnc1-2] | Example 1 (steps 8 & 9) and Example 9 using CAS 167081-25-6 | DMSO-$d_6$ + $D_2O$: 8.45 (s, 1H), 8.05 (d, J = 9.2 Hz, 1H), 7.64 (d, J = 2.8 Hz, 1H), 7.23 (dd, J = 9.2 Hz, 2.8 Hz, 1H), 4.06 (m, 1H), 3.84 (s, 3H), 3.02 (m, 1H), 2.11 (m, 2H), 1.93 (m, 2H), 1.50 (s, 6H), 1.40 (m, 4H) | 2.90 | 382.3 $[M + H]^+$ | TFA |
| 11 | 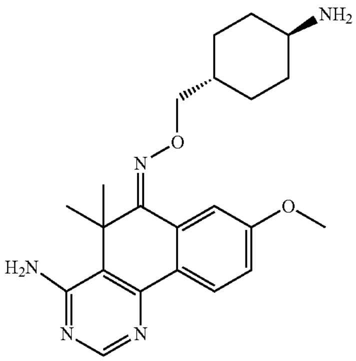 [SMILES: COc1ccc2c(c1)/C(=N\OC[C@H]1CC[C@H](N)CC1)C(C)(C)c1c(N)ncnc1-2] | Example 1 (steps 8 & 9) and Example 9 using CAS 239074-29-4 | DMSO-$d_6$ + $D_2O$: 8.44 (s, 1H), 8.04 (d, J = 8.8 Hz, 1H), 7.60 (d, J = 2.8 Hz, 1H), 7.23 (dd, J = 8.8 Hz, 2.8 Hz, 1H), 3.94 (d, J = 6.8 Hz, 2H), 3.84 (s, 3H), 2.90 (m, 1H), 1.91 (m, 2H), 1.75 (m, 2H), 1.63 (m, 1H), 1.48 (s, 6H), 1.25 (m, 2H), 1.06 (m, 2H) | 3.12 | 396.4 $[M + H]^+$ | TFA |
| 12 | 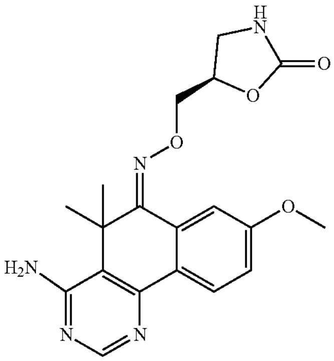 [SMILES: COc1ccc2c(c1)/C(=N\OC[C@H]1CNC(=O)O1)C(C)(C)c1c(N)ncnc1-2] | — | DMSO-$d_6$ + $D_2O$: 8.40 (s, 1H), 8.06 (d, J = 8.8 Hz, 1H), 7.61 (d, J = 2.8 Hz, 1H), 7.21 (dd, J = 8.8 Hz, 2.8 Hz, 1H), 4.85 (m, 1H), 4.25 (m, 2H), 3.84 (s, 3H), 3.57 (d, J = 8.8 Hz, 1H), 3.27 (dd, J = 8.8 Hz, 2.8 Hz, 1H), 1.50 and 1.48 (2s, 6H) | 3.02 | 384.3 $[M + H]^+$ | TFA |
| 13 | 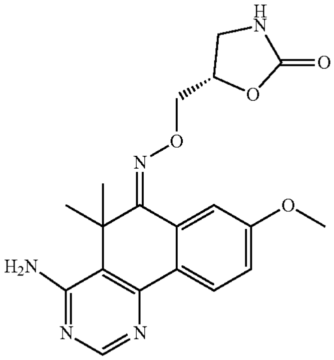 [SMILES: COc1ccc2c(c1)/C(=N\OC[C@@H]1CNC(=O)O1)C(C)(C)c1c(N)ncnc1-2] | Example 12 using CAS 169048-83-3 | DMSO-$d_6$ + $D_2O$: 8.46 (s, 1H), 8.05 (d, J = 9.2 Hz, 1H), 7.63 (d, J =2.8 Hz, 1H), 7.23 (dd, J = 9.2 Hz, 2.8 Hz, 1H), 4.85 (m, 1H), 4.26 (m, 2H), 3.86 (s, 3H), 3.57 (d, J = 8.8 Hz, 1H), 3.27 (dd, J = 8.8 Hz, 2.8 Hz, 1H), 1.51 and 1.49 (2s, 6H) | 3.31 | 384.2 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 14 | 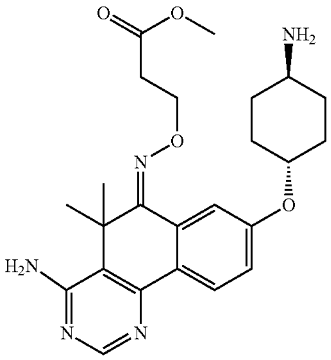 [SMILES: COC(=O)CCO/N=C1\c2cc(O[C@H]3CC[C@H](N)CC3)ccc2-c2ncnc(N)c2C1(C)C] | Example 1 (steps 8 & 9) using CAS 3395-91-3 | DMSO-$d_6$: 8.41 (s, 1H), 8.09 (d, J = 8.8 Hz, 1H), 7.87 (br, 3H), 7.53 (d, J = 2.6 Hz, 1H), 7.23 (dd, J = 8.9, 2.7 Hz, 1H), 4.38 (m, 1H), 4.33 (t, J = 6.0 Hz, 2H), 3.60 (s, 3H), 3.10 (m, 1H), 2.70 (t, J = 6.0 Hz, 2H), 2.16 (m, 2H), 2.00 (m, 2H), 1.50 (m, 10H) | 3.01 | 454.1 $[M + H]^+$ | TFA |
| 15 | 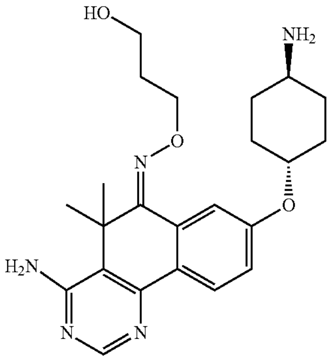 [SMILES: CC1(C)/C(=N/OCCCO)c2cc(O[C@H]3CC[C@H](N)CC3)ccc2-c2ncnc(N)c21] | Example 1 (steps 8 & 9) using CAS 627-18-9 | DMSO-$d_6$: 8.41 (s, 1H), 8.09 (d, J = 8.8 Hz, 1H), 7.87 (br, 3H), 7.61 (d, J = 2.6 Hz, 1H), 7.36 (br, 1H), 7.22 (dd, J = 8.8, 2.7 Hz, 1H), 4.40 (m, 1H), 4.17 (t, J = 6.4 Hz, 2H), 3.50 (m, 2H, overlapped with water peak), 3.11 (m, 1H), 2.15 (m, 2H), 2.00 (m, 2H), 1.79 (t, J = 6.4 Hz, 2H), 1.50 (m, 10H) | 2.66 | 426.1 $[M + H]^+$ | TFA |
| 16 | 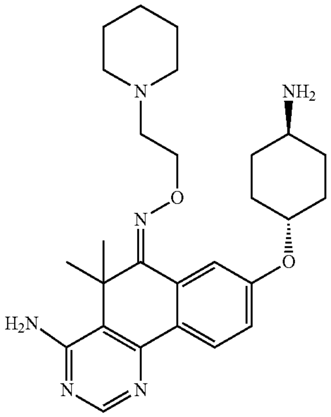 [SMILES: CC1(C)/C(=N/OCCN2CCCCC2)c2cc(O[C@H]3CC[C@H](N)CC3)ccc2-c2ncnc(N)c21] | Example 1 (steps 8 & 9) using CAS 2008-75-5 | DMSO-$d_6$: 8.28 (s, 1H), 8.15 (d, J = 8.7 Hz, 2H), 7.61 (d, J = 2.6 Hz, 1H), 7.18 (dd, J = 8.9, 2.6 Hz, 1H), 6.67 (br, 2H), 4.39 (m, 1H), 4.25 (t, J = 5.8 Hz, 2H), 3.10 (m, 1H), 2.80 (t, J = 5.8 Hz, 2H), 2.60 (m, 4H), 2.16 (m, 2H), 2.02 (m, 2H), 1.52 (m, 12H), 1.40 (m, 4H) | 2.22 | 479.2 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 17 | 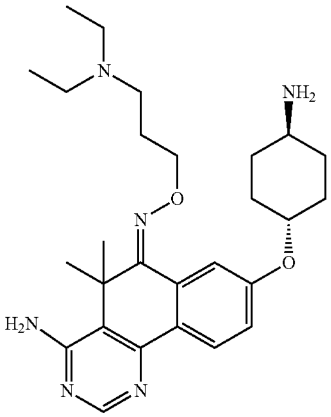 [SMILES: CCN(CC)CCCO/N=C1\c2cc(O[C@H]3CC[C@H](N)CC3)ccc2-c2ncnc(N)c2C1(C)C] | Example 1 (steps 8 & 9) using CAS 104-77-8 | DMSO-$d_6$: 8.26 (s, 1H), 8.14 (d, J = 8.8 Hz, 1H), 7.54 (d, J = 2.4 Hz, 1H), 7.14 (dd, J = 8.8 Hz, 2.4 Hz, 1H), 6.64 (br, 2H), 4.33 (m, 1H), 4.10 (t, J = 6.0 Hz, 2H), 3.00 (m, 1H), 2.44 (m, 6H), 2.13 (m, 2H), 1.98 (m, 2H), 1.71 (m, 2H), 1.47 (m, 10H), 0.90 (t, J = 7.2 Hz, 6H) | 2.31 | 481.2 $[M + H]^+$ | HCOOH |
| 18 | 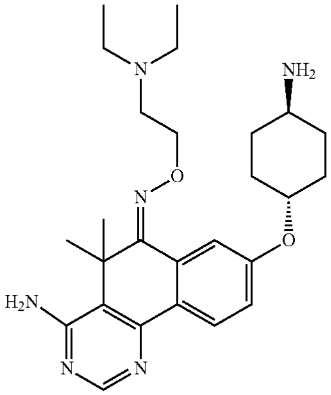 [SMILES: CCN(CC)CCO/N=C1\c2cc(O[C@H]3CC[C@H](N)CC3)ccc2-c2ncnc(N)c2C1(C)C] | Example 1 (steps 8 & 9) using CAS 869-24-9 | DMSO-$d_6$: 8.27 (s, 1H), 8.14 (d, J = 8.8 Hz, 1H), 7.55 (d, J = 2.4 Hz, 1H), 7.18 (dd, J = 8.8 Hz, 2.4 Hz, 1H), 6.67 (br, 2H), 4.36 (m, 1H), 4.23 (t, J = 5.2 Hz, 2H), 3.09 (m, 1H), 3.01 (m, 2H), 2.76 (q, J = 7.2 Hz, 4H), 2.14 (m, 2H), 1.99 (m, 2H), 1.50 (m, 10H), 1.01 (t, J = 7.2 Hz, 6H) | 2.20 | 467.2 $[M + H]^+$ | TFA |
| 19 | 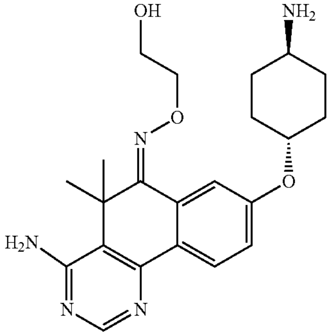 [SMILES: CC1(C)/C(=N/OCCO)c2cc(O[C@H]3CC[C@H](N)CC3)ccc2-c2ncnc(N)c21] | Example 1 (steps 8 & 9) using CAS 540-51-2 | DMSO-$d_6$: 8.26 (s, 1H), 8.12 (d, J = 8.8 Hz, 1H), 7.70 (d, J = 2.8 Hz, 1H), 7.09 (dd, J = 8.8 Hz, 2.8 Hz, 1H), 6.64 (br, 2H), 4.36 (m, 1H), 4.09 (t, J = 4.8 Hz, 2H), 3.63 (t, J = 4.8 Hz, 2H), 2.95 (m, 1H), 2.14 (m, 2H), 1.94 (m, 2H), 1.50 (s, 6H), 1.46 (m, 4H) | 2.51 | 412.1 $[M + H]^+$ | HCOOH |
| 20 | 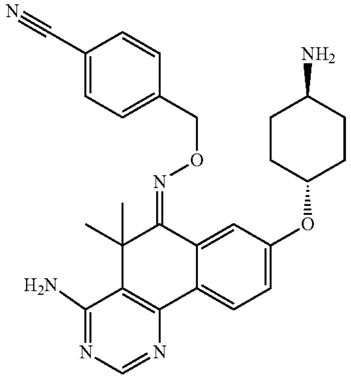 [SMILES: CC1(C)/C(=N/OCc2ccc(C#N)cc2)c2cc(O[C@H]3CC[C@H](N)CC3)ccc2-c2ncnc(N)c21] | Example 1 (steps 8 & 9) using CAS 17201-43-3 | DMSO-$d_6$: 8.26 (s, 1H), 8.13 (d, J = 8.8 Hz, 1H), 7.84 (d, J = 8.0 Hz, 2H), 7.53 (m, 3H), 7.13 (dd, J = 8.8 Hz, 2.8 Hz, 1H), 6.66 (br, 2H), 5.22 (s, 2H), 4.27 (m, 1H), 2.88 (m, 1H), 2.04 (m, 2H), 1.89 (m, 2H), 1.48 (s, 6H), 1.37 (m, 4H) | 3.64 | 483.1 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 21 | 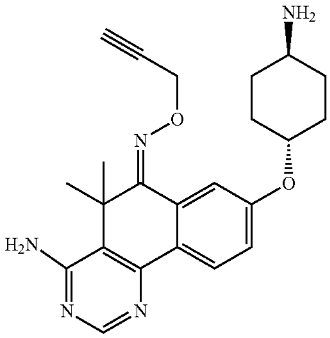 [SMILES: C#CCO/N=C1\c2cc(O[C@H]3CC[C@H](N)CC3)ccc2-c2ncnc(N)c2C1(C)C] | Example 1 (steps 8 & 9) using CAS 106-96-7 | DMSO-$d_6$: 8.32 (s, 1H), 8.15 (d, J = 8.8 Hz, 1H), 7.83 (br, 3H), 7.52 (d, J = 2.6 Hz, 1H), 7.21 (dd, J = 8.8, 2.6 Hz, 1H), 6.83 (br, 2H), 4.77 (s, 2H), 4.39 (m, 1H), 3.49 (m, 1H), 3.11 (m, 1H), 2.19 (m, 2H), 2.01 (m, 2H), 1.50 (m, 10H) | 3.12 | 406.1 $[M + H]^+$ | HCOOH |
| 22 | 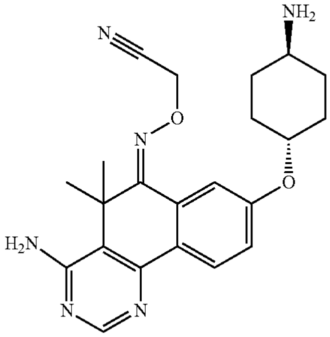 [SMILES: CC1(C)/C(=N/OCC#N)c2cc(O[C@H]3CC[C@H](N)CC3)ccc2-c2ncnc(N)c21] | Example 1 (steps 8 & 9) using CAS 590-17-0 | DMSO-$d_6$: 8.39 (s, 1H), 8.11 (d, J = 8.8 Hz, 1H), 7.86 (br, 3H), 7.43 (d, J = 2.4 Hz, 1H), 7.28 (dd, J = 8.8 Hz, 2.4 Hz, 1H), 5.04 (s, 2H), 4.41 (m, 1H), 3.09 (m, 1H), 2.15 (m, 2H), 1.99 (m, 2H), 1.51 (m, 10H) | 2.88 | 407.1 $[M + H]^+$ | HCOOH |
| 23 | 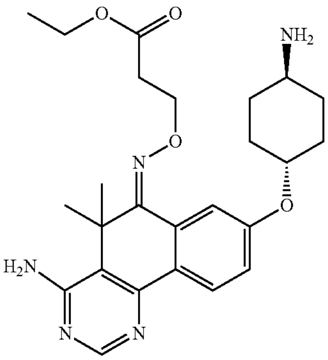 [SMILES: CCOC(=O)CCO/N=C1\c2cc(O[C@H]3CC[C@H](N)CC3)ccc2-c2ncnc(N)c2C1(C)C] | Example 1 (steps 8 & 9) using CAS 539-74-2 | DMSO-$d_6$: 8.26 (s, 1H), 8.12 (d, J = 8.8 Hz, 1H), 7.47 (d, J = 2.4 Hz, 1H), 7.13 (dd, J = 8.8 Hz, 2.4 Hz, 1H), 6.64 (br, 2H), 4.42 (m, 1H), 4.29 (t, J = 6.0 Hz, 2H), 4.03 (q, J = 7.2 Hz, 2H), 3.09 (m, 1H), 2.66 (t, J = 6.0 Hz, 2H), 2.13 (m, 2H), 1.98 (m, 2H), 1.48 (m, 10H), 1.12 (t, J = 7.2 Hz, 3H) | 3.20 | 468.1 $[M + H]^+$ | TFA |
| 24 | 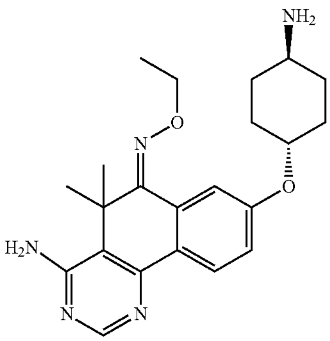 [SMILES: CCO/N=C1\c2cc(O[C@H]3CC[C@H](N)CC3)ccc2-c2ncnc(N)c2C1(C)C] | Example 1 (steps 8 & 9) using CAS 75-03-6 | DMSO-$d_6$: 8.28 (s, 1H), 8.16 (d, J = 8.7 Hz, 1H), 7.87 (br, 3H), 7.60 (d, J = 2.6 Hz, 1H), 7.14 (dd, J = 8.8, 2.6 Hz, 1H), 6.67 (br, 2H), 4.38 (m, 1H), 4.14 (q, J = 7.0 Hz, 2H), 3.11 (m, 1H), 2.15 (m, 2H), 2.00 (m, 2H), 1.52 (m, 10H), 1.23 (t, J = 7.0 Hz, 3H) | 3.16 | 396.2 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 25 | 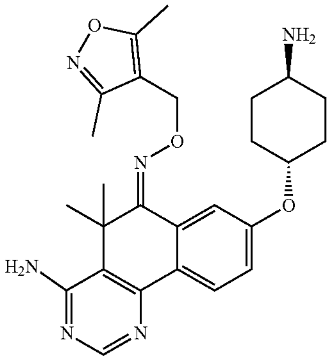 [SMILES: Cc1noc(C)c1CO/N=C1\c2cc(O[C@H]3CC[C@H](N)CC3)ccc2-c2ncnc(N)c2C1(C)C] | Example 1 (steps 8 & 9) using CAS 19788-37-5 | DMSO-$d_6$: 8.26 (s, 1H), 8.11 (d, J = 8.8 Hz, 1H), 7.41 (d, J = 2.4 Hz, 1H), 7.11 (dd, J = 8.8 Hz, 2.4 Hz, 1H), 6.65 (br, 2H), 4.91 (s, 2H), 4.28 (m, 1H), 2.94 (m, 1H), 2.38 (s, 3H), 2.15 (s, 3H), 2.04 (m, 2H), 1.91 (m, 2H), 1.48 (s, 6H), 1.40 (m, 4H) | 3.22 | 477.1 $[M + H]^+$ | HCOOH |
| 26 | 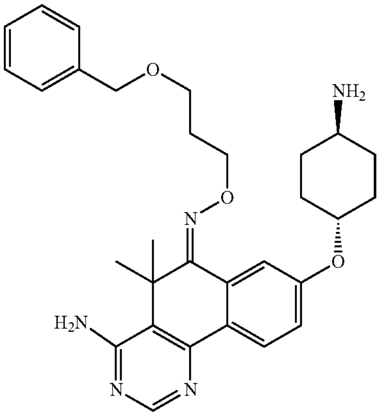 [SMILES: CC1(C)/C(=N/OCCCOCc2ccccc2)c2cc(O[C@H]3CC[C@H](N)CC3)ccc2-c2ncnc(N)c21] | Example 1 (steps 8 & 9) using CAS 54314-84-0 | DMSO-$d_6$: 8.28 (s, 1H), 8.15 (d, J = 8.7 Hz, 1H), 7.52 (s, 1H), 7.30 (m, 5H), 7.14 (dd, J = 8.8, 2.6 Hz, 1H), 6.66 (br, 2H), 4.46 (s, 2H), 4.30 (m, 1H), 4.18 (t, J = 6.4 Hz, 2H), 3.51 (t, J = 6.3 Hz, 2H), 2.93 (m, 1H), 2.11 (m, 2H), 1.92 (m, 4H), 1.51 (s, 6H), 1.40 (m, 4H) | 3.92 | 516.2 $[M + H]^+$ | HCOOH |
| 27 | 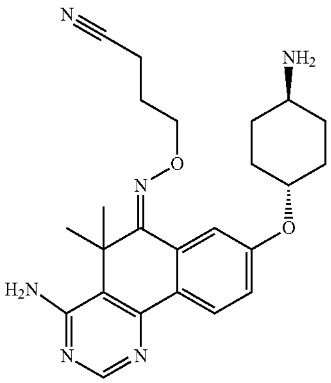 [SMILES: CC1(C)/C(=N/OCCCC#N)c2cc(O[C@H]3CC[C@H](N)CC3)ccc2-c2ncnc(N)c21] | Example 1 (steps 8 & 9) using CAS 5332-06-9 | DMSO-$d_6$: 8.43 (s, 1H), 8.06 (d, J = 8.8 Hz, 1H), 7.90 (br, 3H), 7.60 (d, J = 2.4 Hz, 1H), 7.22 (dd, J = 8.8 Hz, 2.4 Hz, 1H), 4.42 (m, 1H), 4.14 (t, J = 6.0 Hz, 2H), 3.09 (m, 1H), 2.55 (m, 2H), 2.15 (m, 2H), 1.99 (m, 2H), 1.94 (m, 2H), 1.51 (m, 10H) | 2.96 | 435.1 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 28 | 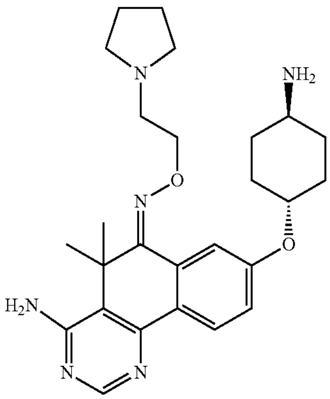 [SMILES: CC1(C)/C(=N/OCCN2CCCC2)c2cc(O[C@H]3CC[C@H](N)CC3)ccc2-c2ncnc(N)c21] | Example 1 (steps 8 & 9) using CAS 7250-67-1 | DMSO-$d_6$: 8.41 (s, 1H), 8.11 (d, J = 8.8 Hz, 1H), 7.97 (br, 3H), 7.58 (d, J = 2.5 Hz, 1H), 7.28 (dd, J = 8.9, 2.6 Hz, 1H), 4.40 (m, 3H), 3.53 (m, 4H), 3.10 (m, 3H), 2.15 (m, 2H), 2.00 (m, 4H), 1.80 (m, 2H), 1.53 (m, 10H) | 2.15 | 465.2 $[M + H]^+$ | TFA |
| 29 | 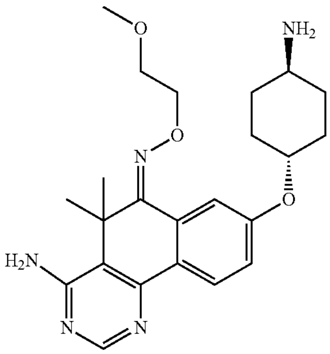 [SMILES: COCCO/N=C1\c2cc(O[C@H]3CC[C@H](N)CC3)ccc2-c2ncnc(N)c2C1(C)C] | Example 1 (steps 8 & 9) using CAS 6482-24-2 | DMSO-$d_6$: 8.27 (s, 1H), 8.15 (d, J = 8.7 Hz, 1H), 7.62 (d, J = 2.6 Hz, 1H), 7.14 (dd, J = 8.8, 2.6 Hz, 1H), 6.67 (br, 3H), 4.34 (m, 1H), 4.20 (t, J = 5.5 Hz, 2H), 3.57 (t, J = 5.5 Hz, 2H), 3.30 (s, 3H), 3.09 (m, 1H), 2.15 (m, 2H), 2.01 (m, 2H), 1.50 (m, 10H) | 2.90 | 426.1 $[M + H]^+$ | HCOOH |
| 30 | 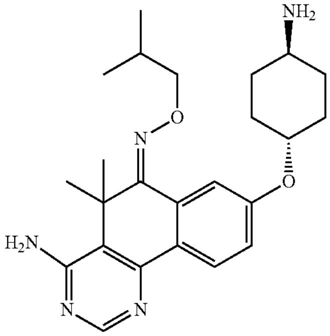 [SMILES: CC(C)CO/N=C1\c2cc(O[C@H]3CC[C@H](N)CC3)ccc2-c2ncnc(N)c2C1(C)C] | Example 1 (steps 8 & 9) using CAS 78-77-3 | DMSO-$d_6$: 8.28 (s, 1H), 8.16 (d, J = 8.7 Hz, 1H), 7.60 (d, J = 2.6 Hz, 1H), 7.14 (dd, J = 8.8, 2.6 Hz, 1H), 6.66 (br, 2H), 4.36 (m, 1H), 3.88 (d, J = 6.7 Hz, 2H), 3.09 (m, 1H), 2.16 (m, 2H), 1.97 (m, 3H), 1.51 (s, 6H), 1.47 (m, 4H), 0.91 (d, J = 6.7 Hz, 6H) | 3.68 | 424.1 $[M + H]^+$ | HCOOH |
| 31 | 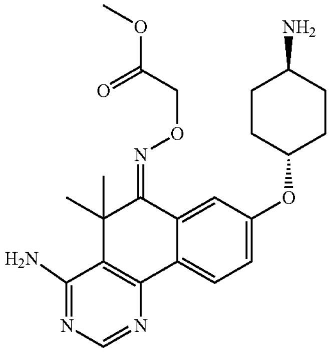 [SMILES: COC(=O)CO/N=C1\c2cc(O[C@H]3CC[C@H](N)CC3)ccc2-c2ncnc(N)c2C1(C)C] | Example 1 (steps 8 & 9) using CAS 96-32-2 | DMSO-$d_6$: 8.27 (s, 1H), 8.13 (d, J = 8.8 Hz, 1H), 7.72 (d, J = 2.8 Hz, 1H), 7.16 (dd, J = 8.8 Hz, 2.8 Hz, 1H), 6.66 (br, 2H), 4.76 (s, 2H), 4.34 (m, 1H), 3.70 (s, 3H), 2.96 (m, 1H), 2.13 (m, 2H), 1.97 (m, 2H), 1.47 (s, 6H), 1.44 (m, 4H) | 2.92 | 440.1 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 32 | 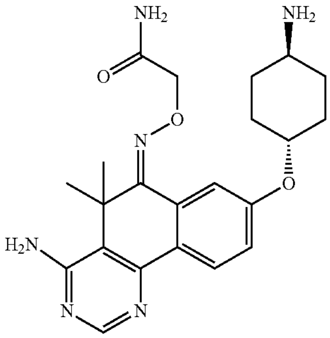 [SMILES: CC1(C)/C(=N/OCC(N)=O)c2cc(O[C@H]3CC[C@H](N)CC3)ccc2-c2ncnc(N)c21] | Example 1 (steps 8 & 9) using CAS 683-57-8 | DMSO-$d_6$: 8.28 (s, 1H), 8.13 (d, J = 8.8 Hz, 1H), 7.85 (d, J = 2.6 Hz, 1H), 7.34 (s, 1H), 7.25 (s, 1H), 7.14 (dd, J = 8.8, 2.6 Hz, 1H), 6.65 (br, 2H), 4.44 (s, 2H), 4.37 (m, 1H), 3.93 (m, 1H), 2.15 (m, 2H), 1.96 (m, 2H), 1.50 (s, 6H), 1.46 (m, 4H) | 2.38 | 425.1 $[M + H]^+$ | HCOOH |
| 33 | 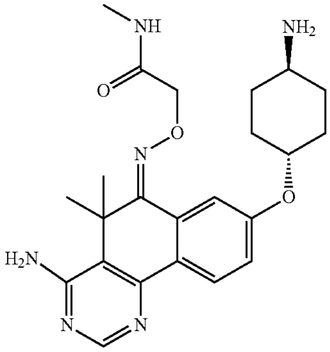 [SMILES: CNC(=O)CO/N=C1\c2cc(O[C@H]3CC[C@H](N)CC3)ccc2-c2ncnc(N)c2C1(C)C] | Example 1 (steps 8 & 9) using CAS 34680-81-4 | DMSO-$d_6$: 8.28 (s, 1H), 8.14 (d, J = 8.8 Hz, 1H), 7.83 (m, 2H), 7.15 (dd, J = 8.8, 2.6 Hz, 1H), 6.65 (br, 2H), 4.47 (s, 2H), 4.38 (m, 1H), 2.94 (m, 1H), 2.66 (d, J = 4.6 Hz, 3H), 2.15 (m, 2H), 1.95 (m, 2H), 1.50 (s, 6H), 1.47 (m, 4H) | 2.45 | 439.1 $[M + H]^+$ | HCOOH |
| 34 | 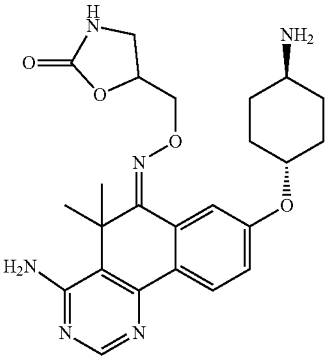 [SMILES: CC1(C)/C(=N/OCC2CNC(=O)O2)c2cc(O[C@H]3CC[C@H](N)CC3)ccc2-c2ncnc(N)c21] | Example 1 (steps 8 & 9) using CAS 22625-57-6 | — | 2.58 | 467.1 $[M + H]^+$ | HCOOH |
| 35 | 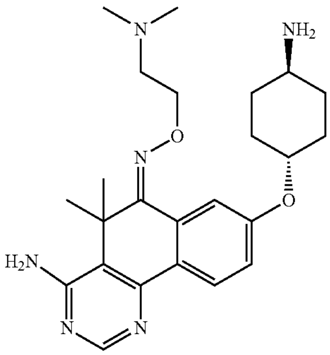 [SMILES: CN(C)CCO/N=C1\c2cc(O[C@H]3CC[C@H](N)CC3)ccc2-c2ncnc(N)c2C1(C)C] | Example 1 (steps 8 & 9) using CAS 2862-39-7 | DMSO-$d_6$: 8.26 (s, 1H), 8.13 (d, J = 8.8 Hz, 1H), 7.59 (d, J = 2.8 Hz, 1H), 7.11 (dd, J = 8.8 Hz, 2.8 Hz, 1H), 6.65 (br, 2H), 4.34 (m, 1H), 4.15 (t, J = 6.0 Hz, 2H), 3.03 (m, 1H), 2.52 (t, J = 6.0 Hz, 2H), 2.16 (s, 6H), 2.14 (m, 2H), 1.98 (m, 2H), 1.50 (s, 6H), 1.46 (m, 4H) | 2.07 | 439.2 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 36 | 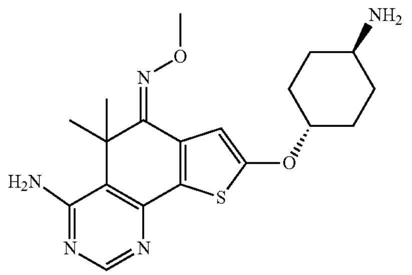 [SMILES: CO/N=C1\c2cc(O[C@H]3CC[C@H](N)CC3)sc2-c2ncnc(N)c2C1(C)C] | Example 1 (steps 5-9) using CAS 5470-11-1 and CAS 74-88-4 | DMSO-$d_6$ + $D_2O$: 8.18 (s, 1H), 7.15 (s, 1H), 4.25 (m, 1H), 3.91 (s, 3H). 3.07 (m, 1H), 2.16 (m, 2H), 1.98 (m, 2H), 1.56 (s, 6H), 1.50 (m, 4H) | 3.57 | 388.3 $[M + H]^+$ | TFA |
| 37 | 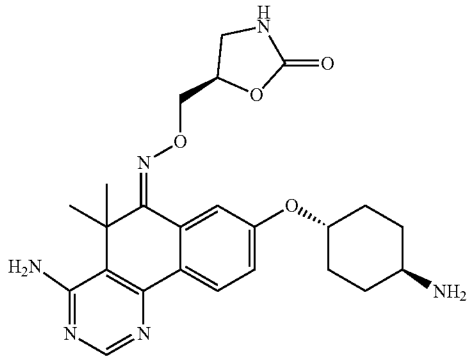 [SMILES: CC1(C)/C(=N/OC[C@H]2CNC(=O)O2)c2cc(O[C@H]3CC[C@H](N)CC3)ccc2-c2ncnc(N)c21] | Example 4 (step 10) | DMSO-$d_6$ + $D_2O$: 8.25 (s, 1H), 8.12 (d, J = 8.8 Hz, 1H), 7.54 (d, J = 2.8 Hz, 1H), 7.13 (dd, J = 8.8 Hz, 2.8 Hz, 1H), 4.83 (m, 1H), 4.35 (m, 1H), 4.22 (m, 2H), 3.60 (m, 1H), 3.25 (m, 1H), 3.00 (m, 1H), 2.14 (m, 2H), 1.94 (m, 2H), 1.50 (m, 10H) | 2.58 | 467.4 $[M + H]^+$ | HCOOH |
| 38 | 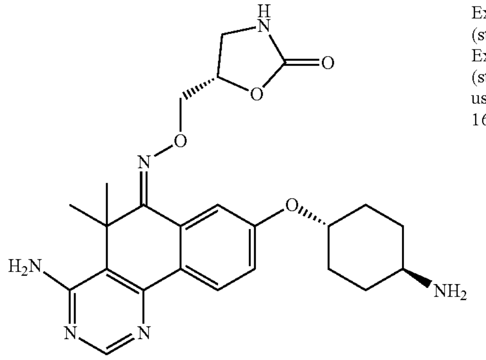 | Example 4 (step 10) and Example 37 (step 1) using CAS 169048-83-3 | DMSO-$d_6$ + $D_2O$: 8.50 (s, 1H), 8.03 (d, J = 8.8 Hz, 1H), 7.59 (d, J = 2.4 Hz, 1H), 7.24 (dd, J = 8.8 Hz, 2.4 Hz, 1H), 4.83 (m, 1H), 4.42 (m, 1H), 4.25 (m, 2H), 3.60 (m, 1H), 3.25 (m, 1H), 3.10 (m, 1H), 2.15 (m, 2H), 1.97 (m, 2H), 1.50 (m, 10H) | 2.60 | 467.3 $[M + H]^+$ | TFA |
| 39 | 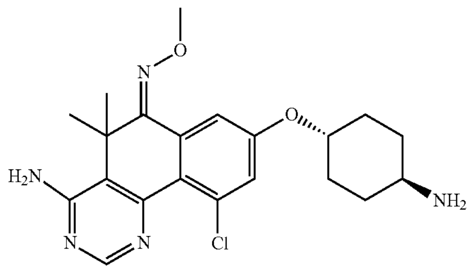 [SMILES: CO/N=C1\c2cc(O[C@H]3CC[C@H](N)CC3)cc(Cl)c2-c2ncnc(N)c2C1(C)C] | Example 1 (step 9) | DMSO-$d_6$ + $D_2O$: 8.36 (s, 1H), 7.31 (d, J = 2.4 Hz, 1H), 7.29 (d, J = 2.4 Hz, 1H), 4.45 (m, 1H), 3.84 (s, 3H), 3.07 (m, 1H), 2.12 (m, 2H), 1.97 (m, 2H), 1.49 (m, 4H), 1.43 (s, 6H) | 2.98 | 416.2, 418.2 $[M + H]^+$ | TFA |
| 40 | 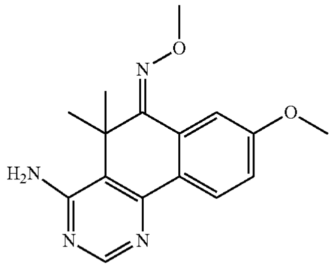 [SMILES: CO/N=C1\c2cc(OC)ccc2-c2ncnc(N)c2C1(C)C] | Example 1 (step 8) using CAS 74-88-4 | DMSO-$d_6$ + $D_2O$: 8.49 (s, 1H), 8.02 (d, J = 8.8 Hz, 1H), 7.57 (d, J = 2.8 Hz, 1H), 7.26 (dd, J = 8.8 Hz, 2.8 Hz, 1H), 3.87 (s, 3H), 3.85 (s, 3H), 1.49 (s, 6H) | 4.28 | 299.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 41 | 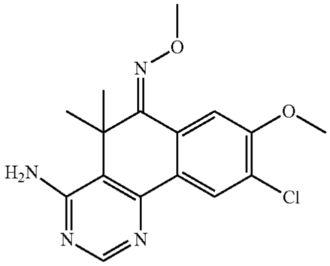 [SMILES: CO/N=C1\c2cc(OC)c(Cl)cc2-c2ncnc(N)c2C1(C)C] | — | DMSO-$d_6$ + $D_2O$: 8.44 (s, 1H), 8.16 (s, 1H), 7.76 (s, 1H), 3.95 (s, 3H), 3.93 (s, 3H), 1.51 (s, 6H) | 5.58 | 333.2, 335.2 $[M + H]^+$ | TFA |
| 42 | 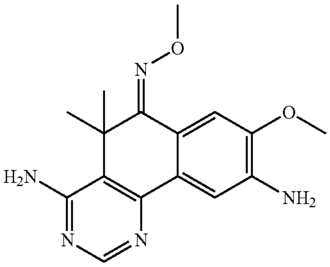 [SMILES: CO/N=C1\c2cc(OC)c(N)cc2-c2ncnc(N)c2C1(C)C] | — | DMSO-$d_6$ + $D_2O$: 8.22 (s, 1H), 7.57 (s, 1H), 7.54 (s, 1H), 3.82 (s, 3H), 3.79 (s, 3H), 1.49 (s, 6H) | 3.83 | 314.2 $[M + H]^+$ | TFA |
| 43 | 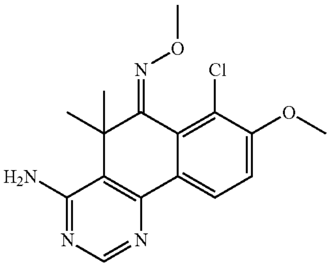 [SMILES: CO/N=C1\c2c(ccc(OC)c2Cl)-c2ncnc(N)c2C1(C)C] | Example 41 (step 2) | DMSO-$d_6$ + $D_2O$: 8.30 (s, 1H), 8.26 (d, J = 8.8 Hz, 1H), 7.30 (d, J = 8.8 Hz, 1H) 3.92 (s, 6H), 1.69 (s, 6H) | 4.90 | 333.2, 335.1 $[M + H]^+$ | Parent |
| 44 | 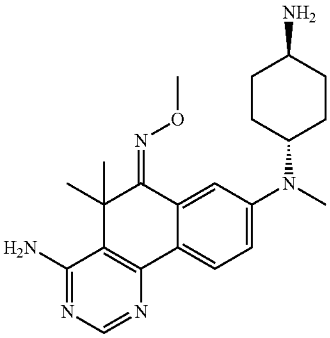 [SMILES: CO/N=C1\c2cc(N(C)[C@H]3CC[C@H](N)CC3)ccc2-c2ncnc(N)c2C1(C)C] | — | DMSO-$d_6$ + $D_2O$: 8.44 (s, 1H), 7.86 (d, J = 8.8 Hz, 1H), 7.37 (d, J = 2.4 Hz, 1H), 7.03 (dd, J = 8.8 Hz, 2.4 Hz, 1H), 3.85 (s, 3H), 3.71 (m, 1H), 3.04 (m, 1H), 2.83 (s, 3H), 2.01 (m, 2H), 1.71 (m, 4H), 1.52 (m, 2H), 1.48 (s, 6H) | 2.93 | 395.3 $[M + H]^+$ | TFA |
| 45 | 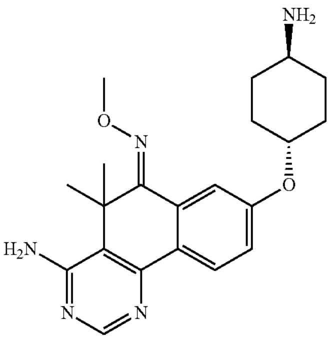 [SMILES: CO/N=C1/c2cc(O[C@H]3CC[C@H](N)CC3)ccc2-c2ncnc(N)c2C1(C)C] | Example 1 (steps 1-9) | DMSO-$d_6$ + $D_2O$: 8.52 (s, 1H), 8.22 (d, J = 9.2 Hz, 1H), 7.59 (d, J = 2.8 Hz, 1H), 7.28 (dd, J = 9.2 Hz, 2.8 Hz, 1H), 4.43 (m, 1H), 4.00 (s, 3H), 3.08 (m, 1H), 2.11 (m, 2H), 1.98 (m, 2H), 1.74 (s, 6H), 1.49 (m, 4H) | 3.09 | 382.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 46 | 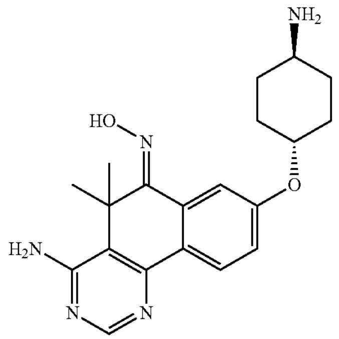 [SMILES: CC1(C)/C(=N\O)c2cc(O[C@H]3CC[C@H](N)CC3)ccc2-c2ncnc(N)c21] | Example 2 (steps 1-2) | DMSO-$d_6$ + $D_2O$: 8.42 (s, 1H), 8.26 (d, J = 9.2 Hz, 1H), 7.55 (d, J = 2.8 Hz, 1H), 7.15 (dd, J = 9.2 Hz, 2.8 Hz, 1H), 4.37 (m, 1H), 3.09 (m, 1H), 2.11 (m, 2H), 1.98 (m, 2H), 1.79 (s, 6H), 1.47 (m, 4H) | 2.53 | 368.3 $[M + H]^+$ | TFA |
| 47 | 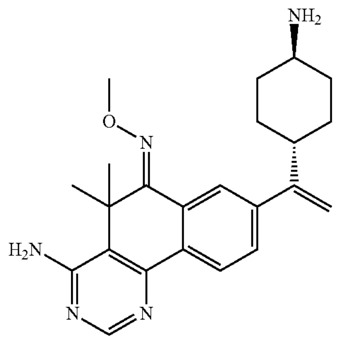 [SMILES: C=C(c1ccc2c(c1)/C(=N/OC)C(C)(C)c1c(N)ncnc1-2)[C@H]1CC[C@H](N)CC1] | Example 4 (steps 1-10) | DMSO-$d_6$ + $D_2O$: 8.41 (s, 1H), 8.40 (d, J = 8.4 Hz, 1H), 8.07 (d, J = 1.6 Hz, 1H), 7.55 (dd, J = 8.4 Hz, 1.6 Hz, 1H), 5.27 (s, 1H), 5.13 (s, 1H), 4.00 (s, 3H), 3.00 (m, 1H), 2.45 (m, 1H), 1.98 (m, 2H), 1.83 (m, 2H), 1.76 (s, 6H), 1.36 (m, 2H), 1.29 (m, 2H) | 3.68 | 392.4 $[M + H]^+$ | TFA |
| 48 | 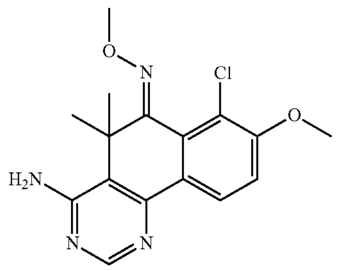 [SMILES: CO/N=C1/c2c(ccc(OC)c2Cl)-c2ncnc(N)c2C1(C)C] | Example 41 (step 2) | DMSO-$d_6$ + $D_2O$: 8.44 (s, 1H), 7.93 (d, J = 8.8 Hz, 1H), 7.76 (d, J = 8.8 Hz, 1H), 3.95 (s, 3H), 3.81 (s, 3H), 1.74 (s, 3H), 1.20 (s, 3H) | 4.74 | 333.2, 335.2 $[M + H]^+$ | TFA |
| 49 | 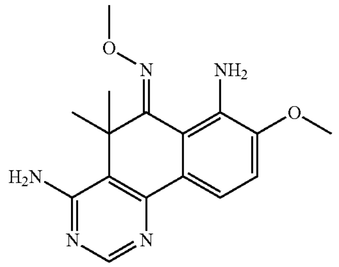 [SMILES: CO/N=C1/c2c(ccc(OC)c2N)-c2ncnc(N)c2C1(C)C] | Example 42 (steps 1-2) | DMSO-$d_6$ + $D_2O$: 8.50 (s, 1H), 7.20 (d, J = 8.4 Hz, 1H), 7.11 (d, J = 8.4 Hz, 1H), 3.89 (d, J = 2.0 Hz, 6H), 1.73 (br, 3H), 1.17 (br, 3H) | 3.83 | 314.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 50 | 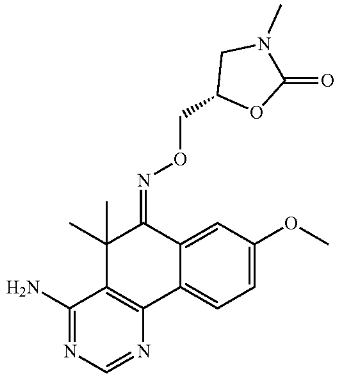 [SMILES: COc1ccc2c(c1)/C(=N\OC[C@@H]1CN(C)C(=O)O1)C(C)(C)c1c(N)ncnc1-2] | Example 12 using CAS 140478-99-5 | DMSO-$d_6$ + $D_2O$: 8.50 (s, 1H), 8.02 (d, J = 9.2 Hz, 1H), 7.58 (d, J = 2.8 Hz, 1H), 7.25 (dd, J = 9.2 Hz, 2.8 Hz, 1H), 4.75 (m, 1H), 4.25 (m, 2H), 3.86 (s, 3H), 3.60 (m, 1H), 3.27 (m, 1H), 2.63 (s, 3H), 1.50 and 1.48 (2s, 6H) | 3.54 | 398.3 $[M + H]^+$ | TFA |
| 51 | 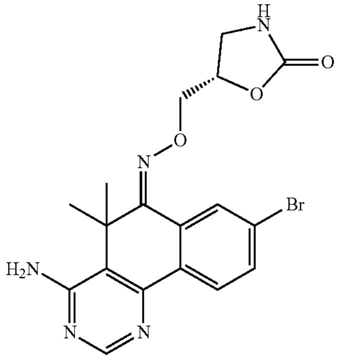 [SMILES: CC1(C)/C(=N/OC[C@@H]2CNC(=O)O2)c2cc(Br)ccc2-c2ncnc(N)c21] | Example 1 (step 7), Example 4 (step 4) and Example 12 using CAS 169048-83-3 | DMSO-$d_6$ + $D_2O$: 8.50 (s, 1H), 8.23 (d, J = 2.0 Hz, 1H), 8.03 (d, J = 8.4 Hz, 1H), 7.88 (dd, J = 8.4 Hz, 2.0 Hz, 1H), 4.84 (m, 1H), 4.27 (m, 2H), 3.57 (m, 1H), 3.25 (m, 1H), 1.50 (s, 6H) | 4.17 | 432.1, 434.1 [M + H]+ | TFA |
| 52 | 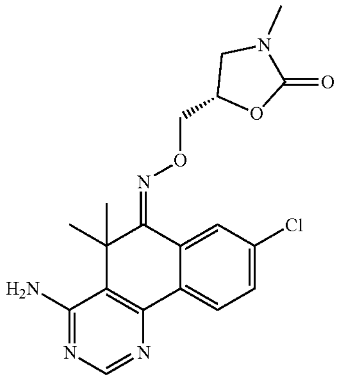 [SMILES: CN1C[C@@H](CO/N=C2\c3cc(Cl)ccc3-c3ncnc(N)c3C2(C)C)OC1=O] | Example 1 (steps 6 & 7) and Example 12 using CAS 140478-99-5 | DMSO-$d_6$ + $D_2O$: 8.44 (s, 1H), 8.13 (d, J = 8.4 Hz, 1H), 8.01 (d, J = 2.0 Hz, 1H), 7.72 (dd, J = 8.4 Hz, 2.0 Hz, 1H), 4.75 (m, 1H), 4.34 (m, 1H), 4.24 (m, 1H), 3.62 (m, 1H), 3.28 (m, 1H), 2.65 (s, 3H), 1.50 (s, 6H) | 4.45 | 402.2, 404.1 $[M + H]^+$ | TFA |
| 53 | 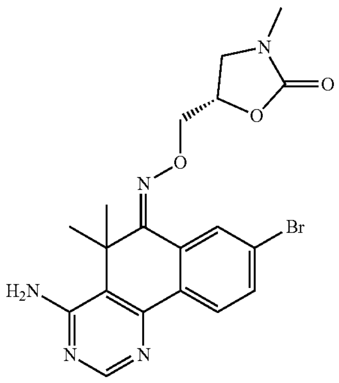 [SMILES: CN1C[C@@H](CO/N=C2\c3cc(Br)ccc3-c3ncnc(N)c3C2(C)C)OC1=O] | Example 1 (step 6 & 7), Example 4 (step 4), Example 12 and Example 51 (step 2) using CAS 140478-99-5 | DMSO-$d_6$ + $D_2O$: 8.45 (s, 1H), 8.15 (d, J = 2.0 Hz, 1H), 8.04 (d, J = 8.8 Hz, 1H), 7.85 (dd, J = 8.8 Hz, 2.0 Hz, 1H), 4.75 (m, 1H), 4.33 (m, 1H), 4.25 (m, 1H), 3.64 (m, 1H), 3.28 (m, 1H), 2.65 (s, 3H), 1.50 (s, 6H) | 4.58 | 446.1, 448.1 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 54 | 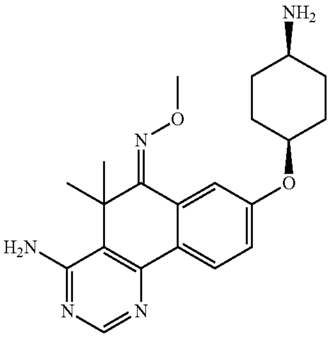 [SMILES: CO/N=C1\c2cc(O[C@H]3CC[C@@H](N)CC3)ccc2-c2ncnc(N)c2C1(C)C] | Example 1 (steps 5-9) using CAS 167081-25-6 | DMSO-$d_6$ + $D_2O$: 8.43 (s, 1H), 8.04 (d, J = 8.8 Hz, 1H), 7.54 (d, J = 2.8 Hz, 1H), 7.22 (dd, J = 8.8 Hz, 2.8 Hz, 1H), 4.70 (m, 1H), 3.85 (s, 3H), 3.13 (m, 1H), 1.98 (m, 2H), 1.70 (m, 6H), 1.48 (s, 6H) | 2.85 | 382.3 $[M + H]^+$ | TFA |
| 55 | 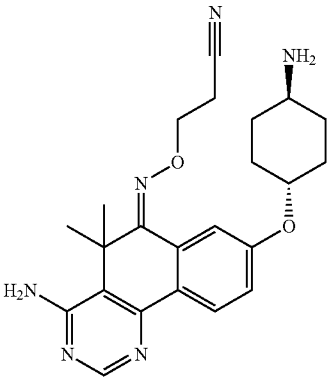 [SMILES: CC1(C)/C(=N/OCCC#N)c2cc(O[C@H]3CC[C@H](N)CC3)ccc2-c2ncnc(N)c21] | Example 1 (steps 8 & 9) using CAS 2517-76-2 | DMSO-$d_6$ + $D_2O$: 8.43 (s, 1H), 8.04 (d, J = 8.8 Hz, 1H), 7.61 (d, J = 2.4 Hz, 1H), 7.24 (dd, J = 8.8 Hz, 2.4 Hz, 1H), 4.43 (m, 1H), 4.26 (t, J = 5.6 Hz, 2H), 3.08 (m, 1H), 2.92 (t, J = 5.6 Hz, 2H), 2.15 (m, 2H), 1.97 (m, 2H), 1.50 (m, 10H) | 2.84 | 421.3 $[M + H]^+$ | TFA |
| 56 | 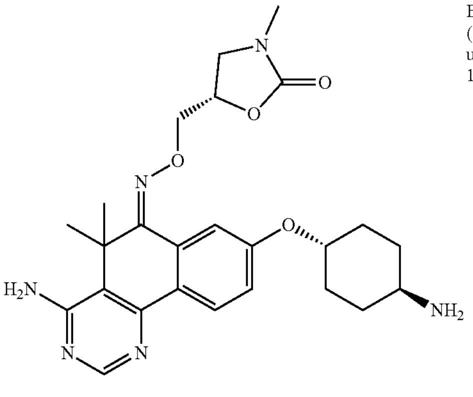 | Example 1 (steps 8 & 9) using CAS 140478-99-5 | DMSO-$d_6$ + $D_2O$: 8.42 (s, 1H), 8.04 (d, J = 8.8 Hz, 1H), 7.51 (d, J = 2.4 Hz, 1H), 7.24 (dd, J = 8.8 Hz, 2.4 Hz, 1H), 4.74 (m, 1H), 4.42 (m, 1H), 4.27 (m, 1H), 4.21 (m, 1H), 3.62 (m, 1H), 3.28 (m, 1H), 3.07 (m, 1H), 2.67 (s, 3H), 2.14 (m, 2H), 1.99 (m, 2H), 1.49 (m, 10H) | 2.71 | 481.3 $[M + H]^+$ | TFA |
| 57 | 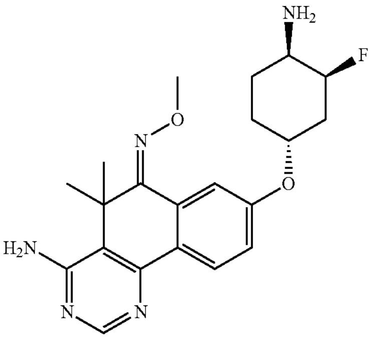 [SMILES: CO/N=C1\c2cc(O[C@@H]3CC[C@@H](N)[C@@H](F)C3)ccc2-c2ncnc(N)c2C1(C)C] | Example 1 (steps 5-9) using CAS 2382633-72-7 | DMSO-$d_6$ + $D_2O$: 8.25 (s, 1H), 8.12 (d, J = 8.8 Hz, 1H), 7.46 (d, J = 2.4 Hz, 1H), 7.11 (dd, J = 8.8 Hz, J = 2.4 Hz, 1H), 4.86 (d, J = 48.0 Hz, 1H), 4.61 (m, 1H), 3.83 (s, 3H), 3.32 (m, 1H), 2.30 (m, 1H), 2.07 (m, 1H), 1.90 (m, 2H), 1.76 (m, 1H), 1.62 (m, 1H), 1.48 (d, J = 7.6 Hz, 6H) | 2.73 | 400.2 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 58 | 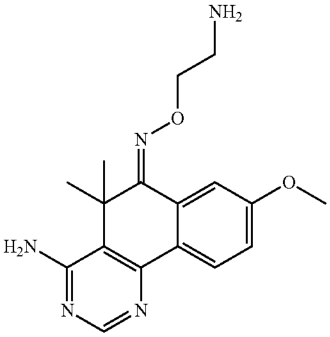 [SMILES: COc1ccc2c(c1)/C(=N\OCCN)C(C)(C)c1c(N)ncnc1-2] | Example 5 (steps 2 & 3) using CAS 39684-80-5 | DMSO-$d_6$ + $D_2O$: 8.43 (s, 1H), 8.06 (d, J = 8.8 Hz, 1H), 7.69 (d, J = 2.8 Hz, 1H), 7.24 (dd, J = 8.8 Hz, 2.8 Hz, 1H), 4.23 (t, J = 5.2 Hz, 2H), 3.85 (s, 3H), 3.15 (t, J = 5.2 Hz, 2H), 1.50 (s, 6H) | 2.52 | 328.2 $[M + H]^+$ | TFA |
| 59 | 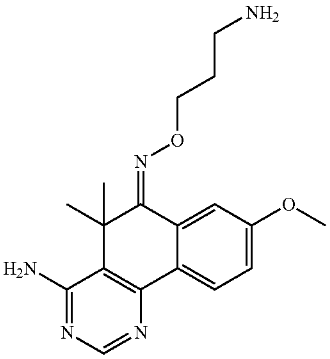 [SMILES: COc1ccc2c(c1)/C(=N\OCCCN)C(C)(C)c1c(N)ncnc1-2] | Example 5 (steps 2 & 3) using CAS 83948-53-2 | DMSO-$d_6$ + $D_2O$: 8.43 (s, 1H), 8.07 (d, J = 8.8 Hz, 1H), 7.57 (d, J =2.8 Hz, 1H), 7.23 (dd, J = 8.8 Hz, 2.8 Hz, 1H), 4.16 (t, J = 6.4 Hz, 2H), 3.85 (s, 3H), 2.83 (t, J = 8.0 Hz, 2H), 1.91 (m, 2H), 1.50 (s, 6H) | 2.67 | 342.2 $[M + H]^+$ | TFA |
| 60 | 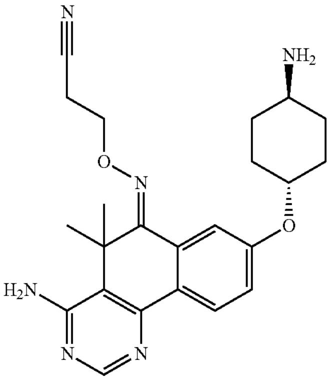 [SMILES: CC1(C)/C(=N\OCCC#N)c2cc(O[C@H]3CC[C@H](N)CC3)ccc2-c2ncnc(N)c21] | Example 1 (steps 8 & 9) using CAS 2517-76-2 | DMSO-$d_6$ + $D_2O$: 8.40 (s, 1H), 8.26 (d, J = 8.8 Hz, 1H), 7.62 (d, J = 2.4 Hz, 1H), 7.21 (dd, J = 8.8 Hz, 2.4 Hz, 1H), 4.40 (m, 3H), 3.05 (m, 1H), 2.95 (t, J = 5.6 Hz, 2H), 2.10 (m, 2H), 1.96 (m, 2H), 1.77 (s, 6H), 1.46 (m, 4H) | 3.02 | 421.3 $[M + H]^+$ | TFA |
| 61 | 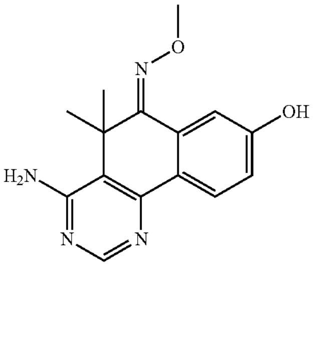 [SMILES: CO/N=C1\c2cc(O)ccc2-c2ncnc(N)c2C1(C)C] | Example 4 | DMSO-$d_6$ + $D_2O$: 8.48 (s, 1H), 7.88 (d, J = 8.8 Hz, 1H), 7.46 (d, J = 2.4 Hz, 1H), 7.03 (dd, J = 8.8 Hz, 2.4 Hz, 1H), 3.86 (s, 3H), 1.48 (s, 6H) | 3.41 | 285.1 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 62 | 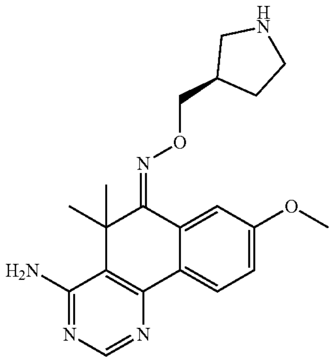 [SMILES: COc1ccc2c(c1)/C(=N\OC[C@@H]1CCNC1)C(C)(C)c1c(N)ncnc1-2] | Example 5 (steps 2 & 3) using CAS 1067230-64-1 | DMSO-$d_6$ + $D_2O$: 8.44 (s, 1H), 8.06 (d, J = 8.8 Hz, 1H), 7.56 (d, J = 2.4 Hz, 1H), 7.24 (dd, J = 8.0 Hz, 2.4 Hz, 1H), 4.13 (m, 2H), 3.85 (s, 3H), 3.25 (m, 1H), 3.19 (m, 1H), 3.12 (m, 1H), 2.89 (m, 1H), 2.61 (m, 1H), 2.02 (m, 1H), 1.65 (m, 1H), 1.49 (s, 6H) | 2.77 | 368.3 $[M + H]^+$ | TFA |
| 63 | 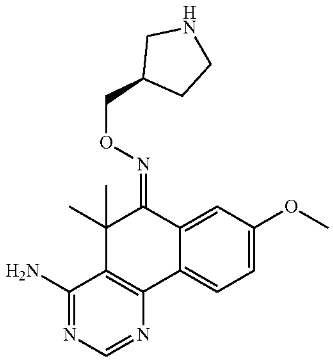 [SMILES: COc1ccc2c(c1)/C(=N/OC[C@@H]1CCNC1)C(C)(C)c1c(N)ncnc1-2] | Example 5 (steps 2 & 3) using CAS 1067230-64-1 | DMSO-$d_6$ + $D_2O$: 8.42 (s, 1H), 8.31 (d, J = 8.8 Hz, 1H), 7.58 (d, J = 2.4 Hz, 1H), 7.18 (dd, J = 8.8 Hz, 2.4 Hz, 1H), 4.28 (m, 2H), 3.84 (s, 3H), 3.36 (m, 1H), 3.26 (m, 1H), 3.17 (m, 1H), 3.01 (m, 1H), 2.74 (m, 1H), 2.15 (m, 1H), 1.73 (m, 1H), 1.70 (s, 6H) | 3.02 | 368.2 $[M + H]^+$ | TFA |
| 64 | 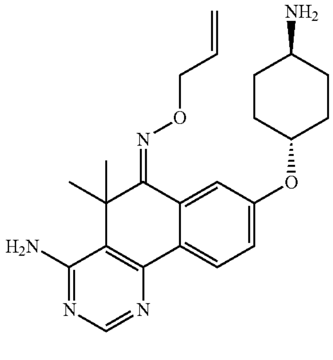 [SMILES: C=CCO/N=C1\c2cc(O[C@H]3CC[C@H](N)CC3)ccc2-c2ncnc(N)c2C1(C)C] | Example 1 (steps 8 & 9) using CAS 106-95-6 | DMSO-$d_6$ + $D_2O$: 8.44 (s, 1H), 8.01 (d, J = 8.8 Hz, 1H), 7.60 (d, J = 2.8 Hz, 1H), 7.23 (dd, J = 8.8 Hz, 2.8 Hz, 1H), 5.96 (m, 1H), 5.28 (dd, J = 17.6 Hz, 1.6 Hz, 1H), 5.21 (dd, J = 10.4 Hz, 1.6 Hz, 1H), 4.60 (d, J = 5.6 Hz, 2H), 4.38 (m, 1H), 3.07 (m, 1H), 2.13 (m, 2H), 1.98 (m, 2H), 1.49 (m, 10H) | 3.29 | 408.3 $[M + H]^+$ | TFA |
| 65 | 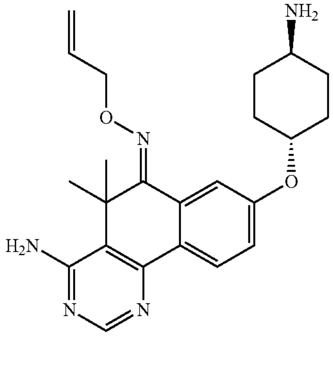 [SMILES: C=CCO/N=C1/c2cc(O[C@H]3CC[C@H](N)CC3)ccc2-c2ncnc(N)c2C1(C)C] | Example 1 (steps 8 & 9) using CAS 106-95-6 | DMSO-$d_6$ + $D_2O$: 8.39 (s, 1H), 8.27 (d, J = 8.8 Hz, 1H), 7.55 (d, J = 2.4 Hz, 1H), 7.20 (dd, J = 8.8 Hz, J = 2.4 Hz, 1H), 6.06 (m, 1H), 5.38 (dd, J = 17.6 Hz, J = 1.6 Hz, 1H), 5.28 (dd, J = 10.4 Hz, J = 1.6 Hz, 1H), 4.73 (d, J = 5.6 Hz, 2H), 4.38 (m, 1H), 3.07 (m, 1H), 2.10 (m, 2H), 1.97 (m, 2H), 1.76 (s, 6H), 1.47 (m, 4H) | 3.49 | 408.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 66 | 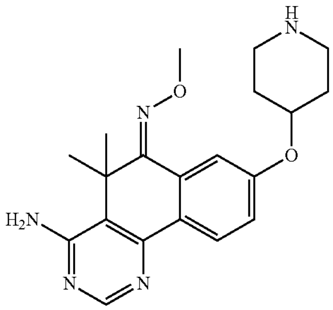 [SMILES: CO/N=C1\c2cc(OC3CCNCC3)ccc2-c2ncnc(N)c2C1(C)C] | Example 1 (steps 8 & 9) using CAS 118811-07-7 | DMSO-$d_6$ + $D_2O$: 8.42 (s, 1H), 8.04 (d, J = 8.8 Hz, 1H), 7.57 (d, J = 2.4 Hz, 1H), 7.28 (dd, J = 8.8 Hz, 2.4 Hz, 1H), 4.76 (m, 1H), 3.85 (s, 3H), 3.27 (m, 2H), 3.10 (m, 2H), 2.14 (m, 2H), 1.86 (m, 2H), 1.48 (s, 6H) | 2.70 | 368.2 $[M + H]^+$ | TFA |
| 67 | 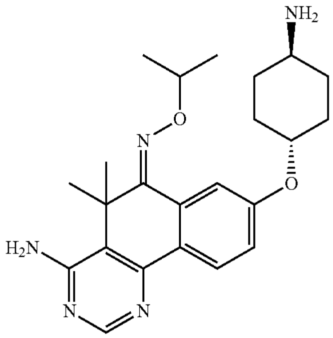 [SMILES: CC(C)O/N=C1\c2cc(O[C@H]3CC[C@H](N)CC3)ccc2-c2ncnc(N)c2C1(C)C] | Example 1 (steps 8 & 9) using CAS 75-30-9 | DMSO-$d_6$ + $D_2O$: 8.45 (s, 1H), 7.99 (d, J = 8.8 Hz, 1H), 7.66 (d, J = 2.4 Hz, 1H), 7.17 (dd, J = 8.8 Hz, 2.4 Hz, 1H), 4.37 (m, 2H), 3.09 (m, 1H), 2.15 (m, 2H), 1.98 (m, 2H), 1.50 (m, 10H), 1.20 (d, J = 6.4 Hz, 6H) | 3.35 | 410.3 $[M + H]^+$ | TFA |
| 68 | 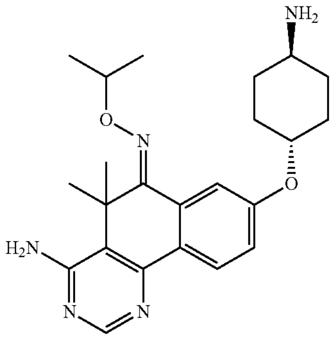 [SMILES: CC(C)O/N=C1/c2cc(O[C@H]3CC[C@H](N)CC3)ccc2-c2ncnc(N)c2C1(C)C] | Example 1 (steps 8 & 9) using CAS 75-30-9 | DMSO-$d_6$ + $D_2O$: 8.42 (s, 1H), 8.27 (d, J = 9.2 Hz, 1H), 7.57 (d, J = 2.8 Hz, 1H), 7.21 (dd, J = 9.2 Hz, 2.8 Hz, 1H), 4.43 (m, 2H), 3.08 (m, 1H), 2.11 (m, 2H), 1.98 (m, 2H), 1.77 (s, 6H), 1.48 (m, 4H), 1.32 (d, J = 6.4 Hz, 6H) | 3.59 | 410.3 $[M + H]^+$ | TFA |
| 69 | 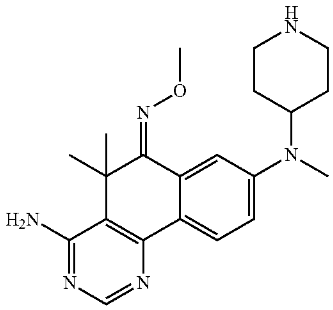 [SMILES: CO/N=C1\c2cc(N(C)C3CCNCC3)ccc2-c2ncnc(N)c2C1(C)C] | — | DMSO-$d_6$ + $D_2O$: 8.43 (s, 1H), 7.87 (d, J = 9.2 Hz, 1H), 7.40 (d, J = 2.4 Hz, 1H), 7.11 (dd, J = 9.2 Hz, 2.4 Hz, 1H), 4.13 (m, 1H), 3.84 (s, 3H), 3.38 (m, 2H), 3.08 (m, 2H), 2.83 (s, 3H), 1.90 (m, 2H), 1.83 (m, 2H), 1.48 (s, 6H) | 2.70 | 381.2 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 70 | 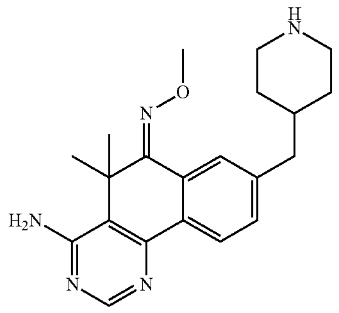 [SMILES: CO/N=C1\c2cc(CC3CCNCC3)ccc2-c2ncnc(N)c2C1(C)C] | — | DMSO-$d_6$ + $D_2O$: 8.43 (s, 1H), 8.03 (d, J = 8.0 Hz, 1H), 7.83 (d, J = 1.2 Hz, 1H), 7.44 (dd, J = 8.0 Hz, 1.2 Hz, 1H), 3.84 (s, 3H), 3.24 (m, 2H), 2.81 (m, 2H), 2.63 (m, 2H), 1.83 (m, 1H), 1.74 (m, 2H), 1.49 (s, 6H), 1.32 (m, 2H) | 2.87 | 366.2 $[M + H]^+$ | TFA |
| 71 | 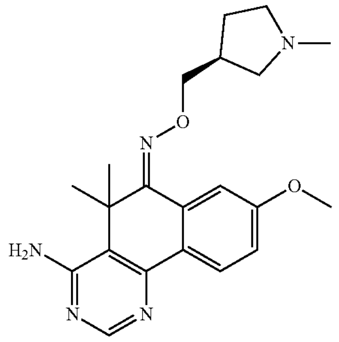 [SMILES: COc1ccc2c(c1)/C(=N\OC[C@H]1CCN(C)C1)C(C)(C)c1c(N)ncnc1-2] | Examples 1 (steps 8 & 9) and 44 (step 3) using CAS 1067230-64-1 and CAS 30525-89-4 | DMSO-$d_6$ + $D_2O$ + Diethylamine: 8.24 (s, 1H), 8.14 (d, J = 8.8 Hz, 1H), 7.55 (d, J = 2.8 Hz, 1H), 7.12 (dd, J = 8.8 Hz, 2.8 Hz, 1H), 3.97 (d, J = 7.6 Hz, 2H), 3.80 (s, 3H), 2.66 (m, 1H), 2.37 (m, 2H), 2.22 (m, 1H), 2.17 (s, 3H), 1.83 (m, 1H), 1.48 (s, 6H), 1.43 (m, 2H) | 2.82 | 382.2 $[M + H]^+$ | TFA |
| 72 | 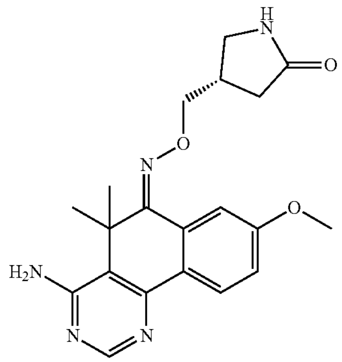 | Example 5 (steps 2 & 3) using CAS 945671-51-2 | DMSO-$d_6$ + $D_2O$: 8.50 (s, 1H), 8.01 (d, J = 8.8 Hz, 1H), 7.58 (d, J = 2.8 Hz, 1H), 7.24 (dd, J = 8.8 Hz, 2.8 Hz, 1H), 4.09 (d, J = 6.4 Hz, 2H), 3.85 (s, 3H), 3.25 (m, 1H), 3.04 (m, 1H), 2.75 (m, 1H), 2.26 (m, 1H), 2.00 (m, 1H), 1.49 (s, 6H) | 3.34 | 382.3 $[M + H]^+$ | TFA |
| 73 | 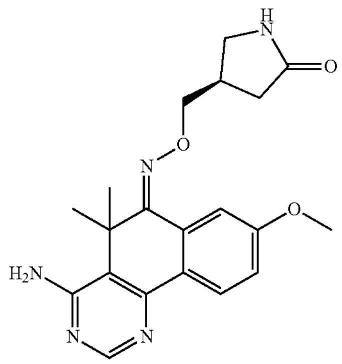 [SMILES: COc1ccc2c(c1)/C(=N\OC[C@H]1CNC(=O)C1)C(C)(C)c1c(N)ncnc1-2] | Example 5 (steps 2 & 3) using CAS 945671-51-2 | DMSO-$d_6$ + $D_2O$: 8.48 (s, 1H), 8.01 (d, J = 8.8 Hz, 1H), 7.58 (d, J = 2.8 Hz, 1H), 7.24 (dd, J = 8.8 Hz, 2.8 Hz, 1H), 4.09 (d, J = 6.4 Hz, 2H), 3.85 (s, 3H), 3.32 (m, 1H), 3.03 (m, 1H), 2.75 (m, 1H), 2.26 (m, 1H), 2.00 (m, 1H), 1.49 (s, 6H) | 3.35 | 382.4 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 74 | 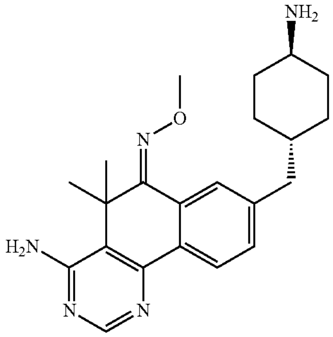 [SMILES: CO/N=C1\c2cc(C[C@H]3CC[C@H](N)CC3)ccc2-c2ncnc(N)c2C1(C)C] | Example 70 using CAS 179321-49-4 | DMSO-$d_6$ + $D_2O$: 8.44 (s, 1H), 8.01 (d, J = 8.0 Hz, 1H), 7.81 (d, J = 1.6 Hz, 1H), 7.42 (dd, J = 8.0 Hz, 1.6 Hz, 1H), 3.83 (s, 3H), 2.91 (m, 1H), 2.56 (d, J = 7.2 Hz, 2H), 1.88 (m, 2H), 1.70 (m, 2H), 1.49 (s, 6H), 1.49 (m, 1H), 1.23 (m, 2H), 1.05 (m, 2H) | 3.20 | 380.3 $[M + H]^+$ | TFA |
| 75 | 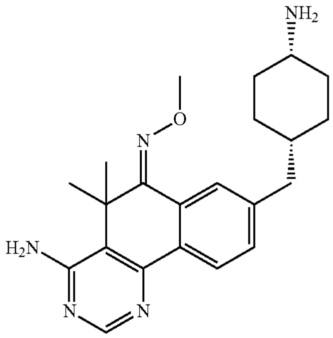 [SMILES: CO/N=C1\c2cc(C[C@H]3CC[C@@H](N)CC3)ccc2-c2ncnc(N)c2C1(C)C] | Example 70 using CAS 179321-49-4 | DMSO-$d_6$ + $D_2O$: 8.43 (s, 1H), 8.04 (d, J = 8.0 Hz, 1H), 7.81 (d, J = 1.6 Hz, 1H), 7.42 (dd, J = 8.0 Hz, 1.6 Hz, 1H), 3.83 (s, 3H), 3.16 (m, 1H), 2.64 (d, J = 7.6 Hz, 2H), 1.79 (m, 1H), 1.64 (m, 4H), 1.49 (s, 6H), 1.42 (m, 4H) | 3.11 | 380.3 $[M + H]^+$ | TFA |
| 76 | 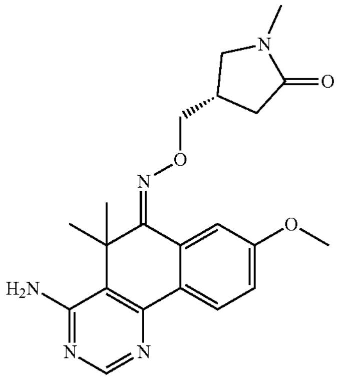 [SMILES: COc1ccc2c(c1)/C(=N\OC[C@H]1CC(=O)N(C)C1)C(C)(C)c1c(N)ncnc1-2] | — | DMSO-$d_6$ + $D_2O$: 8.55 (s, 1H), 7.97 (d, J = 8.8 Hz, 1H), 7.58 (d, J = 2.4 Hz, 1H), 7.28 (dd, J = 8.8 Hz, 2.4 Hz, 1H), 4.11 (d, J = 6.4 Hz, 2H), 3.87 (s, 3H), 3.43 (m, 1H), 3.12 (m, 1H), 2.68 (m, 1H), 2.63 (s, 3H), 2.37 (m, 1H), 2.08 (m, 1H), 1.50 (s, 6H) | 3.57 | 396.3 $[M + H]^+$ | TFA |
| 77 | 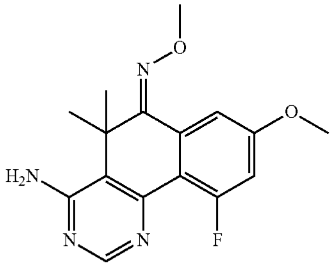 [SMILES: CO/N=C1\c2cc(OC)cc(F)c2-c2ncnc(N)c2C1(C)C] | — | DMSO-$d_6$ + $D_2O$: 8.45 (s, 1H), 7.33 (d, J = 2.4 Hz, 1H), 7.19 (dd, J = 14.0 Hz, 2.4 Hz, 1H), 3.87 (s, 3H), 3.86 (s, 3H), 1.46 (s, 6H) | 2.70 | 317.3 $[M + H]^+$ | TFA |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 78 | 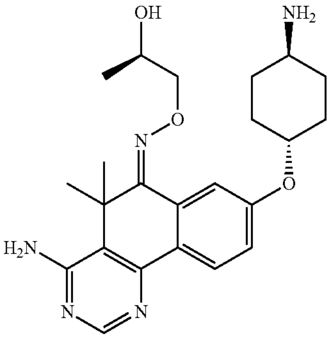 [SMILES: C[C@@H](O)CO/N=C1\c2cc(O[C@H]3CC[C@H](N)CC3)ccc2-c2ncnc(N)c2C1(C)C] | — | DMSO-$d_6$ + $D_2O$: 8.42 (s, 1H), 8.01 (d, J = 8.8 Hz, 1H), 7.72 (d, J = 2.8 Hz, 1H), 7.19 (dd, J = 8.8 Hz, 2.8 Hz, 1H), 4.40 (m, 1H), 3.91 (m, 3H), 3.07 (m, 1H), 2.15 (m, 2H), 1.97 (m, 2H), 1.48 (m, 10H), 1.06 (d, J = 6.0 Hz, 3H) | 3.54 | 426.3 $[M + H]^+$ | TFA |
| 79 | 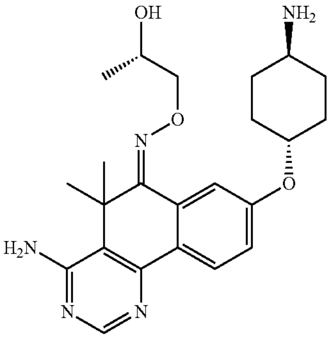 [SMILES: C[C@H](O)CO/N=C1\c2cc(O[C@H]3CC[C@H](N)CC3)ccc2-c2ncnc(N)c2C1(C)C] | Example 78 using CAS 16088-62-3 | DMSO-$d_6$ + $D_2O$: 8.45 (s, 1H), 7.99 (d, J = 8.8 Hz, 1H), 7.73 (d, J = 2.4 Hz, 1H), 7.21 (dd, J = 8.8 Hz, 2.4 Hz, 1H), 4.41 (m, 1H), 3.91 (m, 3H), 3.07 (m, 1H), 2.15 (m, 2H), 1.98 (m, 2H), 1.48 (m, 10H), 1.06 (d, J = 6.0 Hz, 3H) | 5.54 | 426.3 $[M + H]^+$ | TFA |
| 80 | 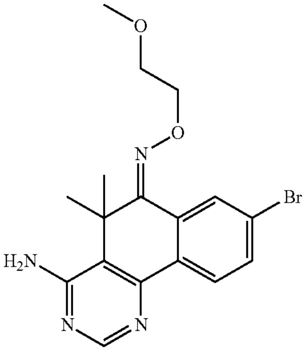 [SMILES: COCCO/N=C1\c2cc(Br)ccc2-c2ncnc(N)c2C1(C)C] | Example 5 (step 2) using CAS 6482-24-2 | DMSO-$d_6$ + $D_2O$: 8.30 (s, 1H), 8.24 (d, J = 2.0 Hz, 1H), 8.14 (d, J = 8.4 Hz, 1H), 7.75 (dd, J = 8.4 Hz, 2.0 Hz, 1H), 4.20 (m, 2H), 3.57 (m, 2H), 3.26 (s, 3H), 1.50 (s, 6H) | 5.70 | 391.2, 393.2 $[M + H]^+$ | Parent |
| 81 | 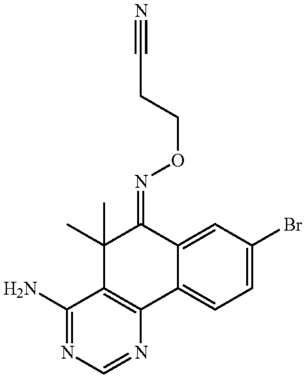 [SMILES: CC1(C)/C(=N/OCCC#N)c2cc(Br)ccc2-c2ncnc(N)c21] | Example 5 (step 2) using CAS 2417-90-5 | DMSO-$d_6$ + $D_2O$: 8.30 (s, 1H), 8.20 (d, J = 2.0 Hz, 1H), 8.13 (d, J = 8.4 Hz, 1H), 7.78 (dd, J = 8.4 Hz, 2.0 Hz, 1H), 4.27 (t, J = 5.6 Hz, 2H), 2.90 (t, J = 5.6 Hz, 2H), 1.50 (s, 6H) | 5.33 | 386.2, 388.2 $[M + H]^+$ | Parent |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 82 | 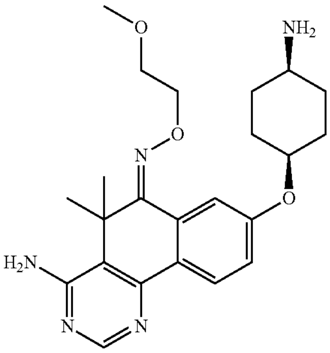 [SMILES: COCCO/N=C1\c2cc(O[C@H]3CC[C@@H](N)CC3)ccc2-c2ncnc(N)c2C1(C)C] | Example 5 (step 2) using CAS 6482-24-2 | DMSO-$d_6$ + $D_2O$: 8.25 (s, 1H), 8.13 (d, J = 8.8 Hz, 1H), 7.62 (d, J = 2.4 Hz, 1H), 7.11 (dd, J = 8.8 Hz, 2.4 Hz, 1H), 4.61 (m, 1H), 4.18 (t, J = 4.8 Hz, 2H), 3.54 (t, J = 4.8 Hz, 2H), 3.23 (s, 3H), 3.10 (m, 1H), 2.00 (m, 2H), 1.69 (m, 6H), 1.48 (s, 6H) | 2.88 | 426.4 $[M + H]^+$ | HCOOH |
| 83 | 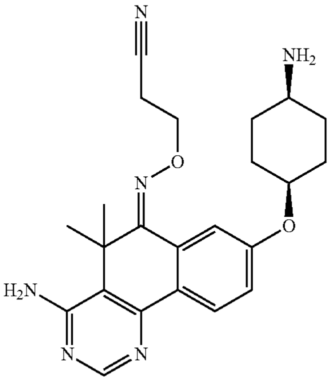 [SMILES: CC1(C)/C(=N/OCCC#N)c2cc(O[C@H]3CC[C@@H](N)CC3)ccc2-c2ncnc(N)c21] | Example 5 (step 2) using CAS 2417-90-5 | DMSO-$d_6$ + $D_2O$: 8.25 (s, 1H), 8.14 (d, J = 8.8 Hz, 1H), 7.58 (d, J = 2.4 Hz, 1H), 7.12 (dd, J = 8.8 Hz, 2.4 Hz, 1H), 4.65 (m, 1H), 4.24 (t, J = 5.6 Hz, 2H), 3.09 (m, 1H), 2.90 (t, J = 5.6 Hz, 2H), 1.99 (m, 2H), 1.73 (m, 6H), 1.50 (s, 6H) | 2.83 | 421.4 $[M + H]^+$ | HCOOH |
| 84 | 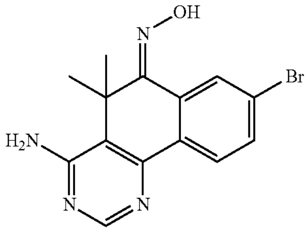 [SMILES: CC1(C)/C(=N/O)c2cc(Br)ccc2-c2ncnc(N)c21] | Example 51 | DMSO-$d_6$ + $D_2O$: 8.30 (s, 1H), 8.26 (d, J = 2.0 Hz, 1H), 8.14 (d, J = 8.4 Hz, 1H), 7.72 (dd, J = 8.4 Hz, 2.0 Hz, 1H), 1.49 (s, 6H) | 4.39 | 333.1, 335.1 $[M + H]^+$ | Parent |
| 85 | 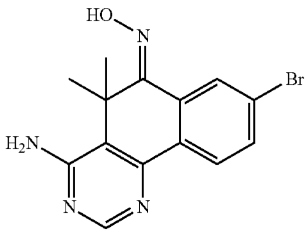 [SMILES: CC1(C)/C(=N\O)c2cc(Br)ccc2-c2ncnc(N)c21] | Example 51 | DMSO-$d_6$ + $D_2O$: 8.37 (d, J = 8.8 Hz, 1H), 8.30 (s, 1H), 8.14 (d, J = 2.0 Hz, 1H), 7.62 (dd, J = 8.8 Hz, 2.0 Hz, 1H), 1.79 (s, 6H) | 5.05 | 333.1, 335.1 $[M + H]^+$ | Parent |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 86 | 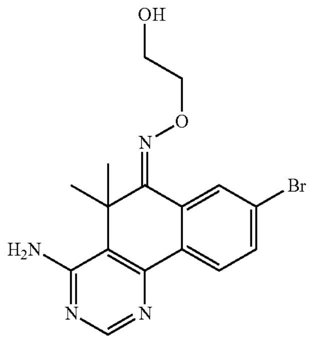 [SMILES: CC1(C)/C(=N/OCCO)c2cc(Br)ccc2-c2ncnc(N)c21] | Example 78 (step 1) using CAS 75-21-8 | DMSO-$d_6$ + $D_2O$: 8.29 (m, 2H), 8.13 (d, J = 8.4 Hz, 1H), 7.74 (dd, J = 8.4 Hz, 2.0 Hz, 1H), 4.10 (m, 2H), 3.61 (m, 2H), 1.49 (s, 6H) | 4.39 | 377.2, 379.2 $[M + H]^+$ | Parent |
| 87 | 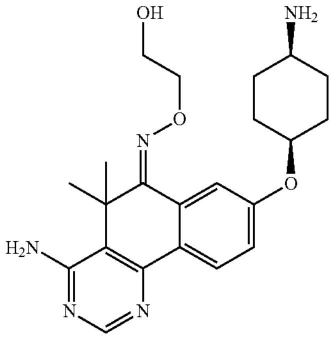 [SMILES: CC1(C)/C(=N/OCCO)c2cc(O[C@H]3CC[C@@H](N)CC3)ccc2-c2ncnc(N)c21] | Example 78 (steps 1 & 2) using CAS 75-21-8 | DMSO-$d_6$ + $D_2O$: 8.25 (s, 1H), 8.13 (d, J = 8.8 Hz, 1H), 7.68 (d, J = 2.4 Hz, 1H), 7.10 (dd, J = 8.8 Hz, 2.4 Hz, 1H), 4.63 (m, 1H), 4.08 (t, J = 5.2 Hz, 2H), 3.62 (t, J = 5.2 Hz, 2H), 3.10 (m, 1H), 2.00 (m, 2H), 1.69 (m, 6H), 1.49 (s, 6H) | 2.54 | 412.4 $[M + H]^+$ | HCOOH |
| 88 | 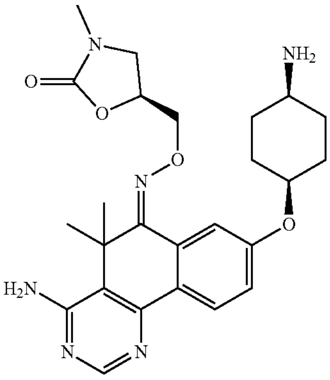 [SMILES: CN1C[C@@H](CO/N=C2\c3cc(O[C@H]4CC[C@@H](N)CC4)ccc3-c3ncnc(N)c3C2(C)C)OC1=O] | Examples 1 & 12 using CAS 167081-25-6 and CAS 140478-99-5 | DMSO-$d_6$ + $D_2O$: 8.26 (s, 1H), 8.14 (d, J = 8.8 Hz, 1H), 7.53 (d, J = 2.4 Hz, 1H), 7.13 (dd, J = 8.8 Hz, 2.4 Hz, 1H), 4.75 (m, 1H), 4.65 (m, 1H), 4.23 (m, 2H), 3.63 (t, J = 8.8 Hz, 1H), 3.28 (d, J = 8.8 Hz, 6.0 Hz, 1H), 3.10 (m, 1H), 2.67 (s, 3H), 1.98 (m, 2H), 1.69 (m, 6H), 1.50 (s, 3H), 1.48 (s, 3H) | 2.70 | 481.4 $[M + H]^+$ | HCOOH |
| 89 | 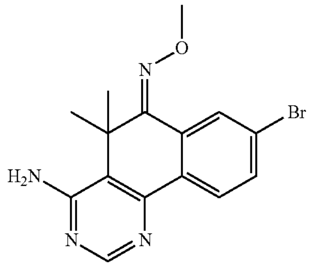 [SMILES: CO/N=C1\c2cc(Br)ccc2-c2ncnc(N)c2C1(C)C] | Example 1 (step 8) using 74-88-4 | DMSO-$d_6$ + $D_2O$: 8.31 (s, 1H), 8.13 (m, 2H), 7.75 (dd, J = 8.4 Hz, 2.0 Hz, 1H), 3.87 (s, 3H), 1.49 (s, 6H) | 5.94 | 347.2, 349.2 $[M + H]^+$ | Parent |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 90 | 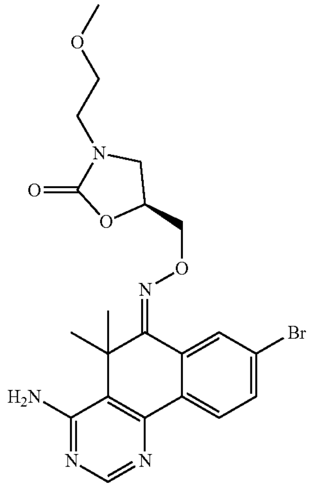 [SMILES: COCCN1C[C@@H](CO/N=C2\c3cc(Br)ccc3-c3ncnc(N)c3C2(C)C)OC1=O] | — | DMSO-$d_6$ + $D_2O$: 8.30 (s, 1H), 8.13 (m, 2H), 7.77 (dd, J = 8.4 Hz, 2.0 Hz, 1H), 4.76 (m, 1H), 4.24 (m, 2H), 3.67 (t, J = 8.8 Hz, 2H), 3.36 (m, 2H), 3.25 (m, 2H), 3.17 (s, 3H), 1.49 (s, 3H), 1.48 (s, 3H) | 4.78 | 490.3, 492.3 [M + H]+ | Parent |
| 91 | 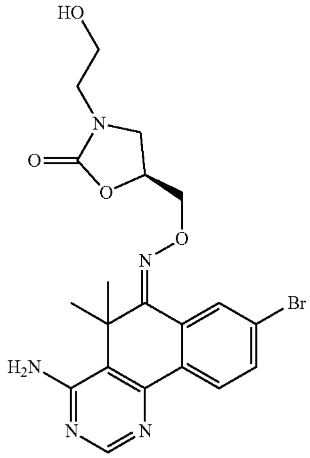 [SMILES: CC1(C)/C(=N/OC[C@@H]2CN(CCO)C(=O)O2)c2cc(Br)ccc2-c2ncnc(N)c21] | Examples 90 & 5 (step 3) using CAS 169048-83-3 and CAS 86864-60-0 | DMSO-$d_6$ + $D_2O$: 8.31 (s, 1H), 8.14 (m, 2H), 7.76 (dd, J = 8.4 Hz, 2.0 Hz, 1H), 4.76 (m, 1H), 4.26 (m, 2H), 3.72 (t, J = 8.8 Hz, 1H), 3.45 (t, J = 5.6 Hz, 2H), 3.35 (dd, J = 8.8 Hz, 6.4 Hz, 1H), 3.20 (m, 1H), 3.04 (m, 1H), 1.49 (s, 6H) | 4.05 | 476.3, 478.2 $[M + H]^+$ | Parent |
| 92 | 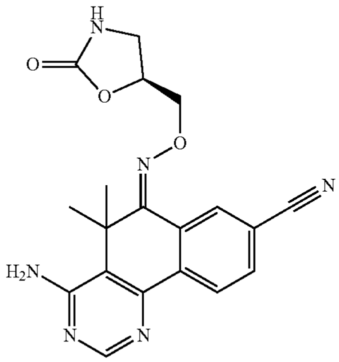 [SMILES: CC1(C)/C(=N/OC[C@@H]2CNC(=O)O2)c2cc(C#N)ccc2-c2ncnc(N)c21] | — | DMSO-$d_6$ + $D_2O$: 8.48 (s, 1H), 8.40 (d, J = 1.6 Hz, 1H), 8.31 (d, J = 8.4 Hz, 1H), 8.09 (dd, J = 8.4 Hz, 1.6 Hz, 1H), 4.85 (m, 1H), 4.31 (m, 2H), 3.59 (m, 1H), 3.27 (m, 1H), 1.51 (s, 6H) | 3.96 | 379.3 $[M + H]^+$ | HCl |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 93 | 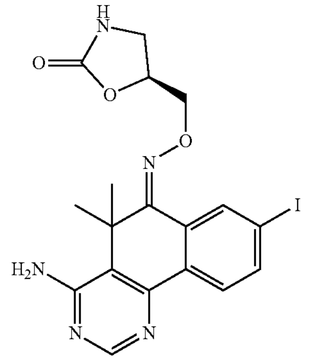 [SMILES: CC1(C)/C(=N/OC[C@@H]2CNC(=O)O2)c2cc(I)ccc2-c2ncnc(N)c21] | — | DMSO-$d_6$ + $D_2O$: 8.52 (s, 1H), 8.42 (d, J = 1.6 Hz, 1H), 8.07(dd, J = 8.4 Hz, 1.6 Hz, 1H), 7.86 (d, J = 8.4 Hz, 1H), 4.85 (m, 1H), 4.30 (m, 2H), 3.60 (m, 1H), 3.27 (m, 1H), 1.50 (s, 3H), 1.49 (s, 3H) | 4.33 | 480.2 $[M + H]^+$ | HCl |
| 94 | 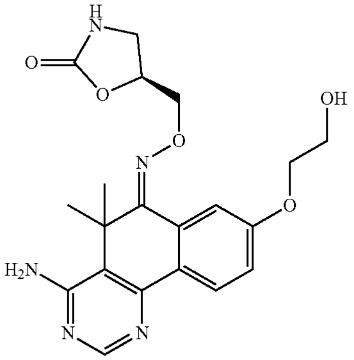 [SMILES: CC1(C)/C(=N/OC[C@@H]2CNC(=O)O2)c2cc(OCCO)ccc2-c2ncnc(N)c21] | — | DMSO-$d_6$ + $D_2O$: 8.13 (d, J = 8.8 Hz, 1H), 7.55 (d, J = 2.4 Hz, 1H), 7.51 (s, 1H), 7.13 (dd, J = 8.8 Hz, 2.4 Hz, 1H), 4.86 (m, 1H), 4.23 (m, 2H), 4.50 (m, 2H), 3.73 (m, 2H), 3.57 (m, 1H), 3.26 (m, 1H), 1.50 (s, 3H), 1.48 (s, 3H) | 2.84 | 414.3 $[M + H]^+$ | Parent |
| 95 | 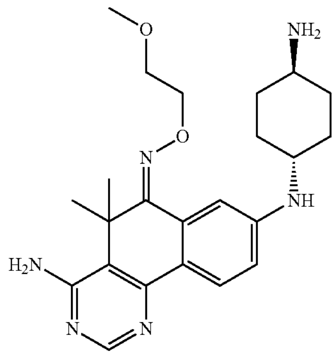 [SMILES: COCCO/N=C1\c2cc(N[C@H]3CC[C@H](N)CC3)ccc2-c2ncnc(N)c2C1(C)C] | Examples 4, 44 & 94 using CAS 6482-24-1 and CAS 2615-25-0 | DMSO-$d_6$ + $D_2O$: 8.18 (s, 1H), 7.91 (d, J = 8.8 Hz, 1H), 7.17 (d, J = 2.0 Hz, 1H), 6.72 (dd, J = 8.8 Hz, 2.0 Hz, 1H), 4.14 (t, J = 4.4 Hz, 2H), 3.56 (t, J = 4.4 Hz, 2H), 3.24 (s, 3H), 3.16 (m, 1H), 2.99 (m, 1H), 2.00 (m, 4H), 1.46 (s, 6H), 1.42 (m, 2H), 1.25 (m, 2H) | 2.66 | 425.4 $[M + H]^+$ | HCOOH |
| 96 | 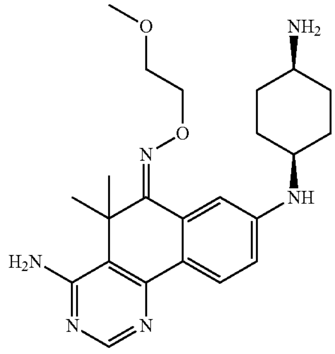 [SMILES: COCCO/N=C1\c2cc(N[C@H]3CC[C@@H](N)CC3)ccc2-c2ncnc(N)c2C1(C)C] | Examples 4, 44 & 94 using CAS 6482-24-1 and CAS 15827-56-2 | DMSO-$d_6$ + $D_2O$: 8.18 (s, 1H), 7.93 (d, J = 8.8 Hz, 1H), 7.21 (d, J = 2.0 Hz, 1H), 6.79 (dd, J = 8.8 Hz, 2.0 Hz, 1H), 4.15 (t, J = 4.4 Hz, 2H), 3.56 (t, J = 4.4 Hz, 2H), 3.29 (m, 1H), 3.23 (s, 3H), 3.11 (m, 1H), 1.73 (m, 8H), 1.47 (s, 6H) | 2.67 | 425.4 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 97 | 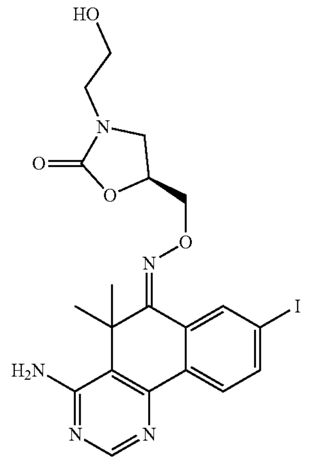 [SMILES: CC1(C)/C(=N/OC[C@@H]2CN(CCO)C(=O)O2)c2cc(I)ccc2-c2ncnc(N)c21] | Examples 90 & 94 using CAS 86864-60-0 (from Example 93) | DMSO-$d_6$ + $D_2O$: 8.32 (d, J = 1.6 Hz, 1H), 8.30 (s, 1H), 7.96 (d, J = 8.4 Hz, 1H), 7.93 (dd, J = 8.4 Hz, 1.6 Hz, 1H), 4.76 (m, 1H), 4.26 (m, 2H), 3.72 (t, J = 8.8 Hz, 1H), 3.45 (t, J = 5.6 Hz, 2H), 3.34 (dd, J = 8.8 Hz, 6.4 Hz, 1H), 3.20 (m, 1H), 3.07 (m, 1H), 1.48 (s, 6H) | 4.07 | 524.3 $[M + H]^+$ | Parent |
| 98 | 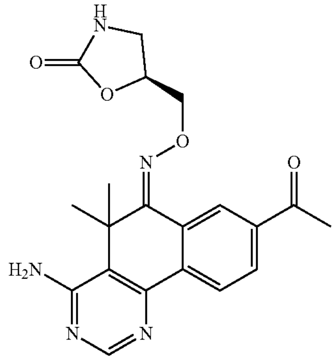 [SMILES: CC(=O)c1ccc2c(c1)/C(=N\OC[C@@H]1CNC(=O)O1)C(C)(C)c1c(N)ncnc1-2] | — | DMSO-$d_6$ + $D_2O$: 8.61 (d, J = 1.6 Hz, 1H), 8.43 (s, 1H), 8.29 (d, J = 8.4 Hz, 1H), 8.14 (dd, J = 8.4 Hz, 1.6 Hz, 1H), 4.85 (m, 1H), 4.32 (m, 2H), 3.59 (m, 1H), 3.30 (m, 1H), 2.62 (s, 3H), 1.52 (s, 3H), 1.51 (s, 3H) | 3.57 | 396.3 $[M + H]^+$ | Parent |
| 99 | 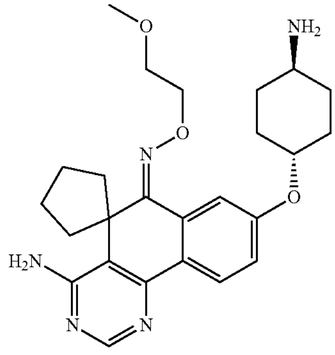 [SMILES: COCCO/N=C1\c2cc(O[C@H]3CC[C@H](N)CC3)ccc2-c2ncnc(N)c2C12CCCC2] | Examples 1 & 94 using CAS 5660-83-3, CAS 111300-06-2 and CAS 6482-24-2 | DMSO-$d_6$ + $D_2O$: 8.27 (s, 1H), 8.12 (d, J = 8.8 Hz, 1H), 7.61 (d, J = 2.4 Hz, 1H), 7.11 (dd, J = 8.8 Hz, 2.4 Hz, 1H), 4.32 (m, 1H), 4.17 (t, J = 4.4 Hz, 2H), 3.58 (t, J = 4.4 Hz, 2H), 3.27 (s, 3H), 3.01 (m, 1H), 2.08 (m, 8H), 1.74 (m, 4H), 1.46 (m, 4H) | 3.28 | 452.4 $[M + H]^+$ | HCOOH |
| 100 | 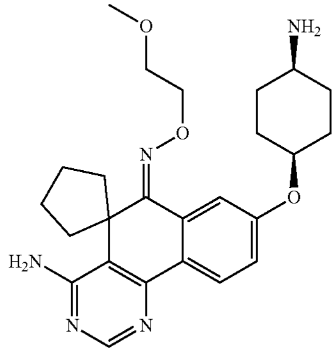 [SMILES: COCCO/N=C1\c2cc(O[C@H]3CC[C@@H](N)CC3)ccc2-c2ncnc(N)c2C12CCCC2] | Examples 1 & 94 using CAS 5660-83-3, CAS 167081-25-6 and CAS 6482-24-2 | DMSO-$d_6$ + $D_2O$: 8.27 (s, 1H), 8.14 (d, J = 8.8 Hz, 1H), 7.64 (d, J = 2.4 Hz, 1H), 7.10 (dd, J = 8.8 Hz, 2.4 Hz, 1H), 4.60 (m, 1H), 4.18 (t, J = 4.4 Hz, 2H), 3.58 (t, J = 4.4 Hz, 2H), 3.25 (s, 3H), 3.07 (m, 1H), 2.06 (m, 6H), 1.67 (m, 10H) | 3.28 | 452.2 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 101 | 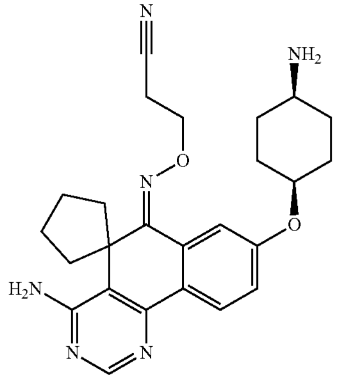 [SMILES: N#CCCO/N=C1\c2cc(O[C@H]3CC[C@@H](N)CC3)ccc2-c2ncnc(N)c2C12CCCC2] | Examples 1 & 94 using CAS 5660-83-3, CAS 167081-25-6 and CAS 2417-90-5 | DMSO-$d_6$ + $D_2O$: 8.27 (s, 1H), 8.14 (d, J = 8.8 Hz, 1H), 7.64 (d, J = 2.4 Hz, 1H), 7.14 (dd, J = 8.8 Hz, 2.4 Hz, 1H), 4.64 (m, 1H), 4.25 (t, J = 4.4 Hz, 2H), 3.07 (m, 1H), 2.90 (t, J = 4.4 Hz, 2H), 2.07 (m, 6H), 1.47 (m, 10H) | 3.19 | 447.1 $[M + H]^+$ | HCOOH |
| 102 | 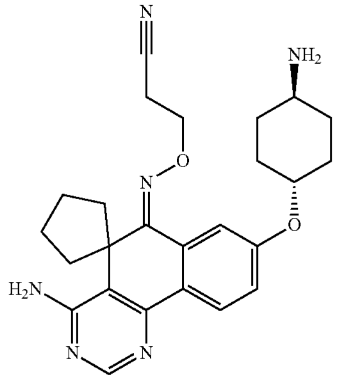 [SMILES: N#CCCO/N=C1\c2cc(O[C@H]3CC[C@H](N)CC3)ccc2-c2ncnc(N)c2C12CCCC2] | Examples 1 & 94 using CAS 5660-83-3, CAS 111300-06-2 and CAS 2417-90-5 | DMSO-$d_6$ + $D_2O$: 8.27 (s, 1H), 8.14 (d, J = 8.8 Hz, 1H), 7.58 (d, J = 2.4 Hz, 1H), 7.14 (dd, J = 8.8 Hz, 2.4 Hz, 1H), 4.37 (m, 1H), 4.25 (t, J = 5.6 Hz, 2H), 3.05 (m, 1H), 2.92 (t, J = 5.6 Hz, 2H), 2.10 (m, 6H), 1.82 (m, 6H), 1.43 (m, 4H) | 3.20 | 447.1 $[M + H]^+$ | HCOOH |
| 103 | 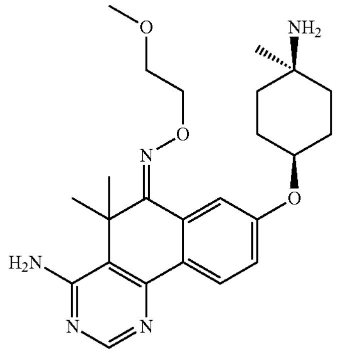 [SMILES: COCCO/N=C1\c2cc(O[C@H]3CC[C@@](C)(N)CC3)ccc2-c2ncnc(N)c2C1(C)C] | Example 1 using CAS 412293-62-0 and CAS 6482-24-2 | DMSO-$d_6$ + $D_2O$: 8.37 (s, 1H), 8.12 (d, J = 8.8 Hz, 1H), 7.60 (d, J = 2.4 Hz, 1H), 7.13 (dd, J = 8.8 Hz, 2.4 Hz, 1H), 4.41 (m, 1H), 4.17 (m, 2H), 3.55 (m, 2H), 3.25 (s, 3H), 2.00 (m, 2H), 1.70 (m, 6H), 1.48 (s, 6H), 1.28 (s, 3H) | 3.06 | 440.1 $[M + H]^+$ | HCOOH |
| 104 | 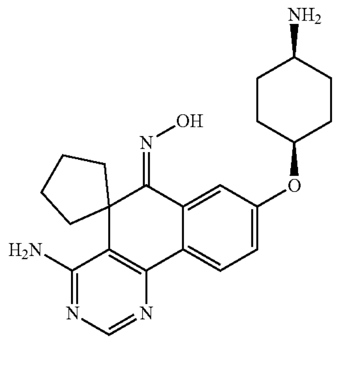 [SMILES: Nc1ncnc2c1C1(CCCC1)/C(=N/O)c1cc(O[C@H]3CC[C@@H](N)CC3)ccc1-2] | Example 1 using CAS 5660-83-3 and CAS 167081-25-6 | DMSO-$d_6$ + $D_2O$: 8.41 (s,1H), 8.13 (d, J = 8.4 Hz, 1H), 7.66 (d, J = 2.4 Hz, 1H), 7.10 (dd, J = 8.8 Hz, 2.4 Hz, 1H), 4.63 (m, 1H), 3.06 (m, 1H), 2.00 (m, 6H), 1.70 (m, 10H) | 2.71 | 394.2 $[M + H]^+$ | HCOOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 105 | 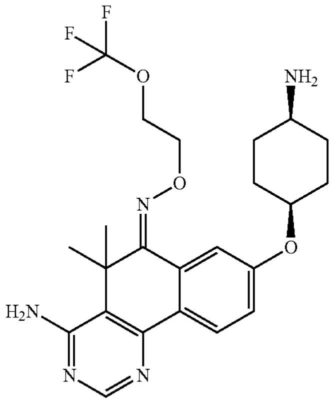 [SMILES: CC1(C)/C(=N/OCCOC(F)(F)F)c2cc(O[C@H]3CC[C@@H](N)CC3)ccc2-c2ncnc(N)c21] | Example 1 using CAS 167081-25-6 and CAS 1645-93-8 | DMSO-$d_6$ + $D_2O$: 8.26 (s, 1H), 8.14 (d, J = 8.8 Hz, 1H), 7.56 (d, J = 2.4 Hz, 1H), 7.12 (dd, J = 8.8 Hz, 2.4 Hz, 1H), 4.58 (m, 1H), 4.31 (m, 4H), 3.07 (m, 1H), 1.98 (m, 2H), 1.67 (m, 6H), 1.49 (s, 6H) | 3.55 | 480.1 $[M + H]^+$ | HCOOH |
| 106 | 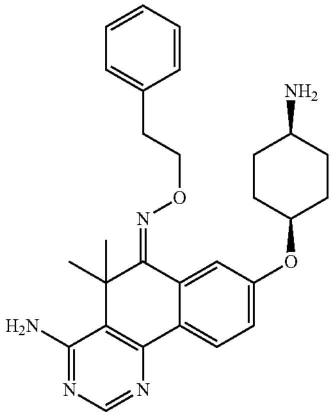 [SMILES: CC1(C)/C(=N/OCCc2ccccc2)c2cc(O[C@H]3CC[C@@H](N)CC3)ccc2-c2ncnc(N)c21] | Example 1 & using CAS 167081-25-6 and CAS 103-63-9 | DMSO-$d_6$: 8.28 (s, 1H), 8.14 (d, J =8.8 Hz, 1H), 7.37 (d, J = 2.6 Hz, 1H), 7.26 (m, 5H), 7.09 (dd, J = 8.8 Hz, 2.6 Hz, 1H), 6.65 (s, 2H), 4.30 (m, 3H), 2.97 (t, J = 6.4 Hz, 2H), 2.79 (m, 1H), 1.87 (m, 2H), 1.60 (m, 4H), 1.49 (s, 6H), 1.45 (m, 2H) | 3.85 | 472.1 $[M + H]^+$ | AcOH |
| 107 | 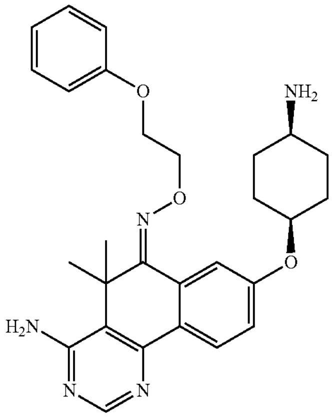 [SMILES: CC1(C)/C(=N/OCCOc2ccccc2)c2cc(O[C@H]3CC[C@@H](N)CC3)ccc2-c2ncnc(N)c21] | Example 1 & using CAS 167081-25-6 and CAS 589-10-6 | DMSO-$d_6$: 8.28 (s, 1H), 8.15 (d, J = 8.8 Hz, 1H), 7.62 (m, 1H), 7.29 (m, 2H), 7.09 (dd, J = 8.8 Hz, 2.4 Hz, 1H), 6.97 (m, 3H), 6.66 (s, 2H), 4.42 (t, J = 4.6 Hz, 2H), 4.26 (m, 3H), 2.69 (m, 1H), 1.87 (m, 2H), 1.53 (s, 6H), 1.47 (m, 6H) | 3.75 | 488.1 $[M + H]^+$ | AcOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 108 | 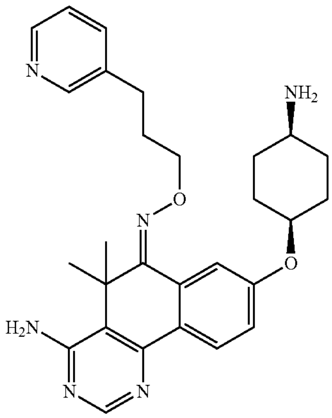 [SMILES: CC1(C)/C(=N/OCCCc2cccnc2)c2cc(O[C@H]3CC[C@@H](N)CC3)ccc2-c2ncnc(N)c21] | Example 1 & using CAS 167081-25-6 and CAS 109839-74-9 | DMSO-$d_6$: 8.41 (m, 2H), 8.29 (s, 1H), 8.18 (d, J = 8.8 Hz, 1H), 7.61 (m, 2H), 7.30 (m, 1H), 7.14 (dd, J = 8.8 Hz, 2.4 Hz, 1H), 6.66 (s, 2H), 4.57 (m, 1H), 4.10 (t, J = 6.4 Hz, 2H), 2.82 (m, 1H), 2.68 (m, 2H), 1.96 (m, 4H), 1.61 (m, 4H), 1.52 (s, 6H), 1.47 (m, 2H) | 2.53 | 487.1 $[M + H]^+$ | AcOH |
| 109 | 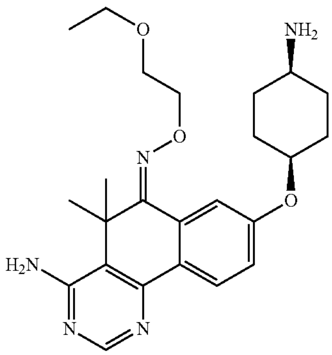 [SMILES: CCOCCO/N=C1\c2cc(O[C@H]3CC[C@@H](N)CC3)ccc2-c2ncnc(N)c2C1(C)C] | Example 1 & using CAS 167081-25-6 and CAS 628-34-2 | DMSO-$d_6$: 8.28 (s, 1H), 8.16 (d, J = 8.8 Hz, 1H), 7.65 (d, J = 2.6 Hz, 1H), 7.14 (dd, J = 8.8 Hz, 2.6 Hz, 1H), 6.65 (s, 2H), 4.56 (m, 1H), 4.19 (m, 2H), 3.62 (m, 2H), 3.45 (m, 2H), 2.87 (m, 1H), 1.95 (m, 2H), 1.65 (m, 4H), 1.52 (s, 6H), 1.49 (m, 2H), 1.10 (m, 3H) | 3.09 | 440.0 $[M + H]^+$ | AcOH |
| 110 | 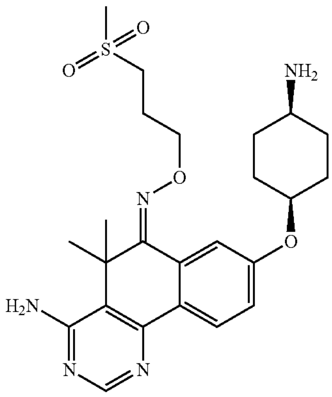 [SMILES: CC1(C)/C(=N/OCCCS(C)(=O)=O)c2cc(O[C@H]3CC[C@@H](N)CC3)ccc2-c2ncnc(N)c21] | Example 1 & using CAS 167081-25-6 and CAS 859940-73-1 | DMSO-$d_6$: 8.28 (s, 1H), 8.17 (d, J = 8.8 Hz, 1H), 7.57 (d, J = 2.6 Hz, 1H), 7.14 (dd, J = 8.8 Hz, 2.6 Hz, 1H), 6.66 (s, 2H), 4.58 (m, 1H), 4.19 (t, J = 6.4 Hz, 2H), 3.17 (m, 2H), 2.98 (s, 3H), 2.82 (m, 1H), 2.08 (m, 2H), 1.94 (m, 2H), 1.65 (m, 4H), 1.52 (s, 6H), 1.49 (m, 2H) | 2.79 | 488.1 $[M + H]^+$ | AcOH |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 111 | 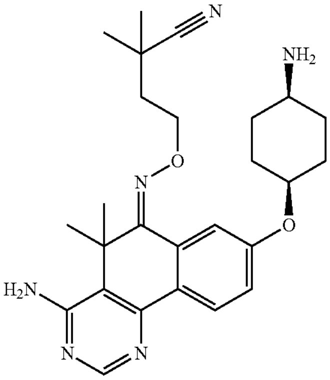 [SMILES: CC(C)(C#N)CCO/N=C1\c2cc(O[C@H]3CC[C@@H](N)CC3)ccc2-c2ncnc(N)c2C1(C)C] | Example 1 & using CAS 167081-25-6 and CAS 1240955-62-7 | DMSO-$d_6$: 8.28 (s, 1H), 8.15 (d, J = 8.8 Hz, 1H), 7.60 d, J = 2.6 Hz, 1H), 7.12 (dd, J = 8.8 Hz, 2.6 Hz, 1H), 6.66 (s, 2H), 4.56 (m, 1H), 4.25 (t, J = 6.6 Hz, 2H), 2.84 (m, 1H), 1.95 (t, J = 6.6 Hz, 4H), 1.64 (m, 4H), 1.52 (s, 6H), 1.47 (m, 2H), 1.34 (s, 6H) | 3.35 | 463.2 $[M + H]^+$ | AcOH |
| 112 | 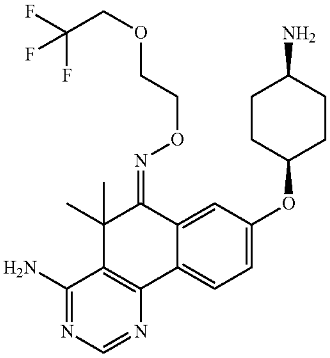 [SMILES: CC1(C)/C(=N/OCCOCC(F)(F)F)c2cc(O[C@H]3CC[C@@H](N)CC3)ccc2-c2ncnc(N)c21] | Example 1 & using CAS 167081-25-6 and CAS 133068-36-7 | DMSO-$d_6$: 8.28 (s, 1H), 8.15 (d, J = 8.8 Hz, 1H), 7.61 (d, J = 2.6 Hz, 1H), 7.13 (dd, J = 8.8 Hz, 2.6 Hz, 1H), 6.65 (s, 2H), 4.51 (m, 1H), 4.23 (m, 2H), 4.07 (q, J = 9.3 Hz, 2H), 3.87 (m, 2H), 2.71 (m, 1H), 1.91 (m, 2H), 1.60 (m, 4H), 1.52 (s, 6H), 1.48 (m, 2H) | 3.46 | 494.1 $[M + H]^+$ | Parent |
| 113 | 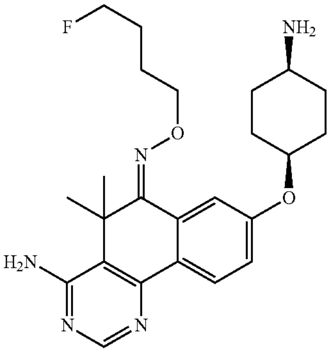 [SMILES: CC1(C)/C(=N/OCCCCF)c2cc(O[C@H]3CC[C@@H](N)CC3)ccc2-c2ncnc(N)c21] | Example 1 & using CAS 167081-25-6 and CAS 462-72-6 | DMSO-$d_6$: 8.28 (s, 1H), 8.16 (d, J = 8.8 Hz, 1H), 7.58 (d, J = 2.6 Hz, 1H), 7.12 (dd, J = 8.8 Hz, 2.6 Hz, 1H), 6.65 (s, 2H), 4.52 (t, J = 5.6 Hz, 2H), 4.40 (t, J = 5.7 Hz, 1H), 4.13 (t, J = 6.0 Hz, 2H), 2.75 (m, 1H), 1.92 (m, 2H), 1.69 (m, 8H), 1.52 (s, 6H), 1.43 (m, 2H) | 3.42 | 442.1 $[M + H]^+$ | Parent |
| 114 | 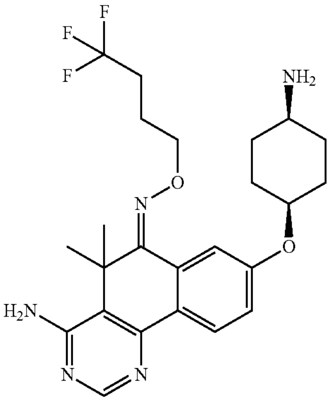 [SMILES: CC1(C)/C(=N/OCCCC(F)(F)F)c2cc(O[C@H]3CC[C@@H](N)CC3)ccc2-c2ncnc(N)c21] | Example 1 & using CAS 167081-25-6 and CAS 406-81-5 | DMSO-$d_6$: 8.28 (s, 1H), 8.16 (d, J = 8.8 Hz, 1H), 7.58 (d, J = 2.6 Hz, 1H), 7.13 (dd, J = 8.8 Hz, 2.6 Hz, 1H), 6.66 (s, 2H), 4.53 (m, 1H), 4.15 (m, 2H), 2.76 (m, 1H), 2.31 (m, 2H), 1.86 (m, 4H), 1.66 (m, 4H), 1.52 (s, 6H), 1.43 (m, 2H) | 3.75 | 478.1 $[M + H]^+$ | Parent |

TABLE 1-continued

| Ex. | Formula | Reference for Preparation | 1H NMR (400 MHz) δ ppm | HPLC Retention time (min) | MS m/z (+ESI) | Salt Form* |
|---|---|---|---|---|---|---|
| 115 | 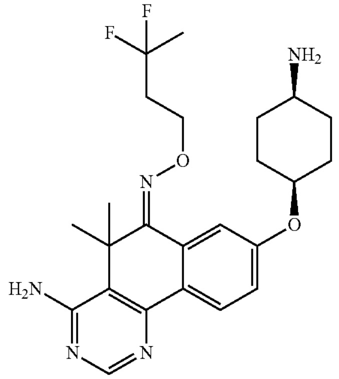 [SMILES: CC(F)(F)CCO/N=C1\c2cc(O[C@H]3CC[C@@H](N)CC3)ccc2-c2ncnc(N)c2C1(C)C] | Example 1 & using CAS 167081-25-6 and CAS 1784544-27-9 | DMSO-$d_6$: 8.29 (s, 1H), 8.16 (d, J = 8.8 Hz, 1H), 7.57 d, J = 2.6 Hz, 1H ), 7.13 (dd, J = 8.8 Hz, 2.6 Hz, 1H), 6.66 (s, 2H), 4.56 (m, 1H), 4.25 (t, J = 6.6 Hz, 2H), 2.83 (m, 1H), 2.33 (m, 2H), 1.94 (m, 2H), 1.62 (m, 7H), 1.52 (s, 6H), 1.49 (m, 2H) | 3.54 | 460.1 $[M + H]^+$ | AcOH |
| 116 | 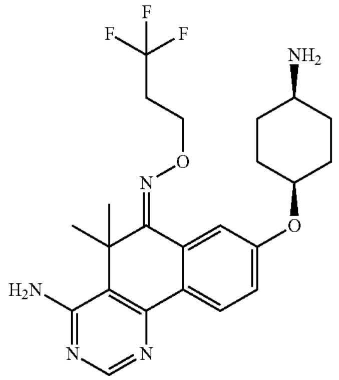 [SMILES: CC1(C)/C(=N/OCCC(F)(F)F)c2cc(O[C@H]3CC[C@@H](N)CC3)ccc2-c2ncnc(N)c21] | Example 1 using CAS 167081-25-6 and CAS 460-32-2 | DMSO-$d_6$ + $D_2O$: 8.26 (s, 1H), 8.15 (d, J = 8.8 Hz, 1H), 7.53 (d, J = 2.8 Hz, 1H), 7.12 (dd, J = 8.8 Hz, 2.8 Hz, 1H), 4.59 (m, 1H), 4.28 (t, J = 5.6 Hz, 2H), 3.10 (m, 1H), 2.68 (m, 2H), 1.98 (m, 2H), 1.68 (m, 6H), 1.50 (s, 6H) | 3.27 | 464.3 $[M + H]^+$ | HCOOH |

A hyphen in the second column indicates that the synthesis procedure is described below.

*Assumption based on the acid used during purification/presence of a basic nitrogen atom in the molecule. For Examples 112, 113, 114 the eluting system used for purification by preparative HPLC was a mixture of acetonitrile and an aqueous solution of ammonium carbonate 50 mM and it is assumed no salt formed..

Preparation of Example 1: (6Z)-8-(trans-4-aminocyclohexoxy)-6-methoxyimino-5,5-dimethyl-benzo[h]quinazolin-4-amine

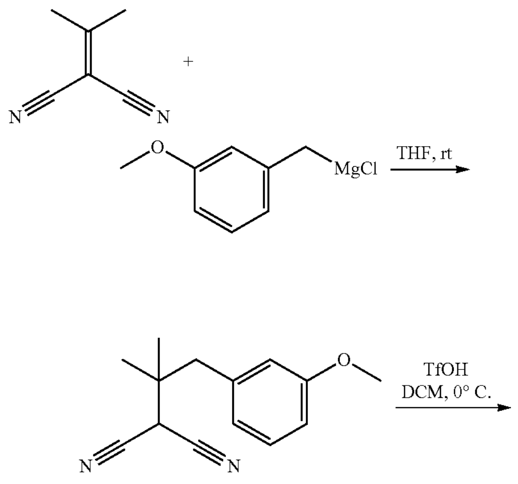

-continued

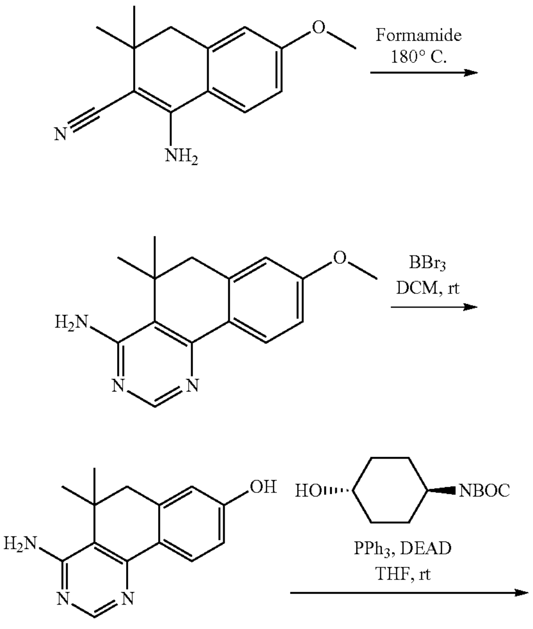

-continued

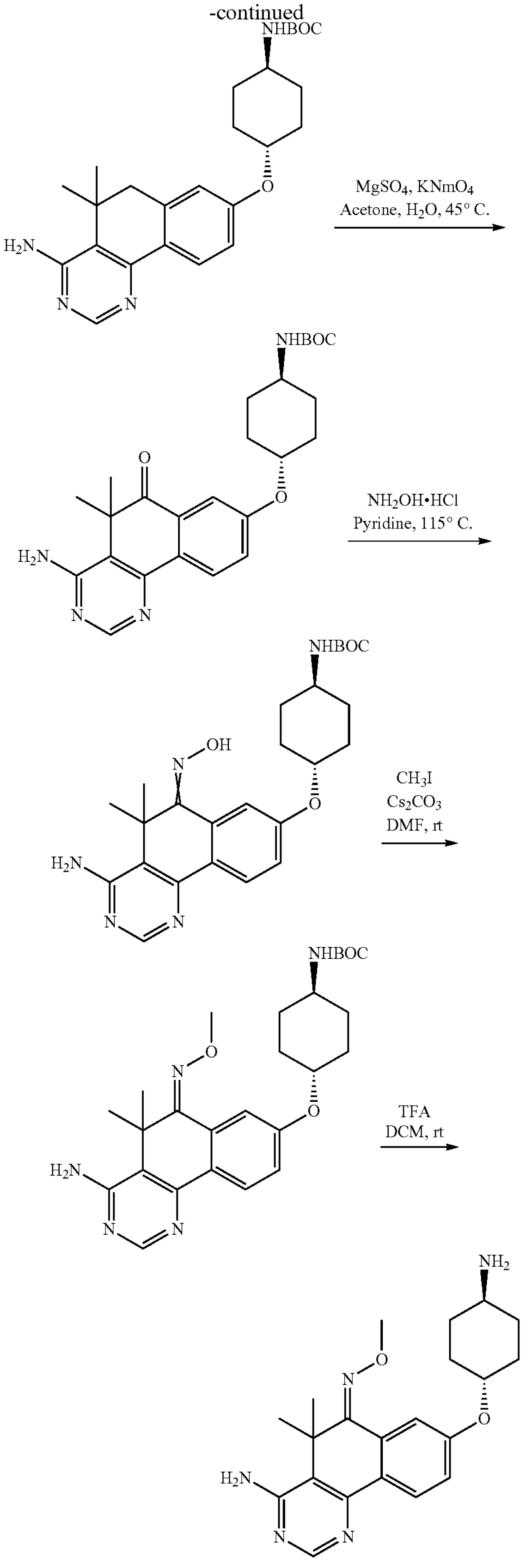

1

Step 1: Preparation of 2-[2-(3-methoxyphenyl)-1,1-dimethyl-ethyl]propanedinitrile 3-Methoxybenzylmagnesium chloride (96.0 mL, 24.0 mmol, 0.25M in THF) was added dropwise at 0° C. to a stirred solution of isopropylidenemalononitrile (2.00 g, 18.5 mmol) in THF (50 mL). The resulting solution was stirred at rt for 3 h. 1N HCl aqueous solution was then added at 0° C., and the resulting mixture was concentrated. The residue was extracted with EA and $H_2O$. The combined organic layers were dried over $Na_2SO_4$, filtered and concentrated. The residue was purified by column chromatography (silica gel; PE:EA; 5:1; v:v) to afford 2-[2-(3-methoxyphenyl)-1,1-dimethyl-ethyl]propanedinitrile as a yellow oil (1.69 g, 38% yield).

$^1$H NMR (400 MHz, $CDCl_3$) δ ppm: 7.27 (m, 1H), 6.86 (m, 1H), 6.79 (d, J=7.6 Hz, 1H), 6.74 (m, 1H), 3.82 (s, 3H), 3.44 (s, 1H), 2.81 (s, 2H), 1.29 (s, 6H).

MS m/z (+ESI): 229.1 $[M+H]^+$.

Step 2: Preparation of 1-amino-6-methoxy-3,3-dimethyl-4H-naphthalene-2-carbonitrile Trifluoromethanesulfonic acid (1.04 g, 6.24 mmol) was added at 0° C. to a stirred solution of 2-[2-(3-methoxyphenyl)-1,1-dimethyl-ethyl]propanedinitrile (300 mg, 1.25 mmol) in DCM (6 mL) and the resulting mixture was stirred at 0° C. for 2 h. Saturated $NaHCO_3$ aqueous solution was added, and the mixture was extracted with DCM. The combined organic layers were dried over $Na_2SO_4$, filtered and concentrated to afford 1-amino-6-methoxy-3,3-dimethyl-4H-naphthalene-2-carbonitrile as a yellow solid (300 mg, 95% yield) that was used in the next step without further purification.

$^1$H NMR (400 MHz, $CDCl_3$) δ ppm: 7.31 (d, J=8.8 Hz, 1H), 6.81 (m, 1H), 6.74 (d, J=2.4 Hz, 1H), 4.51 (br, 2H), 3.85 (s, 3H), 2.69 (s, 2H), 1.17 (s, 6H).

MS m/z (+ESI): 229.1 $[M+H]^+$.

Step 3: Preparation of 8-methoxy-5,5-dimethyl-6H-benzo[h]quinazolin-4-amine

A suspension of 1-amino-6-methoxy-3,3-dimethyl-4H-naphthalene-2-carbonitrile (1.00 g, 3.94 mmol) and formamide (19 mL, 473 mmol) was stirred at 180° C. for 8 h. After being cooled to rt, the reaction mixture was diluted with $H_2O$ and extracted with EA. The combined organic layers were dried over $Na_2SO_4$, filtered and concentrated. The residue was purified by column chromatography (silica gel; PE:EA; 1:1; v:v) to afford 8-methoxy-5,5-dimethyl-6H-benzo[h]quinazolin-4-amine as a light yellow solid (700 mg, 63% yield).

$^1$H NMR (400 MHz, DMSO-$d_6$) δ ppm: 8.24 (s, 1H), 7.99 (d, J=8.8 Hz, 1H), 6.86 (m, 1H), 6.79 (d, J=2.8 Hz, 1H), 6.37 (br, 2H), 3.79 (s, 3H), 2.75 (s, 2H), 1.28 (s, 6H).

MS m/z (+ESI): 256.1 $[M+H]^+$.

Step 4: Preparation of 4-amino-5,5-dimethyl-6H-benzo[h]quinazolin-8-ol $BBr_3$ (4.8 mL, 4.80 mmol, 1M in DCM) was added at −40° C. to a stirred solution of 8-methoxy-5,5-dimethyl-6H-benzo[h]quinazolin-4-amine (450 mg, 1.58 mmol) in DCM (30 mL). The resulting solution was stirred at rt for 18 h. Saturated $NaHCO_3$ aqueous solution was added and the resulting green solid was collected by filtration, washed with $H_2O$ and dried under reduced pressure at 60° C. to afford 4-amino-5,5-dimethyl-6H-benzo[h]quinazolin-8-ol (350 mg, 82% yield).

$^1$H NMR (400 MHz, DMSO-$d_6$) δ ppm: 8.21 (s, 1H), 7.88 (d, J=8.4 Hz, 1H), 6.67 (m, 1H), 6.59 (s, 1H), 6.29 (br, 2H), 2.67 (s, 2H), 1.26 (s, 6H).

MS m/z (+ESI): 242.2 $[M+H]^+$.

Step 5: Preparation of tert-butyl N-[trans-4-[(4-amino-5,5-dimethyl-6H-benzo[h]quinazolin-8-yl) oxylcyclohexyl]carbamate $PPh_3$ (600 mg, 2.24 mmol) was added at 0° C. to a stirred solution of 4-amino-5,5-dimethyl-6H-benzo[h]quinazolin-8-ol (300 mg, 1.12 mmol) and tert-butyl N- (cis-4-hydroxy-cyclohexyl)carbamate (380 mg, 1.68 mmol) in THF (10 mL), followed by DEAD (360 mg, 2.01 mmol). The suspension was stirred at 45° C. for 16 h. The reaction was concentrated and purified by combiflash to afford tert-butyl N-[trans-4-[(4-amino-5,5-dimethyl-6H-benzo[h]quinazolin-8-yl)oxy]cyclohexyl]carbamate as a white solid (200 mg, 28% yield).

MS m/z (+ESI): 439.3 $[M+H]^+$.

Step 6: Preparation of tert-butyl N-[trans-4-(4-amino-5,5-dimethyl-6-oxo-benzo[h]quinazolin-8-yl) oxycyclohexyl]carbamate $KMnO_4$ (362 mg, 2.28 mmol) was added at 0° C. to a stirred suspension of tert-butyl N-[4-[(4-amino-5,5-dimethyl-6H-benzo[h]quinazolin-8-yl)oxy]cyclohexyl]carbamate (250 mg, 0.45 mmol) in acetone (10 mL) and $H_2O$ (2 mL), followed by $MgSO_4$ (137 mg, 1.14 mmol). The resulting suspension was stirred at 45° C. for 24 h. The reaction mixture was extracted with EA and saturated $Na_2S_2O_3$ aqueous solution. The combined organic layers were dried over $Na_2SO_4$, filtered and concentrated to afford tert-butyl N-[trans-4-(4-amino-5,5-dimethyl-6-oxo-benzo[h]quinazolin-8-yl)oxycyclohexyl]carbamate as a white solid (270 mg, 59% yield) that was used in the next step without further purification.

MS m/z (+ESI): 453.4 $[M+H]^+$.

Step 7: Preparation of tert-butyl N-[trans-4-(4-amino-6-hydroxyimino-5,5-dimethyl-benzo[h]quinazolin-8-yl)oxycyclohexyl]carbamate Hydroxylamine hydrochloride (352 mg, 4.97 mmol) was added to a stirred solution of tert-butyl N-[4-(4-amino-5,5-dimethyl-6-oxo-benzo[h]quinazolin-8-yl)oxycyclohexyl] carbamate (250 mg, 0.49 mmol) in pyridine (3 mL). The resulting mixture was stirred at 115° C. for 4 h. Solvent was removed and the residue was purified by combiflash to afford tert-butyl N-[trans-4-(4-amino-6-hydroxyimino-5,5-dimethyl-benzo[h]quinazolin-8-yl)oxycyclohexyl]carbamate as an off-white solid (190 mg, 51% yield).

MS m/z (+ESI): 468.3 $[M+H]^+$.

Step 8: Preparation of (6Z)-tert-butyl N-[trans-4-(4-amino-6-methoxyimino-5,5-dimethyl-benzo[h]quinazolin-8-yl)oxycyclohexyl]carbamate Iodomethane (50 mg, 0.35 mmol) was added to a stirred solution of tert-butyl N-[4-(4-amino-6-hydroxyimino-5,5-dimethyl-benzo[h]quinazolin-8-yl)oxycyclohexyl]carbamate (90 mg, 0.17 mmol) in DMF (2 mL), followed by $Cs_2CO_3$ (115 mg, 0.35 mmol) and the resulting mixture was stirred for 1 h. Solvent was removed and the residue was extracted with DCM and $H_2O$. The combined organic layers were dried over $Na_2SO_4$, filtered and concentrated and the residue was purified by preparative HPLC to afford (6Z)-tert-butyl N-[trans-4-(4-amino-6-methoxyimino-5,5-dimethyl-benzo[h]quinazolin-8-yl)oxycyclohexyl]carbamate as a white solid (40 mg, 46% yield).

MS m/z (+ESI): 482.3 $[M+H]^+$.

Step 9: Preparation of (6Z)-8-(trans-4-aminocyclohexoxy)-6-methoxyimino-5,5-dimethyl-benzo[h] quinazolin-4-amine TFA (0.5 mL) was added to a stirred solution of (6Z)-tert-butyl N-[trans-4-(4-amino-6-methoxyimino-5,5-dimethyl-benzo[h]quinazolin-8-yl)oxycyclohexyl]carbamate (40 mg, 0.08 mmol) in DCM (2 mL). After 3 h, solvent was removed and the crude product was purified by preparative HPLC to afford (6Z)-8-(trans-4-aminocyclohexoxy)-6-methoxyimino-5,5-dimethyl-benzo[h]quinazolin-4-amine as a white solid (28 mg, 93% yield).

$^1$H NMR (400 MHz, DMSO-$d_6$+$D_2O$) 6 ppm: 8.51 (s, 1H), 7.98 (d, J=9.2 Hz, 1H), 7.55 (d, J=2.8 Hz, 1H), 7.29 (dd, J=9.2 Hz, 2.8 Hz, 1H), 4.43 (m, 1H), 3.86 (s, 3H), 3.08 (m, 1H), 2.14 (m, 2H), 1.98 (m, 2H), 1.50 (m, 10H).

MS m/z (+ESI): 382.3 $[M+H]^+$.

Preparation of Example 4: (6Z)-8-[1-(trans-4-aminocyclohexyl)vinyl]-6-methoxyimino-5,5-dimethyl-benzo[h]quinazolin-4-amine

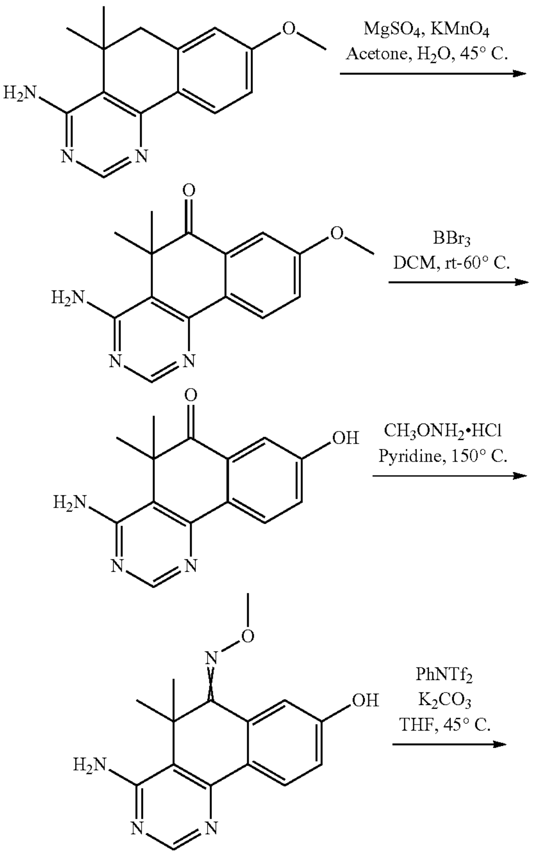

-continued

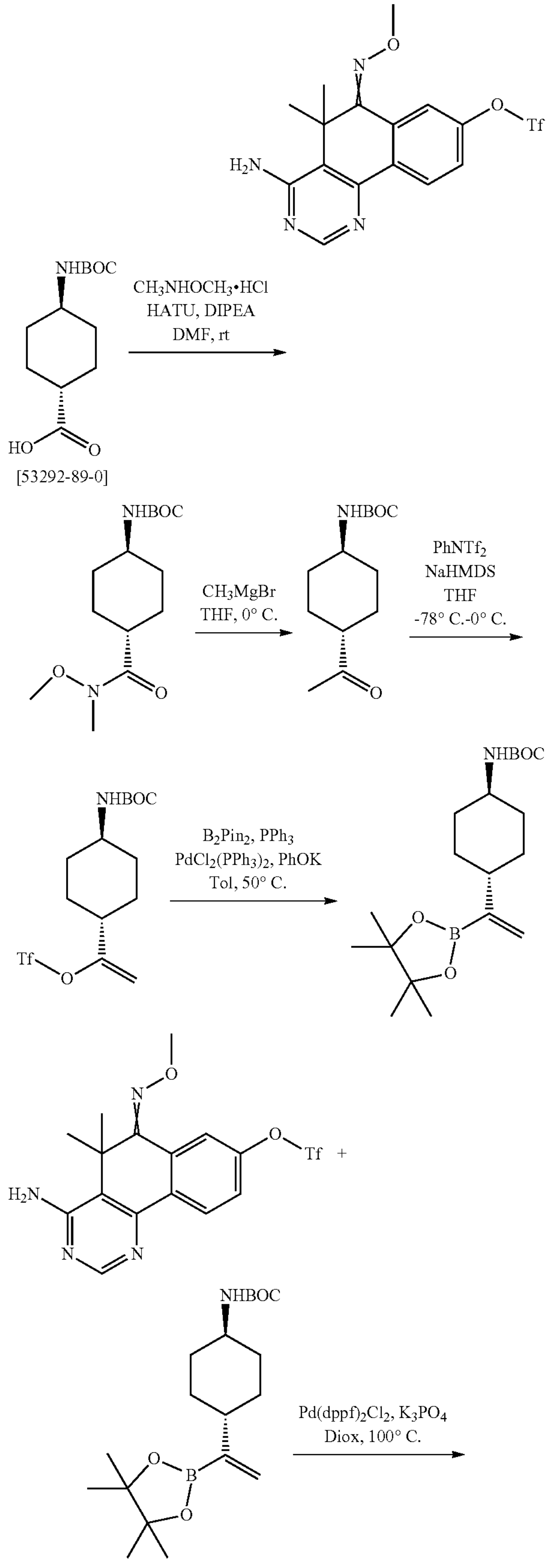

-continued

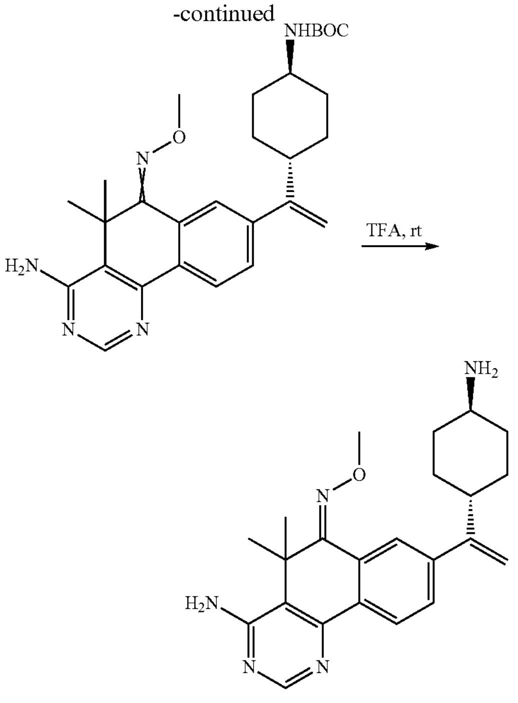

4

Step 1: Preparation of 4-amino-8-methoxy-5,5-dimethyl-benzo[h]quinazolin-6-one $KMnO_4$ (22.4 g, 141 mmol) was added at 0° C. to a stirred solution of 8-methoxy-5,5-dimethyl-6H-benzo[h]quinazolin-4-amine (4 g, 14.10 mmol) in acetone (150 mL) and $H_2O$ (30 mL), followed by $MgSO_4$ (4.28 g, 35.3 mmol). After 5 h stirring at 45° C., the reaction mixture was extracted with EA and saturated $Na_2S_2O_3$ aqueous solution. The combined organic layers were dried over $Na_2SO_4$, filtered and concentrated. The residue was purified by column chromatography (silica gel; PE:EA; 1:1, v:v) to afford 4-amino-8-methoxy-5,5-dimethyl-benzo[h]quinazolin-6-one as a white solid (2.2 g, 57% yield).

$^1H$ NMR (400 MHz, DMSO-$d_6$+$D_2O$) 6 ppm: 8.54 (d, J=8.8 Hz, 1H), 8.37 (s, 1H), 7.48 (d, J=2.8 Hz, 1H), 7.42 (dd, J=8.8 Hz, 2.8 Hz, 1H), 3.88 (s, 3H), 1.50 (s, 6H).

MS m/z (+ESI): 270.2 $[M+H]^+$.

Step 2: Preparation of 4-amino-8-hydroxy-5,5-dimethyl-benzo[h]quinazolin-6-one $BBr_3$ (6.84 mL, 6.84 mmol, 1M in DCM) was added at 0° C. to a stirred solution of 4-amino-8-methoxy-5,5-dimethyl-benzo[h]quinazolin-6-one (1.00 g, 3.34 mmol) in DCM (5 mL). The resulting mixture was stirred at rt for 16 h and at 60° C. for 8 additional hours. The reaction mixture was poured in ice cold water and the pH was adjusted to 7.5 with addition of a saturated $NaHCO_3$ aqueous solution before extraction with EA. The combined organic layers were dried over $Na_2SO_4$, filtered and concentrated to afford 4-amino-8-hydroxy-5,5-dimethyl-benzo[h]quinazolin-6-one as a light yellow solid (825 mg, 87% yield) that was used in the next step without further purification.

MS m/z (+ESI): 256.1 $[M+H]^+$.

Step 3: Preparation of 4-amino-6-methoxyimino-5,5-dimethyl-benzo[h]quinazolin-8-ol Methoxyamine hydrochloride (CAS 593-56-6, 1.82 g, 21.2 mmol) was added to a stirred solution of 4-amino-8-hydroxy-5,5-dimethyl-benzo[h]quinazolin-6-one (300 mg, 1.06 mmol) in pyridine (2 mL). The reaction suspension was stirred at 150° C. for 22 h. The reaction mixture was extracted with EA and $H_2O$. The combined organic layers were dried over $Na_2SO_4$, filtered and concentrated to afford 4-amino-6-methoxyimino-5,5-dimethyl-benzo[h]quinazolin-8-ol as a light yellow solid (300 mg, 90% yield) that was used in the next step without further purification.

MS m/z (+ESI): 285.2 $[M+H]^+$.

Step 4: Preparation of (4-amino-6-methoxyimino-5,5-dimethyl-benzo[h]quinazolin-8-yl) trifluoromethanesulfonate N-Phenyl-bis(trifluoromethanesulfonimide) (350 mg, 0.95 mmol) was added to a stirred suspension of 4-amino-6-methoxyimino-5,5-dimethyl-benzo[h]quinazolin-8-ol (300 mg, 0.95 mmol) in THF (5 mL), followed by $K_2CO_3$ (400 mg, 2.85 mmol). After 1 h at 45° C., the reaction mixture was extracted with EA and $H_2O$. The combined organic layers were dried over $Na_2SO_4$, filtered and concentrated and the crude product was purified by column chromatography (silica gel; PE:EA; 1:1; v:v) to afford (4-amino-6-methoxyimino-5,5-dimethyl-benzo[h]quinazolin-8-yl) trifluoromethanesulfonate as a yellow solid (300 mg, 65% yield).

MS m/z (+ESI): 417.1 $[M+H]^+$.

Step 5: Preparation of tert-butyl N-[trans-4-[methoxy(methyl)carbamoyl]cyclohexyl]carbamate N,O-Dimethylhydroxylamine hydrochloride (648 mg, 6.44 mmol) was added to a stirred solution of BOC-trans-aminocyclohexanecarboxylic acid (CAS 53292-89-0, 1.60 g, 6.44 mmol) in DMF (20 mL), followed by HATU (2.97 g, 7.73 mmol) and DIPEA (3.36 mL, 19.33 mmol). After 18 h stirring, the reaction mixture was extracted with EA and $H_2O$. The combined organic layers were dried over $Na_2SO_4$, filtered and concentrated. The residue was purified by column chromatography (silica gel; PE:EA; 1:1; v:v) to afford tert-butyl N-[trans-4-[methoxy(methyl)carbamoyl]cyclohexyl]carbamate as a white solid (1.53 g, 79% yield).

$^1H$ NMR (400 MHz, $CDCl_3$) δ ppm: 4.38 (br, 1H), 3.69 (s, 3H), 3.43 (br, 1H), 3.17 (s, 3H), 2.61 (m, 1H), 2.10 (m, 2H), 1.83 (m, 2H), 1.62 (m, 2H), 1.44 (s, 9H), 1.14 (m, 2H).

MS m/z (+ESI): 287.2 $[M+H]^+$.

Step 6: Preparation of tert-butyl N-(trans-4-acetylcyclohexyl)carbamate

Methylmagnesium bromide (3.30 mL, 9.90 mmol, 3M in $Et_2O$) was added dropwise at −10° C. to a stirred solution of tert-butyl N-[trans-4-[methoxy(methyl)carbamoyl] cyclohexyl]carbamate (1.00 g, 3.30 mmol) in THF (20 mL). After 4 h stirring at 0° C., saturated $NH_4Cl$ aqueous solution was added and the resulting mixture was extracted with EA. The combined organic layers were dried over $Na_2SO_4$, filtered and concentrated. The residue was purified by column chromatography (silica gel; PE:EA; 3:1; v:v) to afford tert-butyl N-(trans-4-acetylcyclohexyl)carbamate as a white solid (650 mg, 73% yield).

$^1H$ NMR (400 MHz, $CDCl_3$) δ ppm: 4.38 (br, 1H), 3.39 (br, 1H), 2.28 (m, 1H), 2.24 (s, 3H), 2.11 (m, 2H), 1.96 (m, 2H), 1.49-1.38 (m, 11H), 1.18-1.08 (m, 2H).

Step 7: Preparation of 1-[trans-4-(tert-butoxycarbonylamino)cyclohexyl]vinyl trifluoromethanesulfonate NaHMDS (0.41 mL, 0.41 mmol, 1M in THF) was added at −78° C. to a stirred solution of tert-butyl N-(trans-4-acetylcyclohexyl)carbamate (100 mg, 0.37 mmol) in THF (5 mL). After 1 h stirring at −78° C. N-phenyl-bis(trifluoromethanesulfonimide) (149 mg, 0.41 mmol) was added at 0° C. and the resulting mixture was stirred at 0° C. for 3 h. Saturated $NH_4Cl$ aqueous solution was added and the mixture was extracted with EA. The combined organic layers were dried over $Na_2SO_4$, filtered and concentrated. The residue was purified by column chromatography (silica gel; PE:EA; 5:1; v:v) to afford 1-[trans-4-(tert-butoxycarbonylamino)cyclohexyl]vinyl trifluoromethanesulfonate as a white solid (120 mg, 78% yield).

$^1H$ NMR (400 MHz, $CDCl_3$) δ ppm: 5.10 (d, J=3.6 Hz, 1H), 4.92 (m, 1H), 4.40 (br, 1H), 3.42 (br, 1H), 2.18-2.02 (m, 5H), 1.45 (s, 9H), 1.38-1.27 (m, 2H), 1.18-1.11 (m, 2H).

Step 8: Preparation of tert-butyl N-[trans-4-[1-(4,4,5,5-tetramethyl-1,3,2-dioxaborolan-2-yl)vinyl]cyclohexyl]carbamate $B_2Pin_2$ (284 mg, 1.08 mmol) was added to a stirred solution of 1-[trans-4-(tert-butoxycarbonylamino)cyclohexyl]vinyl trifluoromethanesulfonate (300 mg, 0.72 mmol) in toluene (10 mL), followed by $PPh_3$ (39 mg, 0.14 mmol), $PdCl_2(PPh_3)_2$ (52 mg, 0.07 mmol) and PhOK (199 mg, 1.45 mmol). After 5 h at 50° C., the reaction mixture was cooled to rt before extraction with EA and $H_2O$. The combined organic layers were dried over $Na_2SO_4$, filtered and concentrated. The residue was purified by column chromatography (silica gel; PE:EA; 5:1; v:v) to afford tert-butyl N-[trans-4-[1-(4,4,5,5-tetramethyl-1,3,2-dioxaborolan-2-yl)vinyl]cyclohexyl]carbamate as a white solid (180 mg, 64% yield).

$^1H$ NMR (400 MHz, $CDCl_3$) δ ppm: 5.73 (d, J=2.8 Hz, 1H), 5.58 (d, J=2.4 Hz, 1H), 4.38 (br, 1H), 3.40 (br, 1H), 2.04 (m, 3H), 1.75 (m, 2H), 1.46 (s, 9H), 1.38 (m, 2H), 1.27 (s, 12H), 1.15 (m, 2H).

MS m/z (+ESI): 352.3 $[M+H]^+$.

Step 9: Preparation of tert-butyl 2-[trans-4-[1-(4-amino-6-methoxyimino-5,5-dimethyl-benzo[h]quinazolin-8-yl)vinyl]cyclohexyl]acetate tert-Butyl N-[trans-4-[1-(4,4,5,5-tetramethyl-1,3,2-dioxaborolan-2-yl)vinyl]cyclohexyl]carbamate (150 mg, 0.39 mmol) was added to a stirred suspension of (4-amino-6-methoxyimino-5,5-dimethyl-benzo[h]quinazolin-8-yl) trifluoromethanesulfonate (190 mg, 0.39 mmol) in 1,4-dioxane (2 mL), followed by $Pd(dppf)_2Cl_2$ (57 mg, 0.08 mmol) and $K_3PO_4$ (250 mg, 1.15 mmol). After 3 h stirring at 100° C., the reaction mixture was cooled to rt before extraction with EA and $H_2O$. The combined organic layers were dried over $Na_2SO_4$, filtered and concentrated to afford tert-butyl 2-[trans-4-[1-(4-amino-6-methoxyimino-5,5-dimethyl-benzo[h]quinazolin-8-yl)vinyl]cyclohexyl]acetate as a yellow solid (150 mg, 64% yield) that was used in the next step without further purification.

MS m/z (+ESI): 492.3 $[M+H]^+$.

Step 10: Preparation of (6Z)-8-[1-(trans-4-aminocyclohexyl)vinyl]-6-methoxyimino-5,5-dimethyl-benzo[h]quinazolin-4-amine A solution of tert-butyl 2-[trans-4-[1-(4-amino-6-methoxyimino-5,5-dimethyl-benzo[h]quinazolin-8-yl)vinyl]cyclohexyl]acetate (145 mg, 0.23 mmol) in TFA (2 mL) was sonicated for 5 min. The reaction mixture was concentrated and the crude product was purified by preparative HPLC to afford (6Z)-8-[1-(trans-4-aminocyclohexyl)vinyl]-6-methoxyimino-5,5-dimethyl-benzo[h]quinazolin-4-amine as a white solid (24 mg, 25% yield).

$^1H$ NMR (400 MHz, DMSO-$d_6$+$D_2O$) 6 ppm: 8.42 (s, 1H), 8.11 (d, J=8.4 Hz, 1H), 8.02 (d, J=1.6 Hz, 1H), 7.65 (dd, J=8.4 Hz, 1.6 Hz, 1H), 5.38 (s, 1H), 5.16 (s, 1H), 3.85 (s, 3H), 3.01 (m, 1H), 2.50 (m, 1H, overlapped with DMSO signal), 1.98 (m, 2H), 1.87 (m, 2H), 1.50 (s, 6H), 1.37 (m, 2H), 1.30 (m, 2H).

MS m/z (+ESI): 392.4 $[M+H]^+$.

Preparation of Example 5: 2—[(Z)-(4-amino-8-methoxy-5,5-dimethyl-benzo[h]quinazolin-6-ylidene)amino]oxyacetic acid

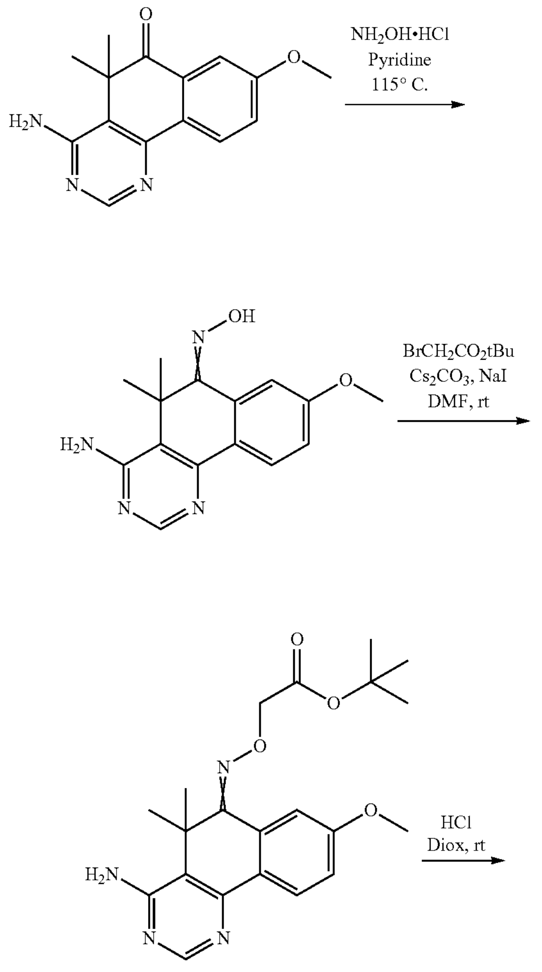

-continued

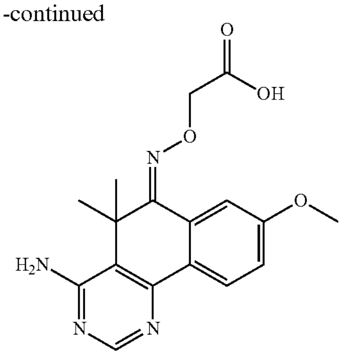

5

Step 1: Preparation of 4-amino-8-methoxy-5,5-dimethyl-benzo[h]quinazolin-6-one oxime The title compound was prepared as a yellow solid (3.7 g, 88% yield) following Scheme 1 and in analogy to Example 1 (step 7) using 4-amino-8-methoxy-5,5-dimethyl-benzo[h]quinazolin-6-one (4.00 g, 13.7 mmol) and hydroxylamine hydrochloride (9.43 g, 134 mmol) as starting materials.

MS m/z (+ESI): 285.2 $[M+H]^+$.

Step 2: Preparation of tert-butyl 2-[(4-amino-8-methoxy-5,5-dimethyl-benzo[h]quinazolin-6-ylidene)amino]oxyacetate tert-Butyl bromoacetate (141 μL, 0.95 mmol) was added to a stirred solution of 4-amino-8-methoxy-5,5-dimethyl-benzo[h]quinazolin-6-one oxime (100 mg, 0.32 mmol) in DMF (1 mL), followed by $Cs_2CO_3$ (316 mg, 0.95 mmol) and NaI (48 mg, 0.32 mmol). After 16 h stirring, solvent was removed and the residue was extracted with EA and $H_2O$. The combined organic layers were dried over $Na_2SO_4$, filtered and concentrated to afford tert-butyl 2-[(4-amino-8-methoxy-5,5-dimethyl-benzo[h]quinazolin-6-ylidene)amino]oxyacetate as a brown oil (130 mg, 93% yield) that was used in the next step without further purification.

MS m/z (+ESI): 399.3 $[M+H]^+$.

Step 3: Preparation of 2-[(Z)-(4-amino-8-methoxy-5,5-dimethyl-benzo[h]quinazolin-6-ylidene)amino]oxyacetic acid A suspension of tert-butyl 2-[(4-amino-8-methoxy-5,5-dimethyl-benzo[h]quinazolin-6-ylidene)amino]oxyacetate (130 mg, 0.29 mmol) in 4N HCl aqueous solution (3 mL) was stirred for 3 h. The reaction mixture was concentrated and the crude product was purified by preparative HPLC to afford 2-[(Z)-(4-amino-8-methoxy-5,5-dimethyl-benzo[h]quinazolin-6-ylidene)amino]oxyacetic acid as a white solid (38 mg, 36% yield).

$^1H$ NMR (400 MHz, DMSO-$d_6$+$D_2O$) 6 ppm: 8.48 (s, 1H), 7.99 (d, J 8.8 Hz, 1H), 7.85 (d, J 2.8 Hz, 1H), 7.27 (dd, J 8.8 Hz, 2.8 Hz, 1H), 4.67 (s, 2H), 3.85 (s, 3H), 1.47 (s, 6H).

MS m/z (+ESI): 343.3 $[M+H]^+$.

Preparation of Example 7: 2—[(Z)-(4-amino-8-methoxy-5,5-dimethyl-benzo[h]quinazolin-6-ylidene)amino]oxyacetamide

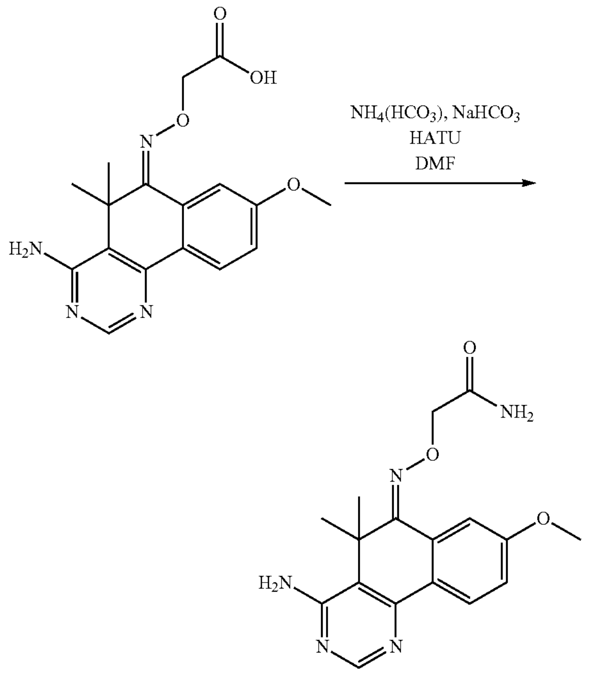

7

$NH_4(HCO_3)$ (64 mg, 0.79 mmol) was added to a stirred solution of 2-(Z)-(4-amino-8-methoxy-5,5-dimethyl-benzo[h]quinazolin-6-ylidene)amino]oxyacetic acid (100 mg, 0.26 mmol) in DMF (2 mL), followed by HATU (206 mg, 0.52 mmol) and $NaHCO_3$ (68 mg, 0.79 mmol). After 16 h stirring, the reaction mixture was concentrated and the crude product was purified by preparative HPLC to afford 2-[(Z)-(4-amino-8-methoxy-5,5-dimethyl-benzo[h]quinazolin-6-ylidene)amino]oxyacetamide as a white solid (33 mg, 35% yield).

$^1$H NMR (400 MHz, DMSO-$d_6$+$D_2O$) 6 ppm: 8.52 (s, 1H), 8.00 (d, J 8.8 Hz, 1H), 7.92 (d, J 2.8 Hz, 1H), 7.28 (dd, J 8.8 Hz, 2.8 Hz, 1H), 4.47 (s, 2H), 3.87 (s, 3H), 1.48 (s, 6H).

MS m/z (+ESI): 342.3 $[M+H]^+$.

Preparation of Example 8: N-(2-aminoethyl)-2-[(Z)-(4-amino-8-methoxy-5,5-dimethyl-benzo[h]quinazolin-6-ylidene)amino]oxy-acetamide

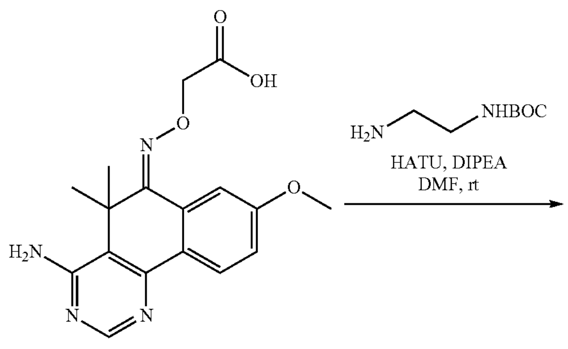

-continued

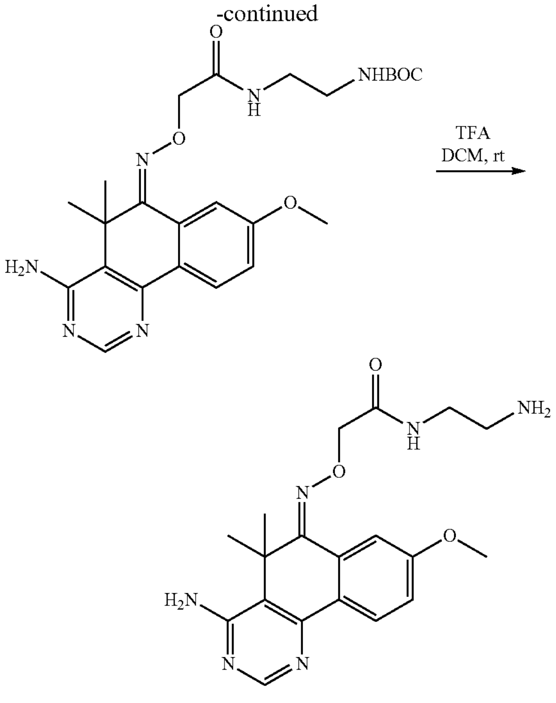

8

Step 1: Preparation of 2-[[2-[(Z)-(4-amino-8-methoxy-5,5-dimethyl-benzo[h]quinazolin-6-ylidene)amino]oxyacetyl]amino]ethyl tert-butyl carbonate N—BOC-ethylene diamine (105 μL, 0.63 mmol) was added to a stirred solution of 2-Z)-(4-amino-8-methoxy-5,5-dimethyl-benzo[h]quinazolin-6-ylidene)amino]oxyacetic acid (120 mg, 0.31 mmol) in DMF (2 mL), followed by HATU (247 mg, 0.63 mmol) and DIPEA (160 μL, 0.95 mmol). After 24 h stirring, the reaction mixture was concentrated and extracted with EA and $H_2O$. The combined organic layers were dried over $Na_2SO_4$, filtered and concentrated to afford 2-[[2-[(Z)-(4-amino-8-methoxy-5,5-dimethyl-benzo[h]quinazolin-6-ylidene)amino]oxyacetyl]amino]ethyl tert-butyl carbonate as a dark brown oil (150 mg, 88% yield) that was used in the next step without further purification.

MS m/z (+ESI): 485.3 [M+H].

Step 2: Preparation of N-(2-aminoethyl)-2-[(Z)-(4-amino-8-methoxy-5,5-dimethyl-benzo[h]quinazolin-6-ylidene)amino]oxy-acetamide The title compound was prepared as a light brown solid (58 mg, 53% yield) following Scheme 1 and in analogy to Example 1 (step 9) using 2-[[2-[(Z)-(4-amino-8-methoxy-5,5-dimethyl-benzo[h]quinazolin-6-ylidene)amino]oxyacetyl]amino]ethyl tert-butyl carbonate (150 mg, 0.28 mmol) as starting material.

$^1$H NMR (400 MHz, DMSO-$d_6$+$D_2O$) 6 ppm: 8.44 (s, 1H), 8.06 (d, J 8.8 Hz, 1H), 7.86 (d, J 2.8 Hz, 1H), 7.25 (dd, J 8.8 Hz, 2.8 Hz, 1H), 4.53 (s, 2H), 3.86 (s, 3H), 3.34 (t, J 6.4 Hz, 2H), 2.85 (t, J 6.4 Hz, 2H), 1.48 (s, 6H).

MS m/z (+ESI): 385.3 $[M+H]^+$.

Preparation of Example 9: (6Z)-6-(cis-4-aminocyclohexoxy)imino-8-methoxy-5,5-dimethyl-benzo[h]quinazolin-4-amine

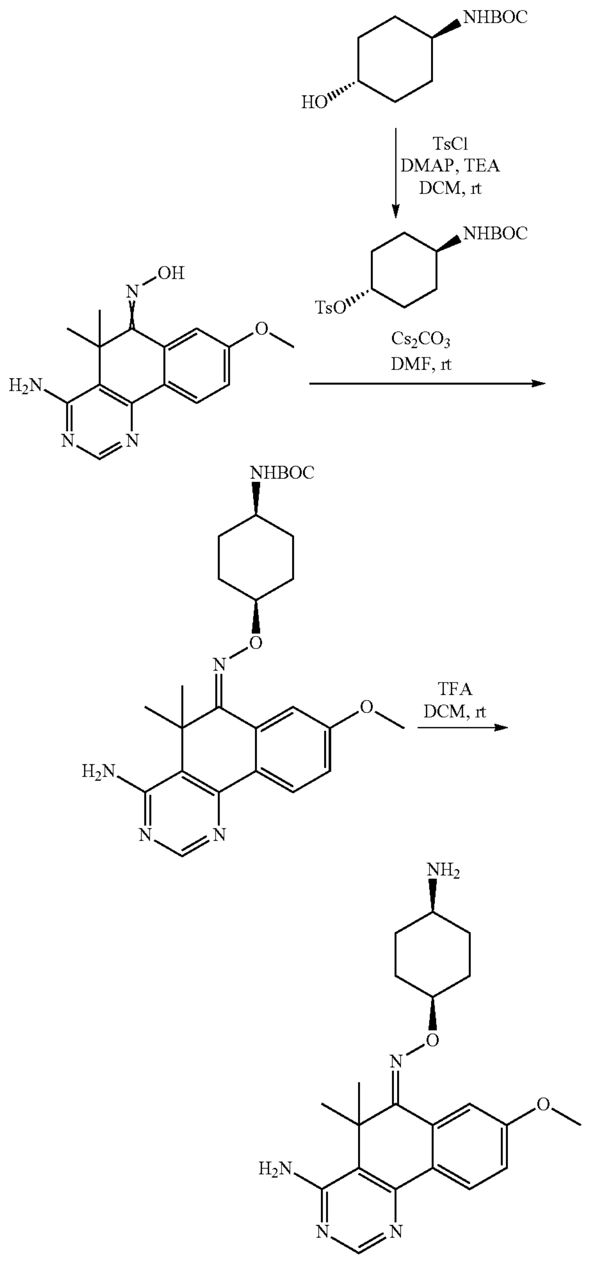

9

Preparation of [trans-4-(tert-butoxycarbonylamino)cyclohexyl]4-methylbenzenesulfonate TsCl (8.50 g, 44.1 mmol) was added to a stirred solution of BOC-trans-4-aminohexanol (5.00 g, 22.0 mmol) in DCM (20 mL), followed by TEA (9.32 mL, 66.2 mmol) and DMAP (275 mg, 2.21 mmol). After 24 h stirring, the solid was filtered off, the solution was concentrated and the residue was purified by column chromatography (silica gel; PE:EA; 1:1; v:v) to afford [trans-4-(tert-butoxycarbonylamino)cyclohexyl] 4-methylbenzenesulfonate as a light yellow solid (7.5 g, 83% yield).

$^1$H NMR (400 MHz, DMSO-$d_6$) δ ppm: 7.79 (d, J 8.0 Hz, 2H), 7.46 (d, J 8.0 Hz, 2H), 6.71 (d, J 7.2 Hz, 1H), 4.34 (m, 1H), 3.20 (m, 1H), 2.41 (s, 3H), 1.73 (m, 4H), 1.46 (m, 2H), 1.35 (s, 9H), 1.18 (m, 2H).

Preparation of Example 9: (6Z)-6-(cis-4-aminocyclohexoxy)imino-8-methoxy-5,5-dimethyl-benzo[h]quinazolin-4-amine The title compound (6Z)-6-(cis-4-aminocyclohexoxy)imino-8-methoxy-5,5-dimethyl-benzo[h]quinazolin-4-amine was prepared as a white solid following Scheme 1 and in analogy to Example 1 (steps 8 and 9) using [trans-4-(tert-butoxycarbonylamino)cyclohexyl] 4-methylbenzenesulfonate and 4-amino-8-methoxy-5,5-dimethyl-benzo[h]quinazolin-6-one oxime as starting materials.

$^1$H NMR (400 MHz, DMSO-$d_6$+$D_2O$) 6 ppm: 8.45 (s, 1H), 8.07 (d, J=8.8 Hz, 1H), 7.77 (d, J=2.8 Hz, 1H), 7.23 (dd, J=8.8 Hz, 2.4 Hz, 1H), 4.25 (m, 1H), 3.86 (s, 3H), 3.06 (m, 1H), 2.05 (m, 2H), 1.67 (m, 4H), 1.50 (s, 6H), 1.44 (m, 2H).

MS m/z (+ESI): 382.3 $[M+H]^+$.

Preparation of Example 12: (5R)-5-[[(Z)-(4-amino-8-methoxy-5,5-dimethyl-benzo[h]quinazolin-6-ylidene)amino]oxymethyl] oxazolidin-2-one

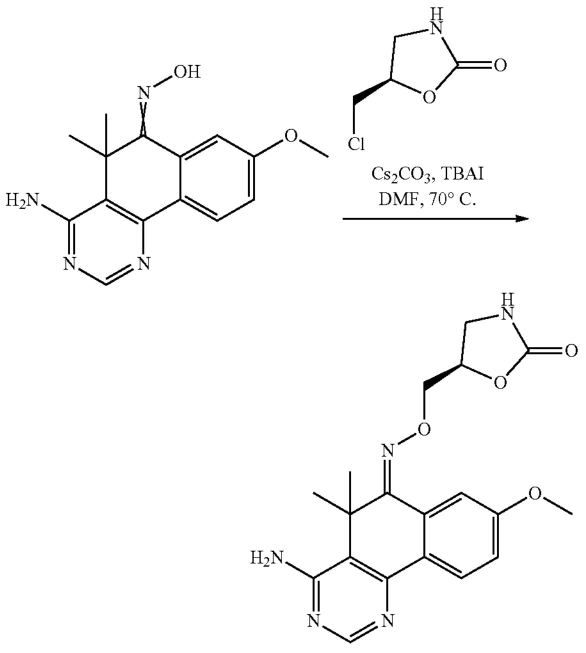

12

(5R)-5-(chloromethyl)oxazolidin-2-one (CAS 169048-79-7, 286 mg, 1.90 mmol) was added to a stirred solution of 4-amino-8-methoxy-5,5-dimethyl-benzo[h]quinazolin-6-one oxime (100 mg, 0.32 mmol) in DMF (2 mL), followed by $Cs_2CO_3$ (316 mg, 0.95 mmol) and TBAI (316 mg, 0.95 mmol). After 2 h stirring at 70° C., the reaction mixture was concentrated and the crude product was purified by preparative HPLC to afford (5R)-5-[[(Z)-(4-amino-8-methoxy-5,5- dimethyl-benzo[h]quinazolin-6-ylidene)amino]oxymethyl] oxazolidin-2-one as a white solid (11 mg, 9% yield).

$^1$H NMR (400 MHz, DMSO-$d_6$+$D_2O$) 6 ppm: 8.40 (s, 1H), 8.06 (d, J=8.8 Hz, 1H), 7.61 (d, J=2.8 Hz, 1H), 7.21 (dd, J=8.8 Hz, 2.8 Hz, 1H), 4.85 (m, 1H), 4.25 (m, 2H), 3.84 (s, 3H), 3.57 (d, J=8.8 Hz, 1H), 3.27 (dd, J=8.8 Hz, 2.8 Hz, 1H), 1.50 and 1.48 (2s, 6H).

MS m/z (+ESI): 384.3 $[M+H]^+$.

Preparation of Example 36: (6Z)-8-(trans-4-amino-cyclohexoxy)-6-methoxyimino-5,5-dimethyl-thieno [3,2-h]quinazolin-4-amine

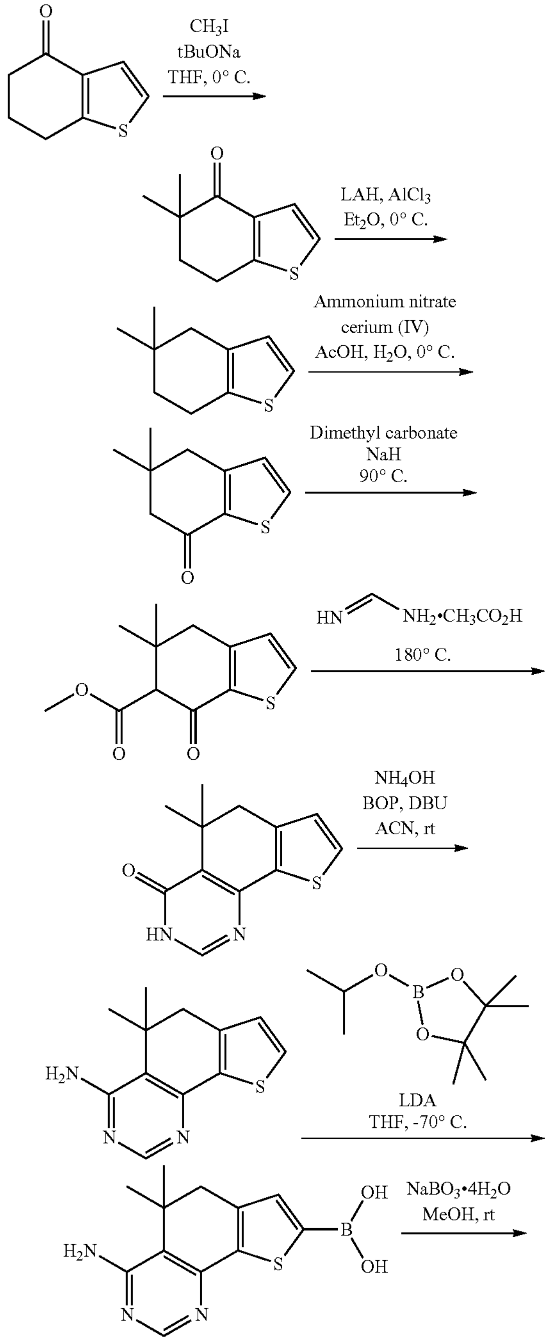

-continued

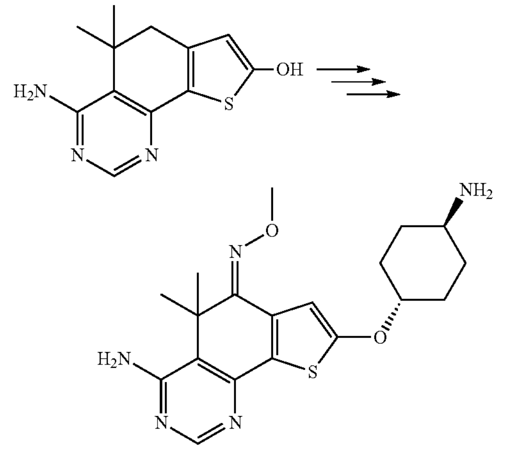

36

Step 1: Preparation of 5,5-dimethyl-6,7-dihydrobenzothiophen-4-one

Iodomethane (5.98 mL, 95.6 mmol) was added at 0° C. to a stirred solution of 6,7-dihydro-5H-benzo[b]thiophen-4-one (5.00 g, 31.9 mmol) in THF (50 mL), followed by tBuONa (9.28 g, 95.6 mmol). After 1 h stirring at 0° C., the reaction mixture was concentrated and extracted with EA and saturated $NH_4Cl$ aqueous solution. The combined organic layers were dried over $Na_2SO_4$, filtered and concentrated to afford 5,5-dimethyl-6,7-dihydrobenzothiophen-4-one as a brown oil (6.00 g, 94% yield).

$^1$H NMR (400 MHz, DMSO-$d_6$) δ ppm: 7.38 (d, J=5.2 Hz, 1H), 7.24 (d, J=5.2 Hz, 1H), 3.04 (t, J=6.4 Hz, 2H), 1.98 (t, J=6.4 Hz, 2H), 1.09 (s, 6H).

MS m/z (+ESI): 181.1 $[M+H]^+$.

Step 2: Preparation of 5,5-dimethyl-6,7-dihydro-4H-benzothiophene

A suspension of LAH (390 mg, 9.99 mmol) in $Et_2O$ (20 mL) was added at 0° C. and under argon to a stirred solution of $AlCl_3$ (2.69 g, 20.0 mmol) in $Et_2O$ (30 mL) and the resulting suspension was stirred at 0° C. for 10 min. A solution of 5,5-dimethyl-6,7-dihydrobenzothiophen-4-one (1 g, 4.99 mmol) in $Et_2O$ (10 mL) was added dropwise at 0° C. to the suspension. After stirring at 0° C. for 30 min, the reaction mixture was deactivated with $H_2O$. The organic layer was washed with brine, dried over $Na_2SO_4$, filtered and concentrated to afford 5,5-dimethyl-6,7-dihydro-4H-benzothiophene as a yellow oil (850 mg, 92% yield) that was used in the next step without further purification.

$^1$H NMR (400 MHz, $CDCl_3$) δ ppm: 7.07 (d, J=5.2 Hz, 1H), 6.72 (d, J=5.2 Hz, 1H), 2.79 (t, J=6.4 Hz, 2H), 2.42 (s, 2H), 1.62 (t, J=6.4 Hz, 2H), 1.01 (s, 6H).

Step 3: Preparation of 5,5-dimethyl-4,6-dihydrobenzothiophen-7-one

A solution of cerium(IV) ammonium nitrate (180 g, 325 mmol) in $H_2O$ (160 mL) was added dropwise at 0° C. to a stirred solution of 5,5-dimethyl-6,7-dihydro-4H-benzothiophene (15 g, 81.19 mmol) in AcOH (160 mL) and $H_2O$ (40 mL). After 3 h stirring at 0° C., the reaction mixture was extracted with EA and $H_2O$. The combined organic layers were dried over $Na_2SO_4$, filtered and concentrated. The residue was purified by column chromatography (silica gel; PE:EA; 100:1 to 50:1; v:v) to afford 5,5-dimethyl-4,6-dihydrobenzothiophen-7-one as a dark brown oil (11 g, 68% yield).

MS m/z (+ESI): 181.0 $[M+H]^+$.

Step 4: Preparation of methyl 5,5-dimethyl-7-oxo-4,6-dihydrobenzothiophene-6-carboxylate NaH (6.59 g, 165 mmol) was added in portions to a stirred solution of 5,5-dimethyl-4,6-dihydrobenzothiophen-7-one (11.0 g, 54.9 mmol) in dimethyl carbonate (60 mL). After 1 h stirring at 90° C., the reaction mixture was extracted with EA and $H_2O$. The combined organic layers were dried over $Na_2SO_4$, filtered and concentrated. The residue was purified by column chromatography (silica gel; PE:EA; 20:1; v:v) to afford methyl 5,5-dimethyl-7-oxo-4,6-dihydrobenzothiophene-6-carboxylate as a yellow oil (13 g, 89% yield).

MS m/z (+ESI): 239.0 $[M+H]^+$.

Step 5: Preparation of 5,5-dimethyl-3,6-dihydrothieno[3,2-h]quinazolin-4-one

A mixture of methyl 5,5-dimethyl-7-oxo-4,6-dihydrobenzothiophene-6-carboxylate (5.00 g, 18.9 mmol) in formamidine acetate (13.0 g, 119 mmol) was stirred at 180° C. for 2 h. The reaction mixture was then cooled to rt and diluted with $H_2O$. The resulting suspension was filtered, the cake was washed with $H_2O$ and dried to afford 5,5-dimethyl-3,6-dihydrothieno[3,2-h]quinazolin-4-one as a brown solid (3.1 g, 64% yield) that was used in the next step without further purification.

$^1H$ NMR (400 MHz, $CDCl_3$) δ ppm: 12.22 (s, 1H), 8.03 (s, 1H), 7.67 (d, J=5.2 Hz, 1H), 7.02 (d, J=5.2 Hz, 1H), 2.74 (s, 2H), 1.32 (s, 6H).

MS m/z (+ESI): 233.1 $[M+H]^+$.

Step 6: Preparation of 5,5-dimethyl-6H-thieno[3,2-h]quinazolin-4-amine

BOP (2.27 g, 5.04 mmol) was added to a stirred solution of 5,5-dimethyl-3,6-dihydrothieno[3,2-h]quinazolin-4-one (1.00 g, 3.87 mmol) in ACN (10 mL), followed by DBU (895 μL, 5.81 mmol). After 30 min stirring, $NH_4OH$ solution (25 mL) was added and the resulting solution was stirred at 80° C. for 16 h. Solvent was removed and crude product was purified by combiflash to afford 5,5-dimethyl-6H-thieno[3,2-h]quinazolin-4-amine as a yellow solid (650 mg, 65% yield).

$^1H$ NMR (400 MHz, DMSO-$d_6$+$D_2O$) δ ppm: 8.36 (s, 1H), 7.81 (d, J=4.8 Hz, 1H), 7.09 (d, J=4.8 Hz, 1H), 2.86 (s, 2H), 1.32 (s, 6H).

MS m/z (+ESI): 232.1 $[M+H]^+$.

Step 7: Preparation of (4-amino-5,5-dimethyl-6H-thieno[3,2-h]quinazolin-8-yl)boronic acid LDA (0.35 mL, 0.69 mmol, 2M in hexane/THF) was added dropwise at −70° C. to a stirred solution of 5,5-dimethyl-6H-thieno[3,2-h]quinazolin-4-amine (200 mg, 0.69 mmol) in THF (12 mL) and the resulting suspension was stirred at −70° C. for 1 h. Isopropoxyboronic acid pinacol ester (CAS 61676-62-8, 291 μL, 1.38 mmol) was added dropwise at −70° C. After 1 h stirring at −70° C., the reaction was deactivated with saturated $NH_4Cl$ aqueous solution and then concentrated to afford (4-amino-5,5-dimethyl-6H-thieno[3,2-h]quinazolin-8-yl)boronic acid as a yellow solid (160 mg, 59% yield) that was used in the next step without further purification.

MS m/z (+ESI): 276.1 $[M+H]^+$.

Step 8: Preparation of 4-amino-5,5-dimethyl-6H-thieno[3,2-h]quinazolin-8-ol $NaBO_3 \times 4H_2O$ (182 mg, 1.14 mmol) was added to a stirred solution of (4-amino-5,5-dimethyl-6H-thieno[3,2-h]quinazolin-8-yl)boronic acid (150 mg, 0.38 mmol) in MeOH (10 mL). After 1 h, solvent was removed and the crude product was purified by column chromatography (silica gel; MeOH:DCM; 1:10; v:v) to afford 4-amino-5,5-dimethyl-6H-thieno[3,2-h]quinazolin-8-ol as a yellow solid (70 mg, 59% yield).

MS m/z (+ESI): 248.2 $[M+H]^+$.

Preparation of Example 36: (6Z)-8-(trans-4-aminocyclohexoxy)-6-methoxyimino-5,5-dimethyl-thieno[3,2-h]quinazolin-4-amine The title compound (6Z)-8-(trans-4-aminocyclohexoxy)-6-methoxyimino-5,5-dimethyl-thieno[3,2-h]quinazolin-4-amine was prepared as a yellow solid following Scheme 1 and in analogy to Example 1 (steps 5-9) using [trans-4-(tert-butoxycarbonylamino)cyclohexyl] 4-methylbenzenesulfonate, 4-amino-5,5-dimethyl-6H-thieno[3,2-h]quinazolin-8-ol, hydroxylamine hydrochloride and iodomethane as starting materials.

$^1H$ NMR (400 MHz, DMSO-$d_6$+$D_2O$) δ ppm: 8.18 (s, 1H), 7.15 (s, 1H), 4.25 (m, 1H), 3.91 (s, 3H). 3.07 (m, 1H), 2.16 (m, 2H), 1.98 (m, 2H), 1.56 (s, 6H), 1.50 (m, 4H).

MS m/z (+ESI): 388.3 $[M+H]^+$.

Preparation of Example 37: (5R)-5-[[(Z)-[4-amino-8-(trans-4-aminocyclohexoxy)-5,5-dimethyl-benzo[h]quinazolin-6-ylidene]amino]oxymethyl]oxazolidin-2-one

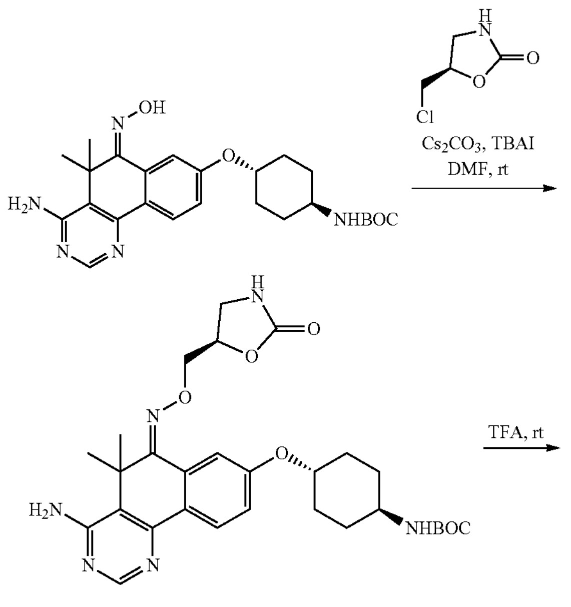

-continued

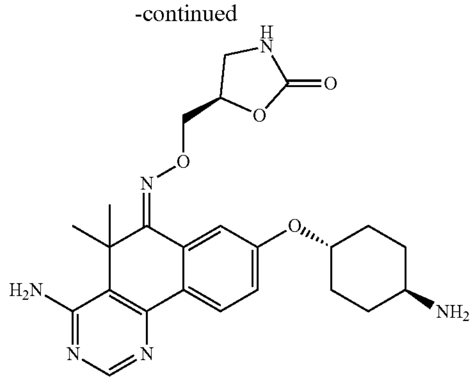

37

Step 1: Preparation of tert-butyl N-[trans-4-[(6Z)-4-amino-5,5-dimethyl-6-[[(5R)-2-oxooxazolidin-5-yl] methoxyimino]benzo[h]quinazolin-8-yl]oxycyclohexyl]carbamate: (5R)-5-(Chloromethyl)-2-oxazolidinone (CAS 169048-79-7, 73 mg, 0.49 mmol) was added to a stirred solution of tert-butyl N-[trans-4-[(6Z)-4-amino-6-hydroxyimino-5,5-dimethyl-benzo[h]quinazolin-8-yl]oxycyclohexyl]carbamate (80 mg, 0.16 mmol) in DMF (2 mL), followed by $Cs_2CO_3$ (162 mg, 0.49 mmol) and TBAI (6 mg, 0.016 mmol). After 36 h stirring, the reaction mixture was concentrated and extracted with EA and $H_2O$. The combined organic layers were dried over $Na_2SO_4$, filtered and concentrated to afford tert-butyl N-[trans-4-[(6Z)-4-amino-5,5-dimethyl-6-[[(5R)-2-oxooxazolidin-5-yl]methoxyimino] benzo[h]quinazolin-8-yl]oxycyclohexyl]carbamate as a light yellow oil (100 mg, 54% yield) that was used in the next step without further purification.

MS m/z (+ESI): 567.3 $[M+H]^+$.

Step 2: Preparation of (5R)-5-[[(Z)-[4-amino-8-(trans-4-aminocyclohexoxy)-5,5-dimethyl-benzo[h] quinazolin-6-ylidene]amino]oxymethyl]oxazolidin-2-one The title compound was prepared as a white solid (12 mg, 23% yield) following Scheme 1 and in analogy to Example 4 (step 10) using tert-butyl N-[trans-4-[(6Z)-4-amino-5,5-dimethyl-6-[[(5R)-2-oxooxazolidin-5-yl]methoxyimino] benzo[h]quinazolin-8-yl]oxycyclohexyl]carbamate (100 mg, 0.09 mmol) as starting material.

$^1$H NMR (400 MHz, DMSO-$d_6$+$D_2O$) 6 ppm: 8.25 (s, 1H), 8.12 (d, J=8.8 Hz, 1H), 7.54 (d, J=2.8 Hz, 1H), 7.13 (dd, J=8.8 Hz, 2.8 Hz, 1H), 4.83 (m, 1H), 4.35 (m, 1H), 4.22 (m, 2H), 3.60 (m, 1H), 3.25 (m, 1H), 3.00 (m, 1H), 2.14 (m, 2H), 1.94 (m, 2H), 1.50 (m, 10H).

MS m/z (+ESI): 467.4 $[M+H]^+$.

Preparation of Example 39: (6Z)-8-(trans-4-amino-cyclohexoxy)-10-chloro-6-methoxyimino-5,5-dimethyl-benzo[h]quinazolin-4-amine

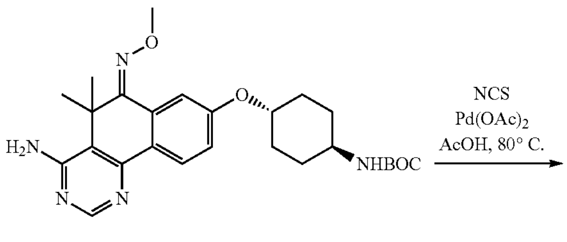

-continued

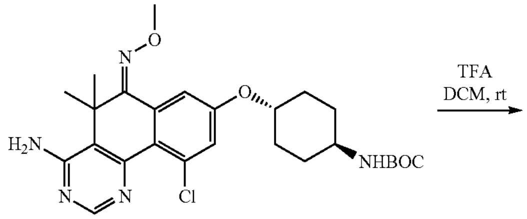

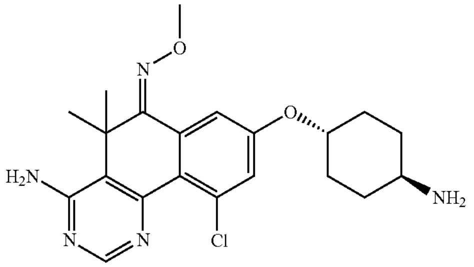

39

Step 1: Preparation of tert-butyl N-[trans-4-[(6Z)-4-amino-10-chloro-6-methoxyimino-5,5-dimethyl-benzo[h]quinazolin-8-yl]oxycyclohexyl]carbamate NCS (5 mg, 0.035 mmol) was added to a stirred solution of (6Z)-tert-butyl N-[trans-4-(4-amino-6-methoxyimino-5,5-dimethyl-benzo[h]quinazolin-8-yl)oxycyclohexyl]carbamate (20 mg, 0.029 mmol) in AcOH (0.2 mL) followed by $Pd(OAc)_2$ (0.5 mg, 0.002 mmol). After 3 h stirring at 80° C., the reaction mixture was extracted with EA and $H_2O$. The combined organic layers were dried over $Na_2SO_4$, filtered and concentrated to afford tert-butyl N-[trans-4-[(6Z)-4-amino-10-chloro-6-methoxyimino-5,5-dimethyl-benzo[h] quinazolin-8-yl]oxycyclohexyl]carbamate as a yellow solid (18 mg, 96% yield) that was used in the next step without further purification.

$^1$H NMR (400 MHz, DMSO-$d_6$) δ ppm: 8.26 (s, 1H), 7.26 (d, J=2.4 Hz, 1H), 7.19 (d, J=2.4 Hz, 1H), 6.64 (s, 2H), 4.39 (m, 1H), 3.30 (m, 1H, overlapped with water signal), 3.82 (s, 3H), 2.06 (m, 2H), 1.82 (m, 2H), 1.43 (m, 4H), 1.38 (s, 9H), 1.23 (s, 6H).

MS m/z (+ESI): 516.3, 518.2 $[M+H]^+$.

Step 2: Preparation of (6Z)-8-(trans-4-aminocyclo-hexoxy)-10-chloro-6-methoxyimino-5,5-dimethyl-benzo[h]quinazolin-4-amine The title compound was prepared as a white solid (10 mg, 52% yield) following Scheme 1 and in analogy to Example 1 (step 9) using tert-butyl N-[trans-4-[(6Z)-4-amino-10-chloro-6-methoxyimino-5,5-dimethyl-benzo[h]quinazolin-8-yl]oxycyclohexyl]carbamate (26 mg, 0.04 mmol) as starting material.

$^1$H NMR (400 MHz, DMSO-$d_6$+$D_2O$) 6 ppm: 8.36 (s, 1H), 7.31 (d, J=2.4 Hz, 1H), 7.29 (d, J=2.4 Hz, 1H), 4.45 (m, 1H), 3.84 (s, 3H), 3.07 (m, 1H), 2.12 (m, 2H), 1.97 (m, 2H), 1.49 (m, 4H), 1.43 (s, 6H).

MS m/z (+ESI): 416.2, 418.2 $[M+H]^+$.

Preparation of Example 41: (6Z)-9-chloro-8-methoxy-6-methoxyimino-5,5-dimethyl-benzo[h]quinazolin-4-amine

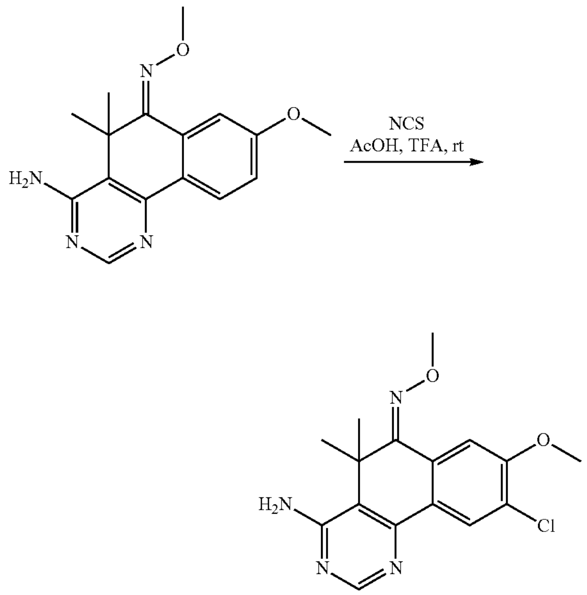

41

NCS (3 mg, 0.22 mmol) was added to a stirred solution of (6Z)-8-methoxy-6-methoxyimino-5,5-dimethyl-benzo[h]quinazolin-4-amine (60 mg, 0.18 mmol) in AcOH (0.9 mL), followed by TFA (0.6 0 mL). After 16 h stirring, the reaction mixture was extracted with DCM and $H_2O$. The combined organic layers were dried over $Na_2SO_4$, filtered and concentrated and the crude product was purified by preparative HPLC to afford (6Z)-9-chloro-8-methoxy-6-methoxyimino-5,5-dimethyl-benzo[h]quinazolin-4-amine as a white solid (8 mg, 13% yield).

$^1$H NMR (400 MHz, DMSO-$d_6$+$D_2O$) 6 ppm: 8.44 (s, 1H), 8.16 (s, 1H), 7.76 (s, 1H), 3.95 (s, 3H), 3.93 (s, 3H), 1.51 (s, 6H).

MS m/z (+ESI): 333.2, 335.2 $[M+H]^+$.

Preparation of Example 42: (6Z)-8-methoxy-6-methoxyimino-5,5-dimethyl-benzo[h]quinazoline-4,9-diamine

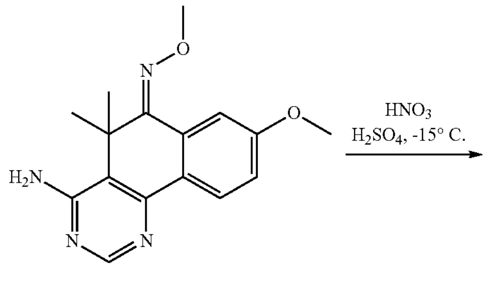

-continued

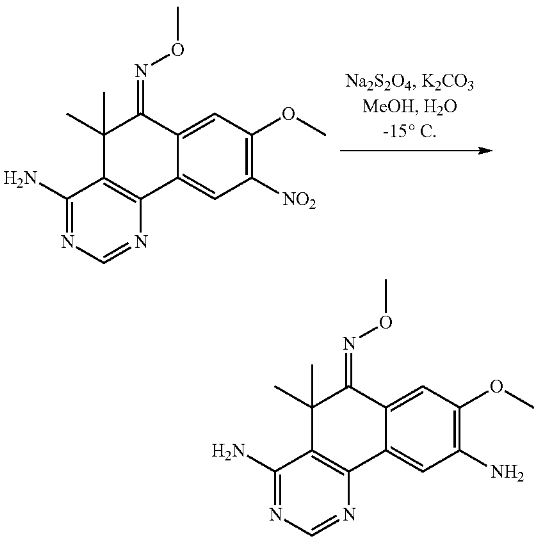

42

Step 1: Preparation of (6Z)-8-methoxy-6-methoxyimino-5,5-dimethyl-9-nitro-benzo[h]quinazolin-4-amine $HNO_3$ (0.5 mL, 11.2 mmol) was added at −15° C. to a stirred solution of (6Z)-8-methoxy-6-methoxyimino-5,5-dimethyl-benzo[h]quinazolin-4-amine (130 mg, 0.39 mmol) in $H_2SO_4$ (0.5 mL). After 30 min stirring at −15° C., saturated $K_2CO_3$ aqueous solution was slowly added at −15° C. to get pH 7, and the resulting mixture was extracted with DCM. The combined organic layers were dried over $Na_2SO_4$, filtered and concentrated and the crude product was purified by preparative HPLC to afford (6Z)-8-methoxy-6-methoxyimino-5,5-dimethyl-9-nitro-benzo[h]quinazolin-4-amine as a yellow solid (30 mg, 20% yield).

MS m/z (+ESI): 344.2 $[M+H]^+$.

Step 2: Preparation of (6Z)-8-methoxy-6-methoxyimino-5,5-dimethyl-benzo[h]quinazoline-4,9-diamine $Na_2S_2O_4$ (104 mg, 0.52 mmol) was added to a stirred solution of (6Z)-8-methoxy-6-methoxyimino-5,5-dimethyl-9-nitro-benzo[h]quinazolin-4-amine (25 mg, 0.06 mmol) in MeOH (0.3 mL) and $H_2O$ (0.1 mL), followed by $K_2CO_3$ (27 mg, 0.20 mmol). After 2 h stirring, the reaction mixture was extracted with DCM and $H_2O$. The combined organic layers were dried over $Na_2SO_4$, filtered and concentrated and the crude product was purified by preparative HPLC to afford (6Z)-8-methoxy-6-methoxyimino-5,5-dimethyl-benzo[h]quinazoline-4,9-diamine as a yellow solid (6 mg, 24% yield).

$^1$H NMR (400 MHz, DMSO-$d_6$+$D_2O$) 6 ppm: 8.22 (s, 1H), 7.57 (s, 1H), 7.54 (s, 1H), 3.82 (s, 3H), 3.79 (s, 3H), 1.49 (s, 6H).

MS m/z (+ESI): 314.2 $[M+H]^+$.

Preparation of Example 44: (6Z)—N8-(trans-4-aminocyclohexyl)-6-methoxyimino-N8,5,5-trimethyl-benzo[h]quinazoline-4,8-diamine

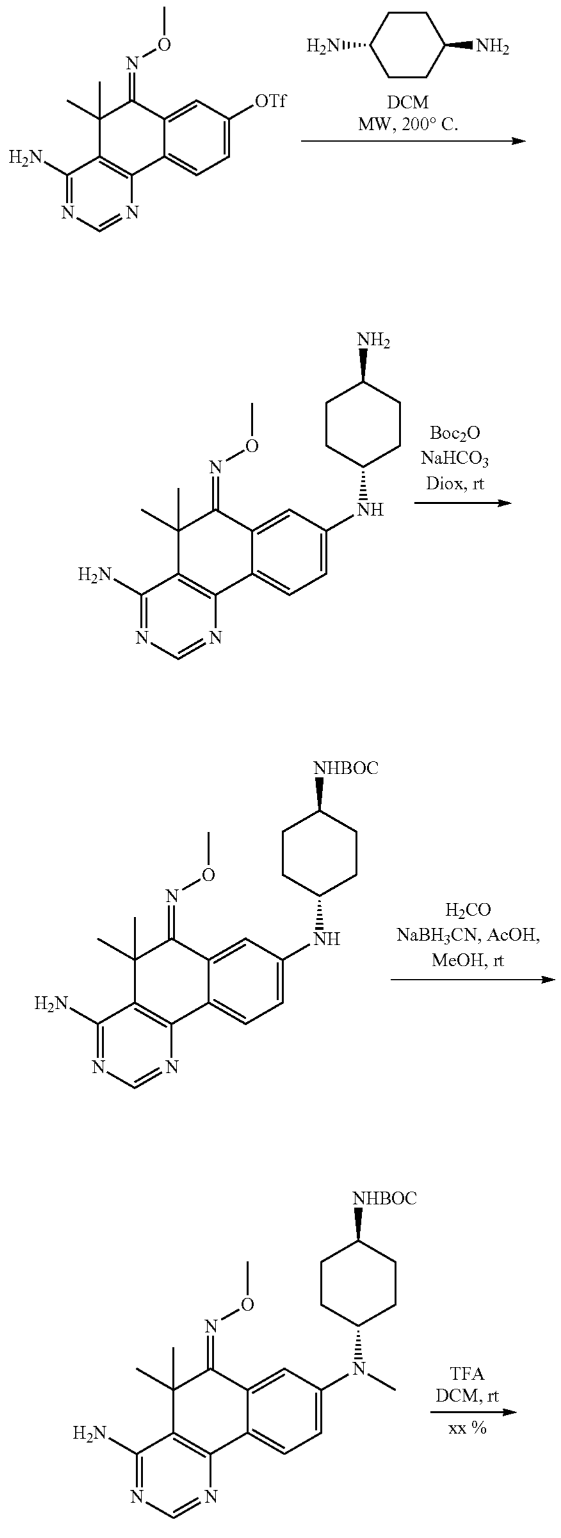

-continued

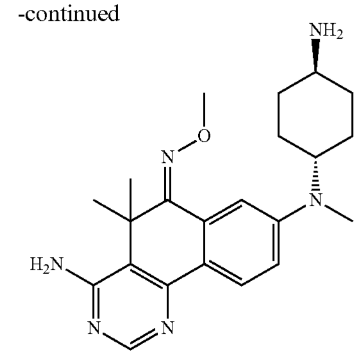

44

Step 1: Preparation of (6Z)—N8-(trans-4-aminocyclohexyl)-6-methoxyimino-5,5-dimethyl-benzo[h]quinazoline-4,8-diamine A mixture of (4-amino-6Z-methoxyimino-5,5-dimethyl-benzo[h]quinazolin-8-yl) trifluoromethanesulfonate (150 mg, 0.31 mmol) and trans-1,4-diaminocyclohexane (1.92 mL, 15.3 mmol) was stirred under microwave irradiation at 200° C. for 30 min. The reaction mixture was extracted with DCM and $H_2O$. The combined organic layers were dried over $Na_2SO_4$, filtered and concentrated to afford (6Z)—N8-(trans-4-aminocyclohexyl)-6-methoxyimino-5,5-dimethyl-benzo[h]quinazoline-4,8-diamine as a yellow semisolid (120 mg, 87% yield) that was used in the next step without further purification.

MS m/z (+ESI): 381.3 $[M+H]^+$.

Step 2: Preparation of tert-butyl N-[trans-4-[[(6Z)-4-amino-6-methoxyimino-5,5-dimethyl-benzo[h]quinazolin-8-yl]aminoleyclohexyl]carbamate $BOC_2O$ (119 mg, 0.54 mmol) was added to a stirred solution of (6Z)—N8-(trans-4-aminocyclohexyl)-6-methoxyimino-5,5-dimethyl-benzo[h]quinazoline-4,8-diamine (120 mg, 0.27 mmol) in 1,4-dioxane (1 mL), followed by a saturated $NaHCO_3$ aqueous solution (0.25 mL). After 2 h stirring, the reaction mixture was extracted with DCM and $H_2O$. The combined organic layers were dried over $Na_2SO_4$, filtered and concentrated. The residue was purified by combiflash to afford tert-butyl N-[trans-4-[[(6Z)-4-amino-6-methoxyimino-5,5-dimethyl-benzo[h]quinazolin-8-yl]amino]cyclohexyl]carbamate as a light yellow solid (85 mg, 43% yield).

MS m/z (+ESI): 481.3 $[M+H]^+$.

Step 3: Preparation of tert-butyl N-[trans-4-[[(6Z)-4-amino-6-methoxyimino-5,5-dimethyl-benzo[h]quinazolin-8-yl]-methyl-amino]cyclohexyl]carbamate Paraformaldehyde (36 mg, 0.44 mmol) was added to a stirred solution of tert-butyl N-[trans-4-[[(6Z)-4-amino-6-methoxyimino-5,5-dimethyl-benzo[h]quinazolin-8-yl]amino]cyclohexyl]carbamate (65 mg, 0.09 mmol) in MeOH (5 mL), followed by AcOH (26 μL, 0.44 mmol) and $NaBH_3CN$ (29 mg, 0.44 mmol). After 1 h stirring, the reaction mixture was extracted with EA and $H_2O$. The combined organic layers were dried over $Na_2SO_4$, filtered and concentrated to afford tert-butyl N-[trans-4-[[(6Z)-4- amino-6-methoxyimino-5,5-dimethyl-benzo[h]quinazolin-8-yl]-methyl-amino]cyclohexyl]carbamate as a yellow oil (65 mg, 75% yield) that was used in the next step without further purification.

MS m/z (+ESI): 495.3 $[M+H]^+$.

Step 4: Preparation of (6Z)—N8-(trans-4-aminocyclohexyl)-6-methoxyimino-N8,5,5-trimethyl-benzo[h]quinazoline-4,8-diamine The title compound was prepared as a yellow solid (6 mg, 17% yield) following Scheme 1 and in analogy to Example 1 (step 9) using tert-butyl N-[trans-4-[[(6Z)-4-amino-6-methoxyimino-5,5-dimethyl-benzo[h]quinazolin-8-yl]-methyl-amino]cyclohexyl]carbamate (85 mg, 0.08 mmol) as starting material.

$^1$H NMR (400 MHz, DMSO-$d_6$+$D_2O$) δ ppm: 8.44 (s, 1H), 7.86 (d, J=8.8 Hz, 1H), 7.37 (d, J=2.4 Hz, 1H), 7.03 (dd, J=8.8 Hz, 2.4 Hz, 1H), 3.85 (s, 3H), 3.71 (m, 1H), 3.04 (m, 1H), 2.83 (s, 3H), 2.01 (m, 2H), 1.71 (m, 4H), 1.52 (m, 2H), 1.48 (s, 6H).

MS m/z (+ESI): 395.3 $[M+H]^+$.

Preparation of Example 51: (5S)-5-[[(Z)-(4-amino-8-bromo-5,5-dimethyl-benzo[h]quinazolin-6-ylidene)amino]oxymethyl]oxazolidin-2-one

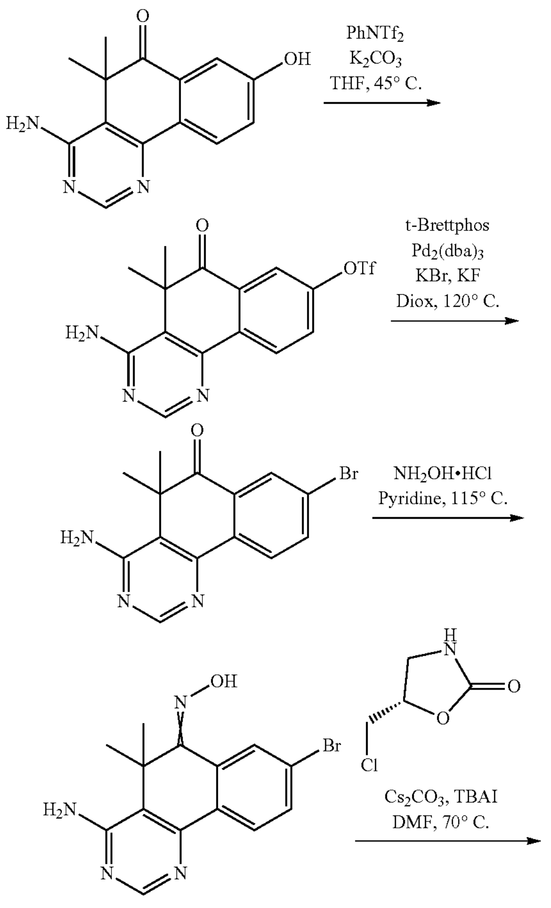

-continued

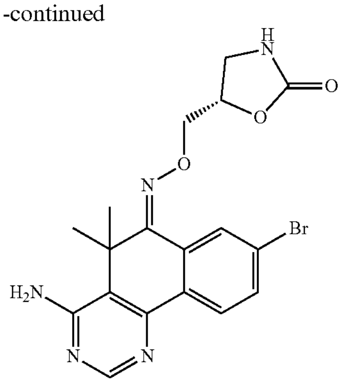

51

Step 1: Preparation of (4-amino-5,5-dimethyl-6-oxo-benzo[h]quinazolin-8-yl)trifluoromethanesulfonate The title compound was prepared as a yellow solid (1.7 g, 62% yield) following Scheme 1 and in analogy to Example 4 (step 4) using 4-amino-8-hydroxy-5,5-dimethyl-benzo[h]quinazolin-6-one (1.7 g, 6.33 mmol) as starting material.

MS m/z (+ESI): 388.0 $[M+H]^+$.

Step 2: Preparation of 4-amino-8-bromo-5,5-dimethyl-benzo[h]quinazolin-6-one t-Brettphos (0.17 g, 0.36 mmol) was added to a stirred solution of (4-amino-5,5-dimethyl-6-oxo-benzo[h]quinazolin-8-yl)trifluoromethanesulfonate (0.75 g, 1.75 mmol) in Diox (6 mL), followed by $Pd_2(dba)_3$ (0.16 g, 0.17 mmol), KBr (2.09 g, 17.4 mmol) and KF (51 mg, 0.87 mmol). After 16 h at 120° C., the reaction mixture was cooled to rt, concentrated and the residue was purified by column chromatography (silica gel; PE:EA; 1:1; v:v) to afford 4-amino-8-bromo-5,5-dimethyl-benzo[h]quinazolin-6-one as a yellow solid (0.25 g, 23% yield).

MS m/z (+ESI): 318.1, 320.1 $[M+H]^+$.

Preparation of (5S)-5-[[(Z)-(4-amino-8-bromo-5,5-dimethyl-benzo[h]quinazolin-6-ylidene)amino]oxymethyl]oxazolidin-2-one The title compound was prepared as a yellow solid following Scheme 1 and in analogy to Example 1 (step 7) and Example 12 using 4-amino-8-bromo-5,5-dimethyl-benzo[h]quinazolin-6-one, hydroxylamine hydrochloride and (5S)-5-(chloromethyl)oxazolidin-2-one (CAS 169048-83-3) as starting materials.

$^1$H NMR (400 MHz, DMSO-$d_6$+$D_2O$) δ ppm: 8.50 (s, 1H), 8.23 (d, J=2.0 Hz, 1H), 8.03 (d, J=8.4 Hz, 1H), 7.88 (dd, J=8.4 Hz, 2.0 Hz, 1H), 4.84 (m, 1H), 4.27 (m, 2H), 3.57 (m, 1H), 3.25 (m, 1H), 1.51 (s, 3H), 1.50 (s, 3H) MS m/z (+ESI): 432.1, 434.1 $[M+H]^+$.

Preparation of Example 52: (5S)-5-[[(Z)-(4-amino-8-chloro-5,5-dimethyl-benzo[h]quinazolin-6-ylidene)amino]oxymethyl]-3-methyl-oxazolidin-2-one

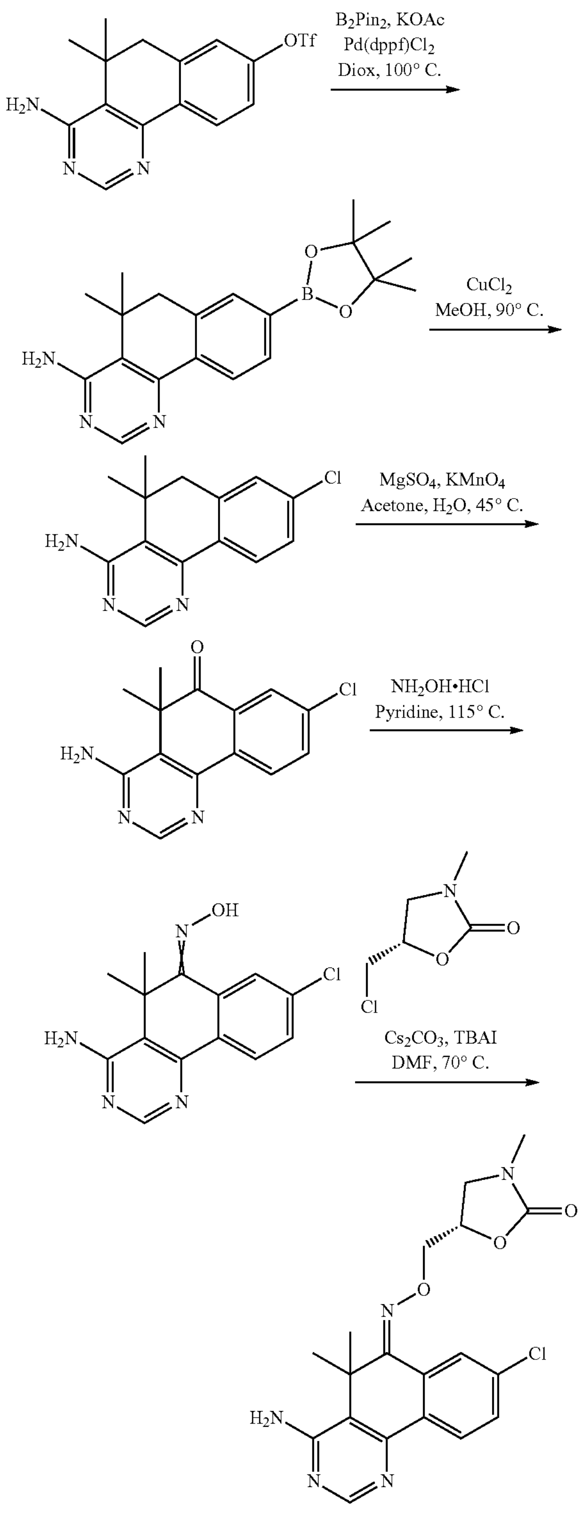

52

Step 1: Preparation of 5,5-dimethyl-8-(4,4,5,5-tetramethyl-1,3,2-dioxaborolan-2-yl)-6H-benzo[h]quinazolin-4-amine $B_2Pin_2$ (197 mg, 0.58 mmol) was added to a stirred solution of (4-amino-5,5-dimethyl-6H-benzo[h]quinazolin-8-yl) trifluoromethanesulfonate (240 mg, 0.58 mmol) in Diox (18 mL), followed by $Pd_2(dppf)Cl_2$ (44 mg, 0.058 mmol) and KOAc (172 mg, 1.74 mmol). After 5 h at 90° C., the reaction mixture was cooled to rt before extraction with EA and $H_2O$. The combined organic layers were dried over $Na_2SO_4$, filtered and concentrated. The residue was purified by column chromatography (silica gel; PE:EA; 3:2; v:v) to afford 5,5-dimethyl-8-(4,4,5,5-tetramethyl-1,3,2-dioxaborolan-2-yl)-6H-benzo[h]quinazolin-4-amine as a dark green solid (210 mg, 93% yield).

$^1H$ NMR (400 MHz, $CDCl_3$) δ ppm: 8.51 (s, 1H), 8.21 (d, J=8.0 Hz, 1H), 7.80 (d, J=8.0 Hz, 1H), 7.63 (s, 1H), 5.24 (br, 2H), 2.87 (s, 2H), 1.37 (s, 12H), 1.25 (s, 6H).

MS m/z (+ESI): 352.2 $[M+H]^+$.

Step 2: Preparation of 8 chloro-5,5-dimethyl-6H-benzo[h]quinazolin-4-amine $CuCl_2$ (52 mg, 0.38 mmol) was added to a solution of 5,5-dimethyl-8-(4,4,5,5-tetramethyl-1,3,2-dioxaborolan-2-yl)-6H-benzo[h]quinazolin-4-amine (0.15 g, 0.38 mmol) in t-BuOH (1 mL) and MeOH (4 mL). After 2 h at 90° C., the solid was removed by filtration and the filtrate was concentrated. The crude product was purified by preparative HPLC (Note 2) to afford 8 chloro-5,5-dimethyl-6H-benzo[h]quinazolin-4-amine as a white solid. (140 mg, 99% yield).

$^1H$ NMR (400 MHz, DMSO-$d_6$+$D_2O$) 6 ppm: 8.61 (s, 1H), 7.87 (d, J=8.4 Hz, 1H), 7.55 (dd, J=8.4 Hz, 2.0 Hz, 1H), 7.51 (d, J=2.0 Hz, 1H), 2.89 (s, 2H), 1.29 (s, 6H).

MS m/z (+ESI): 260.1, 262.1 $[M+H]^+$.

Preparation of (5S)-5-[[(Z)-(4-amino-8-chloro-5,5-dimethyl-benzo[h]quinazolin-6-ylidene)amino]oxymethyl]-3-methyl-oxazolidin-2-one The title compound was prepared as a yellow solid following Scheme 1 and in analogy to Example 1 (steps 6 & 7) and Example 12 using 8 chloro-5,5-dimethyl-6H-benzo[h]quinazolin-4-amine, hydroxylamine hydrochloride and (5S)-5-(chloromethyl)-3-methyl-oxazolidin-2-one (CAS 140478-99-5) as starting materials.

$^1H$ NMR (400 MHz, DMSO-$d_6$+$D_2O$) 6 ppm: 8.44 (s, 1H), 8.13 (d, J=8.4 Hz, 1H), 8.01 (d, J=2.0 Hz, 1H), 7.72 (dd, J=8.4 Hz, 2.0 Hz, 1H), 4.75 (m, 1H), 4.34 (m, 1H), 4.24 (m, 1H), 3.62 (m, 1H), 3.28 (m, 1H), 2.65 (s, 3H), 1.50 (s, 6H).

MS m/z (+ESI): 402.2, 404.1 $[M+H]^+$.

Preparation of Example 69: (6Z)-6-methoxyimino-N8,5,5-trimethyl-N8-(4-piperidyl)benzo[h]quinazoline-4,8-diamine

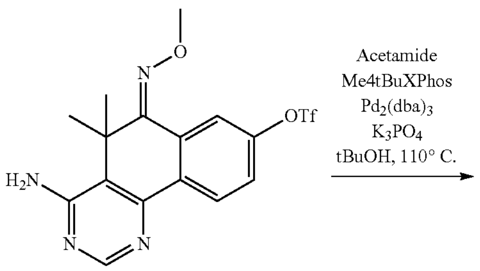

-continued

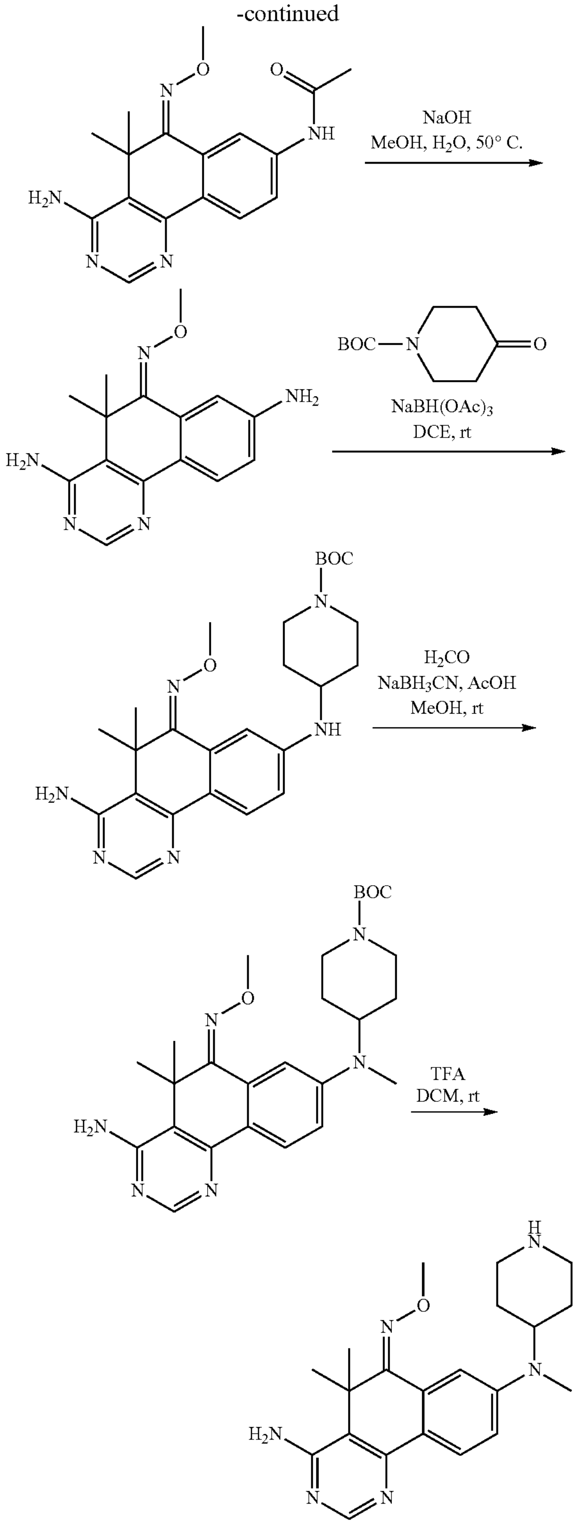

69

Step 1: Preparation of N-[(6Z)-4-amino-6-methoxy-imino-5,5-dimethyl-benzo[h]quinazolin-8-yl]acet-amide Acetamide (781 mg, 12.96 mmol) was added to a stirred solution of [(6Z)-4-amino-6-methoxyimino-5,5-dimethyl-benzo[h]quinazolin-8-yl] trifluoromethanesulfonate (300 mg, 0.65 mmol) in tBuOH (20 mL), followed by $K_3PO_4$ (699 mg, 3.24 mmol), $Pd_2(dba)_3$ (121 mg, 0.13 mmol) and $Me_4$tBuXPhos (127 mg, 0.26 mmol). After 2 h stirring at 110° C., the reaction mixture was extracted with DCM and $H_2O$. The combined organic layers were dried over $Na_2SO_4$, filtered and concentrated. The residue was purified by column chromatography (silica gel; DCM:MeOH; 10:1; v:v) to afford N-[(6Z)-4-amino-6-methoxyimino-5,5-dimethyl-benzo[h]quinazolin-8-yl]acetamide as a brown foam (200 mg, 85% yield).

MS m/z (+ESI): 326.2 $[M+H]^+$.

Step 2: Preparation of (6Z)-6-methoxyimino-5,5-dimethyl-benzo[h]quinazoline-4,8-diamine NaOH (805 mg, 19.92 mmol) was added to a stirred solution of N-[(6Z)-4-amino-6-methoxyimino-5,5-dimethyl-benzo[h]quinazolin-8-yl]acetamide (180 mg, 0.50 mmol) in MeOH (3 mL) and $H_2O$ (3 mL). After 16 h stirring at 50° C., the reaction mixture was extracted with EA and brine. The combined organic layers were dried over $Na_2SO_4$, filtered and concentrated to afford (6Z)-6-methoxyimino-5,5-dimethyl-benzo[h]quinazoline-4,8-diamine as a yellow semisolid (170 mg, 72% yield) that was used in the next step without further purification.

MS m/z (+ESI): 284.1 $[M+H]^+$.

Step 3: Preparation of tert-butyl 4-[[(6Z)-4-amino-6-methoxyimino-5,5-dimethyl-benzo[h]quinazolin-8-yl]aminolpiperidine-1-carboxylate N-(tert-butoxycarbonyl)-4-piperidone (80 mg, 0.39 mmol) was added to a stirred solution of (6Z)-6-methoxy-imino-5,5-dimethyl-benzo[h]quinazoline-4,8-diamine (170 mg, 0.36 mmol) in DCE (5 mL), followed by NaBH(OAc)$_3$ (236 mg, 1.08 mmol). After 16 h stirring, the reaction mixture was deactivated with a saturated $NH_4Cl$ aqueous solution and extracted with EA. The combined organic layers were dried over $Na_2SO_4$, filtered and concentrated. The residue was purified by column chromatography (silica gel; DCM:MeOH; 10:1; v:v) to afford tert-butyl 4-[[(6Z)-4-amino-6-methoxyimino-5,5-dimethyl-benzo[h]quinazolin-8-yl]amino]piperidine-1-carboxylate as a yellow solid (168 mg, 81% yield).

MS m/z (+ESI): 467.2 $[M+H]^+$.

Preparation of Example 69: (6Z)-6-methoxyimino-N8,5,5-trimethyl-N8-(4-piperidyl)benzo[h]quinazoline-4,8-diamine The title compound was prepared as a yellow solid (18 mg, 34% yield) following Scheme 1 and in analogy to Examples 1 (step 9) and 44 (step 3) using tert-butyl 4-[[(6Z)-4-amino-6-methoxyimino-5,5-dimethyl-benzo[h]quinazolin-8-yl]amino]piperidine-1-carboxylate and paraformaldehyde as starting materials.

$^1H$ NMR (400 MHz, DMSO-$d_6$+$D_2O$) 6 ppm: 8.43 (s, 1H), 7.87 (d, J=9.2 Hz, 1H), 7.40 (d, J=2.4 Hz, 1H), 7.11 (dd, J=9.2 Hz, 2.4 Hz, 1H), 4.13 (m, 1H), 3.84 (s, 3H), 3.38 (m, 2H), 3.08 (m, 2H), 2.83 (s, 3H), 1.90 (m, 2H), 1.83 (m, 2H), 1.48 (s, 6H).

MS m/z (+ESI): 381.2 $[M+H]^+$.

Preparation of Example 70: (6Z)-6-methoxyimino-5,5-dimethyl-8-(4-piperidylmethyl)benzo[h]quinazolin-4-amine

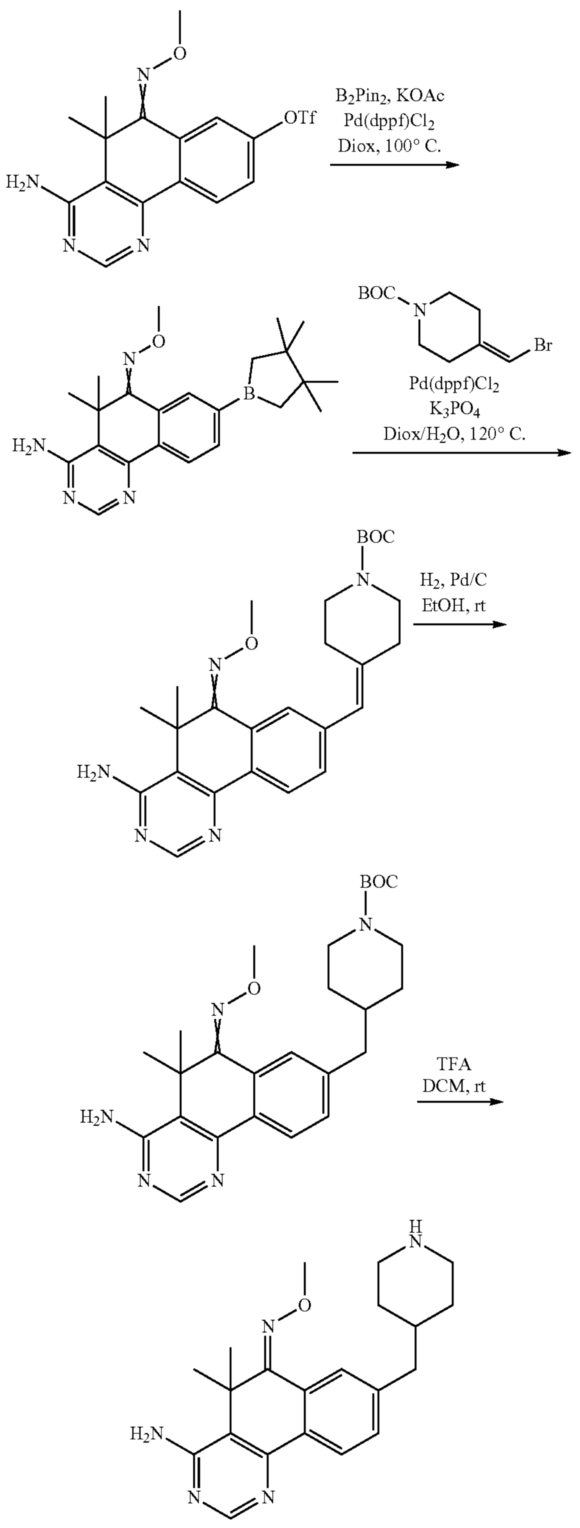

70

Step 1: Preparation of 6-methoxyimino-5,5-dimethyl-8-(4,4,5,5-tetramethyl-1,3,2-dioxaborolan-2-yl)benzo[h]quinazolin-4-amine The title compound was prepared as a brown semisolid (220 mg, 93% yield) following Scheme 1 and in analogy to Example 52 (step 1) using (4-amino-6-methoxyimino-5,5-dimethyl-benzo[h]quinazolin-8-yl) trifluoromethanesulfonate (250 mg, 0.54 mmol) as starting material.

MS m/z (+ESI): 395.3 $[M+H]^+$.

Step 2: Preparation of tert-butyl 4-[(4-amino-6-methoxyimino-5,5-dimethyl-benzo[h]quinazolin-8-yl)methylene]piperidine-1-carboxylate tert-Butyl 4-(bromomethylene)piperidine-1-carboxylate (190 mg, 0.67 mmol) was added to a stirred solution of 6-methoxyimino-5,5-dimethyl-8-(4,4,5,5-tetramethyl-1,3,2-dioxaborolan-2-yl)benzo[h]quinazolin-4-amine (260 mg, 0.51 mmol) in Diox (3 mL) and $H_2O$ (0.4 mL), followed by $Pd(dppf)Cl_2$ (38 mg, 0.05 mmol) and $K_3PO_4$ (0.33 g, 1.54 mmol). After 1 h stirring at 120° C., the reaction mixture was concentrated and the residue was purified by combiflash (ACN:$H_2O$ with 0.1% HCOOH) to afford tert-butyl 4-[(4-amino-6-methoxyimino-5,5-dimethyl-benzo[h]quinazolin-8-yl)methylene]piperidine-1-carboxylate as a dark brown solid (250 mg, 84% yield).

MS m/z (+ESI): 464.3 $[M+H]^+$.

Step 3: Preparation of tert-butyl 4-[(4-amino-6-methoxyimino-5,5-dimethyl-benzo[h]quinazolin-8-yl)methyl]piperidine-1-carboxylate 10% Palladium on activated carbon (37 mg, 0.03 mmol) was added to a stirred solution of tert-butyl 4-[(4-amino-6-methoxyimino-5,5-dimethyl-benzo[h]quinazolin-8-yl) methylene]piperidine-1-carboxylate (200 mg, 0.34 mmol) in EtOH (5 mL). After 16 h stirring under hydrogen flow, the catalyst was removed by filtration and the solution was concentrated to afford tert-butyl 4-[(4-amino-6-methoxyimino-5,5-dimethyl-benzo[h]quinazolin-8-yl)methyl]piperidine-1-carboxylate as light yellow semisolid (20 mg, 62% yield) that was used in the next step without further purification.

MS m/z (+ESI): 466.3 $[M+H]^+$.

Step 4: Preparation of (6Z)-6-methoxyimino-5,5-dimethyl-8-(4-piperidylmethyl)benzo[h]quinazolin-4-amine The title compound was prepared as a white solid (15 mg, 19% yield) following Scheme 1 and in analogy to Example 1 (step 9) using tert-butyl 4-[(4-amino-6-methoxyimino-5,5-dimethyl-benzo[h]quinazolin-8-yl)methyl]piperidine-1-carboxylate (190 mg, 0.20 mmol) as starting material.

$^1H$ NMR (400 MHz, DMSO-$d_6$+$D_2O$) δ ppm: 8.43 (s, 1H), 8.03 (d, J=8.0 Hz, 1H), 7.83 (d, J=1.2 Hz, 1H), 7.44 (dd, J=8.0 Hz, 1.2 Hz, 1H), 3.84 (s, 3H), 3.24 (m, 2H), 2.81 (m, 2H), 2.63 (m, 2H), 1.83 (m, 1H), 1.74 (m, 2H), 1.49 (s, 6H), 1.32 (m, 2H).

MS m/z (+ESI): 366.2 $[M+H]^+$.

Preparation of Example 76: (4S)-4-[[(Z)-(4-amino-8-methoxy-5,5-dimethyl-benzo[h]quinazolin-6-ylidene)amino]oxymethyl]-1-methyl-pyrrolidin-2-one

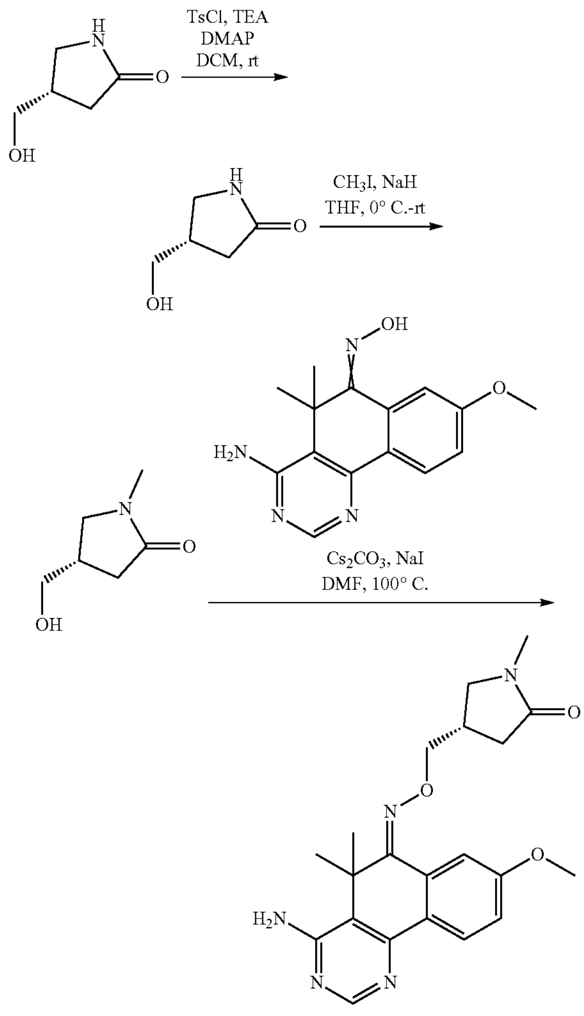

76

Step 1: Preparation of [(3S)-5-oxopyrrolidin-3-yl]methyl 4-methylbenzenesulfonate The title compound was prepared as a light yellow liquid (140 mg, 12% yield) following Scheme 1 and in analogy to Example 9 (step 1) using (4S)-4-(hydroxymethyl)pyrrolidin-2-one (900 mg, 3.91 mmol) as starting material.

MS m/z (+ESI): 270.2 $[M+H]^+$.

Step 2: Preparation of [(3S)-1-methyl-5-oxo-pyrrolidin-3-yl]methyl 4-methylbenzenesulfonate NaH (35 mg, 0.87 mmol) was added at 0° C. to a stirred solution of [(3S)-5-oxopyrrolidin-3-yl]methyl 4-methylbenzenesulfonate (130 mg, 0.43 mmol) in THF (5 mL), followed by iodomethane (33 μL, 0.74 mmol). After 30 min stirring at rt, the reaction mixture was extracted with DCM and $H_2O$. The combined organic layers were dried over $Na_2SO_4$, filtered and concentrated to afford [(3S)-1-methyl-5-oxo-pyrrolidin-3-yl]methyl 4-methylbenzenesulfonate as an off-white semisolid (120 mg, 88% yield) that was used in the next step without further purification.

MS m/z (+ESI): 284.1 $[M+H]^+$.

Step 3: Preparation of (4S)-4-[[(Z)-(4-amino-8-methoxy-5,5-dimethyl-benzo[h]quinazolin-6-ylidene)amino]oxymethyl]-1-methyl-pyrrolidin-2-one

[(3S)-1-methyl-5-oxo-pyrrolidin-3-yl]methyl 4-methylbenzenesulfonate (120 mg, 0.57 mmol) was added to a stirred solution of 4-amino-8-methoxy-5,5-dimethyl-benzo[h]quinazolin-6-one oxime (180 mg, 0.57 mmol) in DMF (5 mL), followed by $Cs_2CO_3$ (380 mg, 1.14 mmol) and NaI (58 mg, 0.38 mmol). After 20 min stirring at 100° C. the reaction mixture was concentrated and the residue was purified by preparative HPLC to afford (4S)-4-[[(Z)-(4-amino-8-methoxy-5,5-dimethyl-benzo[h]quinazolin-6-ylidene)amino]oxymethyl]-1-methyl-pyrrolidin-2-one as a white solid (22 mg, 14% yield).

$^1H$ NMR (400 MHz, DMSO-$d_6$+$D_2O$) δ ppm: 8.55 (s, 1H), 7.97 (d, J=8.8 Hz, 1H), 7.58 (d, J=2.4 Hz, 1H), 7.28 (dd, $J_1$=8.8 Hz, $J_2$=2.4 Hz, 1H), 4.11 (d, J=6.4 Hz, 2H), 3.87 (s, 3H), 3.43 (m, 1H), 3.12 (m, 1H), 2.68 (m, 1H), 2.63 (s, 3H), 2.37 (m, 1H), 2.08 (m, 1H), 1.50 (s, 6H).

MS m/z (+ESI): 396.3 $[M+H]^+$.

Preparation of Example 77: (6Z)-10-fluoro-8-methoxy-6-methoxyimino-5,5-dimethyl-benzo[h]quinazolin-4-amine

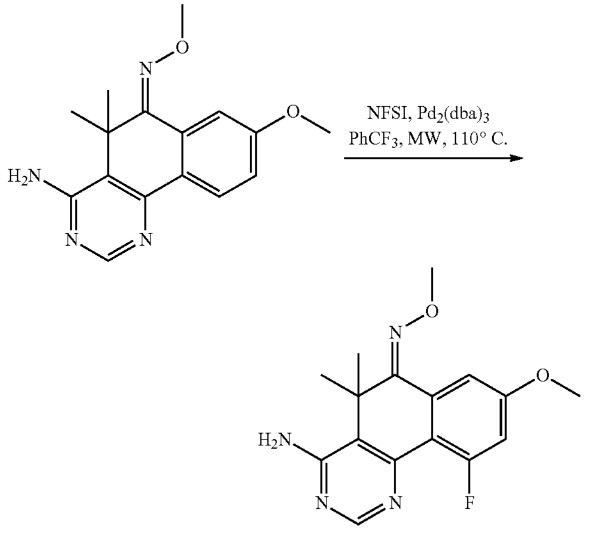

77

A mixture of (6Z)-8-methoxy-6-methoxyimino-5,5-dimethyl-benzo[h]quinazolin-4-amine (20 mg, 0.06 mmol), NFSI (59 mg, 0.18 mmol) and $Pd_2(dba)_3$ (10 mg, 0.02 mmol) in $PhCF_3$ (1.2 mL) was stirred under microwave irradiation at 110° C. for 1 h. The reaction mixture was extracted with DCM and $H_2O$. The combined organic layers were dried over $Na_2SO_4$, filtered and concentrated. The residue was purified by preparative HPLC to afford (6Z)-

10-fluoro-8-methoxy-6-methoxyimino-5,5-dimethyl-benzo[h]quinazolin-4-amine as a white solid (7 mg, 5% yield).

$^1$H NMR (400 MHz, DMSO-$d_6$+$D_2O$) 6 ppm: 8.45 (s, 1H), 7.33 (d, J=2.4 Hz, 1H), 7.19 (dd, J=14.0 Hz, 2.4 Hz, 1H), 3.87 (s, 3H), 3.86 (s, 3H), 1.46 (s, 6H).

MS m/z (+ESI): 317.3 $[M+H]^+$.

Preparation of Example 78: (2R)-1-[(Z)-[4-amino-8-(trans-4-aminocyclohexoxy)-5,5-dimethyl-benzo[h]quinazolin-6-ylidene]amino]oxypropan-2-ol

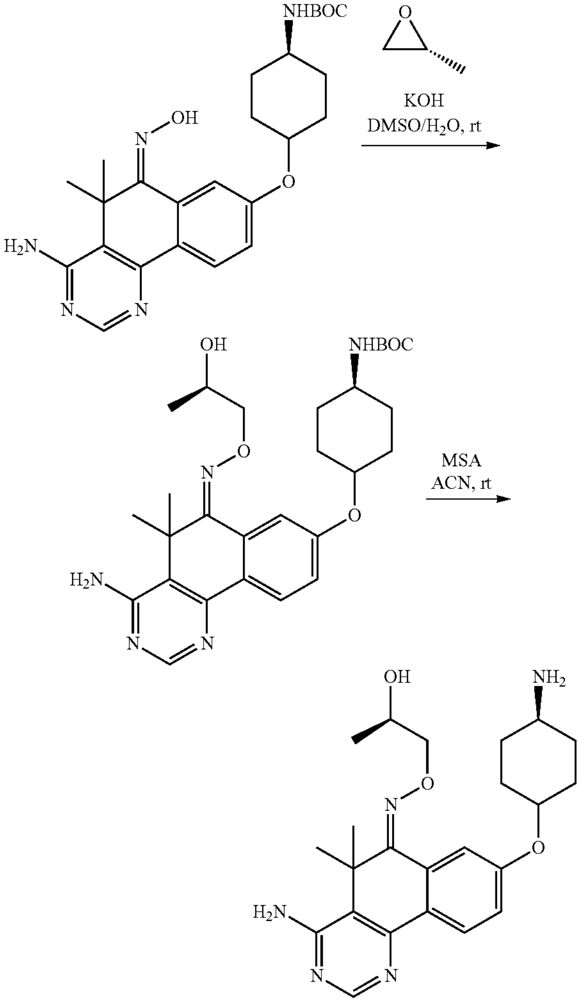

78

Step 1: Preparation of tert-butyl N-[4-[(6Z)-4-amino-6-[(2R)-2-hydroxypropoxy]imino-5,5-dimethyl-benzo[h]quinazolin-8-yl]oxycyclohexyl]carbamate KOH (6 mg, 0.11 mmol) was added to a stirred solution of tert-butyl N-[4-[(6Z)-4-amino-6-hydroxyimino-5,5-dimethyl-benzo[h]quinazolin-8-yl]oxycyclohexyl]carbamate (50 mg, 0.09 mmol) and (R)-(+)—1,2-epoxypropane (9 mg, 0.14 mmol) in $H_2O$ (0.3 mL) and DMSO (0.9 mL). After 48 h stirring, the reaction mixture was extracted with EA and $H_2O$. The combined organic layers were dried over $Na_2SO_4$, filtered and concentrated to afford tert-butyl N-[4-[(6Z)-4-amino-6-[(2R)-2-hydroxypropoxy]imino-5,5-dimethyl-benzo[h]quinazolin-8-yl]oxycyclohexyl]carbamate as a light yellow solid (55 mg, 92% yield) that was used in the next step without further purification.

MS m/z (+ESI): 526.4 $[M+H]^+$.

Step 2: Preparation of (2R)-1-[(Z)-[4-amino-8-(trans-4-aminocyclohexoxy)-5,5-dimethyl-benzo[h]quinazolin-6-ylidene]amino]oxypropan-2-ol MSA (174 mg, 1.78 mmol) was added to a stirred solution of tert-butyl N-[4-[(6Z)-4-amino-6-[(2R)-2-hydroxypropoxy]imino-5,5-dimethyl-benzo[h]quinazolin-8-yl]oxycyclohexyl]carbamate (110 mg, 0.18 mmol) in ACN (1.2 mL). After 18 h stirring, the reaction mixture was diluted with $H_2O$, adjusted to pH 7 with a $NaHCO_3$ aqueous solution, and then extracted with DCM/MeOH (20:1, v/v). The combined organic layers were dried over $Na_2SO_4$, filtered and concentrated. The residue was purified by preparative HPLC to afford (2R)-1-[(Z)-[4-amino-8-(trans-4-aminocyclohexoxy)-5,5-dimethyl-benzo[h]quinazolin-6-ylidene]amino]oxypropan-2-ol as a white solid (23 mg, 28% yield). $^1$H NMR (400 MHz, DMSO-$d_6$+$D_2O$) 6 ppm: 8.42 (s, 1H), 8.01 (d, J=8.8 Hz, 1H), 7.72 (d, J=2.8 Hz, 1H), 7.19 (dd, J=8.8 Hz, 2.8 Hz, 1H), 4.40 (m, 1H), 3.91 (m, 3H), 3.07 (m, 1H), 2.15 (m, 2H), 1.97 (m, 2H), 1.48 (m, 10H), 1.06 (d, J=6.0 Hz, 3H).

LC-MS m/z (+ESI): 426.3 $[M+H]^+$.

Preparation of Example 90: (5S)-5-[[(Z)-(4-amino-8-bromo-5,5-dimethyl-benzo[h]quinazolin-6-ylidene)amino]oxymethyl]-3-(2-methoxyethyl)oxazolidin-2-one

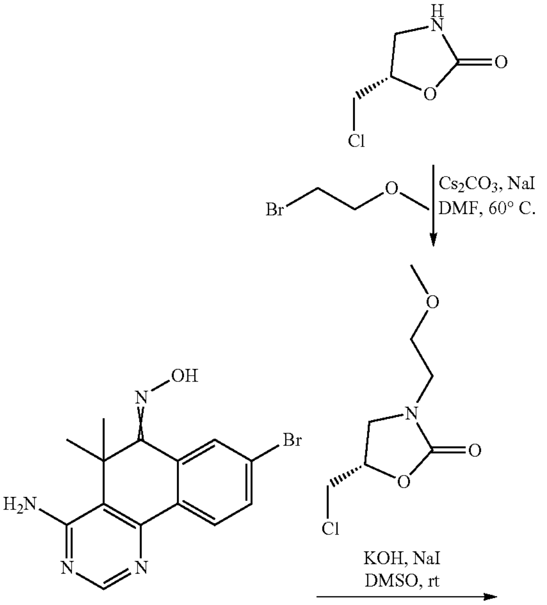

-continued

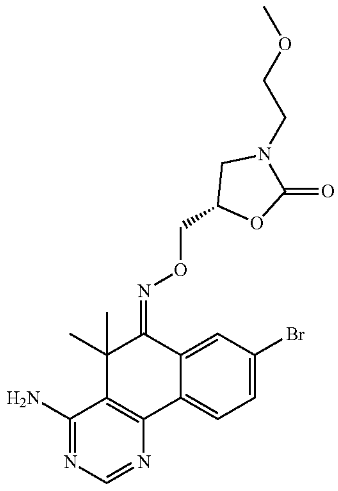

90

Step 1: Preparation of (5S)-5-(chloromethyl)-3-(2-methoxyethyl)oxazolidin-2-one

1-Bromo-2-methoxyethane (596 mg, 4.20 mmol) was added to a stirred solution of (5S)-5-(chloromethyl)oxazolidin-2-one (500 mg, 3.50 mmol) in DMF (4 mL), followed by $Cs_2CO_3$ (2.33 g, 7.01 mmol) and NaI (804 mg, 5.25 mmol). After 18 h stirring at 60° C., the reaction mixture was deactivated with a saturated $NH_4Cl$ aqueous solution and extracted with EA. The combined organic layers were dried over $Na_2SO_4$, filtered and concentrated to afford (5S)-5-(chloromethyl)-3-(2-methoxyethyl)oxazolidin-2-one as a yellow oil (370 mg, 38% yield) that was used in the next step without further purification.

Step 2: Preparation of (5S)-5-[[(Z)-(4-amino-8-bromo-5,5-dimethyl-benzo[h]quinazolin-6-ylidene)amino]oxymethyl]-3-(2-methoxyethyl)oxazolidin-2-one NaI (98 mg, 0.65 mmol) was added to a stirred solution of 4-amino-8-bromo-5,5-dimethyl-benzo[h]quinazolin-6-one oxime (120 mg, 0.32 mmol) and (5S)-5-(chloromethyl)-3-(2-methoxyethyl)oxazolidin-2-one (358 mg, 1.29 mmol) in DMSO (3 mL), followed by KOH (64 mg, 0.97 mmol). After 8 h stirring, the reaction mixture was purified by preparative HPLC to afford (5S)-5-[[(Z)-(4-amino-8-bromo-5,5-dimethyl-benzo[h]quinazolin-6-ylidene)amino]oxymethyl]-3-(2-methoxyethyl)oxazolidin-2-one as a yellow solid (33 mg, 18% yield).

$^1H$ NMR (400 MHz, DMSO-$d_6$+$D_2O$) 6 ppm: 8.30 (s, 1H), 8.13 (m, 2H), 7.77 (dd, J=8.4 Hz, 2.0 Hz, 1H), 4.76 (m, 1H), 4.24 (m, 2H), 3.67 (t, J=8.8 Hz, 2H), 3.36 (m, 2H), 3.25 (m, 2H), 3.17 (s, 3H), 1.49 (s, 3H), 1.48 (s, 3H).

MS m/z (+ESI): 490.3, 492.3 $[M+H]^+$.

Preparation of Example 92: (6Z)-4-amino-5,5-dimethyl-6-[[(5S)-2-oxooxazolidin-5-yl]methoxyimino]benzo[h]quinazoline-8-carbonitrile

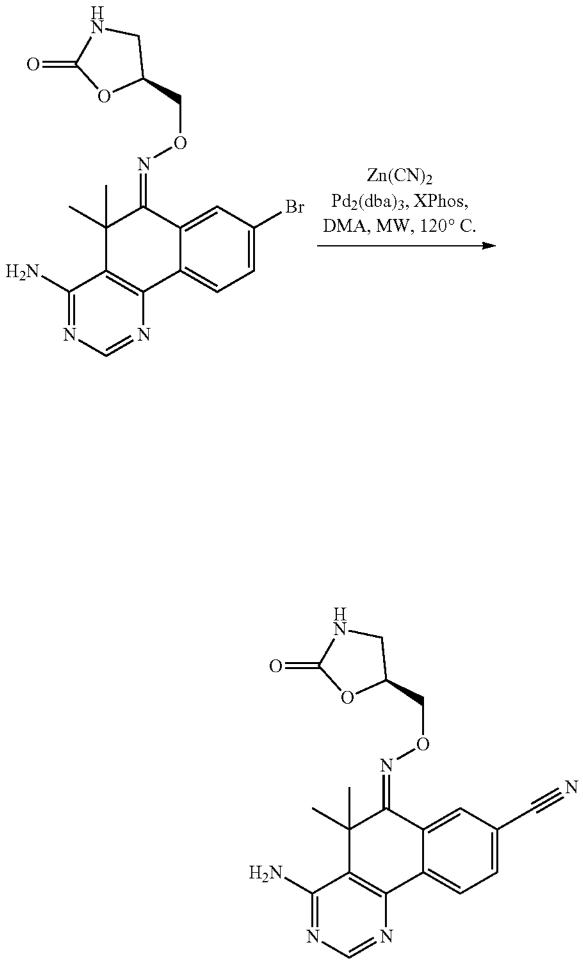

92

$Zn(CN)_2$ (75 mg, 0.62 mmol) was added to a stirred suspension of (5S)-5-[[(Z)-(4-amino-8-bromo-5,5-dimethyl-benzo[h]quinazolin-6-ylidene)amino]oxymethyl]oxazolidin-2-one (100 mg, 0.21 mmol) in DMA (5 mL), followed by $Pd_2(dba)_3$ (19 mg, 0.02 mmol) and XPhos (10 mg, 0.02 mmol). The resulting suspension was stirred under microwave irradiation at 120° C. for 30 min. The reaction mixture was extracted with EA and $H_2O$. The combined organic layers were dried over $Na_2SO_4$, filtered and concentrated. The residue was purified by preparative HPLC to afford (6Z)-4-amino-5,5-dimethyl-6-[[(5S)-2-oxooxazolidin-5-yl]methoxyimino]benzo[h]quinazoline-8-carbonitrile as a white solid (56 mg, 62% yield).

$^1H$ NMR (400 MHz, DMSO-$d_6$+$D_2O$) 6 ppm: 8.48 (s, 1H), 8.40 (d, J=1.6 Hz, 1H), 8.31 (d, J=8.4 Hz, 1H), 8.09 (dd, J=8.4 Hz, 1.6 Hz, 1H), 4.85 (m, 1H), 4.31 (m, 2H), 3.59 (m, 1H), 3.27 (m, 1H), 1.51 (s, 6H).

LC-MS m/z (+ESI): 379.3 $[M+H]^+$.

Preparation of Example 93: (5S)-5-[[(Z)-(4-amino-8-iodo-5,5-dimethyl-benzo[h]quinazolin-6-ylidene)amino]oxymethyl]oxazolidin-2-one

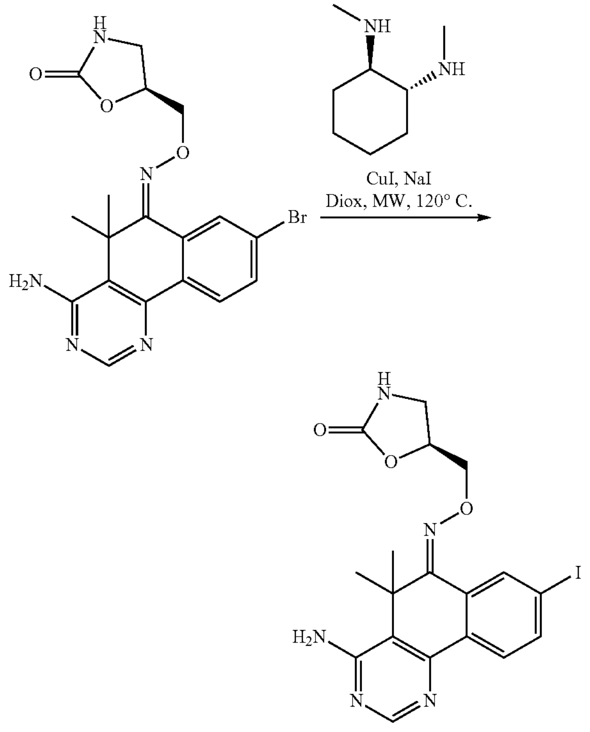

93

NaI (95 mg, 0.62 mmol) was added to a stirred suspension of (5S)-5-[[(Z)-(4-amino-8-bromo-5,5-dimethyl-benzo[h]quinazolin-6-ylidene)amino]oxymethyl]oxazolidin-2-one (150 mg, 0.31 mmol) in 1,4-dioxane (1 mL), followed by (1R,2R)—N1,N2-dimethylcyclohexane-1,2-diamine (13 mg, 0.09 mmol) and CuI (12 g, 0.06 mmol). The resulting suspension was stirred under microwave irradiation at 120° C. for 1 h, then filtered, washed with DCM and purified by preparative HPLC to afford (5S)-5-[[(Z)-(4-amino-8-iodo-5,5-dimethyl-benzo[h]quinazolin-6-ylidene)amino]oxymethyl]oxazolidin-2-one as a white solid (62 mg, 40% yield).

$^1$H NMR (400 MHz, DMSO-$d_6$+$D_2O$) 6 ppm: 8.52 (s, 1H), 8.42 (d, J=1.6 Hz, 1H), 8.07 (dd, J=8.4 Hz, 1.6 Hz, 1H), 7.86 (d, J=8.4 Hz, 1H), 4.85 (m, 1H), 4.30 (m, 2H), 3.60 (m, 1H), 3.27 (m, 1H), 1.50 (s, 3H), 1.49 (s, 3H).

LC-MS m/z (+ESI): 480.2 $[M+H]^+$.

Preparation of Example 94: (5S)-5-[[(Z)-[4-amino-8-(2-hydroxyethoxy)-5,5-dimethyl-benzo[h]quinazolin-6-ylidene]amino]oxymethyl]oxazolidin-2-one

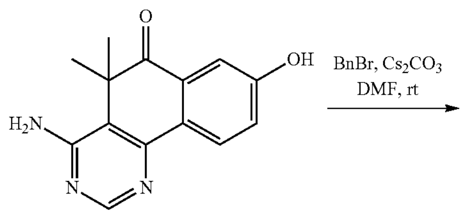

-continued

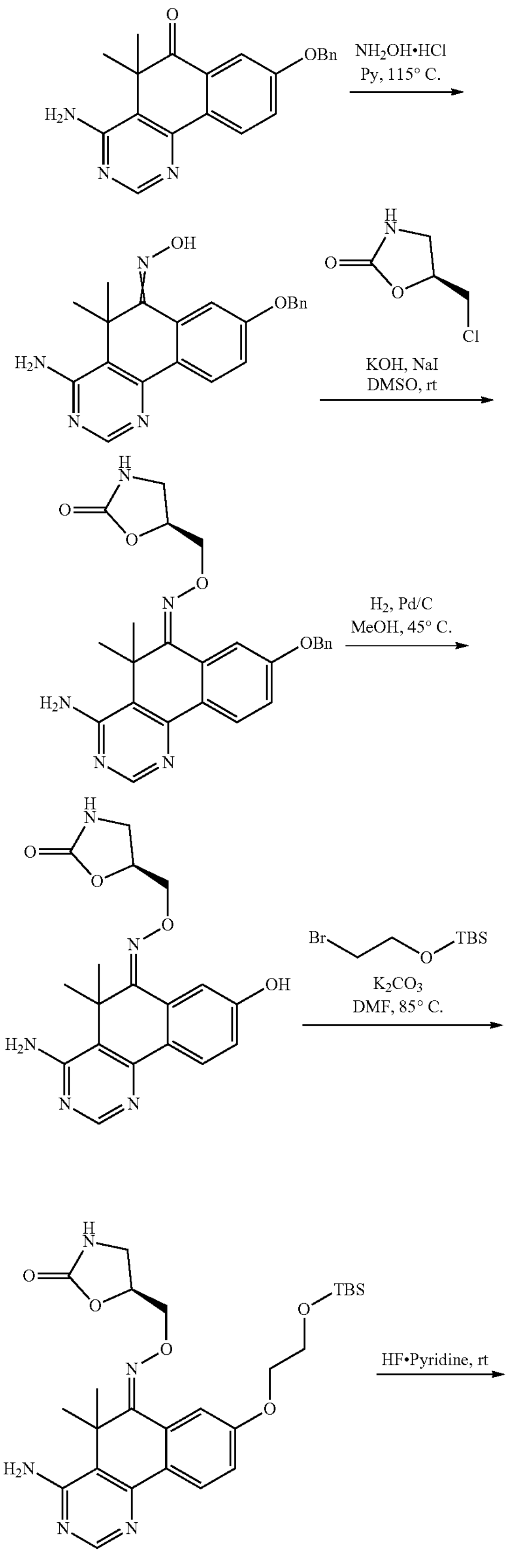

-continued

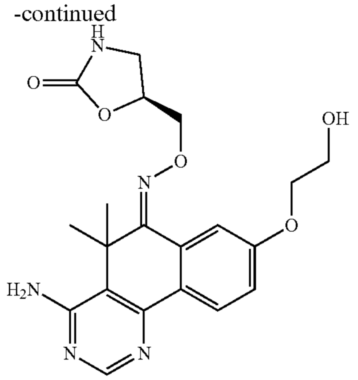

94

Step 1: Preparation of 4-amino-8-benzyloxy-5,5-dimethyl-benzo[h]quinazolin-6-one Benzyl bromide (2.7 g, 15.67 mmol) was added to a stirred solution of 4-amino-8-hydroxy-5,5-dimethyl-benzo[h]quinazolin-6-one (5 g, 9.79 mmol) in DMF (50 mL), followed by $Cs_2CO_3$ (9.77 g, 29.38 mmol). After 1 h stirring the reaction mixture was extracted with EA and $H_2O$. The combined organic layers were dried over $Na_2SO_4$, filtered and concentrated. The residue was purified by column chromatography (silica gel; PE:EA; 2:1, v:v) to afford 4-amino-8-benzyloxy-5,5-dimethyl-benzo[h]quinazolin-6-one as a yellow solid (2.3 g, 61% yield).

$^1H$ NMR (400 MHz, DMSO-$d_6$) δ ppm: 8.56 (d, J=8.8 Hz, 1H), 8.38 (s, 1H), 7.56 (d, J=2.8 Hz, 1H), 7.49 (m, 3H), 7.39 (m, 2H), 7.35 (m, 1H), 6.87 (s, 2H), 5.26 (s, 2H), 1.50 (s, 6H).

LC-MS m/z (+ESI): 346.3 $[M+H]^+$.

Step 2: Preparation of 4-amino-8-benzyloxy-5,5-dimethyl-benzo[h]quinazolin-6-one oxime The title compound was prepared as a yellow solid (450 mg, 82% yield) following Scheme 1 and in analogy to Example 1 (step 7) using 4-amino-8-benzyloxy-5,5-dimethyl-benzo[h]quinazolin-6-one (500 mg, 1.37 mmol) and hydroxylamine hydrochloride (970 mg, 13.7 mmol) as starting materials.

LC-MS m/z (+ESI): 361.2 $[M+H]^+$.

Step 3: Preparation of (5S)-5-[[(Z)-[4-amino-5,5-dimethyl-8-(2-phenylethyl)benzo[h]quinazolin-6-ylidene]amino]oxymethyl]oxazolidin-2-one (5S)-5-(Chloromethyl)oxazolidin-2-one (CAS 169048-83-3, 1.07 g, 7.49 mmol) was added to a stirred suspension of 4-amino-8-benzyloxy-5,5-dimethyl-benzo[h]quinazolin-6-one oxime (1 g, 2.50 mmol) in DMSO (20 mL), followed by KOH (429 mg, 7.49 mmol) and NaI (756 mg, 4.99 mmol). After 16 h stirring, the reaction mixture was extracted with EA and $H_2O$. The combined organic layers were dried over $Na_2SO_4$, filtered and concentrated. The residue was purified by combiflash to afford (5S)-5-[[(Z)-[4-amino-5,5-dimethyl-8-(2-phenylethyl)benzo[h]quinazolin-6-ylidene]amino]oxymethyl]oxazolidin-2-one as a light yellow solid (350 mg, 27% yield).

LC-MS m/z (+ESI): 460.2 $[M+H]^+$.

Step 4: Preparation of: (5S)-5-[[(Z)-(4-amino-8-hydroxy-5,5-dimethyl-benzo[h]quinazolin-6-ylidene)amino]oxymethyl]oxazolidin-2-one 10% Palladium on activated carbon (365 mg, 0.34 mmol) was added to a stirred solution of (5S)-5-[[(Z)-[4-amino-5,5-dimethyl-8-(2-phenylethyl)benzo[h]quinazolin-6-ylidene]amino]oxymethyl]oxazolidin-2-one (350 mg, 0.69 mmol) in MeOH (15 mL). After 16 h stirring under hydrogen flow, the catalyst was removed by filtration and the solution was concentrated to afford (5S)-5-[[(Z)-(4-amino-8-hydroxy-5,5-dimethyl-benzo[h]quinazolin-6-ylidene)amino]oxymethyl]oxazolidin-2-one as a light yellow viscous oil (280 mg, 99% yield) that was used in the next step without further purification.

LC-MS m/z (+ESI): 370.2 $[M+H]^+$.

Step 5: Preparation of (5S)-5-[[(Z)-[4-amino-8-[2-[tert-butyl(dimethyl)silyl]oxyethoxy]-5,5-dimethyl-benzo[h]quinazolin-6-ylidene]amino]oxymethyl]oxazolidin-2-one (2-Bromoethoxy)(tert-butyl)dimethylsilane (CAS 86864-60-0, 589 mg, 2.39 mmol) was added to a stirred solution of (5S)-5-[[(Z)-(4-amino-8-hydroxy-5,5-dimethyl-benzo[h]quinazolin-6-ylidene)amino]oxymethyl]oxazolidin-2-one (280 mg, 0.68 mmol) in DMF (5 mL), followed by $K_2CO_3$ (476 mg, 3.41 mmol). After 3 h stirring at 85° C., the reaction mixture was extracted with EA and $H_2O$. The combined organic layers were dried over $Na_2SO_4$, filtered and concentrated. The residue was purified by combiflash to afford (5S)-5-[[(Z)-[4-amino-8-[2-[tert-butyl(dimethyl)silyl]oxyethoxy]-5,5-dimethyl-benzo[h]quinazolin-6-ylidene]amino]oxymethyl]oxazolidin-2-one as a colorless liquid (200 mg, 53% yield).

LC-MS m/z (+ESI): 528.4 $[M+H]^+$.

Step 6: Preparation of (5S)-5-[[(Z)-[4-amino-8-(2-hydroxyethoxy)-5,5-dimethyl-benzo[h]quinazolin-6-ylidene]amino]oxymethyl]oxazolidin-2-one Pyridine hydrofluoride (497 mg, 3.51 mmol) was added to a stirred solution of (5S)-5-[[(Z)-[4-amino-8-[2-[tert-butyl(dimethyl)silyl]oxyethoxy]-5,5-dimethyl-benzo[h]quinazolin-6-ylidene]amino]oxymethyl]oxazolidin-2-one (195 mg, 0.35 mmol) in THF (10 mL) and the resulting solution was sonicated for 10 min. The reaction mixture was concentrated and the residue was purified by preparative HPLC to afford (5S)-5-[[(Z)-[4-amino-8-(2-hydroxyethoxy)-5,5-dimethyl-benzo[h]quinazolin-6-ylidene]amino]oxymethyl]oxazolidin-2-one as a white solid (58 mg, 36% yield).

$^1H$ NMR (400 MHz, DMSO-$d_6$+$D_2O$) 6 ppm: 8.13 (d, J=8.8 Hz, 1H), 7.55 (d, J=2.4 Hz, 1H), 7.51 (s, 1H), 7.13 (dd, J=8.8 Hz, 2.4 Hz, 1H), 4.86 (m, 1H), 4.23 (m, 2H), 4.50 (m, 2H), 3.73 (m, 2H), 3.57 (m, 1H), 3.26 (m, 1H), 1.50 (s, 3H), 1.48 (s, 3H).

LC-MS m/z (+ESI): 414.3 $[M+H]^+$.

Preparation of Example 98: (5S)-5-[[(Z)-(8-acetyl-4-amino-5,5-dimethyl-benzo[h]quinazolin-6-ylidene)amino]oxymethyl]oxazolidin-2-one

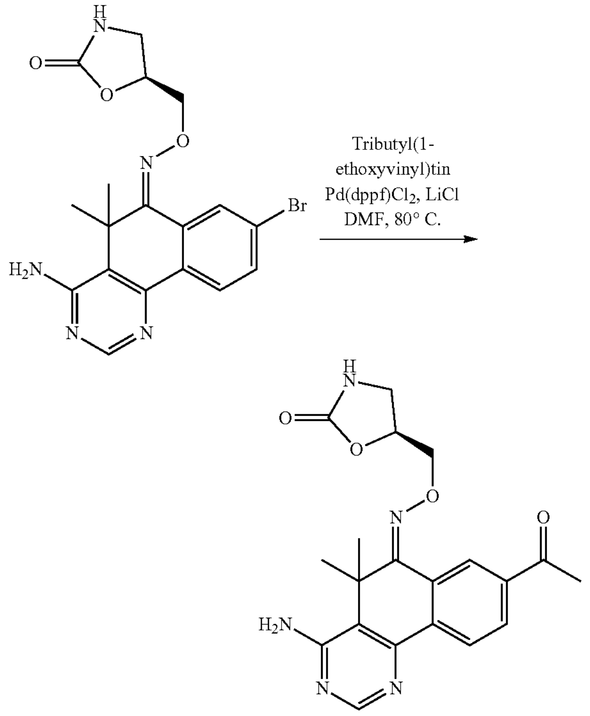

98

Tributyl(1-ethoxyvinyl)tin (CAS 97674-02-7, 310 mg, 0.83 mmol) was added to a stirred solution of (5S)-5-[[(Z)-(4-amino-8-bromo-5,5-dimethyl-benzo[h]quinazolin-6-ylidene)amino]oxymethyl]oxazolidin-2-one (200 mg, 0.42 mmol) in DMF (5 mL), followed by LiCl (18 mg, 0.42 mmol) and $Pd(dppf)Cl_2$ (31 mg, 0.04 mmol). The resulting suspension was stirred at 80° C. for 16 h. Solvent was removed and the residue was extracted with EA and $H_2O$. The combined organic layers were dried over $Na_2SO_4$, filtered and concentrated. The crude product was dissolved in THF (2 mL) and 1N HCl aqueous solution (1 mL) was added. After 1 h stirring solvent was removed and the residue was purified by preparative HPLC to afford (5S)-5-[[(Z)-(8-acetyl-4-amino-5,5-dimethyl-benzo[h]quinazolin-6-ylidene)amino]oxymethyl]oxazolidin-2-one as a white solid (106 mg, 25% yield).

$^1H$ NMR (400 MHz, DMSO-$d_6$+$D_2O$) 6 ppm: 8.61 (d, J=1.6 Hz, 1H), 8.43 (s, 1H), 8.29 (d, J=8.4 Hz, 1H), 8.14 (dd, J=8.4 Hz, 1.6 Hz, 1H), 4.85 (m, 1H), 4.32 (m, 2H), 3.59 (m, 1H), 3.30 (m, 1H), 2.62 (s, 3H), 1.52 (s, 3H), 1.51 (s, 3H).

LC-MS m/z (+ESI): 396.3 $[M+H]^+$.

Biological Examples

CLK3 Kinase Assay

CLK3 kinase activity was measured using the LANCE® Ultra technology (PerkinElmer) essentially as recommended by the supplier. Briefly, 2.5 μL of test sample at 4× the desired final concentration in 4% DMSO were dispensed into white, low volume, round bottom, 384 well plates (Corning, cat. no. 4512). 5 μL of a mixture containing recombinant human CLK3 (Thermo Fisher Scientific, cat. no. PV3826) and the labeled peptide substrate ULight™-CREBtide (PerkinElmer, cat. no. TRF0107) prepared in 1.33× kinase buffer (Thermo Fisher Scientific, cat. no. PV3189) were then added. Finally, the reactions were started by adding 2.5 μL of a 4× solution of ATP in kinase buffer. The plates were sealed with adhesive foils and incubated for 3 hours at 30° C. in the dark. The final concentrations of CLK3, ULight™—CREBtide, and ATP were 0.5 nM, 50 nM, and 300 μM, respectively. 5 μL of 40 mM EDTA were then added to terminate the reactions. The Eu-anti-phospho-CREB antibody (PerkinElmer, cat. no. TRF0200) diluted in LANCE® detection buffer (PerkinElmer, cat. no. CR97) was then added to a final concentration of 2 nM and the reactions were incubated for 1 hour at room temperature in the dark. The signals were measured using a Synergy 4 reader (BioTek) with a 320/80 nm filter for the excitation and 620/10 nm and 665/8 nm filters for the donor and acceptor emission, respectively. Relative inhibition values were calculated by normalizing the raw data using solvent control wells (0% inhibition) and wells that received no ATP (100% inhibition). $IC_{50}$ values were calculated by fitting the concentration-response data to a sigmoidal 4-parameter logistic model. Results are shown in Table 2 below.

MDA-MB-231 Proliferation Assay

MDA-MB-231 cells were cultivated in DMEM High Glucose (4.5 g/L) with L-Glutamine (BioConcept, cat. no. 1-26F03-I) supplemented with 1% Na-pyruvate (Sigma, cat. no. S8636), 1% Penicillin-Streptomycin (BioConcept, cat. no. 4-01F00H), and 10% FBS (Sigma, cat. no. F9665) using standard techniques. Cells were seeded in black, clear-bottom 384 well plates for tissue culture (Greiner Bio-One, cat. no. 781091) at a density of 750 cells per well in 20 μL medium and the plates were incubated overnight at 37° C. with 5% $CO_2$ prior to treatment. Experimental compounds were serially diluted in DMSO to 200× the desired final concentrations. The solutions were then diluted 1:40 with culture medium and 5 μL aliquots were mixed into the wells containing the cells. The final concentration of DMSO was 0.5%. The plates were incubated for 72 hours and cell numbers were then measured using YO-PRO™-1 Iodide (ThermoFisher Scientific, cat. no. Y3603) essentially as recommended by the manufacturer. Briefly, a 12.5 μM solution of YO-PRO™-1 Iodide in 5×YO-PRO buffer (100 mM Na-citrate, 130 mM NaCl, pH 4) was combined with an equal volume of lysis buffer (0.6% NP-40, 30 mM EDTA, 30 mM EGTA, 0.33× YO-PRO buffer) and 12.5 μL of the mixture were dispensed into each well. The plates were incubated at room temperature in the dark for 30 minutes. Fluorescence intensity signals were then measured on a Synergy 4 reader (BioTek) using 485/20 nm and 530/25 nm filters for the excitation and emission, respectively. Relative proliferation values were calculated by normalizing the raw data using DMSO-treated cells (100% proliferation) and the signals obtained from cells that were evaluated at the time of compound addition (0% proliferation). The concentration-response data were fitted to a sigmoidal 4-parameter logistic model with the maximum constrained to 100%. $GI_{50}$ values were calculated from the curves as the compound concentrations reducing proliferation to 50%. Results are shown in Table 2 below:

TABLE 2

| CLK3 biochemical results and growth inhibition of MDA-MB-231 cells | | |
|---|---|---|
| Example | CLK3 $IC_{50}$ (nM) | MDA-MB-231 $GI_{50}$ (nM) |
| 1 | 9.1 | 407 |
| 2 | 16.6 | 742 |
| 3 | 200 | 1960 |
| 4 | 2.1 | 271 |
| 5 | 227 | nt |
| 6 | 32.1 | >2000 |
| 7 | 115 | nt |
| 8 | 73.2 | >2000 |
| 9 | 90.2 | 1050 |
| 10 | 75.8 | >2000 |
| 11 | 437 | nt |
| 12 | 129 | >2000 |
| 13 | 4.3 | 1200 |
| 14 | 23.9 | 597 |
| 15 | 29.8 | 714 |
| 16 | 265 | >2000 |
| 17 | 410 | nt |
| 18 | 478 | nt |
| 19 | 20.2 | 445 |
| 20 | 237 | >2000 |
| 21 | 27.2 | 569 |
| 22 | 34.5 | 691 |
| 23 | 26.5 | 647 |
| 24 | 37.7 | 743 |
| 25 | 151 | 1600 |
| 26 | 42.6 | 1360 |
| 27 | 16.1 | 269 |
| 28 | 279 | >2000 |
| 29 | 15.4 | 378 |
| 30 | 93.9 | 1560 |
| 31 | 76.2 | 1580 |
| 32 | 29.6 | 1490 |
| 33 | 23.3 | 1190 |
| 34 | 10.9 | 620 |
| 35 | 144 | 1480 |
| 36 | 56.4 | 1150 |
| 37 | 59 | >2000 |
| 38 | 4.16 | >2000 |
| 39 | 120 | >2000 |
| 40 | 21.7 | >2000 |
| 41 | 92.8 | >2000 |
| 42 | 90.2 | >2000 |
| 43 | 90.5 | >2000 |
| 44 | 15.8 | >2000 |
| 45 | 104 | 1460 |
| 46 | 12.7 | 470 |
| 47 | 77.3 | 443 |
| 48 | 4.9 | >2000 |
| 49 | 14.4 | >2000 |
| 50 | <1.5 | 761 |
| 51 | 7.26 | 511 |
| 52 | <1.5 | 445 |
| 53 | <1.5 | 194 |
| 54 | 1.9 | nt |
| 55 | 15.6 | 169 |
| 56 | <1.5 | 332 |
| 57 | 2.76 | 207 |
| 58 | 90.4 | >2000 |
| 59 | 265 | >2000 |
| 60 | 116 | >2000 |
| 61 | 53.6 | >2000 |
| 62 | 372 | nt |
| 63 | 313 | nt |
| 64 | 74.1 | >2000 |
| 65 | 572 | nt |
| 66 | 13 | 1750 |
| 67 | 108 | >2000 |
| 68 | 778 | nt |
| 69 | 20.6 | >2000 |
| 70 | 9.1 | 630 |
| 71 | 173 | nt |
| 72 | 79.3 | >2000 |
| 73 | 385 | >2000 |
| 74 | 4.8 | 255 |
| 75 | 3.4 | 472 |

TABLE 2-continued

| CLK3 biochemical results and growth inhibition of MDA-MB-231 cells | | |
|---|---|---|
| Example | CLK3 $IC_{50}$ (nM) | MDA-MB-231 $GI_{50}$ (nM) |
| 76 | <41 | >2000 |
| 77 | 84.8 | >2000 |
| 78 | 66.3 | >2000 |
| 79 | 40.7 | 971 |
| 80 | 51.5 | >2000 |
| 81 | 15.8 | >2000 |
| 82 | 9.7 | 98.5 |
| 83 | 4.9 | 96.2 |
| 84 | 10.6 | >2000 |
| 85 | 125 | >2000 |
| 86 | 63.0 | >2000 |
| 87 | 18.7 | 255 |
| 88 | 8.8 | nt |
| 89 | 98.6 | nt |
| 90 | 9.37 | 863 |
| 91 | 5.1 | 459 |
| 92 | 142 | >2000 |
| 93 | 6.2 | 240 |
| 94 | 18.6 | >2000 |
| 95 | 62.5 | 1040 |
| 96 | 43.6 | 670 |
| 97 | 1.7 | 158 |
| 98 | 26 | >2000 |
| 99 | 5.8 | 27.6 |
| 100 | 3.7 | 10.5 |
| 101 | 1.2 | 4.5 |
| 102 | 2.9 | 10.1 |
| 103 | 28.3 | 184 |
| 104 | 10.4 | 41.3 |
| 105 | 14.9 | 82 |
| 106 | 23.4 | 307 |
| 107 | 35.4 | 319 |
| 108 | 87.9 | 942 |
| 109 | 17.7 | 156 |
| 110 | 31.8 | >2000 |
| 111 | 21.8 | 106 |
| 112 | 8.8 | 66.2 |
| 113 | 21.2 | 167 |
| 114 | 48.9 | 373 |
| 115 | 19.4 | 102 |
| 116 | 28.9 | 71.7 |

nt = not tested

Assessment of Inhibition of Phospho-SRSF6 Levels in MDA-MB-468 Cells

MDA-MB-468 cells (ATCC, HTB-132) were cultured in DMEM (BioConcept cat. no. 1-26F03) supplemented with 10% FBS (Sigma cat. no. F9665), 1% Na-pyruvate (Sigma cat. no. S8636), 1% Penicillin-Streptomycin (BioConcept cat. no. 4-01F00-H). When cells reached a density of 70% in 6-well plates (TPP cat. no. 92006), they were treated either with the test compound vehicle DMSO, or with experimental compounds at a final concentration of 100 nM for 2 hours. Thereafter, the culture medium was removed and cells were collected by scraping in Lysis Buffer (20 mM Tris HCl pH7.5, 150 mM NaCl, 1 mM EGTA, 1 mM EDTA, 1% Triton and 1% NP-40) containing protease and phosphatase inhibitors (Halt™ Protease&Phosphatase inhibitor cocktail 100× ThermoScientific cat. no. 1861281) and 1 mM PMSF (Fluka cat. no. 93482). Cleared lysates were stored in Eppendorf tubes at −80° C. until use, and protein concentration in lysates was determined using Pierce 660 nm Protein Assay Reagent (ThermoScientific cat. no. 22660). 20 μg proteins were diluted in 4× Laemmli buffer (Biorad cat. no. 161-0747) containing 10% beta-mercaptoethanol, separated by SDS-PAGE using 10% gels, and then transferred to PVDF membranes (Trans Blot Turbo Transfer Pack BioRad cat. no. 1704156) by Trans-Blot® Turbo™ System semidry blotting methodology (BioRad). Primary antibodies were incubated in TBS-0.1% Tween-20 buffer containing 3% BSA Bovine Albumin Fr.V (Millipore cat. no. 81-053-3) overnight at 4° C. The following primary antibodies were used: Mouse anti-phosphoepitope SR proteins clone 1H4 (Millipore cat. no. MABE50) diluted 1:5000, and rabbit anti-GAPDH clone 14C10 (Cell Signaling cat. no. 2118S) to control for equal protein loading, diluted 1:2000. HRP-conjugated secondary antibodies were incubated one hour at room temperature diluted 1:5000 in TBS-0.1% Tween-20 buffer containing 5% nonfat-dried bovine milk (Sigma cat. no. M7409). The following secondary antibodies were used: Goat anti-mouse-HRP (Jackson cat. no. 115-035-146) and goat anti-rabbit-HRP (Jackson cat. no. 111-035-144). Membranes were incubated with ECL Prime Western Blot Detection Reagent (Amersham cat. no. RPN2236) to detect specific signals using Fusion SOLO S device (Vilber Lourmat). Pixel intensity of the phopsho-SRSF6 (MW 55 kDa in reference to markers) and GAPDH (MW 37 kDa) signals in the Western blots were determined using Evolution-Capt image analysis software (v17.01, Vilber Lourmat). DMSO control was used to set the phospho-SRSF6 signal at baseline, phospho-SRSF6 signals for each sample were normalized by the respective GAPDH signals and percent intensity of P-SRSF6 signal at 100 nM compound compared to DMSO control was calculated (see FIG. 1).

Several examples of the invention were tested for inhibition of phospho-SRSF6 levels in MDA-MB-468 cells and showed an inhibition level of more than 50% compared to DMSO control when tested at a concentration of 100 nM. Results are shown in Table 3 below.

TABLE 3

Phospho-SRSF6 levels in MDA-MB-468 cells

| Example | % Intensity of p-SRSF6 signal at 100 nM compared to DMSO control |
|---|---|
| 1 | 19 |
| 4 | 32 |
| 6 | 41 |
| 13 | 28 |
| 19 | 25 |
| 21 | 12 |
| 27 | 26 |
| 29 | 12 |
| 38 | 48 |
| 40 | 45 |
| 70 | 34 |
| 74 | 28 |
| 79 | 34 |
| 82 | 15 |
| 83 | 9 |
| 87 | 10 |
| 88 | 21 |
| 90 | 29 |
| 91 | 15 |
| 93 | 19 |
| 97 | 21 |
| 99 | 17 |
| 101 | 8 |
| 102 | 7 |
| 109 | 21 |
| 111 | 16 |
| 115 | 17 |

Mouse Xenograft Models

The efficacy of Example 29 was assessed in a mouse xenograft model. To this end, the CAL-51 triple-negative breast cancer xenograft model was used, in which the tumor cells are injected subcutaneously into the flanks of immunodeficient NCG mice (lack functional/mature T, B, and NK cells, and have reduced macrophage and dendritic cell function). CAL-51 cells (DSMZ, #ACC 302) were cultured in Dulbecco's Modified Eagle Medium high glucose medium supplemented with 10% heat-inactivated fetal bovine serum at 37° C. CAL-51 cells were harvested when they were growing exponentially.

Female NCG mice were used for the study at 8-12 weeks of age (Charles River Laboratories). Mice were inoculated subcutaneously in the flank region with $1\times10^7$ CAL-51 cells in 50% Matrigel™ in a final injection volume of 0.1 mL/mouse. Once tumors reached an average size of 100-150 $mm^3$, a pair match was carried out to distribute mice to the different treatment groups. The mice in the control group were administered the vehicle (5% Ethanol; 85.5% Citrate buffer 50 mM pH 3; 9.5% Tween 80) daily orally in an application volume of 10 mL/kg. The formic acid salt of Example 29 was freshly formulated on days of dosing in the vehicle above. The solutions of Example 29 were administered orally in an application volume of 10 mL/kg either daily at 25 mg/kg, or three times a week at 60 mg/kg, or twice a week at 85 mg/kg (doses represent free base equivalent).

Figure 2:
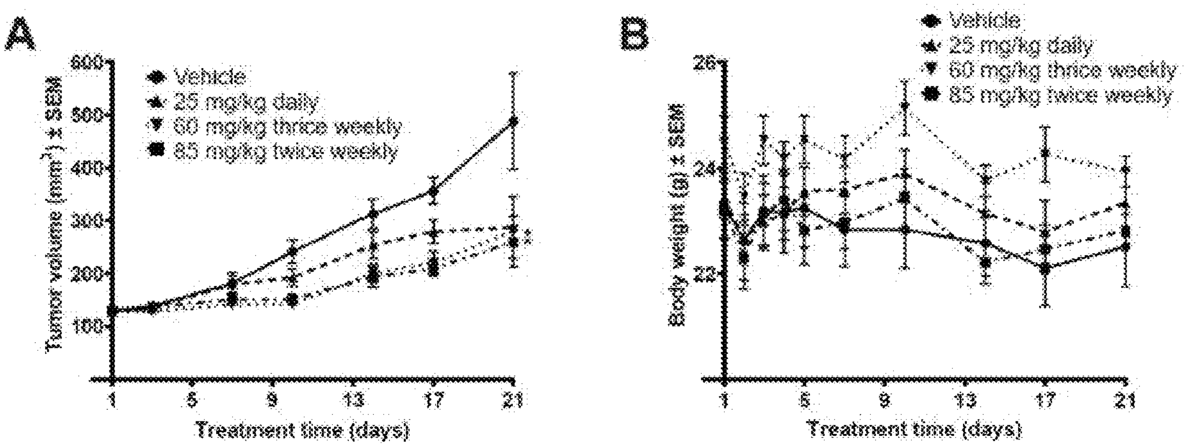
FIG. 2.

Tumor volumes (expressed in $mm^3$) were measured in two dimensions using a caliper on days 1, 3, 7, 10, 14, 17 and 21 of the treatment period. FIG. 2 depicts the tumor growth and body weight changes during the treatment period. Results represent mean values±SEM. Tumor volumes at the conclusion of the study were analyzed by one-way ANOVA analysis to compare treatment groups to the vehicle group. The significance level was set to $P<0.05$. Calculations were conducted using GraphPad™ Prism version 9. At study endpoint (day 21), tumor volumes of mice treated with Example 29 either at 60 mg/kg thrice weekly or at 85 mg/kg twice weekly were significantly smaller as compared with tumor volumes of vehicle-treated animals. At day 21 of the treatment period and compared to the vehicle-treated group, tumor volumes were 41.8%, 42.7% and 46.8% smaller for the 25 mg/kg, 60 mg/kg and 85 mg/kg groups of Example 29, respectively, (FIG. 2A). The treatment with Example 29 was well tolerated, as evidenced by body weight assessments on days 1, 2, 3, 4, 5, 7, 10, 14, 17 and 21 of the treatment period (FIG. 2B).

The invention claimed is:

1. A compound of formula (IB)

(IB)

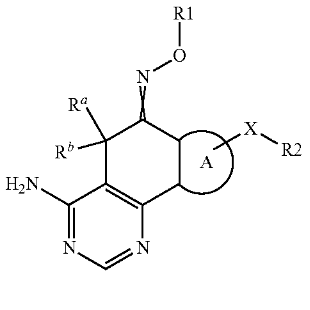

or a pharmaceutically acceptable salt thereof; wherein A is selected from group (A1) and group (A2):

(A1)

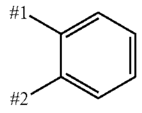

-continued

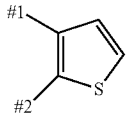

(A2)

wherein #1 is attached to the carbon atom forming the oxime moiety and wherein group (A1) is optionally substituted by one or two R10 and group (A2) is optionally substituted by one R10; each R10 is independently halogen or —$NH_2$;

X is —O—, —C(═O)—, —C(═$CH_2$)—, —$CH_2$—, —NH— or —N(C1-C4alkyl)- and wherein X is a bond when R2 is halogen or —CN and wherein when X is —C(═O)—R2 is not hydrogen;

or X—R2 is hydrogen;

Ra and Rb are both methyl, or together form a —$CH_2$—$CH_2$—$CH_2$— or a —$CH_2$—$CH_2$—$CH_2$—$CH_2$-bridging moiety;

R1 is —Y—R3;

Y is a bond or C1-C6alkylene wherein one non-terminal —$CH_2$-moiety may be replaced by —O—;

R3 is hydrogen, —CN, —OH, C1-C4haloalkyl, C2-C4alkenylene-R4, C2-C4alkynylene-R4, —O-C1-C4alkylene-R4, —O-C1-C4haloalkyl, —$NH_2$, —NH(C1-C4alkylene-R4), —N(C1-C4alkylene-R4)$_2$, —C(═O)—OH, —C(═O)—O—C1-C4alkylene-R4, —C(═O)—$NH_2$, —C(═O)—NH(C1-C4alkylene-R4), —C(═O)—N(C1-C4alkylene-R4)$_2$, Cycle P, Cycle Q, —O-Cycle P, —O-Cycle Q or —S($O_2$)-C1-C4alkyl;

R4 is hydrogen, —$NH_2$, —NH(C1-C2alkyl) or —N(C1-C2alkyl)$_2$;

Cycle P is a 5-6-membered saturated or partially unsaturated carbocyclic ring optionally substituted by one to three R5 or is a 5-6-membered saturated or partially unsaturated heterocyclic ring containing one to two heteroatoms selected from N and O optionally substituted by one to three R5;

each R5 is independently —$NH_2$, —OH, —CN, C1-C4alkyl, C1-C4alkylene-R11, —O-C1-C2alkyl or oxo;

each R11 is independently halogen, —$NH_2$, —OH, —CN or —O-C1-C2alkyl;

Cycle Q is phenyl optionally substituted by one to three R6, or is a 5-6-membered heteroaryl containing one to two heteroatoms selected from N, S and O optionally substituted by one to three R6;

each R6 is independently —$NH_2$, —OH, —CN, C1-C2alkyl or —O-C1-C2alkyl;

R2 is hydrogen, halogen, —CN, C1-C4alkyl optionally substituted by one or two R7, or is a 4- to 7-membered saturated carbocyclic ring optionally substituted by one or two R8, or is a 4- to 7-membered saturated heterocyclic ring containing one-N(R9)-moiety as ring member and otherwise containing only carbon atoms as ring members;

each R7 is independently —OH, halogen, —$NH_2$, —NH(C1-C2alkyl), —N(C1-C2alkyl)$_2$ or —NH(—C(═O)—C1-C2alkyl);

each R8 is independently —OH, halogen, —$NH_2$, —NH(C1-C2alkyl), —N(C1-C2alkyl)$_2$, —NH(—C(═O)—C1-C2alkyl) or C1-C2alkyl; and R9 is hydrogen, C1-C4alkyl or —C(═O)—C1-C2alkyl.

2. The compound of claim 1 or a pharmaceutically acceptable salt thereof, wherein when A is group (A1) X is connected to the carbon atom which is at the para position relative to #2 and when A is group (A2) X is connected to the carbon atom adjacent to the S atom.

3. The compound of claim 1 or a pharmaceutically acceptable salt thereof, wherein X is —O—, —C(═O)—, —C(═$CH_2$)—, —$CH_2$—, —NH— or —N (C1-C4alkyl)- and wherein X is a bond when R2 is halogen or —CN and wherein when X is —C(═O)—R2 is not hydrogen.

4. The compound of claim 1 or a pharmaceutically acceptable salt thereof, wherein R1 is hydrogen or C1-C6alkylene-R3 wherein one non-terminal-$CH_2$-moiety may be replaced by —O—, or R1 is Cycle P.

5. The compound of claim 1 or a pharmaceutically acceptable salt thereof, wherein R1 is hydrogen or C1-C3alkylene-R3.

6. The compound of claim 5 or a pharmaceutically acceptable salt thereof, wherein R3 is hydrogen, —CN, —OH, C1-C4haloalkyl, —O-C1-C4alkyl, —O-C1-C4haloalkyl, C2-C4alkynyl, —C(═O)—OH, —C(═O)—O—C1-C4alkyl, —C(═O)—$NH_2$ or —C(═O)—NH(C1-C4alkyl).

7. The compound of claim 5 or a pharmaceutically acceptable salt thereof, wherein R3 is oxazolidinyl-2-one optionally substituted by one R5, wherein R5 is C1-C4alkyl or C1-C4alkylene-R11.

8. The compound of claim 5 or a pharmaceutically acceptable salt thereof, wherein R3 is hydrogen, —CN, —OH, C1-C4haloalkyl, C2-C4alkenyl, C2-C4alkynyl, —O-C1-C4alkyl, —O-C1-C4haloalkyl, —$NH_2$, —C(═O)—OH, —C(═O)—O—C1-C4alkyl, —C(═O)—$NH_2$, —C(═O)—NH(C1-C4alkylene-R4), Cycle P, Cycle Q, —O-Cycle P, —O-Cycle Q or —S(O2)-C1-C4alkyl.

9. The compound of claim 6 or a pharmaceutically acceptable salt thereof, wherein R2 is hydrogen, halogen, C1-C4alkyl optionally substituted by one or two R7, or is a 6-membered saturated carbocyclic ring optionally substituted by one or two R8, or is a 6-membered saturated heterocyclic ring containing one-N(R9)-moiety as ring member and otherwise containing only carbon atoms as ring members.

10. The compound of claim 1 or a pharmaceutically acceptable salt thereof, wherein A is selected from group (A1) and group (A2) and wherein group (A1) is optionally substituted by one or two R10 and group (A2) is optionally substituted by one R10;

each R10 is independently fluoro, chloro or —$NH_2$; X is —O—, —C(═O)—, —C(═$CH_2$)—, —$CH_2$—, —NH— or —N (C1-C4alkyl)- and wherein X is a bond when R2 is halogen or —CN and wherein when X is —C (—O)—R2 is not hydrogen;

Ra and Rb together form a —$CH_2$—$CH_2$—$CH_2$—$CH_2$-bridging moiety;

R1 is —Y—R3;

Y is a bond or C1-C6alkylene wherein one non-terminal-$CH_2$-moiety may be replaced by —O—;

R3 is hydrogen, —CN, —OH, C1-C4haloalkyl, C2-C4alkenyl, C2-C4alkynyl, —O-C1-C4alkyl, —O-C1-C4haloalkyl, —$NH_2$, —C(═O)—OH, —C(═O)—O—C1-C4alkyl, —C(═O)—$NH_2$, —C(═O)—NH(C1-C4alkylene-R4), Cycle P, Cycle Q, —O-Cycle P, —O-Cycle Q or —S($O_2$)-C1-C4alkyl;

R4 is hydrogen, —$NH_2$ or —NH($CH_3$);

Cycle P is a 6-membered saturated carbocyclic ring optionally substituted by one to two R5 or is a 5-membered saturated heterocyclic ring containing one to two heteroatoms selected from N and O optionally substituted by one to two R5;

each R5 is independently —$NH_2$, —OH, —CN, C1-C2alkyl, —C1-C2alkyl-R11, —O-C1-C2alkyl or oxo;

each R11 is independently halogen, —$NH_2$, —OH, —CN or —O-C1-C2alkyl;

Cycle Q is phenyl optionally substituted by one or two R6, or is a 6-membered heteroaryl containing one to two heteroatoms selected from N, S and O optionally substituted by one or two R6; each R6 is independently —$NH_2$, —OH, —CN, —$CH_3$ or —$OCH_3$;

R2 is hydrogen, halogen, C1-C4alkyl optionally substituted by one or two R7, or is a 6-membered saturated carbocyclic ring optionally substituted by one or two R8 or is a 6-membered saturated heterocyclic ring containing one-N(R9)-moiety as ring member and otherwise containing only carbon atoms as ring members;

each R7 is independently halogen-$NH_2$ or —OH;

each R8 is independently halogen, —$NH_2$ or —$CH_3$;

and R9 is hydrogen or —$CH_3$.

11. The compound of claim 1 or a pharmaceutically acceptable salt thereof, wherein A is group (A1) optionally substituted by one R10;

R10 is chloro or —$NH_2$;

X is connected to the carbon atom which is at the para position relative to #2;

X is —O—, —C(=O)—, —C(=$CH_2$)—, —$CH_2$— or —N($CH_3$)— and wherein X is a bond when R2 is halogen and wherein when X is —C(—O)—R2 is not hydrogen;

Ra and Rb together form a —$CH_2$—$CH_2$—$CH_2$—$CH_2$-bridging moiety;

R1 is hydrogen or C1-C6alkylene-R3; R3 is hydrogen, —CN, —OH, C1-C4haloalkyl, —O-C1-C4alkyl, —O-C1-C4haloalkyl, C2-C4alkynyl, —C(=O)—OH, —C(=O)—O—C1-C4alkyl, —C(=O)—$NH_2$, —C(=O)—NH (C1-C4alkyl), phenyl, oxazolidinyl-2-one or oxazolidinyl-2-one substituted by one R5;

R5 is C1-C2alkyl or C1-C2alkyl-R11;

R11 is halogen, —$NH_2$, —OH, —CN or —O-C1-C2alkyl;

R2 is fluoro, chloro, bromo, iodo, —$CH_3$, C1-C4alkyl-R7, a 6-membered saturated carbocyclic ring substituted by one or two R8 wherein at least one R8 is —$NH_2$ and is at the para position with respect to X, or piperidin-4-yl;

R7 is fluoro, —$NH_2$ or —OH; and each R8 is independently fluoro, —$NH_2$ or —$CH_3$.

12. The compound of claim 1 or a pharmaceutically acceptable salt thereof, wherein the compound is a compound of formula (IAa) or a compound of formula (IBa)

(IAa)

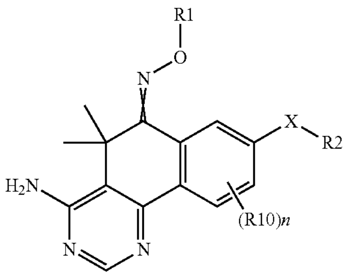

-continued (IBa)

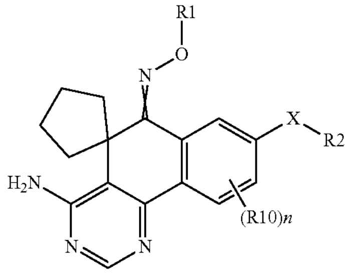

wherein

R10 is chloro or —$NH_2$;

X is —O—, —C(=O)—, —C(—$CH_2$)—, —$CH_2$— or —N($CH_3$)— and wherein X is a bond when R2 is halogen and wherein when X is —C(=O)—R2 is not hydrogen;

R1 is hydrogen or C1-C6alkylene-R3;

R3 is hydrogen, —CN, —OH, C1-C4haloalkyl, —O-C1-C4alkyl, —O-C1-C4haloalkyl, C2-C4alkynyl, —C(=O)—OH, —C(=O)—O—C1-C4alkyl, —C(=O)—$NH_2$, —C(—O)—NH(C1-C4alkyl), phenyl, oxazolidinyl-2-one or oxazolidinyl-2-one substituted by one R5;

R5 is C1-C2alkyl or C1-C2alkyl-R11;

R11 is halogen, —$NH_2$, —OH, —CN or —O-C1-C2alkyl;

R2 is fluoro, chloro, bromo, iodo, —$CH_3$, C1-C4alkyl-R7, a 6-membered saturated carbocyclic ring substituted by one or two R8 wherein at least one R8 is —$NH_2$ and is at the para position with respect to X, or piperidin-4-yl;

R7 is fluoro, —$NH_2$ or —OH;

each R8 is independently fluoro, —$NH_2$ or —$CH_3$; and n is 0 or 1.

13. The compound of claim 1 or a pharmaceutically acceptable salt thereof, wherein the compound of formula (IB) is the Z isomer of the oxime moiety:

(IB-(Z))

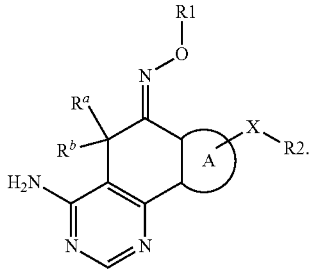

14. The compound of claim 1 or a pharmaceutically acceptable salt thereof, wherein the compound of formula (IB) is the E isomer of the oxime moiety:

(IB-(E))

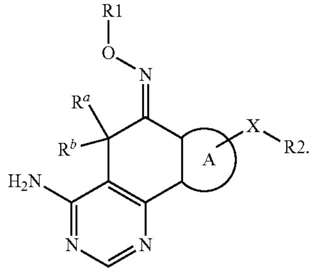

15. The compound of claim 1 or a pharmaceutically acceptable salt thereof, wherein the compound is selected from one of the following compounds:

(6E)-8-(trans-4-aminocyclohexoxy)-6-methoxyimino-5,5-dimethyl-benzo[h] quinazolin-4-amine;
(6Z)-8-(trans-4-aminocyclohexoxy)-6-benzyloxyimino-5,5-dimethyl-benzo[h] quinazolin-4-amine;
(6Z)-8-(trans-4-aminocyclohexoxy)-6-methoxyimino-5,5-dimethyl-benzo[h] quinazolin-4-amine;
(6E)-4-amino-8-(trans-4-aminocyclohexoxy)-5,5-dimethyl-benzo[h] quinazolin-6-one oxime;
(6Z)-4-amino-8-(trans-4-aminocyclohexoxy)-5,5-dimethyl-benzo[h] quinazolin-6-one oxime;
methyl 3-[(Z)-[4-amino-8-(trans-4-aminocyclohexoxy)-5,5-dimethyl-benzo[h] quinazolin-6-ylidene] amino] oxypropanoate;
3-[(Z)-[4-amino-8-(trans-4-aminocyclohexoxy)-5,5-dimethyl-benzo[h] quinazolin-6-ylidene] amino] oxypropan-1-ol;
(6Z)-8-(trans-4-aminocyclohexoxy)-5,5-dimethyl-6-[2-(1-piperidyl) ethoxyimino] benzo[h] quinazolin-4-amine;
(6Z)-8-(trans-4-aminocyclohexoxy)-6-[3-(diethylamino) propoxyimino]-5,5-dimethyl-benzo[h] quinazolin-4-amine;
(6Z)-8-(trans-4-aminocyclohexoxy)-6-[2-(diethylamino) ethoxyimino]-5,5-dimethyl-benzo[h] quinazolin-4-amine;
2-[(Z)-[4-amino-8-(trans-4-aminocyclohexoxy)-5,5-dimethyl-benzo[h] quinazolin-6-ylidene] amino] oxyethanol;
4-[[(Z)-[4-amino-8-(trans-4-aminocyclohexoxy)-5,5-dimethyl-benzo[h] quinazolin-6-ylidene] amino] oxymethyl] benzonitrile;
(6Z)-8-(trans-4-aminocyclohexoxy)-5,5-dimethyl-6-prop-2-ynoxyimino-benzo[h] quinazolin-4-amine;
[(Z)-[4-amino-8-(trans-4-aminocyclohexoxy)-5,5-dimethyl-benzo[h] quinazolin-6-ylidene] amino] oxyacetonitrile;
ethyl 3-[(Z)-[4-amino-8-(trans-4-aminocyclohexoxy)-5,5-dimethyl-benzo[h] quinazolin-6-ylidene] amino]oxypropanoate;
(6Z)-8-(trans-4-aminocyclohexoxy)-6-ethoxyimino-5,5-dimethyl-benzo[h] quinazolin-4-amine;
(6Z)-8-(trans-4-aminocyclohexoxy)-6-[(3,5-dimethylisoxazol-4-yl) methoxyimino]-5,5-dimethyl-benzo[h] quinazolin-4-amine;
(6Z)-8-(trans-4-aminocyclohexoxy)-6-(3-benzyloxypropoxyimino)-5,5-dimethyl-benzo[h] quinazolin-4-amine;
4-[(Z)-[4-amino-8-(trans-4-aminocyclohexoxy)-5,5-dimethyl-benzo[h] quinazolin-6-ylidene] amino] oxybutanenitrile;
(6Z)-8-(trans-4-aminocyclohexoxy)-5,5-dimethyl-6-(2-pyrrolidin-1-ylethoxyimino) benzo[h] quinazolin-4-amine;
(6Z)-8-(trans-4-aminocyclohexoxy)-6-(2-methoxyethoxyimino)-5,5-dimethyl-benzo[h] quinazolin-4-amine;
(6Z)-8-(trans-4-aminocyclohexoxy)-6-isobutoxyimino-5,5-dimethyl-benzo[h] quinazolin-4-amine;
methyl 2-[(Z)-[4-amino-8-(trans-4-aminocyclohexoxy)-5,5-dimethyl-benzo[h] quinazolin-6-ylidene] amino] oxyacetate;
2-[(Z)-[4-amino-8-(trans-4-aminocyclohexoxy)-5,5-dimethyl-benzo[h] quinazolin-6-ylidene]amino]oxyacetamide;
2-[(Z)-[4-amino-8-(trans-4-aminocyclohexoxy)-5,5-dimethyl-benzo[h] quinazolin-6-ylidene] amino] oxy-N-methyl-acetamide;
5-[[(Z)-[4-amino-8-(trans-4-aminocyclohexoxy)-5,5-dimethyl-benzo[h] quinazolin-6-ylidene] amino]oxymethyl] oxazolidin-2-one;
(6Z)-8-(trans-4-aminocyclohexoxy)-6-[2-(dimethylamino) ethoxyimino]-5,5-dimethyl-benzo[h] quinazolin-4-amine;
(6Z)-8-[1-(trans-4-aminocyclohexyl) vinyl]-6-methoxyimino-5,5-dimethyl-benzo[h] quinazolin-4-amine;
(6E)-8-[1-(trans-4-aminocyclohexyl) vinyl]-6-methoxyimino-5,5-dimethyl-benzo[h] quinazolin-4-amine;
2-[(Z)-(4-amino-8-methoxy-5,5-dimethyl-benzo[h] quinazolin-6-ylidene) amino] oxyacetic acid;
(6Z)-6-[(trans-4-aminocyclohexyl) methoxyimino]-8-methoxy-5,5-dimethyl-benzo[h] quinazolin-4-amine;
(6Z)-6-(cis-4-aminocyclohexoxy) imino-8-methoxy-5,5-dimethyl-benzo[h] quinazolin-4-amine;
(6Z)-6-(trans-4-aminocyclohexoxy) imino-8-methoxy-5,5-dimethyl-benzo[h] quinazolin-4-amine; 2-[(Z)-(4-amino-8-methoxy-5,5-dimethyl-benzo[h] quinazolin-6-ylidene) amino] oxyacetamide;
4-[(Z)-(4-amino-8-methoxy-5,5-dimethyl-benzo[h] quinazolin-6-ylidene) amino] oxybutanenitrile;
N-(2-aminoethyl)-2-[(Z)-(4-amino-8-methoxy-5,5-dimethyl-benzo[h] quinazolin-6-ylidene) amino]oxy-acetamide;
(5S)-5-[[(Z)-[4-amino-8-(trans-4-aminocyclohexoxy)-5,5-dimethyl-benzo[h] quinazolin-6-ylidene] amino] oxymethyl] oxazolidin-2-one;
(5R)-5-[[(Z)-(4-amino-8-methoxy-5,5-dimethyl-benzo[h] quinazolin-6-ylidene) amino] oxymethyl] oxazolidin-2-one;
(5S)-5-[[(Z)-(4-amino-8-methoxy-5,5-dimethyl-benzo[h] quinazolin-6-ylidene) amino] oxymethyl] oxazolidin-2-one;
(6Z)-8-methoxy-6-methoxyimino-5,5-dimethyl-benzo[h] quinazolin-4-amine;
(6Z)-8-(trans-4-aminocyclohexoxy)-10-chloro-6-methoxyimino-5,5-dimethyl-benzo[h] quinazolin-4-amine;
(5R)-5-[[(Z)-[4-amino-8-(trans-4-aminocyclohexoxy)-5,5-dimethyl-benzo[h] quinazolin-6-ylidene] amino] oxymethyl] oxazolidin-2-one;
(6Z)-9-chloro-8-methoxy-6-methoxyimino-5,5-dimethyl-benzo[h] quinazolin-4-amine;
(6E)-7-chloro-8-methoxy-6-methoxyimino-5,5-dimethyl-benzo[h] quinazolin-4-amine;
(6E)-8-methoxy-6-methoxyimino-5,5-dimethyl-benzo[h] quinazoline-4,7-diamine;
(6Z)-8-methoxy-6-methoxyimino-5,5-dimethyl-benzo[h] quinazoline-4,9-diamine;

(6Z)-7-chloro-8-methoxy-6-methoxyimino-5,5-dimethyl-benzo[h] quinazolin-4-amine;

(6Z)—N8-(trans-4-aminocyclohexyl)-6-methoxyimino-N8,5,5-trimethyl-benzo[h] quinazoline-4,8-diamine;

(6Z)-8-(trans-4-aminocyclohexoxy)-6-methoxyimino-5,5-dimethyl-thieno[3,2-h] quinazolin-4-amine;

(5S)-5-[[(Z)-(4-amino-8-methoxy-5,5-dimethyl-benzo[h] quinazolin-6-ylidene) amino] oxymethyl]-3-methyl-oxazolidin-2-one;

(5S)-5-[[(Z)-(4-amino-8-bromo-5,5-dimethyl-benzo[h] quinazolin-6-ylidene) amino] oxymethyl] oxazolidin-2-one;

(5S)-5-[[(Z)-(4-amino-8-chloro-5,5-dimethyl-benzo[h] quinazolin-6-ylidene) amino] oxymethyl]-3-methyl-oxazolidin-2-one;

(5S)-5-[[(Z)-(4-amino-8-chloro-5,5-dimethyl-benzo[h] quinazolin-6-ylidene) amino] oxymethyl]-3-methyl-oxazolidin-2-one;

(6Z)-8-(cis-4-aminocyclohexoxy)-6-methoxyimino-5,5-dimethyl-benzo[h] quinazolin-4-amine 3-[(Z)-[4-amino-8-(trans-4-aminocyclohexoxy)-5,5-dimethyl-benzo[h] quinazolin-6-ylidene] amino] oxypropanenitrile;

(5S)-5-[[(Z)-[4-amino-8-(trans-4-aminocyclohexoxy)-5,5-dimethyl-benzo[h] quinazolin-6-ylidene] amino] oxymethyl]-3-methyl-oxazolidin-2-one;

(6Z)-6-methoxyimino-5,5-dimethyl-8-[-(1R,3S,4R)-4-amino-3-fluoro-cyclohexoxy] benzo[h] quinazolin-4-amine;

(6Z)-6-(2-aminoethoxyimino)-8-methoxy-5,5-dimethyl-benzo[h] quinazolin-4-amine;

(6Z)-6-(3-aminopropoxyimino)-8-methoxy-5,5-dimethyl-benzo[h] quinazolin-4-amine;

3-[(E)-[4-amino-8-(trans-4-aminocyclohexoxy)-5,5-dimethyl-benzo[h] quinazolin-6-ylidene] amino] oxypropanenitrile;

(6Z)-4-amino-6-methoxyimino-5,5-dimethyl-benzo[h] quinazolin-8-ol;

(6Z)-8-methoxy-5,5-dimethyl-6-[[(3R)-pyrrolidin-3-yl] methoxyimino] benzo[h] quinazolin-4-amine;

(6E)-8-methoxy-5,5-dimethyl-6-[[(3R)-pyrrolidin-3-yl] methoxyimino] benzo[h] quinazolin-4-amine;

(6Z)-6-allyloxyimino-8-(trans-4-aminocyclohexoxy)-5,5-dimethyl-benzo[h] quinazolin-4-amine;

(6E)-6-allyloxyimino-8-(trans-4-aminocyclohexoxy)-5,5-dimethyl-benzo[h] quinazolin-4-amine;

(6Z)-6-methoxyimino-5,5-dimethyl-8-(4-piperidyloxy) benzo[h] quinazolin-4-amine;

(6Z)-8-(trans-4-aminocyclohexoxy)-6-isopropoxyimino-5,5-dimethyl-benzo[h] quinazolin-4-amine;

(6E)-8-(trans-4-aminocyclohexoxy)-6-isopropoxyimino-5,5-dimethyl-benzo[h] quinazolin-4-amine;

(6Z)-6-methoxyimino-N8,5,5-trimethyl-N8-(4-piperidyl) benzo[h] quinazoline-4,8-diamine;

(6Z)-6-methoxyimino-5,5-dimethyl-8-(4-piperidylmethyl) benzo[h] quinazolin-4-amine;

(6Z)-8-methoxy-5,5-dimethyl-6-[[(3S)-1-methylpyrrolidin-3-yl] methoxyimino] benzo[h] quinazolin-4-amine;

(4S)-4-[[(Z)-(4-amino-8-methoxy-5,5-dimethyl-benzo[h] quinazolin-6-ylidene) amino] oxymethyl] pyrrolidin-2-one;

(4R)-4-[[(Z)-(4-amino-8-methoxy-5,5-dimethyl-benzo[h] quinazolin-6-ylidene) amino] oxymethyl] pyrrolidin-2-one;

(6Z)-8-[(trans-4-aminocyclohexyl) methyl]-6-methoxyimino-5,5-dimethyl-benzo[h] quinazolin-4-amine;

(6Z)-8-[(cis-4-aminocyclohexyl) methyl]-6-methoxyimino-5,5-dimethyl-benzo[h] quinazolin-4-amine;

(4S)-4-[[(Z)-(4-amino-8-methoxy-5,5-dimethyl-benzo[h] quinazolin-6-ylidene) amino] oxymethyl]-1-methyl-pyrrolidin-2-one;

(6Z)-10-fluoro-8-methoxy-6-methoxyimino-5,5-dimethyl-benzo[h] quinazolin-4-amine;

(2R)-1-[(Z)-[4-amino-8-(trans-4-aminocyclohexoxy)-5,5-dimethyl-benzo[h] quinazolin-6-ylidene] amino] oxypropan-2-ol;

(2S)-1-[(Z)-[4-amino-8-(trans-4-aminocyclohexoxy)-5,5-dimethyl-benzo[h] quinazolin-6-ylidene]amino]oxypropan-2-ol;

(6Z)-8-bromo-6-(2-methoxyethoxyimino)-5,5-dimethyl-benzo[h] quinazolin-4-amine;

3-[(Z)-(4-amino-8-bromo-5,5-dimethyl-benzo[h] quinazolin-6-ylidene) amino] oxypropanenitrile;

(6Z)-8-(cis-4-aminocyclohexoxy)-6-(2-methoxyethoxyimino)-5,5-dimethyl-benzo[h] quinazolin-4-amine;

3-[(Z)-[4-amino-8-(cis-4-aminocyclohexoxy)-5,5-dimethyl-benzo[h] quinazolin-6-ylidene] amino]oxypropanenitrile;

(Z)-4-amino-8-bromo-5,5-dimethyl-benzo[h] quinazolin-6-one oxime;

(E)-4-amino-8-bromo-5,5-dimethyl-benzo[h] quinazolin-6-one oxime;

2-[(Z)-(4-amino-8-bromo-5,5-dimethyl-benzo[h] quinazolin-6-ylidene) amino] oxyethanol;

2-[(Z)-[4-amino-8-(cis-4-aminocyclohexoxy)-5,5-dimethyl-benzo[h] quinazolin-6-ylidene] amino] oxyethanol;

(5S)-5-[[(Z)-[4-amino-8-(cis-4-aminocyclohexoxy)-5,5-dimethyl-benzo[h] quinazolin-6-ylidene] amino] oxymethyl]-3-methyl-oxazolidin-2-one;

(6Z)-8-bromo-6-methoxyimino-5,5-dimethyl-benzo[h] quinazolin-4-amine;

(5S)-5-[[(Z)-(4-amino-8-bromo-5,5-dimethyl-benzo[h] quinazolin-6-ylidene) amino] oxymethyl]-3-(2-methoxyethyl) oxazolidin-2-one;

(5S)-5-[[(Z)-(4-amino-8-bromo-5,5-dimethyl-benzo[h] quinazolin-6-ylidene) amino] oxymethyl]-3-(2-hydroxyethyl) oxazolidin-2-one;

(6Z)-4-amino-5,5-dimethyl-6-[[(5S)-2-oxooxazolidin-5-yl] methoxyimino] benzo[h] quinazoline-8-carbonitrile;

(5S)-5-[[(Z)-(4-amino-8-iodo-5,5-dimethyl-benzo[h] quinazolin-6-ylidene) amino]oxymethyl] oxazolidin-2-one;

(5S)-5-[[(Z)-[4-amino-8-(2-hydroxyethoxy)-5,5-dimethyl-benzo[h] quinazolin-6-ylidene] amino] oxymethyl] oxazolidin-2-one;

(6Z)—N8-(trans-4-aminocyclohexyl)-6-(2-methoxyethoxyimino)-5,5-dimethyl-benzo[h] quinazoline-4,8-diamine;

(6Z)—N8-(cis-4-aminocyclohexyl)-6-(2-methoxyethoxyimino)-5,5-dimethyl-benzo[h] quinazoline-4,8-diamine;

(5S)-5-[[(Z)-(4-amino-8-iodo-5,5-dimethyl-benzo[h] quinazolin-6-ylidene) amino] oxymethyl]-3-(2-hydroxyethyl) oxazolidin-2-one;

(5S)-5-[[(Z)-(8-acetyl-4-amino-5,5-dimethyl-benzo[h] quinazolin-6-ylidene) amino]oxymethyl] oxazolidin-2-one;

(6Z)-8-(trans-4-aminocyclohexoxy)-6-(2-methoxyethoxyimino) spiro[benzo[h] quinazoline-5,1'-cyclopentane]-4-amine;

(6Z)-8-(cis-4-aminocyclohexoxy)-6-(2-methoxyethoxyimino) spiro[benzo[h] quinazoline-5,1'-cyclopentane]-4-amine;

3-[(Z)-[4-amino-8-(cis-4-aminocyclohexoxy) spiro [benzo[h] quinazoline-5,1'-cyclopentane]-6-ylidene] amino]oxypropanenitrile;

3-[(Z)-[4-amino-8-(trans-4-aminocyclohexoxy) spiro [benzo[h] quinazoline-5,1'-cyclopentane]-6-ylidene] amino] oxypropanenitrile;

(6Z)-8-(cis-4-amino-4-methyl-cyclohexoxy)-6-(2-methoxyethoxyimino)-5,5-dimethyl-benzo[h] quinazoline-4-amine;

4-amino-8-(cis-4-aminocyclohexoxy) spiro[benzo[h] quinazoline-5,1'-cyclopentane]-6-one oxime;

(6Z)-8-(cis-4-aminocyclohexoxy)-5,5-dimethyl-6-[2-(trifluoromethoxy) ethoxyimino] benzo[h] quinazoline-4-amine;

(6Z)-8-(cis-4-aminocyclohexoxy)-5,5-dimethyl-6-(2-phenylethoxyimino) benzo[h] quinazoline-4-amine;

(6Z)-8-(cis-4-aminocyclohexoxy)-5,5-dimethyl-6-(2-phenoxyethoxyimino) benzo[h] quinazoline-4-amine;

(6Z)-8-(cis-4-aminocyclohexoxy)-5,5-dimethyl-6-[3-(3-pyridyl) propoxyimino] benzo[h] quinazoline-4-amine;

(6Z)-8-(cis-4-aminocyclohexoxy)-6-(2-ethoxyethoxyimino)-5,5-dimethyl-benzo[h] quinazoline-4-amine;

(6Z)-8-(cis-4-aminocyclohexoxy)-5,5-dimethyl-6-(3-methylsulfonylpropoxyimino) benzo[h] quinazoline-4-amine;

4-[(Z)-[4-amino-8-(cis-4-aminocyclohexoxy)-5,5-dimethyl-benzo[h] quinazolin-6-ylidene]amino]oxy-2,2-dimethyl-butanenitrile;

(6Z)-8-(cis-4-aminocyclohexoxy)-5,5-dimethyl-6-[2-(2,2,2-trifluoroethoxy) ethoxyimino] benzo[h] quinazolin-4-amine;

(6Z)-8-(cis-4-aminocyclohexoxy)-6-(4-fluorobutoxyimino)-5,5-dimethyl-benzo[h] quinazolin-4-amine;

(6Z)-8-(cis-4-aminocyclohexoxy)-5,5-dimethyl-6-(4,4,4-trifluorobutoxyimino) benzo[h] quinazolin-4-amine;

(6Z)-8-(cis-4-aminocyclohexoxy)-6-(3,3-difluorobutoxyimino)-5,5-dimethyl-benzo[h] quinazolin-4-amine; and (6Z)-8-(cis-4aminocyclohexoxy)-5,5-dimethyl-6-(3,3,3-trifluoropropoxyimino) benzo[h] quinazoline-4-amine.

16. A method of treating a neoplastic disease in a mammal, comprising administering an effective amount of a compound of formula (IB) as defined in claim 1 or a pharmaceutically acceptable salt thereof to said mammal.

17. A pharmaceutical composition comprising i) a compound of formula (IB) as defined in claim 1 or a pharmaceutically acceptable salt thereof; and ii) one or more pharmaceutically acceptable excipients.

18. A compound of formula (Int-IB)

(Int-IB)

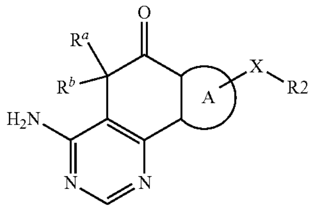

or a salt thereof, wherein A, X, Ra, Rb and R2 are as defined for the compound of formula (IB) in claim 1.

19. A compound of formula (Int-IIB)

(Int-IIB)

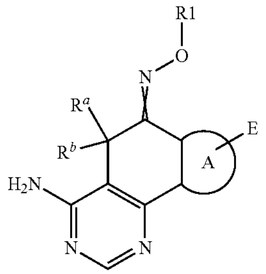

or a salt thereof, wherein A, Ra, Rb and R1 are as defined for the compound of formula (IB) in claim 1 and E is halogen or —O-L1, and —O-L1 is a leaving group in which L1 is selected from a perfluoroalkylsulfonyl such as triflyl (trifluoromethansulfonyl) and a sulfonyl such as tosyl (p-toluenesulfonyl) or mesyl (methanesulfonyl).

20. The method of claim 16, wherein the neoplastic disease is cancer, and the mammal is a human.

* * * * *